US005994109A

United States Patent [19]
Woo et al.

[11] Patent Number: 5,994,109
[45] Date of Patent: Nov. 30, 1999

[54] NUCLEIC ACID TRANSPORTER SYSTEM AND METHODS OF USE

[75] Inventors: Savio L. C. Woo; Louis C. Smith, both of Houston; Richard J. Cristiano, Pearland; Stephen Gottchalk; Jim Sparrow, both of Houston, all of Tex.

[73] Assignee: Baylor College of Medicine, Houston, Tex.

[21] Appl. No.: 08/460,890

[22] Filed: Jun. 3, 1995

Related U.S. Application Data

[60] Division of application No. 08/167,641, Dec. 14, 1993, which is a continuation-in-part of application No. 07/855,389, Mar. 20, 1992, abandoned, said application No. 08/167,641, is a continuation-in-part of application No. PCT/US93/02725, Mar. 19, 1993.

[51] Int. Cl.$^6$ .............................. C12N 15/63; C12N 7/00; C07K 4/00; C07H 21/00
[52] U.S. Cl. .................................. 435/172.3; 435/235.1; 435/325; 530/350; 536/23.1
[58] Field of Search .............................. 435/172.3, 173.4, 435/235.1, 325; 530/395, 350; 536/23.1

[56] References Cited

U.S. PATENT DOCUMENTS

| | | | |
|---|---|---|---|
| 4,490,529 | 12/1984 | Rosowsky | 544/260 |
| 4,801,575 | 1/1989 | Pardridge | 514/4 |
| 4,891,219 | 1/1990 | Karr et al. | 424/145.1 |
| 5,108,921 | 4/1992 | Low et al. | 435/375 |
| 5,166,320 | 11/1992 | Wu et al. | 530/395 |
| 5,547,932 | 8/1996 | Curiel et al. | 435/85 |

FOREIGN PATENT DOCUMENTS 8805077   7/1988   WIPO .

OTHER PUBLICATIONS

Wagner et al. Transferrin–polycation cinjugates as carriers for DNA uptake into cells. Proc. Natl. Acad. Sci. U.S.A. vol. 87, 3410 3414, 1990.
Orkin et al. Report and recommendations of the panel to assess the NIH investment in research on gene therapy, 1995.
Paralkar et al. Identification and characterization of cellular binding proteins (receptors) for recombinant heman bone mmorphogenetic protein 2B, an initiator of bone differentiation cascade Proc. Natl. Acad. Sci. USA vol. 88 3397–3401, 1991.
Abiko, "Syntheses and Structure–Activity Relationships of Thymopoietin," 153–155.
Anderson, "Prospects for Human Gene Therapy," 226 *Science* 401, 1984.
Audhya et al., "Isolation and Complete Amino Acid Sequence of Human Thymopoietin and Splenin," 84 *Proc. Natl. Acad. Sci. USA* 3545, 1987.
Baeza et al., "Electron Microscopy and Biochemical Properties of Polyamine–Compacted DNA," 26 *Biochemistry* 6387, 1987.
Bayne et al., "The C Region of Human Insulin–like Growth Factor (IGF) I is Required for High Affinity Binding to the Type 1 IGF Receptor," 264 *J. Biol. Chem.* 11004, 1988.
Behr et al., "Efficient Gene Transfer into Mammalian Primary Endocrine Cells with Lipopolyamine–coated DNA," 86 *Proc. Natl. Acad. Sci. USA* 6982, 1989.
Berstein et al., "A Deeply Recessed Active Site in Angiotensin–Converting Enzyme is Indicated from the Binding Characteristics of Biotin–Spacer–Inhibitor Reagents," 167 *Biochem. Biophys. Res. Comm.* 310, 1990.
Beukers et al., "[Leu$^{27}$] Insulin–Like Growth Factor II is Highly Selective for the Type–II IGF Receptor in Binding, Cross–Linking and Thymidine Incorporation Experiments," 128 *Endocrinology* 1201, 1991.
Bielecki et al., "*Bacillus Subtilis* Expressing a Haemolysin Gene from Listeria Monocytogenes Can Grow in Mammalian Cells," 345 *Nature* 175, 1990.
Braulin et al., "Equilibrium Dialysis Studies of Polyamine Binding to DNA," 21(7) *Biopolymers* 1301, 1982.
Campbell et al., "Folate–Binding Protein Is a Marker for Ovarian Cancer" 51 *Cancer Res.* 5329, 1991.
Carlsson et al., "Protein Thiolation and Reversible Protein—Protein Conjugation," 173 *Biochem. J.* 723, 1978 (Printed in Great Britain).
Carswell et al., "Simian Virus 40 Agnoprotein Facilitates Perinuclear–Nuclear Localization of VP1, the Major Capsid Protein," 60(3) *J. Virology* 1055, 1986.
Cascieri et al., "Structural Analogs of Human Insulin–like Growth Factor (IGF) I with Altered Affinity for Type 2 IGF Receptors," 264 *J. Biol. Chem.* 2199, 1989.
Cascieri et al., "Characterization of the Biological Activity of IGF I Analogs with Reduced Affinity for IGF Receptors and Binding Proteins," 293 *Adv. Exp. Med. Biol.* 23, 1991.
Chantry et al., "Cross–reactivity of Amylin with Calcitonin–Gene–Related Peptide Minding Sites in Rat Liver and Skeletal Muscle Membranes," 277 *Biochem. J.* 139, 1991 (Printed in Great Britain).
Chiba et al., "Calcitonin Gene–Related Peptide Receptor Antagonist Human CGRP — (8–37)," *American Physiological Society*, (0193–1849/89), pp. E331–E335 (1989).
Coney et al., "Cloning of a Tumor–Associated Antigen: MOv18 and MOv19 Antibodies Recognize a Folate–Binding Protein," 51 *Cancer Res.* 6125, 1991.
Cossart and Mengaud, "*Listeria Monocytogenes*: A Model System for the Molecular Study in Intracellular Parasitism," 6 *Mol. Biol. Med.* 463, 1989.

(List continued on next page.)

*Primary Examiner*—John L. LaGuyader
*Assistant Examiner*—John S. Brusca
*Attorney, Agent, or Firm*—Lyon & Lyon LLP

[57] ABSTRACT

Nucleic acid transporter systems for delivery of nucleic acid to a cell. The nucleic acid transporter includes a binding complex. The binding complex contains a binding molecule which non-covalently binds to the nucleic acid and covalently links to a surface ligand, nuclear ligand and/or a lysis agent. These may be linked to the binding molecule by spacers.

25 Claims, 40 Drawing Sheets

OTHER PUBLICATIONS

Cotten et al., "Transferrin–Polycation–Mediated Introduction of DNA into Human Leukemic Cells: Stimulation by Agents that Affect the Survival of Transfected DNA or Modulate Transferrin Receptor Levels," 87 *Proc. Natl. Acad. Sci. USA* 4033, 1990.

Curiel et al., "Gene Transfer to Respiratory Epithelial Cells via the Receptor–Mediated Endocytosis Pathway," 6 *Am. J. Respir. Cell Mol. Biol.* 247, 1992.

Curiel et al., "Adenovirus Enhancement of Transferrin–Polylysine–Mediated Gene Delivery,"88 *Proc. Natl. Acad. Sci. USA* 8850, 1991.

Dennis et al., "Structure–Activity Profile of Calcitonin Gene–Related Peptide in Peripheral and Brain Tissues. Evidence for Receptor Multiplicity," 251 *J. Pharm. Exper. Ther.* 718, 1989.

Dingwall and Laskey, "Nuclear Targeting Sequences — a Consensus?", 16 *Trend in Biochem. Sc* 478, 1991.

Distler et al., "The Binding Specificity of High and Low Molecular Weight Phosphomannosyl Receptors from Bovine Testes," 266 *J. Biol. Chem.* 21687, 1991.

Durland et al., "Binding of Triple Helix Forming Oligonucleotides to Sites in Gene Promoters," 30 *Biochemistry* 9246, 1991.

Dyer et al., "A Synthetic Peptide Mimic of Plasma Apolipoprotein E that Binds the LDL Receptor," 266 *J. Biol. Chem.* 22803, 1991.

Feener et al., "Cleavage of Disulfide Bonds in Endocytosed Macromolecules," 265 *J. Biol. Chem.* 18780–18785, 1990.

Felgner et al., "Gene Therapeutics," 349 *Nature* 351, 1991.

Foyt et al., "The IFG–I Gene: Structure, Expression, and Gene Products," In: Insulin–Like Growth Factors: Molecular and Cellular Aspects, *CRC Press* (1991).

Friedman, "Progress Toward Human Gene Therapy," 244 *Science* 1275, 1989.

Garcia–Bustos et al., "Nuclear Protein Localization," 1071 *Biochim. Biophys. Acta* 83, 1991.

Geoffroy et al., "Alveolysin, the Thiol–Activated Toxin of *Bacillus alvei*, Is Homologous to Listeriolysin O, Perfringolysin O, Pneumolysin, and Streptolysin O and Contains a Single Cysteine," 172 *J. Bacteriol.* 7301, 1990.

Gilardi et al., "Expression of Human $\alpha_1$–Antitrypsin Using a Recombinant Adenovirus Vector," 267 *FEBS* 60, 1990.

Goldfard et al., "Synthetic Peptides as Nuclear Localization Signals," 322 *Nature* 641, 1986.

Goldstein et al., "Coated Pits, Coated Vesicles, and Receptor–Mediated Endocytosis," 279 *Nature* 679, 1979.

Hardy et al., "Different Modes of Ligand Binding to the Hepatic Galactose/N–Acetygalactosamine Lectin on the Surface of Rabbit Hepatocytes," 24 *Biochemistry* 22, 1985.

Henderson, "Folate–Binding Proteins," 10 *Annu. Rev. Nutr.* 319, 1990.

Hobbs et al., "The LDL Receptor Locus in Familial Hypercholesterolemia: Mutational Analysis of a Membrane Protein," 24 *Annu. Rev. Genet.* 133, 1990.

Ichikawa et al., "Synthesis of a Branched Glycopeptide Derivative Containing Terminal $_D$–Mannose 6–Phosphate Residues," 198 *Carbohydrate Research* 235, 1990.

Inman et al., "Controlled Primary Functionalization of Agarose Affinity Supports by Carboxymethylation and Subsequent Addition of Spacer Units," 376 *J. Chromat.* 273, 1986.

Israel et al., "Analogs of Spermine and Spermidine," 94 *Methods in Enzymology* 411, 1983.

Jaffe et al., "Adenovirus–Mediated In Vivo Gene Transfer and Expression in Normal Rat Liver," 1 *Nature–Genetics* 372, 1992.

Jennings et al., "Chick Myotubes in Culture Express High–Affinity Receptors for Calcitonin Gene–Related Peptide," 504 *Brain Research* 199, 1989.

Kaleko et al., "Persistent Gene Expression After Retroviral Gene Transfer into Liver Cells In Vivo," 2 *Human Gene Therapy* 27, 1991.

Kempen et al., "A Water–Soluble Cholesteryl–Containing Trisgalactoside: Synthesis, Properties, and Use in Directing Lipid–Containg Particles to the Liver," 27 *J. Med. Chem.* 1306, 1984.

Kiess et al., "Insulin–Like Growth Factor–II (IGF–11) Inhibits Both the Cellular Uptake of $\beta$–Galactosidase and the Binding of $\beta$–Galactosidase to Purified IGF–II/Mannose 6–Phosphate Receptor," 264 *J. Biol. Chem.* 4710, 1989.

Lanford et al., "Effect of Basic and Nonbasic Amino Acid Substitutions on Transport Induced by Simian Virus 40 T–Antigen Synthetic Peptide Nuclear Transport Signals," 8 *Mol. Cell. Biol.* 2722, 1988.

Leamon and Low, "Delivery of Macromolecules into Living Cells: A Method that Exploits Folate Receptor Endocytosis," 88 *Proc. Natl. Acad. Sci. USA* 5572, 1991.

Leamon and Low, "Cytotoxicity of Momordin–Folate Conjugates in Cultured Human Cells," 267 *J. Biol. Chem.* 24966, 1992.

Lee et al., "Cluster Glycosides," 138 *Meth. Enzym.* 424, 1987.

Lee et al., "New Synthetic Cluster Ligands for Galactose/N–Acetylgalactosamine–Specific Lectin of Mammalian Liver," 23 *Biochemistry* 4255, 1984.

Leonetti et al., "Biological Activity of Oligonucleotide–oly(L–lysine) Conjugates: Mechanism of Cell Uptake," 1 *Bioconjugate Chemistry* 149, 1990.

Ling et al., "Isolation, Primary Structure, and Synthesis of Human Hypothalamic Somatocrinin: Growth Hormone–Releasing Factor," 81 *Proc. Natl. Acad. Sci. USA* 4302, 1984.

Lowe, Jr., "Biological Actions of the Insulin–Like Growth Factors," Insulin–Like Growth Factors: Molecular and Cellular Aspects, CRC Press (1991).

Lukas et al., "Interactions of the Thymic Polypeptide Hormone Thymopietin with Neuronal Nicontinic $\alpha$–Bungarotoxin Binding Sites and with Muscle–Type, but Not Ganglia–Type, Nicontinic Acetylcholine Receptor Ligand–Gated Ion Channels," 38 *Am. Soc. Pharm. Exper. Ther.* 887, 1990.

Marsh and Helenius, "Virus Entry Into Animal Cells," 36 *Adv. Virus Res.* 107, 1989.

McGraw et al., "Human Transferrin Receptor Internalization is Partially Dependent Upon an Aromatic Amino Acid on the Cytoplasmic Domain," 1 *Cell Regulation* 369, 1990.

Mellman et al., "Acidification of the Endocytic and Exocytic Pathways," 55 *Ann. Rev. Biochem.* 663, 1986.

Morita et al., "Structure–Activity Relationship of Calcitonin Gene Related Peptide," 21 *Horm. Metabol. Res.* 66, 1989.

Moulder, "Comparative Biology of Intracellular Parasitism," 49 *Microbiol. Rev.* 298, 1985.

Neda et al., "Chemical Modification of an Ecotropic Murine Leukemia Virus Results in Redirection of Its Target Cell Specificity," 266 *J. Biol. Chem.* 14143, 1991.

Noda et al., "Synthesis of an Analog of Human Calcitonin ene Related Peptide, [$Asu^{2,7}$]–h–CGRP," *Experientia* 890, Birkhauser Verlag, Ch–4010 Basel/Switzerland (1987).

Oh et al., "Altered Affinity of Insulin–Like Growth Factor II (IGF–II) for Receptors and IGF–Binding Proteins, Resulting from Limited Modifications of the IGF–II Molecule," 278 *Biochem. J.* 249, 1991.

Oshima, "Novel Polyamines in *Thermus thermophilus:* Isolation, Identification, and Chemical Synthesis," 94 *Methods in Enzymology* 401, 1983.

Pearse and Bretscher, "Membrane Recycling by Coated Vesicles," 50 *Annu. Rev. Biochem.* 85, 1981.

Peinado et al., "Hepatic Lipoate Uptake," 273, *Archives of Biochemistry and Biophysics* 389, 1989.

Poorman et al., "Bile Acid Excretion and Cholesterol 7α–Hydroxylase Activity in Hypercholesterolemia–Resistant Rabbits," 11 *Arterioscl. Throm.* 1413a, 1991.

Pastan and Willingham, "Receptor–Mediated Endocytosis of Hormones in Cultured Cells," 43 *Annu. Rev. Physiol.* 239, 1981.

Quik et al., "Thymopoietin Interacts at the α–Bungarotoxin Site of and Induces Process Formation in PC12 Pheochromocytoma Cells," 39 *Neuroscience* 139, 1990.

Quik et al., "Thymopoietin, a Potent Antagonist at Nicotinic Receptors in C2 Muscle Cell Cultures," 39 *Molecular Pharmacology* 324.

Rechler, "Insulin–Like Growth Factor II: Gene Structure and Expression into Messenger RNA and Protein," Insulin–Like Growth Factors: Molecular and Cellular Aspects, CRC Press (1991).

Rosenfeld et al., "Adenovirus–Mediated Transfer of a Recombinant α1–Antitrypsin Gene to the Lung Epithelium In Vivo," 252 *Science* 431, 1991.

Rosenfeld et al., "In Vivo Transfer of the Human Cystic Fibrosis Transmembrane Conductance Regulator Gene to the Airway Epithelium," 68 *Cell* 143, 1992.

Ross et al., "Insulin–Like Growth Factor (IGF)–Binding Proteins Inhibit the Biological Activities of IGF–1 and IGF–2 but Not des–(1–3)–IGF–1," 258 *Biochem. J.* 267, 1989.

Roth et al., "Mutants of Human Insulin–Like Growth Factor II: Expression and Characterization of Analogs With a Substitution of TYR$^{27}$ and/or a Deletion of Residues 62–67," 181 *Biochem. Biophys. Res. Comm.* 907, 1991.

Rothberg et al., "The Glycophospholipid–Linked Folate Receptor Internalizes Folate Without Entering the Clathrin–Coated Pit Endocytic Pathway," 110 *J. Cell Biol.* 637, 1990.

Sakano et al., "The Design, Expression, and Characterization of Human Insulin–Like Growth Factor II (IGF–II) Mutants Specific for Either the IGF–II/Cation–Independent Mannose 6–Phosphate Receptor or IGF–I Receptor," 266 *J. Biol. Chem.* 20626, 1991.

Sara et al., "Insulin–Like Growth Factors and Their Binding Proteins," 70 *Amer. Physiol. Soc.* 591, 1990.

Schwartz et al., "The Hepatic Asialoglycoprotein Receptor," 16 *CRC Crit. Rev Biochem.* 207, 1989.

Shen, "Acid–Sensitive Dissociation Between Poly(lysine) and Histamine–Modified Poly(glutamate) as a Model for Drug–Releasing from Carriers in Endosomes," 1034 *Biochim. Biophys. Acta* 122, 1990.

Shepherd, "Intracellular Pathways and Mechanisms of Sorting in Receptor–Mediated Endocytosis," Elsevier Science Publishers Ltd. (UK), 10 *Trends in Pharmacol. Sci.* 458, 1989.

Shitara et al., "Application of Anti–Sialyl Le$^a$ Monoclonal Antibody, KM231, for Immunotherapy of Cancer," 11 *Anticancer Research* 2003, 1991.

Silver, "How Proteins Enter the Nucleus," 64 *Cell.* 489, 1991.

Silverstein et al., "Endocytosis," 46 *Ann. Rev. Biochem.* 669, 1977.

Simionescu et al., "Permeability of Muscle Capillaries to Small Heme–Peptides: Evidence for the Existence of Patent Transendothelial Channels," 64 *J. Cell Biol.* 586, 1975.

Slinkin et al., "Terminal–Modified Polylysine–Based Chelating Polymers: Highly Efficient Coupling to Antibody with Minimal Loss in Immunoreactivity," 2 *Bioconjugate Chem.* 342, 1991.

Stangl et al., "Characterization and Photoaffinity Labeling of a Calcitonin Gene–Related Peptide Receptor Solubilized from Human Cerebellum," *Biochemistry* 8605, 1991.

Stewart, "The Effect of Structural Changes in a Polyamine Backbone on its DNA–Binding Properties," 152 *Biochem. Biophys. Res. Comm.* 1441, 1988.

Stowell et al., "Neoglycoproteins The Preparation and Application of Synthetic Glycoproteins," 37 *Advances in Carbohydrate Chemistry and Biochemistry* 225.

Stratford–Perricaudet et al., "Evaluation of the Transfer and Expression in Mice of an Enzyme–Encoding Gene Using a Human Adenovirus Vector," 1 *Hum. Gene Ther.* 242, 1990.

Takeuchi et al., "B–Z Transition of Poly(dG–m$^5$dC) induced by binding of Lys–Containing Peptides," 279 *FEBS Letters* 253, 1991, Published by Elsevier Science Publishers B.V.

Tavis et al., "Nucleotide Sequence of the Human Polyomavirus AS Virus, and Antigenic Variant of BK Virus," 63(2) *J. Virology* 901, 1989.

Thiebaud et al., "Structure–Activity Relationships in Calcitonin Gene–Related Peptide: Cyclic AMP Response in a Preosteoblast Cell Line (KS–4)," 6 *Journal of Bone and Mineral Research* 1137, 1991.

Thorpe et al., "New Coupling Agents for the Synthesis of Immunotoxins Containing a Hindered Disulfide Bond with Improved Stability In Vivo," 47 *Cancer Research* 5924, 1987.

Tilney and Portnoy, "Actin Filaments and the Growth, Movement, and Spread of the Intracellular Bacterial Parasite, Listeria Monocytogens," 109 *J. Cell Bio.* 1597, 1989.

Tong et al., "Ligand Interactions of the Cation–Independent Mannose 6–Phosphate Receptor," 264 *J. Biol. Chem.* 7962, 1989.

Trubetskaya et al., "Monoclonal Antibody to Human Endothelial Cell Surface Internalization and Liposome Delivery in Cell Culture," 228 *FEBS Letters* 131, 1988, Elsevier Science Publishers B.V. (Biomedical Division).

Tung et al., "An Acridine Amino Acid Derivative for Use in Fmoc Peptide Synthesis," 5 *Peptide Research* 115, 1992.

Van der Ploeg et al., "Intravenous Administration of Phosphorylated Acid α–Glucosidase Leads to Uptake of Enzyme in Heart and Skeletal Muscle of Mice," 87 The American Society for Clinical Investigation, Inc. 513, 1991.

Wagner et al., "Transferrin–Polycation Conjugates as Carriers for DNA Uptake into Cells," 87 *Proc. Natl. Acad. Sci. USA* 3410, 1990.

Wagner et al., "DNA–Binding Transferrin Conjugates as Functional Gene–Delivery Agents: Synthesis of Linkage of Polylysine or Ethidium Homodimer to the Transferrin Carbohydrate Moiety," 2(4) *Bioconjugate Chemistry* 226, 1991.

Wagner et al., "Tranferrin–Polycation–DNA Complexes: The Effect of Polycations on the Structure of the Complex and DNA Delivery to Cells," 88 *Proc. Natl. Acad. Sci. USA* 4255, 1991.

Wang et al., "8 37h–CGRP Antagonizes Actions of Amylin on Carbohydrate Metabolism In Vitro and In Vivo," 291 *FEBS Letters* 195, 1991, Elsevier Science Publishers B.V.

Waser et al., "Isolation and Purification of Acetylcholine Receptor Proteins by Affinity Chromatography," 172 *European Journal of Pharmacology —Molecular Pharmacology Section* 231, 1989.

Weiner et al., "Biotin Uptake in Cultured Hepatocytes from Normal and Biotin–Deficient Rats," 44 *Biochemical Medicine and Metabolic Biology* 271, 1990.

Weitman et al., "Distribution of the Folate Receptor GP38 in Normal and Malignant Cell Lines and Tissues," 52 *Cancer Res.* 3396, 1992.

Weitman et al., "Cellular Localization of the Folate Receptor: Potential Role in Drug Toxicity and Folate Homeostasis," 52 *Cancer Res.* 6708, 1992.

Wilson et al., "Counterion–Induced Condensation of Deoxyribonucleic Acid. A Light–Scattering Study," *Biochemistry*, pp. 2192–2196, 1979.

Wu et al., "Receptor–Mediated In Vitro Gene Transformation by a Soluble DNA Carrier System," 262(10) *J. Biol. Chem.* 4429, 1987.

Wu and Wu, "Receptor–Mediated Gene Delivery and Expression In Vivo," 263 *J. Biol. Chem.* 14621, 1988.

Wu et al., "Targeting Genes: Delivery and Persistent Expression of a Foreign Gene Driven by Mammalian Regulatory Elements In Vivo," 264 *J. Biol. Chem.* 16985, 1989.

Wu et al., "Receptor–Mediated Gene Delivery In Vivo," 266 *J. Biol. Chem.* 14338, 1991.

Wu and Wu, "Evidence for Targeted Gene Delivery to Hep G2 Hepatoma Cells In Vitro," 27 *Biochem.* 887, 1988.

Wu et al., "Delivery Systems for Gene Therapy," 3 *Biotherapy* 87, 1991.

Yakubov et al., "Mechanism of Oligonucleotide Uptake by Cells: Involvement of Specific Receptors?", 86 *Proc. Natl. Acad. Sci. USA* 6454, 1989.

Zaidi et al., "Structure–Activity Relationship of Human Calcitonin–Gene–Related Peptide," 269 *Biochem. J.* 775, 1990.

Zenke et al., "Receptor–Mediated Endocytosis of Transferrin–Polycation Conjugates: An Efficient Way to Introduce DNA Into Hematopoietic Cells," 87 *Proc. Natl. Acad. Sci. USA* 3655, 1990.

Kaneda et al., "Increased Expression of DNA Cointroduced with Nuclear Protein in Adult Rat Liver," *Science* 243:375–378 (1989).

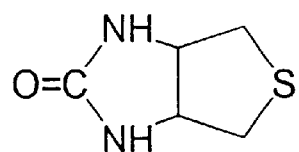
(CH$_2$)$_4$-COOH + H$_2$N-CH$_2$CH$_2$-S-S-CH$_2$CH$_2$-NH$_2$,EDC
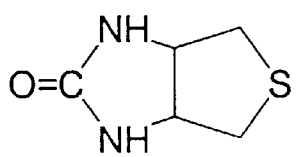
(CH$_2$)$_4$-CONH-CH$_2$CH$_2$-S-S-CH$_2$CH$_2$-NH$_2$     (B)
+ DITHIOTHREITOL
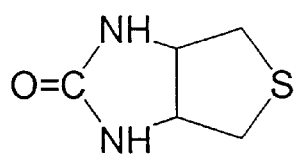
(CH$_2$)$_4$-CONH-CH$_2$CH$_2$-SH
+ 2,2'-DITHIODIPYRIDINE
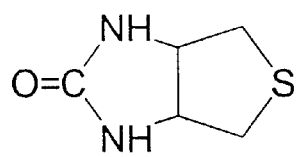
(CH$_2$)$_4$-CONH-CH$_2$CH$_2$-SS-C$_5$H$_4$N     (B')
*Fig. 2*

SOLID PHASE SYNTHESIS:          XXIIIa    XXVIIh    XXXi     XXXIi
                                XXIIIb              XXXj     XXXIj
                                XXIIIc              XXXk     XXXIk
                                                    XXXl     XXXIl

XXIV → XXV → { XXVId
              XXVIe
              XXVIf

XXVIII → XXIXg

*Fig. 6*

XXXVIIa  →  XXXIXa
                                      { XXXVIIb  →  XXXIXb
                                        XXXVIIc  →  XXXIXc

XLIId
IV → XXXII → XXXIII → XXXIV → XXXV → XXXVI → XXXVIII → XL → XLI → XLIIe
                              ↓  ↘         ↘                        XLIIf
                            XLIII   XLIX   XLVII
                              ↓       ↘      ↘
                            XLIV       L      XLVIIIh
                              ↘        ↘
                                XLV              LIi
              XXXIXa           ↘               { LIj
        XLI → { XXXIXb         XLVIg             LIk
                XXXIXc                           LIl

*Fig. 7*

```
                          CXIa  → CXIIa  → CXVIIa
                          CXIb  → CXIIb  → CXVIIb
                          CXIc  → CXIIc  → CXVIIc

LXXXI  → CIX → CX  → CXIII → CXIV →    CXVIIIg
                                            CXVIIIh
                ↘
                    CXV
                        ↘                       CXXd
                            CXVI → CXIX →      CXXe
                                                CXXf

CXXIVg                     CXXVId
    CXXIII →    CXXIVh      CXXV →        CXXVIe
                                            CXXVIf

SOLID PHASE SYNTHESIS:    CXXIIa, CXXIIb, CXXIIc
```

Fig. 12

```
                                              CXXXId
    CXXXIX  → CXXXIIIg      CXXX →          CXXXIe
                                              CXXXIf

SOLID PHASE SYNTHESIS:    CXXVIIa, CXXVIIb, CXXVIIc,
CXXXIIh
```

Fig. 13

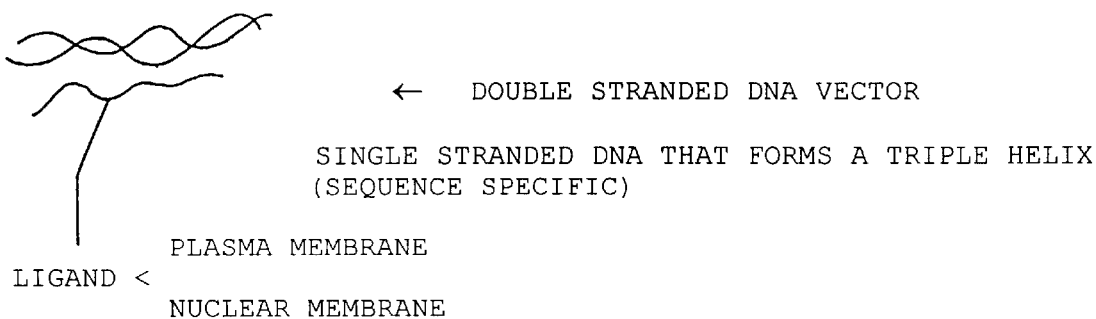

← DOUBLE STRANDED DNA VECTOR

SINGLE STRANDED DNA THAT FORMS A TRIPLE HELIX (SEQUENCE SPECIFIC)

PLASMA MEMBRANE

LIGAND <

NUCLEAR MEMBRANE

Fig. 14 where R1 and R2 are spacer molecules; n is the number of repeating units ranging from 20 to 40; and B may be N-carboxymethyl derivatives of thymine, cytosine, adenine, guanine and/or derivatives and analogs thereof where $R_1$, $R_2$, and $R_3$ can be H or other substituents.

where Y and Z may be spacers terminated in a ligand or an intercalating group.

DNA BINDING OLIGONUCLEOTIDE

GENOMIC TARGET

5' X-TGGGGAGGGAGGGAGGGAAGG-2 3'        C-MYC PROMOTER
         |
         Y
        -148      -122

5' X-TAGAGAGGCCGCAGGGGCTGGGCAGGAAGGAGGTGAAT        CHOLESTERYL ESTER TRANSFER PROTEIN PROMOTER
         |
         Y
        -145      -98

1. LIGAND FOR C-MYC PROMOTER:

5' X-$^m$CT$^m$CTTT$^m$C$^m$CCT$^m$CT$^m$CTTTT$^m$T$^m$C$^m$C$^m$C$^m$C-NHCO-CH$_2$CH$_2$-SS-CH$_2$CH$_2$-CONH-TGGGGAGGGAGGGAGGGAAGG-2 3'
         |                                                                                    |
         $Y_a$                                                                                $Y_b$

Fig. 17A

WHERE

X = (2-METHOXY-6-CHLOROACRIDINYL)-NH
$Y_a$ = $(CH_2)_3$-NH-CO$(CH_2)_5$-NH-$R_a$
$Y_b$ = H ON THE METHYL GROUP OF THE THYMIDINE MOIETY
Z = CO-$(CH_2)_5$ -NH-$CH_2CH_2$-S-$R_z$

WHERE $R_a$

= PRO-ASP-GLU-VAL-LYS-ARG-LYS-LYS-LYS-PRO-PRO-THR-SER-TYR-GLY-$NH_2$ (CXLIi)
= PRO-ARG-ARG-ARG-THR-LYS-PRO-PRO-THR-SER-TYR-GLY-$NH_2$ (CXLIj)
= ARG-LYS-LYS-ARG-GLY-PRO-THR-SER-TYR-GLY-$NH_2$ (CXLIk)
= TRP-ARG-ARG-ARG-ASN-ARG-ARG-PRO-THR-SER-TYR-GLY-$NH_2$ (CXLIl)
= GLY-TYR-SER-THR-PRO-LYS-LYS-ARG-LYS-VAL-GLU-ASP-PRO-CON$H_2$ (CXLIIi)
= GLY-TYR-SER-THR-PRO-PRO-LYS-THR-ARG-ARG-ARG-PRO-CON$H_2$ (CXLIIj)
= GLY-THR-SER-THR-PRO-GLY-ARG-LYS-LYS-ARG-CON$H_2$ (CXLIIk)
= GLY-TYR-SER-THR-PRO-ARG-ARG-ASN-ARG-ARG-ARG-ARG-TRP-CON$H_2$ (CXLIIl)

WHERE $R_z$

= -S-$CH_2CH_2$-NH-Y-AMIDE OF THE GLUTAMYL MOIETY OF METHOTREXATE (CXLIII)

*Fig. 17B*

```
                                    Pep1
         his-leu-arg-arg-leu-arg-arg-arg-leu-leu-arg-glu-ala-glu-glu-gly
                                    Pep2
           his-leu-arg-arg-leu-arg-arg-arg-leu-leu-arg-glu-ala-glu-glu
                                    Pep3
            gly-tyr-ser-thr-pro-pro-lys-lys-lys-arg-lys-val-glu-asp-pro
                                    Pep4
                 gly-tyr-ser-thr-pro-pro-lys-thr-arg-arg-arg-pro
                                    Pep5
                     gly-tyr-ser-thr-pro-gly-arg-lys-lys-arg
                                    Pep6
                 gly-tyr-ser-thr-pro-arg-arg-asn-arg-arg-arg-trp
                                    Pep7
            pro-asp-glu-val-lys-arg-lys-lys-lys-pro-pro-thr-ser-tyr-gly
                                    Pep8
                   pro-arg-arg-arg-thr-lys-pro-pro-thr-ser-tyr-gly
                                    Pep9
                      arg-lys-lys-arg-gly-pro-thr-ser-tyr-gly
                                    Pep10
              trp-arg-arg-arg-arg-asn-arg-arg-pro-thr-ser-tyr-gly
                                    Pep11
                           lys-ala-lys-ala-lys-ala-lys
```

A = γ-amide of the glutaryl moiety of folic acid (Figure 1)

B - biotin (Figure 2)

G = lipoic acid (Figure 3)

D = NH-CH-CONH-(CH$_2$)$_5$-COHN-Pep1-CONH$_2$
    |
    CH2-CONH-(CH$_2$)$_5$-COHN-Pep1-CONH$_2$

E = NH-CH-CONH-(CH$_2$)$_5$-CONH-C-(CH$_2$-O-Lac)$_3$
    |
    CH$_2$-CONH-(CH$_2$)$_5$-CONH-C-(CH$_2$-O-Lac)$_3$

F = fusion competent virus (Figure 4)

Fab' = fragment of IgG

M = γ-amide of the glutaryl moiety of methotrexate (Figure (1)

t-Boc = (CH)$_3$COCO                  z = C$_6$H$_5$CH$_2$OCO

Fig. 18

COMPOUND Q

WHERE M6P IS THE ω-[2-(6-0-PHOSPHORYL-α-D-MANNOPYRANOSYL)OXY]ALKANOYL MOIETY ON THE ε-AMINO GROUP OF LYS IN THE POLYCATION; ALKANOYL IS $(CH_2)_N$ AND n RANGES FROM 3 TO 20.

Pep 12

Gln-Ala-Tyr-Arg-Pro-Ser-Glu-Thr-Leu-Cys-Gly-Gly-Glu-Leu-Val-Asp-Thr-Leu-Gln-
Phe-Val-Cys-Gly-Asp-Arg-Gly-Phe-Leu-Phe-Ser-Arg-Pro-Ala-Ser-Arg-Val-Ser-Arg-
Arg-Ser-Arg-Gly-Ile-Val-Glu-Glu-Cys-Cys-Phe-Arg-Ser-Cys-Asp-Leu-Ala-Leu-Leu-
Glu-Thr-Tyr-Cys-Ala-Thr-Pro-Ala-ε-X-Lys-Ser-Glu

Pep 13

Gln-Ala-Tyr-ε-X-Lys-Pro-Ser-Glu-Thr-Leu-Cys-Gly-Gly-Glu-Leu-Val-Asp-Thr-Leu-
Gln-Phe-Val-Cys-Gly-Asp-Arg-Gly-Phe-Leu-Phe-Ser-Arg-Pro-Ala-Ser-Arg-Val-Ser-
Arg-Arg-Ser-Arg-Gly-Ile-Val-Glu-Glu-Cys-Cys-Phe-Arg-Ser-Cys-Asp-Leu-Ala-Leu-
Leu-Glu-Thr-Tyr-Cys-Ala-Thr-Pro-Ala-Arg-Ser-Glu

Pep 14

Tyr-Ala-Cys-Asp-Thr-Ala-Thr-Cys-Val-Thr-His-Arg-Leu-Ala-Gly-Leu-Leu-Ser-Arg-

Ser-Gly-Gly-Val-Val-ε-X-Lys-Asn-Asn-Phe-Val-Pro-Thr-Asn-Val-Gly-Ser-Lys-Ala-

Phe-NH₂

Pep 15

Ser-Gly-Gly-Val-Val-ε-X-Lys-Asn-Asn-Phe-Val-Pro-Thr-Asn-Val-Gly-Ser-Lys-Ala-

Phe-NH₂

Pep 16

Gln-Ala-Tyr-Arg-Pro-Ser-Glu-Thr-Leu-Cys-Gly-Gly-Glu-Leu-Val-Asp-Thr-Leu-Gln-
Phe-Val-Cys-Gly-Asp-Arg-Gly-Phe-Leu-Phe-Ser-Arg-Pro-Ala-Ser-Arg-Val-Ser-Arg-
Arg-Ser-Arg-Gly-Ile-Val-Glu-Glu-Cys-Cys-Phe-Arg-Ser-Cys-Asp-Leu-e-X-Lys-Arg-
Leu-Glu-Thr-Tyr-Cys-Ala-Thr-Pro-Ala-Arg-Ser-Glu

*Fig. 20A*

Pep 17

Asn-X-Thr-Leu-Cys-Gly-Ala-Glu-Leu-Val-Asp-Ala-Leu-Gln-Phe-Val-Cys-Gly-Asp-Arg-
Gly-Phe-Tyr-Phe-Asn-Lys-Pro-Thr-Gly-Tyr-Gly-Ser-Ser-Ser-Arg-Arg-Ala-Pro-
Gln-Thr-Gly-Ile-Val-Asp-Glu-Cys-Cys-Phe-Arg-Ser-Cys-Asp-Leu-Arg-Arg-Leu-Glu-
Met-Tyr-Cys-Ala-Pro-Leu-Arg-Pro-Ala-Arg-Ser-Ala-Arg-Ser-Val-Arg-Ala-Gln-Arg-
His-Thr-Asp

Pep 18 e-X-Lys-Gly-Leu-Pro-Lys-Glu-Val-Pro-Ala-Val-Leu-Thr-Lys-Gln-Lys-Leu-Lys-Ser-
Glu-Leu-Val-Ala-Asn-Gly-Val-Thr-Leu-Pro-Ala-Gly-Glu-Met-Arg-Lys-Asp-Val-Tyr-
Val-Glu-Leu-Tyr-Leu-Gln-His-Leu-Thr-Ala-Leu-His

Pep 19

Gly-Leu-Pro-e-X-Lys-Glu-Val-Pro-Ala-Val-Leu-Thr-Lys-Gln-Lys-Leu-Lys-Ser-Glu-
Leu-Val-Ala-Asn-Gly-Val-Thr-Leu-Pro-Ala-Gly-Glu-Met-Arg-Lys-Asp-Val-Tyr-Val-
Glu-Leu-Tyr-Leu-Gln-His-Leu-Thr-Ala-Leu-His

*Fig. 20B*

Pep 20

```
Gln-Arg-Lys-Arg-Arg-Asn-Thr-Ile-His-Glu-Phe-Lys-Lys-Ser-Ala-Lys-Thr-Thr-
Leu-Ile-Lys-Ile-Asp-Pro-Ala-Leu-Lys-Ile-Lys-Thr-Lys-Lys-Val-Asn-Thr-Ala-
Asp-Gln-Cys-Ala-Asn-Arg-Cys-Thr-Arg-Asn-Lys-Gly-Leu-Pro-Phe-Thr-Cys-Lys-
Ala-Phe-Val-Phe-Asp-Lys-Ala-Arg-Lys-Gln-Cys-Leu-Trp-Phe-Pro-Phe-Asn-Ser-
Met-Ser-Ser-Gly-Val-Lys-Lys-Glu-Phe-Gly-His-Glu-Phe-Asp-Leu-Tyr-Glu-Asn-
Lys-Asp-Tyr-Ile-Arg-Asn-Cys-Ile-Ile-Gly-Lys-Gly-Arg-Ser-Tyr-Lys-Gly-Thr-
Val-Ser-Ile-Thr-Lys-Ser-Gly-Ile-Lys-Cys-Gln-Pro-Trp-Ser-Ser-Met-Ile-Pro-
His-Glu-His-Ser-Phe-Leu-Pro-Ser-Ser-Tyr-Arg-Gly-Lys-Asp-Leu-Gln-Glu-Asn-
Tyr-Cys-Arg-Asn-Pro-Arg-Gly-Glu-Glu-Gly-Gly-Pro-Trp-Cys-Phe-Thr-Ser-Asn-
Pro-Glu-Val-Arg-Tyr-Glu-Val-Cys-Asp-Ile-Pro-Gln-Cys-Ser-Glu-Val-Glu-Cys-
Met-Thr-Cys-Asn-Gly-Glu-Ser-Tyr-Arg-Gly-Leu-Met-Asp-His-Thr-Glu-Ser-Gly-
Lys-Ile-Cys-Gln-Arg-Trp-Asp-His-Gln-Thr-Pro-His-Arg-His-Lys-Phe-Leu-Pro-
Glu-Arg-Tyr-Pro-Asp-Lys-Gly-Phe-Asp-Asp-Asn-Tyr-Cys-Arg-Asn-Pro-Asp-Gly-
Gln-Pro-Arg-Pro-Trp-Cys-Tyr-Thr-Leu-Asp-Pro-His-Thr-Arg-Trp-Glu-Tyr-Cys-
Ala-Ile-Lys-Thr-Cys-Ala-Asp-Asn-Thr-Met-Asn-Asp-Thr-Asp-Val-Pro-Leu-Glu-
Thr-Thr-Glu-Cys-Ile-Gln-Gly-Gln-Gly-Glu-Gly-Tyr-Arg-Gly-Thr-Val-Asn-Thr-
Ile-Trp-Asn-Gly-Ile-Pro-Cys-Gln-Arg-Trp-Asp-Ser-Gln-Tyr-Pro-His-Glu-His-
Asp-Met-Thr-Pro-Glu-Asn-Phe-Lys-Cys-Lys-Asp-Leu-Arg-Glu-Asn-Tyr-Cys-Arg-
Asn-Pro-Asp-Gly-Ser-Glu-Ser-Pro-Trp-Cys-Phe-Thr-Thr-Asp-Pro-Asn-Ile-Arg-
Val-Gly-Tyr-Cys-Ser-Gln-Ile-Pro-Asn-Cys-Asp-Met-Ser-His-Gly-Gln-Asp-Cys-
Tyr-Arg-Gly-Asn-Gly-Lys-Asn-Tyr-Met-Gly-Asn-Leu-Ser-Gln-Thr-Arg-Ser-Gly-
Leu-Thr-Cys-Ser-Met-Trp-Asp-Lys-Asn-Met-Glu-Asp-Leu-His-Arg-His-Ile-Phe-
Trp-Glu-Pro-Asp-Ala-Ser-Lys-Leu-Asn-Glu-Asn-Tyr-Cys-Arg-Asn-Pro-Asp-Asp-
Asp-Ala-His-Gly-Pro-Trp-Cys-Tyr-Thr-Gly-Asn-Pro-Leu-Ile-Pro-Trp-Asp-Tyr-
Cys-Pro-Ile-Ser-Arg-Cys-Glu-Gly-Asp-Thr-Thr-Pro-Thr-Ile-Val-Asn-Leu-Asp-
His-Pro-Val-Ile-Ser-Cys-Ala-Lys-Thr-Lys-Gln-Leu-Arg-Val-Val-Asn-Gly-Ile-
Pro-Thr-Arg-Thr-Asn-Ile-Gly-Trp-Met-Val-Ser-Leu-Arg-Tyr-Arg-Asn-Lys-His-
Ile-Cys-Gly-Gly-Ser-Leu-Ile-Lys-Glu-Ser-Trp-Val-Leu-Thr-Ala-Arg-Gln-Cys-
Phe-Pro-Ser-Arg-Asp-Leu-Lys-Asp-Tyr-Glu-Ala-Trp-Leu-Gly-Ile-His-Asp-Val-
His-Gly-Arg-Gly-Asp-Glu-Lys-Cys-Lys-Gln-Val-Leu-Asn-Val-Ser-Gln-Leu-Val-
Tyr-Gly-Pro-Glu-Gly-Ser-Asp-Leu-Val-Leu-Met-Lys-Leu-Ala-Arg-Pro-Ala-Val-
Leu-Asp-Asp-Phe-Val-Ser-Thr-Ile-Asp-Leu-Pro-Asn-Tyr-Gly-Cys-Thr-Ile-Pro-
Glu-Lys-Thr-Ser-Cys-Ser-Val-Tyr-Gly-Trp-Gly-Tyr-Thr-Gly-Leu-Ile-Asn-Tyr-
Asp-Gly-Leu-Leu-Arg-Val-Ala-His-Leu-Tyr-Ile-Met-Gly-Asn-Glu-Lys-Cys-Ser-
Gln-His-His-Arg-Gly-Lys-Val-Thr-Leu-Asn-Glu-Ser-Glu-Ile-Cys-Ala-Gly-Ala-
Glu-Lys-Ile-Gly-Ser-Gly-Pro-Cys-Glu-Gly-Asp-Tyr-Gly-Gly-Pro-Leu-Val-Cys-
Glu-Gln-His-Lys-Met-Arg-Met-Val-Leu-Gly-Val-Ile-Val-Pro-Gly-Arg-Gly-Cys-
Ala-Ile-Pro-Asn-Arg-Pro-Gly-Ile-Phe-Val-Arg-Val-Ala-Tyr-Tyr-Ala-Lys-Trp-
Ile-His-Lys-Ile-Ile-Leu-Thr-Tyr-Lys-Val-Pro-Gln-Ser
```

*Fig. 23A*

Pep 21

Cys-Ser-Cys-Ser-Ser-Leu-Met-Asp-Lys-Glu-Cys-Val-Tyr-Phe-Cys-His-Leu-Asp-
Ile-Ile-Trp

Pep 22

HOOCCH$_2$CH$_2$CONH-Asp-Glu-Glu-Ala-Val-Tyr-Phe-Ala-His-Leu-Asp-Ile-Ile-Trp

Pep 23

Ser-Leu-Arg-Arg-Ser-Ser-Cys-Phe-Gly-Gly-Arg-Met-Asp-Arg-Ile-Gly-Ala-Gln-
Ser-Gly-Leu-Gly-Cys-Asn-Ser-Phe-Arg-Tyr

Pep 24

Gly-Leu-Phe-Glu-Ala-Ile-Ala-Asp-Phe-Ile-Glu-Asn-Gly-Trp-Glu-Gly-Met-Ile-
Asp-Gly-Gly-Gly-Cys

Pep 25

Lys-Val-Tyr-Thr-Gly-Val-Tyr-Pro-Phe-Met-Trp-Gly-Gly-Ala-Tyr-Cys-Phe-Cys-
Asp

Pep 26

Gly-Gly-Tyr-Cys-Leu-Thr-Arg-Trp-Met-Leu-Ile-Glu-Ala-Glu-Leu-Lys-Cys-Phe-
Gly-Asn-Thr-Ala-Val

*Fig. 23B*

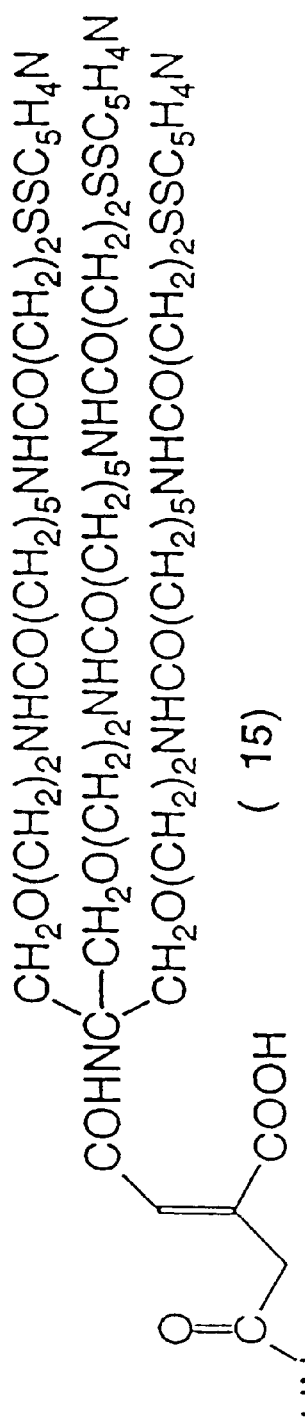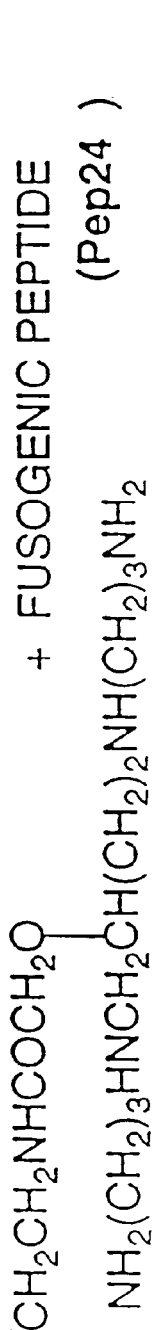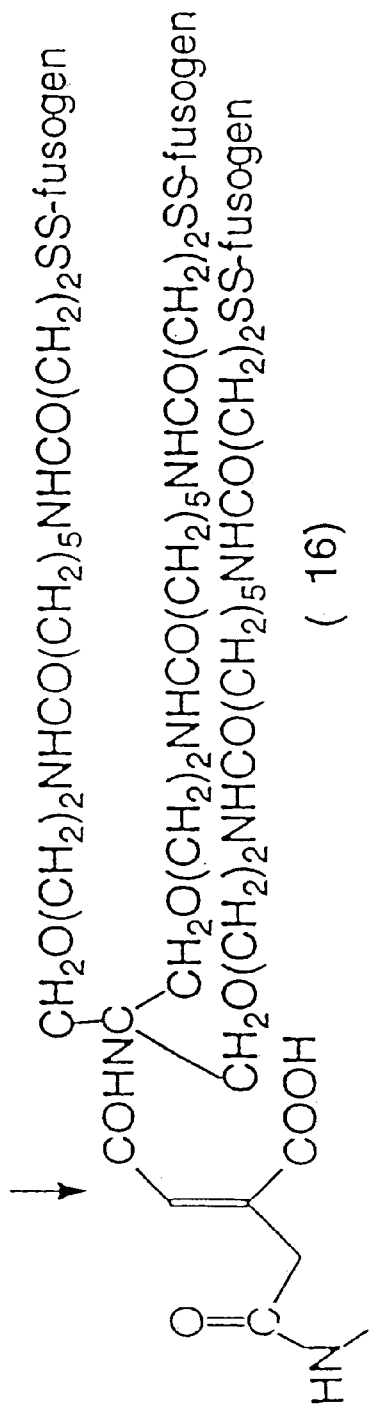
Fig. 25D

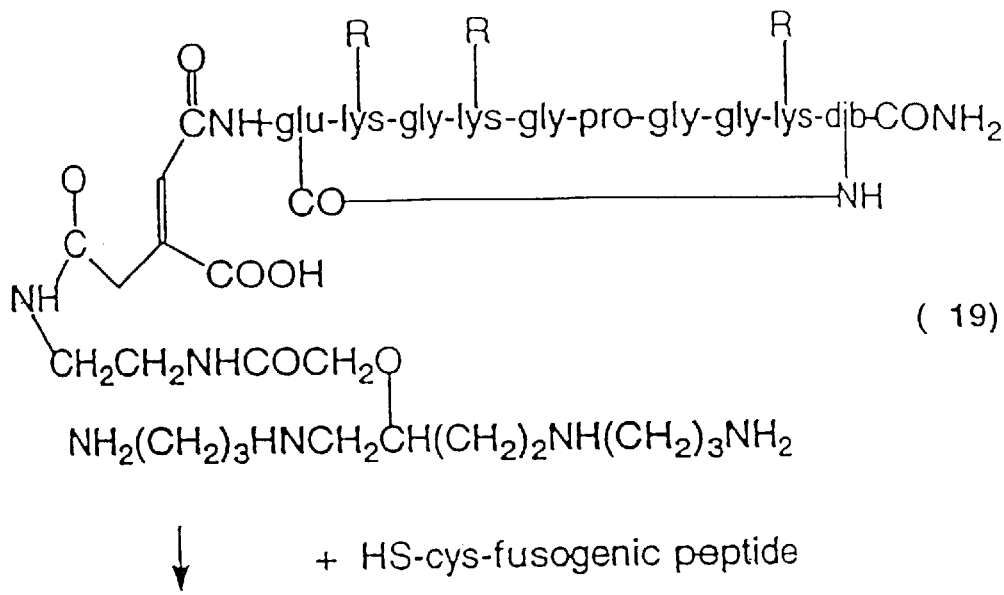
(19)
↓ + HS-cys-fusogenic peptide
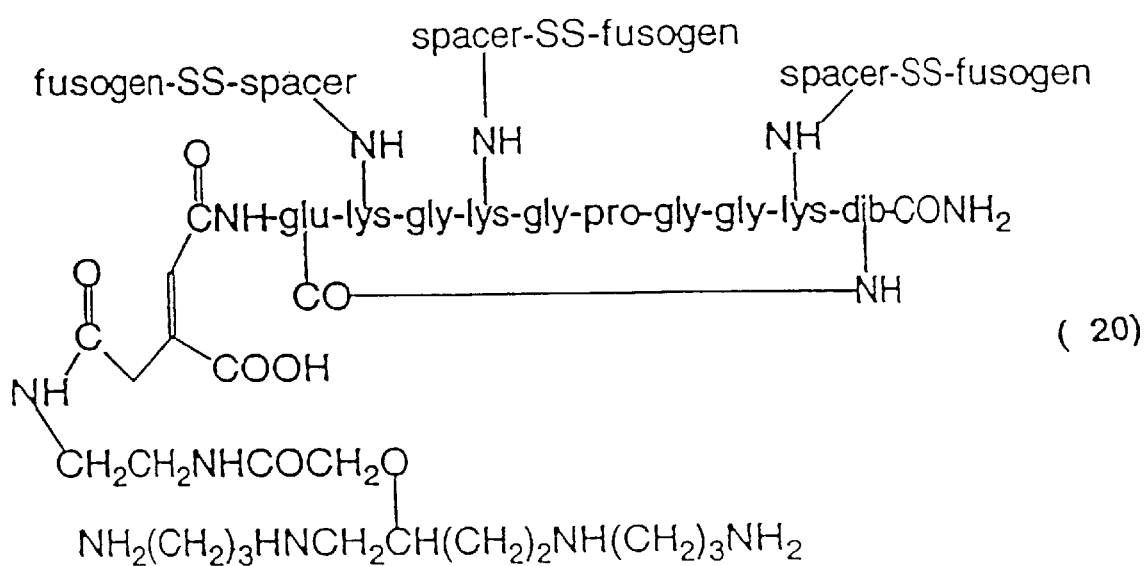
(20)
where dib = 2,4-diaminobutyric acid
Fig. 26B

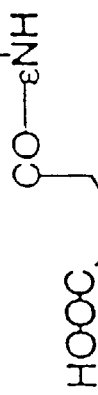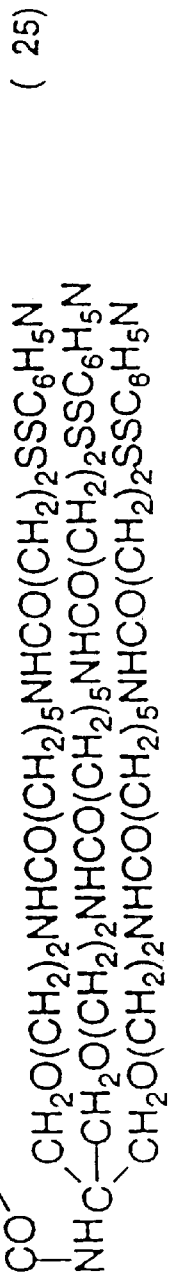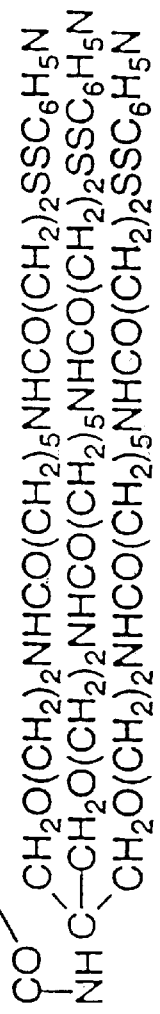
Fig. 28B

NUCLEIC ACID TRANSPORTER SYSTEM AND METHODS OF USE

This application is a divisional of co-pending application Ser. No. 08/167,641, by Woo et al., filed Dec. 14, 1993, entitled "Nucleic Acid Transporter Systems and Methods of Use," the whole of which (including drawings) is hereby incorporated by reference. The Ser. No. 08/167,641 application is a continuation-in-part of Woo et al., application Ser. No. 07/855,389, filed Mar. 20, 1992, now abandoned, entitled "A DNA Transporter System and Method of Use," the whole of which (including drawings) is hereby incorporated by reference. Application Ser. No. 08/167,641 is also a continuation-in-part of Woo et al., International Application No. PCT/US93/02725, filed Mar. 19, 1993 (designating U.S. and other countries), entitled "A DNA Transporter System and Methods of Use," the whole of which is hereby incorporated by reference.

The invention was partially supported by a grant from the United States government under H.L.-23741 awarded by the National Institute of Health. The U.S. government may have rights in the invention.

BACKGROUND OF THE INVENTION

This invention relates to gene therapy using transporter systems for delivering nucleic acid into a cell.

Recombinant retroviral vectors have been used for delivery of genes to cells of living animals. Retroviral vectors permanently integrate the transfered gene into the host chromosal DNA. Studies have demonstrated that retroviral vectors can be transduced into liver cells in vivo by direct injection of the virus into the parenchyma after carbon tetrachloride treatment. Kaleko et al., *Human Gene Therapy*, Vol. 2, pp. 27–32 (1991). Analysis of transduced liver cells indicated a transduction frequency of about 1 out of 160 liver cells. Id.

Retroviral vectors can be transduced into rat hepatocytes after partial hepatectomy followed by a surgical procedure involving isolation and perfusion of the liver with a viral vector. Poorman et al., *Arterioscl. Throm.*, Vol. 11, p. 1413A (1991); Hobbs et al., *Annu. Rev. Genet.*, Vol. 24, pp. 133–70 (1990). The transduced hepatocytes from the above studies were detectable six months after gene transduction. Id.

Another virus used for gene delivery is adenovirus. It has been developed as a means for gene transfer into epithelial derived tissues. Stratford-Perricaudet et al., *Hum. Gene. Ther.*, Vol. 1, pp. 241–256 (1990); Gilardi et al., *FEBS*, Vol. 267, pp. 60–62 (1990); Rosenfeld et al., *Science*, Vol. 252, pp. 431–434 (1991). Vectors have been constructed in which the 35 Kb genome in the E3 and E1 regions have been deleted, such that recombinant gene constructs can be inserted into the adenovirus vector. Id. Since adenovirus has a natural tropism for the lung epithelium it was used for gene transfer into this tissue. Gilardi et al., *FEBS*, Vol. 20 267, pp. 60–62 (1990); Rosenfeld et al., *Cell*, Vol. 68, pp. 143–155 (1992).

Recombinant adenoviral vectors have the advantage over retroviruses of being able to transduce non-poliferating cells as well as an ability to produce purified high titer virus. Studies using an adenoviral vector to deliver genes to liver demonstrated that mouse hepatocytes can be transduced in vivo with the vector. Stratford-Perricaudet, *Hum. Gene Ther.*, Vol. 1, pp. 241–256 (1990). Use of adenoviral-mediated transfer of orninthine transcarbamylase cDNA allowed the transfer of enzyme activity to the mouse liver. These studies resulted in phenotypic correction of enzyme deficiency. Id. Other studies have demonstrated human α-1-antitrypsin production from rat liver after transduction with a recombinant adenoviral vector. Jaffe et al., *Nature-Genetics*, Vol. 1, pp. 372–378 (1992). These studies determined that 1% of hepatocytes were transduced in vivo. Id.

In addition to retroviral-mediated gene delivery, a more recent means for DNA delivery has been receptor-mediated endocytosis. Endocytosis is the process by which eucaryotic cells continually ingest segments of the plasma membrane in the form of small endocytotic vesicles. Alberts et al., *Mol. Biol. of Cell*, Garland Publishing Co., New York, 1983. Extracellular fluid and everything dissolved in it becomes trapped in the vesicle and is ingested into the cell. Id. This process of bulk fluid-phase endocytosis can be visualized and quantified using a tracer such as enzyme peroxidase introduced into the extra-cellular fluid. Id. The rate of constitutive endocytosis varies from cell type to cell type.

Endocytotic vesicles form in a variety of sizes and shapes and are usually enlarged by fusing with each other and/or with other intra-cellular vesicles. Stryer, Bioch., Freeman and Co., New York (1988). In most cells the great majority of endocytotic vesicles ultimately fuse with small vesicles called primary lysosomes to form secondary lysosomes which are specialized sites of intra-cellular digestion. Id. The lysosomes contain a wide variety of degradative enzymes to digest the macromolecular contents of the vesicles. Silverstein, et al., *Ann. Rev. Biochem.*, Vol. 46, pp. 669–722 (1977); Simionescu, et al., *J. Cell Biol.*, Vol. 64, pp. 586–607 (1975).

Many of the endocytotic vesicles are coated and are formed by invagination of coated regions of the plasma membrane called coated pits. Coated pits and vesicles provide a specialized pathway for taking up specific macromolecules from the extracellular fluid. This process is called receptor-mediated endocytosis. Goldstein et al., *Nature*, Vol. 279, pp. 679–685 (1979); Pearse, et al., *Annu. Rev. Biochem.*, Vol. 50, pp. 85–101 (1981); Pastan, et al., *Annu. Rev. Physiol.*, Vol. 43, pp. 239–250 (1981). The macromolecules that bind to specific cell surface receptors are internalized via coated pits. Goldstein, supra. Receptor-mediated endocytosis is a selective mechanism enabling cells to ingest large amounts of specific ligands without taking in correspondingly large amounts of extra-cellular fluid. Goldstein, supra.

One such macromolecule is low density lipoprotein ("LDL"). Numerous studies have been performed involving LDL and the receptor-mediated endocytotic pathway. In addition to LDL, many other cell surface receptors have been discovered to be associated with coated pits and receptor-mediated endocytosis. Pastan et al., *Annu. Rev. Physiol.*, Vol. 43, pp. 239–250 (1981). For example, studies have analyzed the hormone insulin binding to cell surface receptors and entering the cell via coated pits. Stryer et al., *Biochemistry*, Freeman & Co., New York (1988); Alberts et al., *Molecular Biology of the Cell*, Garland Publishing, New York (1983). In addition, it has been determined that some cell surface receptors associate with coated pits only after ligand binding. Pastan, supra.

Taking advantage of receptor-mediated endocytosis, the asialoglycoprotein receptor has been used in targeting DNA to HepG2 cells in vitro and liver cells in vivo. Wu and Wu, *J. Biol. Chem.*, Vol. 262, pp. 4429–4432 (1987); Wu and Wu, *Bio.*, Vol. 27, pp. 887–892 (1988); Wu et al., *J. Biol. Chem.*, Vol. 263, pp. 14621–14624 (1988); Wu et al., *J. Biol. Chem.*, Vol. 264, pp. 16985–16987 (1989); Wu et al., *J. Biol. Chem.*, Vol. 266, pp. 14338–14342 (1991). These studies used asialoorosomucoid covalently linked to polylysine with water soluble carbodiimide, 1-ethyl-3-(3-dimethylaminopropyl)carbodiimide or with 3'(2'pyridyldithio)propionic acid n-hydroxysuccinimide ester. Polylysine in the studies above bound DNA through ionic interaction. The DNA was ingested by endocytosis.

Other studies have utilized transferrin and the transferrin receptor for delivery of DNA to cells in vitro. Wagner et al., *P.N.A.S.*, Vol. 87, pp. 3410–3414 (1990). These studies modified transferrin by covalently coupling transferrin to polylysine. Id. The polylysine interacted ionically with DNA. Delivery of DNA occurred to cells through the transferrin receptor. Such analyses were performed in vitro. Id. Cotten et al., *P.N.A.S.*, Vol. 87, pp. 4033–4037 (1990); Zenke et al., *P.N.A.S.*, Vol. 87, pp. 3655–3659 (1990).

In addition to DNA, macromolecules can also be delivered by receptor-ligand systems. Leamon et al., *P.N.A.S.*, Vol. 88, pp. 5572–5576 (1991); Leamon et al., *J. Biol. Chem.*, Vol. 267, pp. 24966–24971 (1992). In particular these studies have involved the folate receptor, an anchored glycosylphosphatidyl protein, which is excluded from coated pits and cycles in and out of the cells by caveolae. Hill and Dessler, *Science*, Vol. 252, pp. 410–414 (1991). This uptake mechanism has been called potocytosis. Id. Folate conjugated enzymes have been delivered into cells through this receptor system and retained activity for at least 6 hours. Leamon et al., *P.N.A.S.*, Vol. 88, pp. 5572–5576 (1991). Folate receptors have limited tissue distribution and are overexpressed in several malignant cell lines derived from many tissues. Weitman et al., *Cancer Res.*, Vol. 52, pp. 3396–3401 (1992); Weitman et al., *Cancer Res.*, Vol. 52, pp. 6708–6711 (1992); Campbell, *Cancer Res.*, Vol. 51, pp. 5329–5338 (1991); Coney, *Cancer Res.*, Vol. 51, pp. 6125–6132 (1991). Other studies have also used biotin or folate conjugated to proteins by biotinylation for protein delivery to the cell. Low et al., U.S. Pat. No. 5,108,921.

DNA and macromolecule delivery is hindered by lysosomal degradation. Studies have analyzed the endosomal/lysosomal degradation process. It has been determined that organisms which are internalized via receptor-mediated endocytosis or receptor:ligand systems, like viruses and other microorganisms, escape lysosomal degradation in order to function. The entry mechanism of some viruses have been studies extensively. For some viruses outer membrane proteins have been demonstrated to be important for endosomal escape. Marsh et al., *Adv. Virus Res.*, Vol. 36, pp. 107–151 (1989). Other studies have focused on methods to prevent lysosomal degradation. These studies have used substances which pertubate endosomal/lysosomal function. Mellmann et al., *Ann. Rev. Biochem.*, Vol. 55, pp. 663–700 (1986). These substances have only been used in vitro. In addition, studies show that the entire virus-shell is necessary for efficient endosomal lysis. Marsh et al., *Adv. Virus Res.*, Vol. 36, pp. 107–151 (1989). Studies have also demonstrated that adenovirus will enhance transferrin-polylysine mediated gene delivery. Curiel *P.N.A.S.*, Vol. 88, pp. 8850–8854 (1991).

A number of bacteria are also internalized via receptor-mediated endocytosis and are liberated from the endosome by production of toxins. These toxins lyse the endosomal membrane. Moulder, *Microbiol. Rev.*, Vol. 49, pp. 298–337 (1985). *Listeria monocytogenes* produce a membranolytic toxin called listeriolysin. Cossart et al., *Mol. Biol. Med.*, Vol. 6, pp. 463–474 (1989); Tilney et al., *J. Cell Bio.*, Vol. 109 pp. 1597–1608 (1989). Studies have shown that no other cofactors are needed for endosomal escape of *Listeria monocytogenes*. Bielecki et al., *Nature* Vol. 345 pp. 175–176 (1990).

The listeriolysin toxin forms pores in membranes which contain cholesterol. These pores are large enough for macromolecules like immunoglobulins to pass. Ahnert-Hilger et al., *Mol. Cell Biol.*, Vol. 31 pp. 63–90 (1989); Geoffroy et al., *J. of Bacteriol.*, Vol. 172, pp. 7301–7305 (1990).

SUMMARY OF THE INVENTION

Applicant has determined that it is useful to construct nucleic acid transporter systems for delivering nucleic acid into the cell. Specifically, these transporter systems deliver nucleic acid into the cellular interior as well as the nucleus. These are useful in targeting nucleic acid to specific cells. These transporters can be used to treat diseases by targeting specific nucleic acid accordingly. These transporters can also be used to create transgenic animals for assessing human disease in an animal model.

The present invention takes advantage of the unique targeting ability to deliver nucleic acid to specific cells, the unique ability to release nucleic acid into the cellular interior and the unique ability to direct nucleic acid into the nucleus of a cell. The present invention features use of nucleic acid binding complexes containing surface ligands which are capable of binding to a cell surface receptor and entering a cell through cytosis (e.g., endocytosis, potocytosis, pinocytosis). In particular, the present invention demonstrates that by using surface ligands specific to certain cells, nucleic acid can be delivered using the nucleic acid transporter systems directly to the desired tissue. In addition, the present invention features use of a nucleic acid binding complex with a nuclear ligand capable of recognizing and transporting nucleic acid through the nuclear membrane to the nucleus of a cell.

Furthermore, to avoid the problems of endosomal/lysosomal degradation, the present invention takes advantage of lysis agents. In particular, the present invention features use of a nucleic acid binding complex which includes a lysis agent capable of releasing nucleic acid into the cellular interior from the endosome. The nucleic acid can be efficiently released without endosomal/lysosomal degradation.

The unique targeting ability to specific cells and to the nucleus also allows transgenic animal models to be used for the dissection of molecular carcinogenesis and disease, assessing potential chemical and physical carcinogens and tumor promoters, exploring model therapeutic avenues as well as livestock agricultural purposes. Furthermore, the above nucleic acid transporter system advantages allow methods for administration and treatment of various diseases. In addition, the above nucleic acid transporter systems can be used to transform cells to produce particular proteins, polypeptides, and/or RNA. Likewise, the above nucleic acid transporter systems can be used in vitro with tissue culture cells. In vitro uses allow the role of various nucleic acids to be studied by targeting specific expression into specifically targeted tissue culture cells.

In the first aspect, the present invention features a nucleic acid transporter system for delivering nucleic acid into a cell. The nucleic acid transporter includes a nucleic acid binding complex. This nucleic acid binding complex includes a binding molecule which is noncovalently bound to nucleic acid. In addition, the binding molecule is covalently linked to a surface ligand.

The term "nucleic acid transporter system" as used herein refers to a molecular complex which is capable of efficiently transporting nucleic acid through the cell membrane. This molecular complex is bound to nucleic acid noncovalently.

In addition to nucleic acid, other macromolecules including but not limited to, proteins, lipids and carbohydrates can also be delivered using the transporter system. The nucleic acid transporter system is capable of releasing the noncovalently bound nucleic acid into the cellular interior. Although not necessary, the nucleic acid transporter system can also efficiently transport the nucleic acid through the nuclear membrane. Furthermore, the nucleic acid transporter may also prevent degradation of the nucleic acid by endosomal lysis.

The nucleic acid transporter system as described herein can contain but is not limited to five components. It comprises, consists or consists essentially of: (1) a nucleic acid or other macromolecule with a known primary sequence that contains the genetic information of interest or a known chemical composition; (2) a moiety that recognizes and binds to a cell surface receptor or antigen or is capable of entering a cell through cytosis; (3) a nucleic acid or macromolecular molecule binding moiety; (4) a moiety that is capable of moving or initiating movement through a nuclear membrane; and/or (5) a lysis moiety that enables the transport of the entire complex from the cell surface directly into the cytoplasm of the cell. The term "consisting of" is used herein as it is recognized in the art. The transporter "consisting essentially of" the five moieties above includes variation of the above moieties. Such a variation may be use of only three moieties instead of all five. This is only an example and is non-limiting.

The term "nucleic acid" as used herein refers to DNA or RNA. This would include naked DNA, a nucleic acid cassette, naked RNA, or nucleic acid contained in vectors or viruses. These are only examples and are not meant to be limiting.

The term "vector" as used herein refers to nucleic acid, e.g., DNA derived from a plasmid, cosmid, plasmid or bacteriophage into which fragments of nucleic acid may be inserted or cloned. The vector can contain one or more unique restriction sites for this purpose, and may be capable of autonomous replication in a defined host or organism such that the cloned sequence is reproduced. The vector molecule can confer some well-defined phenotype on the host organism which is either selectable or readily detected. Some components of a vector may be a DNA molecule incorporating DNA, a sequence encoding a therapeutic or desired product, and regulatory elements for transcription, translation, RNA stability and replication. A viral vector in this sense is one that contains a portion of a viral genome, e.g. a packaging signal, and is not merely DNA or a located gene within a viral particle.

Expression includes the efficient transcription of an inserted gene or nucleic acid sequence within the vector. Expression products may be proteins, polypeptides or RNA. The gene insert or nucleic acid sequence may be contained in a nucleic acid cassette.

The term "nucleic acid cassette" as used herein refers to the genetic material of interest which can express a protein, polypeptide or RNA. The nucleic acid cassette can be naked DNA or positionally and sequentially oriented within a vector such that the nucleic acid in the cassette can be expressed, i.e., transcribed into RNA, and when necessary, translated into a protein or a polypeptide.

A variety of proteins and polypeptides can be encoded by the sequence in a nucleic acid cassette. Those proteins or polypeptides which can be expressed include hormones, growth factors, enzymes, clotting factors, apolipoproteins, receptors, drugs, oncogenes, tumor antigens, tumor suppressors, viral antigens, parasitic antigens and bacterial antigens. Specific examples of these compounds include proinsulin, insulin, growth hormone, androgen receptors, insulin-like growth factor I, insulin-like growth factor II, insulin growth factor binding proteins, epidermal growth factor, TGF-$\alpha$, TGF-$\beta$, dermal growth factor (PDGF), angiogenesis factors (acidic fibroblast growth factor, basic fibroblast growth factor and angiogenin), matrix proteins (Type IV collagen, Type VII collagen, laminin), oncogenes (ras, fos, myc, erb, src, sis, jun), E6 or E7 transforming sequence, p53 protein, cytokine receptor, IL-1, IL-6, IL-8, viral capsid protein, and proteins from viral, bacterial and parasitic organisms. Other specific proteins or polypeptides which can be expressed include: phenylalanine hydroxylase, $\alpha$-1-antitrypsin, cholesterol-7$\alpha$-hydroxylase, truncated apolipoprotein B, lipoprotein lipase, apolipoprotein E, apolipoprotein A1, LDL receptor, molecular variants of each, and combinations thereof. One skilled in the art readily appreciates that these proteins belong to a wide variety of classes of proteins, and that other proteins within these classes can also be used. In addition, the nucleic acid cassette can code for antisense RNA or ribozymes as well. These are only examples and are not meant to be limiting in any way.

The term "nucleic acid binding complex" as used herein refers to a complex which includes a binding molecule. The binding molecule is capable of noncovalently binding to nucleic acid. The binding molecule is also capable of covalently linking to a surface ligand, a nuclear ligand and/or a lysis agent. The binding molecule can include but is not limited to spermine, spermine derivative, spermidine, histones, polylysine, polyamines and cationic peptides. In addition, this includes but is not limited to analogs or derivatives of the above compounds.

The term "spermine" refers to a cation capable of non-covalent binding with nucleic acid through electrostatic components. Such binding can include ionic interaction, hydrogen bonding, and hydrophobic bonding. The term "derivative" as used herein refers to a compound produced from another compound of similar structure in one or more steps. For example, this includes spermine analogs and any chemical variation of spermine. This would also include any change in the structure of spermine but with the desired activity still remaining. Such a change, for example, could be a change in a chemical bond, or a change in a hydrogen placement. This is only an example and is nonlimiting. In addition, "analog" as used herein refers to a compound that resembles another structure, e.g., spermine, but is not necessarily an isomer.

Spermine derivatives include compounds IV, VII, XXI, XXXIII, XXXVI, LIV, LVI, LXXXII, LXXXIV and CX as described below. When used with the nucleic acid transporter system, the binding molecules, whether attached to a surface ligand, nuclear ligand or a lysis agent, can be different or similar binding molecules. In a preferred embodiment the binding molecule is a spermine derivative labeled below as D, as shown in FIG. 18.

Spermine and spermine derivatives have advantages over poly-1-lysine as used for the binding molecule. The binding properties of the spermine derivatives will approximate most closely those of spermine. The intranuclear spermine concentration is approximately 3 to 10 mmol. Spermine and spermine derivatives of this present invention are advantageous to use for two main reasons. First, the spacing of the amino groups of spermine is such that this naturally occurring polycation fits into the major groove of the DNA double helix with an exact fit. While the polycationic polylysine interacts electrostatically with the phosphates in the groove of DNA, the fit is not as precise. Second, the theoretical association/disassociation kinetics of the DNA/spermine interaction are more rapid for the DNA/spermine interactions than for DNA/polylysine. This is advantageous in the spermine/DNA mix for the release of the DNA inside the cell.

The term "surface ligand" as used herein refers to a chemical compound or structure which will bind to a surface receptor of a cell. The term "cell surface receptor" as used herein refers to a specific chemical grouping on the surface of a cell for which the ligand can attach. Cell surface receptors can be specific for a particular cell, i.e., found predominantly in one cell rather than in another type of cell (e.g., LDL and asialoglycoprotein receptors are specific for hepatocytes). The receptor facilitates the internalization of the ligand and attached molecules. A cell surface receptor includes but is not limited to a folate receptor, biotin receptor, lipoic acid receptor, low-density lipoprotein receptor, asialoglycoprotein receptor, insulin-like growth factor type II/cation-independent mannose-6-phosphate receptor, calcitonin gene-related peptide receptor, insulin-like growth factor I receptor, nicotinic acetylcholine receptor, hepatocyte growth factor receptor, endothelin receptor, bile acid receptor, bone morphogenetic protein receptor, cartilage induction factor receptor or glycosylphosphatidylinositol (GPI)-anchored proteins (e.g., β andrenargic receptor, T-cell activating protein, Thy-1 protein, GPI-anchored 5' nucleotidase). These are nonlimiting examples.

A receptor is a molecule to which a ligand binds specifically and with relatively high affinity. It is usually a protein or a glycoprotein, but may also be a glycolipid, a lipidpolysaccharide, a glycosaminoglycan or a glycocalyx. For purposes of this invention, epitopes to which an antibody or its fragments binds is construed as a receptor since the antigen:antibody complex undergoes endocytosis. Furthermore, surface ligand includes anything which is capable of entering the cell through cytosis (e.g. endocytosis, potocytosis, pinocytosis).

As used herein, the term "ligand" refers to a chemical compound or structure which will bind to a receptor. This includes but is not limited to ligands such as asialoorosomucoid, asialoglycoprotein, folate (compound A; FIG. 1), lipoic acid (compound G; FIG. 3), biotin (compound B; FIG. 2), apolipoprotein E sequence (Pep2; (SEQ ID NO:32) FIG. 18), compound D (FIG. 18), compound E (Asp (bis-LacAHT)) (FIG. 18), Fab__ (FIG. 18), compound P L-tyrosyl-L-aspartoyl-bis-{N-[6-([[6-O-phosphoryl-α-D-mannopyranosyl]oxy]hexyl]-L-alaninamide] (FIG. 19), compound J 3-{N-[3,4,5-tris-(2-triethylammoniumethoxy)benzoic acid, Pep12 (SEQ ID NO:42)-Pep19 (SEQ ID NO:49) (X is the 3(2-pyridyldithio) propionyl moiety (FIG. 20)), Pep12 (SEQ ID NO:42) ([Gln$^0$, Leu$^{27}$, ε-X-Lys$^{67}$]-insulin-like growth factor II), Pep13 (SEQ ID NO:43) ([Gln$^0$, ε-X-Lys$^3$, Leu$^{27}$, Arg$^{67}$]-insulin-like growth factor II), Pep14 (SEQ ID NO:44) (Y$^0$-ε-X-Lys$^{24}$-calcitonin gene-related peptide), Pep15 (SEQ ID NO:45) ([Asu$^{2,7}$, Y$^8$, ε-X-K$^{24}$]-calcitonin gene-related peptide), Pep16 (SEQ ID NO:46) ((Gln$^0$, Leu$^{27}$, ε-X-Lys$^{54}$, Arg$^{55}$, Arg$^{67}$)-insulin-like growth factor II), Pep17 (SEQ ID NO:47) (N-X-des-(1-3)-[Arg$^{65}$, Arg$^{67}$]-insulin-like growth factor I), Pep18 (SEQ ID NO:48) (ε-X-K$^0$-thymopoietin), Pep19 (SEQ ID NO:49) (ε-X-K$^4$-thymopoietin, 7α,12α-dihydroxy-3β-(ω)-aminoalkoxy)-5-β-cholan-24-oic acid), Pep20 (SEQ ID NO:50) (hepatocyte growth factor), Pep21 (SEQ ID NO:51) (endothelin-1), Pep22 (SEQ ID NO:52) (N-succinyl-[glu$^9$,ala$^{11,15}$]-endothelin-1(8-21)), and Pep23 (SEQ ID NO:53) (r-atrial natriuretic factor). The ligand E can be used for delivering nucleic acid to hepatocytes and P for delivering nucleic acid to muscle cells.

One skilled in the art will readily recognize that the ligand chosen will depend on which receptor is being bound. Since different types of cells have different receptors, this provides a method of targeting nucleic acid to specific cell types, depending on which cell surface ligand is used. Thus, the preferred cell surface ligand may depend on the targeted cell type.

The term "nuclear ligand" as used herein refers to a ligand which will bind a nuclear receptor. The term "nuclear receptor" as used herein refers to a chemical grouping on the nuclear membrane which will bind a specific ligand and help transport the ligand through the nuclear membrane. Nuclear receptors can be but are not limited to those receptors which bind nuclear localization sequences. Nonlimiting examples of nuclear ligands include those shown on FIG. 18 below, as well as, Pep3 (SEQ ID NO:33), Pep4 (SEQ ID NO:34), Pep5 (SEQ ID NO:35), Pep6 (SEQ ID NO:36), Pep7 (SEQ ID NO:37), Pep8 (SEQ ID NO:38), Pep9 (SEQ ID NO:39), and Pep10 (SEQ ID NO:40). In a preferred embodiment, the nuclear ligand, GYGPPKKKRKVEAPYKA(K)$_{40}$WK, (SEQ ID NO:60) is used to transport nucleic acid to the nucleus.

The term "lysis agent" as used herein refers to a molecule, compound, protein or peptide which is capable of breaking down an endosomal membrane and freeing the DNA transporter into the cytoplasm of the cell. This term includes but is not limited to viruses, synthetic compounds, lytic peptides, or derivatives thereof. The term "lytic peptide" refers to a chemical grouping which penetrates a membrane such that the structural organization and integrity of the membrane is lost. As a result of the presence of the lysis agent, the membrane undergoes lysis, fusion or both.

In the present invention, useful lysis agents include but are not limited to peptides of the Othromyxoviridae, Alphaviridae and Arenaviridae. Lysis agents also can include Pep24 (SEQ ID NO:54), Pep25 (SEQ ID NO:55), Pep26 (SEQ ID NO:56), any appropriate bacteria toxin, bacteria, adenovirus, parainflunza virus, herpes virus, retrovirus, hepatitis virus, or any appropriate lytic peptide or protein from a virus or bacteria. This includes use of any subfragments of the above which will provide endosomal escape activity. Particular bacterial toxins may include cytolytic toxins or active fragments from alveolysin, bifermentolysin, botulinolysin, capriciolysin, cereolysin O, chauveolysin, histolyticolysin O, ivanolysin, laterosporolysin, oedematolysin O, listeriolysin O, perfringolysin O, pneumolysin, sealigerolysin, septicolysin O, sordellilysin, streptoslysin O, tetanolysin or thuringolysin O.

The lysis agent can be a replication deficient virus. In one preferred embodiment, adenovirus of the structure F (FIG. 4) is used. As used herein, the term "replication deficient" refers to a virus lacking one or more of the necessary elements for replication. In another embodiment of the present invention, useful lytic peptides are Pep24 (SEQ ID NO:54) (influenza; GLFEAIAGFIEDGWEGMIDGGGC), Pep25 (SEQ ID NO:55) (SFV E1; KVYTGVYPFMWGGAYCFCD), and Pep26 (SEQ ID No:56) (Lassa gp2; GGYCLTRWMLIEAELKCFGNTAV). In still another embodiment, bacteria toxins listeriolysin or perfringolysin can be used. The above are only examples and are nonlimiting.

Lysis agents as used herein are pH sensitive. After cointernalization of the nucleic acid complex containing the lysis agent throughout the same coated pit on the plasma membrane of the cell, the decrease in pH that occurs immediately after endosome formation causes spontaneous lysis of the endosome. The nucleic acid is then released into the cytoplasm. The above is a nonlimiting example.

The surface ligand, the nuclear ligand and/or the lysis agent can be attached directly to the binding molecule by covalent bonding or can be connected to the binding molecule via a spacer. The term "spacer" as used herein refers to a chemical structure which links two molecules to each other. The spacer normally binds each molecule on a different part of the spacer molecule. The spacer can be hydrophilic molecule and comprised of about 6 to 30 carbon atoms. The spacer can also contain between 6 to 16 carbon atoms. The spacer can include but is not limited to a hydrophilic, polymer of $[(gly)_i(ser)_j]_k$ wherein i ranges from 1 to 6, j ranges from 1 to 6, and k ranges from 3 to 20. In addition, the spacer and binding molecule compounds include but are not limited to those compounds expressed herein as XI, XII, XL, XLI, LX, LXI, LXXVIII, XC, CXVIV, CXVI, XV, XVI, XVIII, XXI, XLV, LXVII, XLVII, L, LXV, LXX, XCIV, XCVI, XCIX, XXIV, XXV, LXXIII, LXXIV, CII, or CV. Furthermore, the spacer may include but is not limited to repeating omega-amino acid of the structure $[NH—(CH_2CH_2)_n—CO—]_m$, where n=1–3 and m=1–20, a disulfide structure $(CH_2CH_2—S—S—CH_2CH_2—)_n$, or an acid sensitive bifunctional molecule with the structure

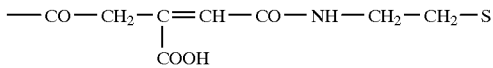

A second aspect of the present invention is a nucleic acid transporter system for delivering nucleic acid into a cell. The transporter includes a nucleic acid binding complex containing a binding molecule noncovalently bound to nucleic acid and covalently linked to a surface ligand. In addition, the transporter includes a second nucleic acid binding complex containing a binding molecule noncovalently bound to nucleic acid and covalently linked to a nuclear ligand. The nucleic acid binding complexes can be non-covalently bound to the nucleic acid at the same time, i.e., simultaneously, and in various proportions. The binding molecules can be the same molecule or a combination of a different molecule as discussed above. Furthermore, the surface ligand and nuclear ligand can be directly attached to the binding molecule or attached by a spacer as defined above. In one embodiment of the present invention, the surface ligand can be one of those disclosed herein and the nuclear ligand is the peptide GYGPPKKKRKVEAPYKA (K)$_{40}$WK.(SEQ ID NO:60)

In a third aspect, the present invention features a nucleic acid transporter for delivering nucleic acid into a cell. The transporter includes a nucleic acid binding complex containing a binding molecule noncovalently bound to nucleic acid and covalently linked to a surface ligand. The transporter includes a second nucleic acid binding complex containing a binding molecule noncovalently bound to nucleic acid and covalently linked to a nuclear ligand. In addition, the transporter includes a third nucleic acid binding complex containing a binding molecule noncovalently bound to nucleic acid and covalently linked to a lysis agent. The binding complexes above can be noncovalently bound to the nucleic acid at the same time, i.e., simultaneously, and in various proportions. As described above, the binding molecules can be the same or different molecules and the binding molecules may attach to the ligands or lysis agent directly or by spacers.

A fourth related aspect of the present invention features a nucleic acid transporter system with a nucleic acid binding complex containing a binding molecule noncovalently bound to nucleic acid and covalently linked to a surface ligand, and a second nucleic acid binding complex with a binding molecule noncovalently bound to nucleic acid and covalently linked to a lysis agent. In one preferred embodiment, folate is used as the surface ligand and replication-deficient adenovirus is used as the lysis agent. This transporter, as well as the other nucleic acid transporters described in this invention, can deliver to the cytosol other macromolecules besides nucleic acid including but not limited to, proteins, lipids and carbohydrates. The binding complexes of this aspect can be noncovalently bound to the nucleic acid at the same time, i.e., simultaneously, and in various proportions. The binding molecules can be the same or different and may attach to the ligands or lysis gents directly or by spacers as described above.

In another preferred embodiment an asialoglycoprotein can be used as the surface agent and listeriolysin or perfringolysin as the lysis agent. Listeriolysin, perfringolysin or only a part of the toxins harboring the active subfragments need be used. Similarly, all microbial toxins and their active subfragments can be incorporated into the transporters of the present invention for endosomal escape.

In addition, a fifth related aspect features a nucleic acid transporter system containing a plurality of a common nucleic acid binding complex with a binding molecule noncovalently bound to nucleic acid and attached to both a surface ligand and a nuclear ligand. A lysis agent may also be bound to the binding molecule along with the surface ligand and nuclear ligand. As above, spacers can be used to connect the surface ligand, nuclear ligand or lysis agent.

A sixth aspect of the present invention features a cell transformed with the nucleic acid transporter system as described above for expression of nucleic acid targeted to the cell. As defined above, the nucleic acid may include nucleic acid containing genetic material and coding for a variety of proteins, polypeptides or RNA.

As used herein "transformation" is a mechanism of gene transfer which involves the uptake of nucleic acid by a cell or organism. Following entry into the cell, the transforming nucleic acid may recombine with that of the host or may replicate independently as a plasmid or a temperate phage. Cells which are able to take up nucleic acid are described as competent. Particular cells may not be naturally competent, but require various treatments in order to induce the transfer of nucleic acid across the cell membrane. This would include but is not limited to the surface ligand receptor interaction of the present invention.

Transformation can be performed by in vivo techniques as described below, or by ex vivo techniques in which cells are cotransfected with a nucleic acid transporter system containing nucleic acid and also containing a selectable marker. This selectable marker is used to select those cells which have become transformed. It is well known to those skilled in the art the type of selectable markers to be used with transformation studies.

The transformed cells can produce a variety of compounds selected from proteins, polypeptides or RNA, including hormones, growth factors, enzymes, clotting factors, apolipoproteins, receptors, drugs, tumor antigens, viral antigens, parasytic antigens, and bacterial antigens. Other examples can be found above in the discussion of nucleic acid. The product expressed by the transformed cell depends on the nucleic acid used. The above are only examples and are not meant to be limiting.

A seventh aspect of the present invention features methods for transformation of cells. These methods comprise the steps of contacting a cell with a nucleic acid transporter system as described above for a sufficient time to transform the cell. Cell types of interest can include but are not limited to liver, muscle, endothelium and skin.

In an eighth aspect, the present invention features a transgenic animal whose cells contain the nucleic acid referenced above delivered via the nucleic acid transporter system. These cells include germ or somatic cells. Transgenic animal models can be used for dissection of molecular carcinogenesis and disease, assessing potential chemical and physical carcinogens and tumor promoters, exploring model therapeutic avenues and livestock agricultural purposes.

The genetic material which is incorporated into the cells from the above nucleic acid transporter system includes (1) nucleic acid not normally found in the cells; (2) nucleic acid which is normally found in the cells but not expressed at physiological significant levels; (3) nucleic acid normally found in the cells and normally expressed at physiological desired levels; (4) other nucleic acid which can be modified for expression in cells; and (5) any combination of the above.

A ninth related aspect of the present invention features compounds relating to the nucleic acid transporter systems above. These include but are not limited to compounds which are related to the nucleic acid binding complex, the binding molecule, surface ligands, nuclear ligands or lysis agents. These compounds are described below in more detail.

A tenth related aspect of the present invention features a method for delivering nucleic acid into a hepatocyte. This method includes contacting a hepatocyte with the above referenced nucleic acid transporters. The surface ligand used with the nucleic acid transporter is one specific for recognition by hepatocyte receptors. In particular, the asialoorosomucoid protein is used as a cell surface ligand, spermine derivative as a binding molecule and a replication-defective adenovirus as a lysis agent. The term "hepatocyte" as used herein refers to cells of the liver.

An eleventh related aspect of the present invention features a method for delivering nucleic acid to muscle cells. This method includes contacting the muscle cell with the above referenced nucleic acid transporter system. The surface ligand used is specific for receptors contained on the muscle cell. In particular, the surface ligand can be insulin-like growth factor-I. In addition, the binding molecule can be a spermine derivative and the lysis agent can be a replication-defective adenovirus. The term "muscle cell" as used herein refers to cells associated with striated muscle, smooth muscle or cardiac muscle.

A twelfth related aspect of the present invention features a method for delivering nucleic acid to bone-forming cells. This method includes contacting the bone-forming cell with the above-referenced nucleic acid transporter system. The surface ligand used with the nucleic acid transporter system is specific for receptors associated with bone-forming cells. In particular, the surface ligands can include but are not limited to bone morphogenetic protein or cartilage induction factor. In addition, the binding molecule of the nucleic acid transporter can be a spermidine derivative and the lysis agent a replication defective adenovirus. As used herein the term "bone-forming cell" refers to those cells which promote bone growth. Nonlimiting examples include osteoblasts, stromal cells, inducible osteoprogenitor cells, determined osteoprogenitor cells, chondrocytes, as well as other cells capable of aiding bone formation.

Another related aspect of the present invention features a method for delivering nucleic acid to a cell using the above-referenced nucleic acid transporter system. The nucleic acid transporter system uses folate as a ligand. In addition, the nucleic acid transporter can use a replication defective adenovirus as a lysis agent and as a binding molecule a spermine derivative. This method targets cells which contain folate receptors, including but not limited to, hepatocytes.

The nucleic acid transporters of the above methods may be administered by various routes. The term "administration" refers to the route of introduction of the nucleic acid transporter or carrier of the transporter into the body. Administration may be intravenous, intramuscular, topical, or oral. Administration can be directly to a target tissue or through systemic delivery. In particular, administration may be by direct injection to the cells. In another embodiment, administration may be intravenously. Routes of administration include intramuscular, aerosol, oral, topical, systemic, ocular, intraperitoneal and/or intrathecal.

Other features and advantages of the invention will be apparent from the following detailed description of the invention in conjunction with the accompanying drawings and from the claims.

BRIEF DESCRIPTION OF THE DRAWINGS

FIGS. 1–3 show the schematic synthesis of the receptor ligands.

FIGS. 5–13 show a schematic flow chart for the synthesis of the nucleic acid transporter systems.

FIG. 14 is a schematic diagram of insertion of a triplex forming oligonucleotide or peptidyl nucleic acid by attachment of a ligand.

FIG. 15A is a schematic representation using a ligand to target a triplex forming peptidyl oligonucleotide to a duplex nucleic acid.

FIGS. 17A–17B show the targeting with a ligand of a sequence to the c-myc promoter region (single stranded nucleic acid sequences (top of page.) represent Seq. ID Nos. 19, 20, and 21 respectively (reading top to bottom); peptide sequence (bottom of page) represents Seq. ID Nos. 22–29 respectively (reading top to bottom)).

FIG. 18 (SEQ ID NOS:31–41) is a schematic of the peptide ligands and other ligands and shows the abbreviations used herein for the ligands.

FIGS. 20A (SEQ ID NOS:42–46) and 20B (SEQ ID NOS:47–49) shows specific ligands for targeting to muscle.

FIGS. 23A (SEQ ID NO:50) and 23B (SEQ ID NOS:51–56) is a schematic of the peptide ligands and other ligands and shows the abbreviations used herein for the ligands.

FIGS. 25A, 25B, 25C, and 25D is a schematic representation of a trimeric fusogenic peptide.

FIGS. 28A, 28B, and 28C is a schematic representation of a synthetic route for a trimeric fusogenic peptide.

The drawings are not necessarily to scale. Certain features of the invention may be exaggerated in scale or shown in schematic form in the interest of clarity and conciseness.

DETAILED DESCRIPTION OF THE INVENTION

The following are examples of the present invention using nucleic acid transporter systems for delivery of nucleic acid to a cell. These examples are offered by way of illustration and are not intended to limit the invention in any manner.

The following are specific examples of preferred embodiments of the present invention. These examples demonstrate how specific surface and nuclear ligands can be used with a nucleic acid binding moiety to target nucleic acid into the cellular interior and/or the cell nucleus. Furthermore, these examples demonstrate use of a lysis agent to release nucleic acid into the cellular interior. These examples include in vivo and in vitro techniques, various cellular or animal models and how nucleic acid can be inserted into cells. The utility of such nucleic acid transporter systems is noted herein and is amplified upon in copending applications by Woo et al., entitled "A DNA Transporter System and Method of Use", supra, and such sections are hereby specifically incorporated by reference herein.

Below are provided examples of specific nucleic acid transporter systems that can be used to provide certain functionalities to the associated nucleic acid in the nucleic acid transporter system, and thus within a transformed cell or animal containing such associated nucleic acid. Those in the art will recognize that specific moieties of the nucleic acid transporter system can be identified as that containing the functional region providing the desirable properties of the nucleic acid transporter system. Such regions can be readily minimized using routine deletion, mutation, or modification techniques or their equivalent.

Synthesis of Components of Receptor Ligands

Examples of the specific components of the receptor ligands are shown in FIGS. 1–4, 18.

Figure 1:
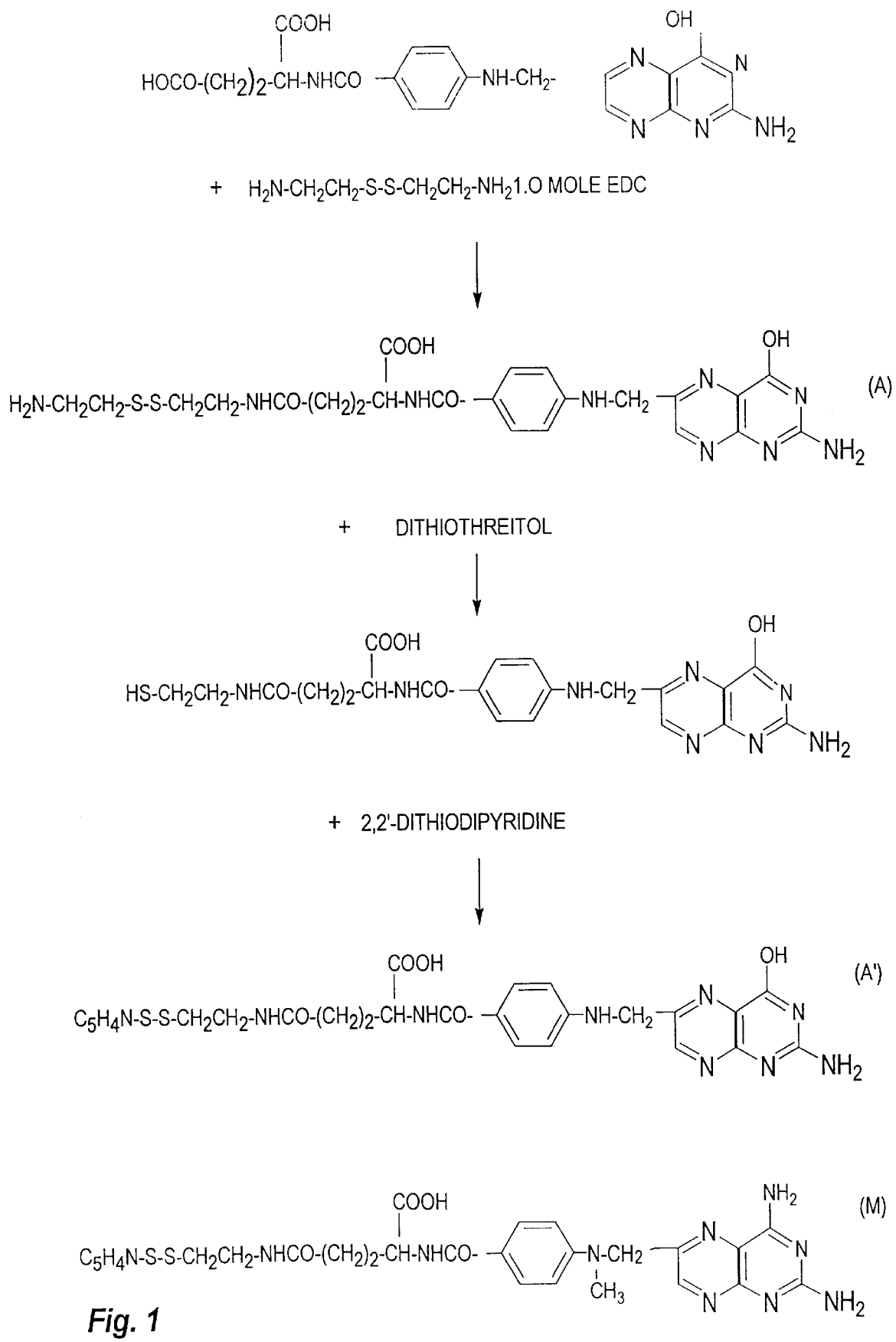
Figure 3:
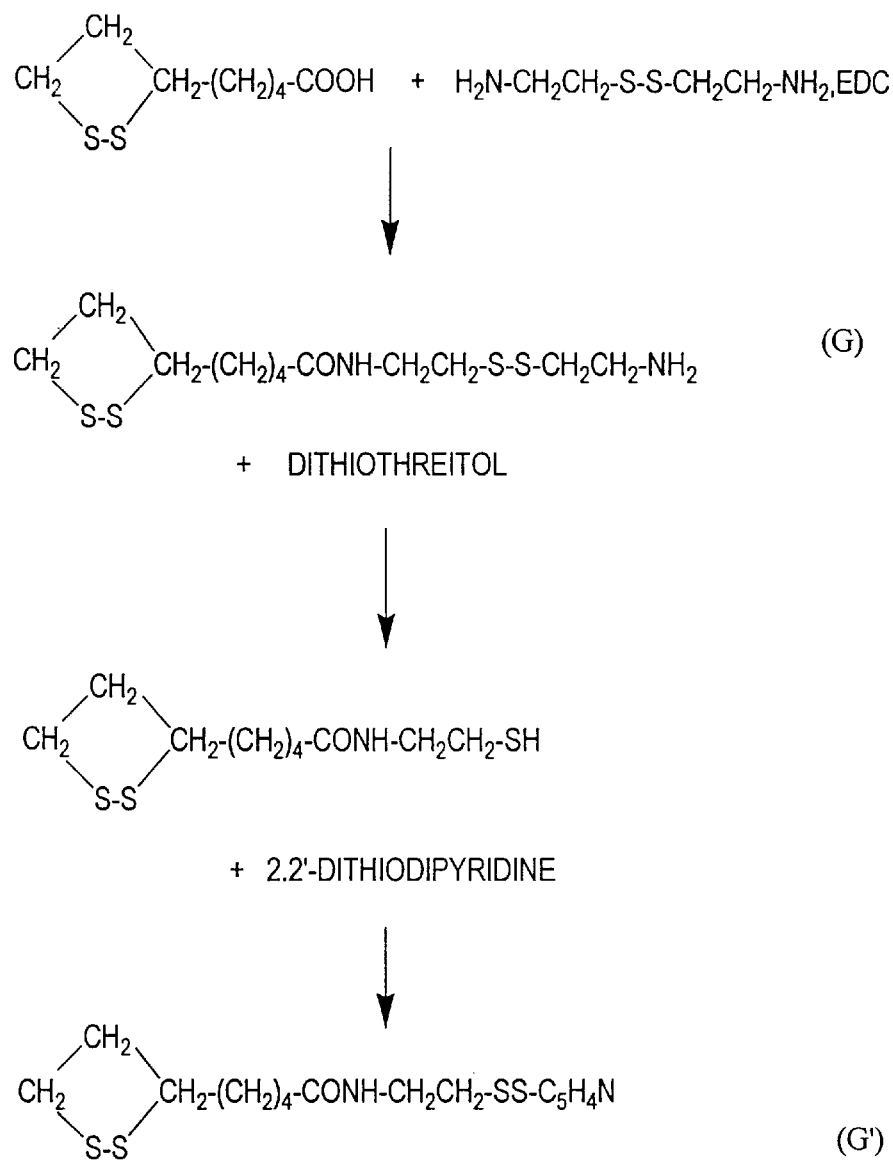

A. In FIGS. 1–3 the schematic synthesis of A, B, G, P, J and M are shown. The actual synthesis for A, B, G, P, J and M are very similar. As an example, for the preparation of A, dissolve 1 mmol of folic acid in 2 ml dry dimethylformamide (DMF), add 1.3 mmol 1-ethyl-3-[3-(dimethylamino) propyl)carbodiimide and stir in the dark under N$_2$ overnight at 4°, then add 1.3 mmol N-hydroxysuccinimide with stirring continued for another 6 hr at 4°. Add bis(2-aminoethane)disulfide, 1 mmol in 0.5 ml dry dimethylformamide, dropwise to the reaction mixture and stir for an additional 4 hr. Add 15 ml water to precipitate the product. After centrifugation, the precipitate is washed and dissolved in oxygen-free 0.1 M NH$_4$OH. This solution is applied to an anion exchange resin and equilibrated in degassed 0.05 M NH$_4$CO$_3$ containing 20% acetonitrile. The γ-isomer is separated from unreacted starting materials and the α-isomer by chromatography in 0.1 M NH$_4$CO$_3$ containing 20% acetonitrile. The appropriate fractions are pooled and lyophilized to obtain the product.

The synthesis of the nicotinic acetylcholine receptor ligand, component J, 3-{N-[3,4,5-tris-(2-triethylammoniumethoxy)benzoic acid, is the same as for folic acid, component A, except the 1 mmol of folic acid in 2 ml dry DMF is replaced with 1 mmol 3-{N-[3,4,5-tris-(2-triethylammoniumethoxy)benzoic acid in 2 ml dry DMF. The synthesis of the nicotinic acetylcholine receptor ligand, component J, 3-{N-[3,4,5-tris-(2-triethylammoniumethoxy) benzoic acid, is the same as for folic acid, component A except the 1 mmol of folic acid in 2 ml dry DMF is replaced with 1 mmol 3-{N-[3,4,5-tris-(2-triethylammoniumethoxy) benzoic acid in 2 ml dry DMF.

This compound can be further reacted to yield A__. dissolve 2 mmol A in 10 ml oxygen-free 0.01 M NH$_4$CO$_3$ containing 2 mmol dithioerythritol, stir for 2 hr. The solution is applied to an anion exchange resin equilibrated in degassed 0.1 M NH$_4$CO$_3$ containing 20% acetonitrile. The reduced folate derivative is separated from unreacted starting materials by chromatography in 0.1 M NH$_4$CO$_3$ containing 20% acetonitrile. The appropriate fractions are pooled, lyophilized, and then dissolved in 10 ml dry dimethylformamide for dropwise addition to a vigorously stirred solution of 2,2'-dipyridinedisulfide, 4 mmol dissolved in 10 ml ethanol containing 0.4 ml glacial acetic acid. After overnight at room temperature protected from light, the solvent is removed in vacuo. Add degassed 0.1 M NH$_4$CO$_3$ to effect solution and then chromatograph as before to obtain the desired product. Both the original A, B and G and the further reacted A__, B__ and G__ have been used. The synthesis of the nicotinic acetylcholine receptor ligand, component J, 3-(N-[3,4,5-tris-(2-triethylammoniumethoxy) benzoic acid is the same as for folic acid, component A except the 1 mmol of folic acid in 2 ml dry DMF is replaced with 1 mmol 3-{N-[3,4,5-tris-(2-triethylammoniumethoxy) benzoic acid in 2 ml dry DMF.

One skilled in the art will recognize that other vitamins and analogs of these vitamins can be used. Since the different vitamins and analogs will have different affinities, uptake and selectivity for the membrane receptors, the specific vitamin or analog is chosen to maximize the specificity and uptake.

B. The peptides including Pep1 (SEQ ID NO:31) through Pep11 (SEQ ID NO:41) and Pep21 (SEQ ID NO:51) through Pep26 (SEQ ID NO:56) can be synthesized by a variety of methods. In the present invention solid phase synthesis on a support is preferred, except for Pep12 (SEQ ID NO:42), Pep13 (SEQ ID NO:43), Pep16 (SEQ ID NO:46), Pep17 (SEQ ID NO:47) and Pep20 (SEQ ID NO:50) which are recombinant proteins produced by expression vectors in bacteria, yeast, baclovirus or mammalian systems.

Peptides Pep1 (SEQ ID NO:31) through Pep6 (SEQ ID NO:36) and Pep12 (SEQ ID NO:42) through Pep23 (SEQ ID NO:43) are examples of peptides or peptide analogs. These peptides target and bind to membrane receptors. One skilled in the art recognizes that other peptides or analogs to other membrane receptors can be used, and that the order of the amino acid sequence can be reversed, inverted and/or repeated, while still maintaining the transporter characteristics. The selection of a specific peptide will depend on the tissue and membrane receptor which is targeted. By selecting specific peptides, one skilled in the art recognizes the binding efficiency, uptake and specificity can be regulated. This can be used for tissue specificity.

Peptides Pep24 (SEQ ID NO:54) through Pep26 (SEQ ID NO:56) are examples of peptides or peptide analogs. These peptides lyse membranes. One skilled in the art recognizes that other peptides or analogs to other lytic peptides can be used, and that the order of the amino acid sequence can be reversed, inverted and/or repeated, and still maintain the lytic characteristics. The selection of a specific peptide will depend on the tissue and membrane receptor which is be targeted.

C. Spermine Template

C1. Monomeric fusogenic peptide covalently linked to a polycation through an acid sensitive, reducible spacer.

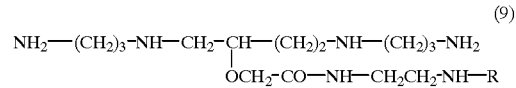

(9)

where R=Pep24 (SEQ ID NO:54)-SS—CH$_2$CH$_2$NH-α-CO-aconityl-γ-CO—

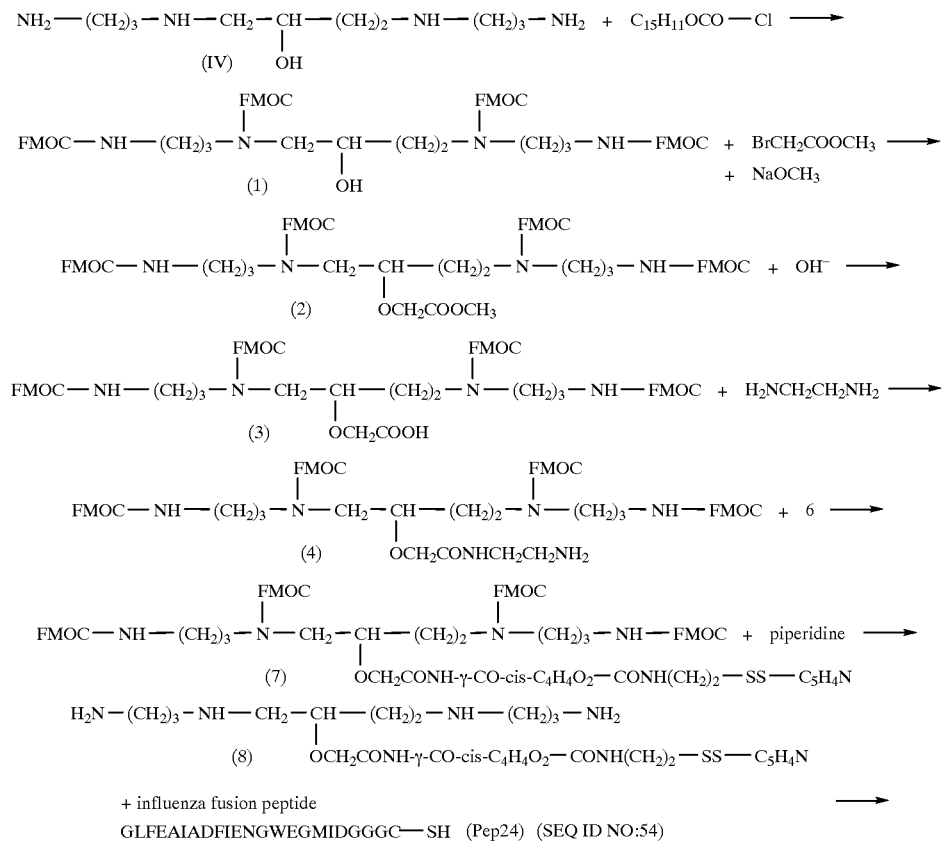

where R=GLFEAIADFIENGWEGMIDGGGC-SS—CH$_2$CH$_2$NH-α-CO-aconi- (SEQ ID NO:54) tyl-γ-CO—(SEQ ID NO:54)

Detailed preparative procedures are as follows: Combine 2 mmol (S)-hydroxyspermine (IV), 4 mmol 4-pyrrolidinopyridine and 4.1 mmol 9-fluorenylmethyl chloroformate in 40 ml anhydrous benzene and stir overnight at room temperature under N$_2$. Separate the desired product (1) by solid phase extraction on phenyl-silica and elution with a linear gradient of ethyl acetate to 50% in hexane. Pool the appropriate fractions and evaporate the solvent to obtain the product as an amorphous solid.

Add 4 ml of dry benzene to 1 mmol K$_2$CO$_3$ and 2 mmol 18-crown-6 and stir for 20 min. Add 2 mmol of 1 in 4 ml of dry benzene, followed by 2 mmol methyl bromoacetate in 2 ml benzene. After 4 hr, add 25 ml of water and extract with 3 portions of 25 ml benzene. Remove the solvent in vacuo and dissolve the residue in 10 ml ethanol containing 2 mmol potassium hydroxide. After overnight at room temperature, the solution is transferred to a separatory funnel, to which 2 mmol of HCl, 5 ml of water and 25 ml of benzene is added. After extraction with 3 additional portions of benzene, the combined organic phase is taken to dryness in vacuo, redissolved in a minimum volume of ethyl acetate, diluted with enough petroleum ether to create slight turbidity and cooled at 4° to promote crystallization of 3.

Dissolve 1 mmol of 3 in 2 ml dry dimethylformamide, add 3.0 mmol 1-ethyl-3-[3-(dimethylamino)propyl]carbodiimide and stir 2 hr, then add 1.1 mmol N-hydroxysuccinimide and continue stirring for another 6 hr at room temperature. This solution is added dropwise to 10 mmol of 1,2-diaminoethane in 0.5 ml dry dimethylformamide, and stirring continued for an additional 4 hr, when the reaction is complete as monitored by thin layer chromatography. The solution is applied to an cation exchange resin equilibrated in degassed water. The product is separated from unreacted starting materials by a gradient from 0.0005 to 2.0 M HCl. The appropriate fractions are pooled and lyophilized to obtain the product (4).

Figure 24:
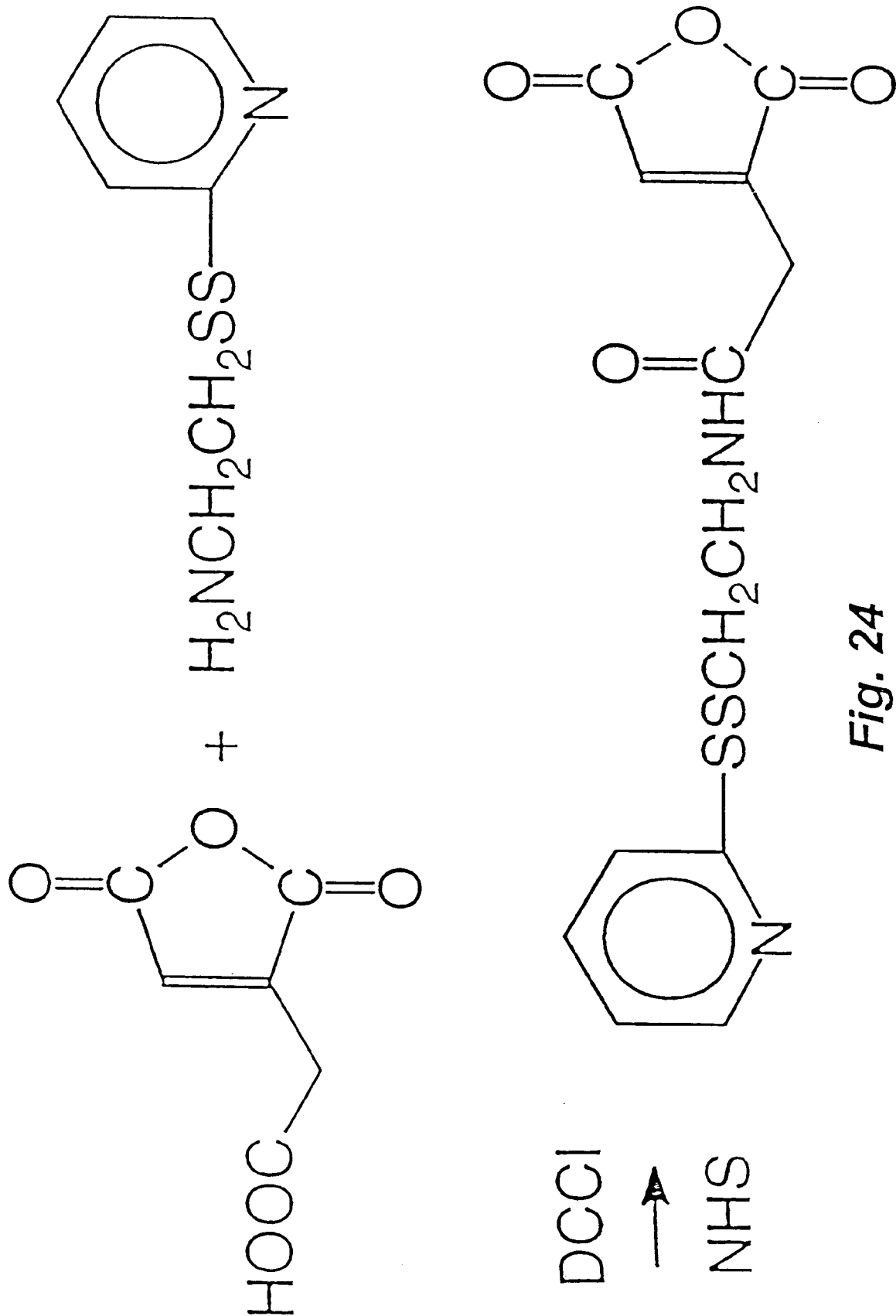
FIG. 24 is a schematic representation of a synthetic route for bifunctional acid sensitive linkers.

The Synthetic route for the bifunctional acid sensitive linker 6 is shown in FIG. 24. Detailed procedures are as follows:

Combine 10 mmol cis-aconityl anhydride 10 mmol with 2-(2'-aminoethyldithio)-pyridine in 20 ml dry DMF under N$_2$ protected from light at room temperature for 18 hr. Remove the solvent in vacuo, dissolve the residue in the minimum amount of 3M NH$_4$CO$_3$, dilute 10 fold and apply to an anion exchange resin equilibrated in degassed 0.05 M NH$_4$CO$_3$ and elute with a gradient to 1.OM NH$_4$CO$_3$. The appropriate fractions are pooled, lyophilized and the residue 5 dissolved in 2-propanol and crystallized at 4° after the solution is made turbid by the addition of diethyl ether. The product 5 is collected by filtration.

Dissolve 1 mmol of 5 in 2 ml dry DMF, add 1.1 mmol N-hydroxysuccinimide and 1.1 mmol dicyclohexylcarbodiimide and continue stirring for another 24 hr at 4°. Remove the solvent in vacuo, dissolve the residue in the minimum amount of 2-propanol and crystallize at 4° after the solution is made turbid by the addition of diethyl ether. The product 6 is collected by filtration.

Dissolve 1 mmol of 6 in 2 ml dry DMF, add 1.1 mmol N-hydroxysuccinimide and 1.1 mmol dicyclohexylcarbodiimide and continue stirring for another 6 hr at 4°. One mmol of 4 in 0.5 ml dry dimethylformamide, is added dropwise to the preceding reaction mixture and stirring continued for an additional 4 hr. Remove the solvent in vacuo and dissolve the residue in 10 ml 50% piperidine in DMF (v/v). Again remove the solvents in vacuo, solubilize the residue 7 in 0.1 M NH$_4$OH, and apply to an anion exchange resin equilibrated in degassed 0.05 M NH$_4$CO$_3$ containing 20% acetonitrile and eluted with a gradient of 0 to 0.25 M acetonitrile in 0.1 M NH$_4$CO$_3$. The appropriate fractions are pooled and lyophilized to obtain the product 8.

To a stirred solution of 0.5 mmol of lytic peptide Pep24 (SEQ ID NO:54) in 5 ml PBS, pH 7.4, at 4°, add 0.1 mmol of 8 in PBS dropwise. After 18 hrs, chromatograph over a molecular sieve to separate the product 9 from unreacted starting materials.

C2. Trimeric fusogenic peptide covalently linked to a polycation through an acid sensitive, reducible spacer.

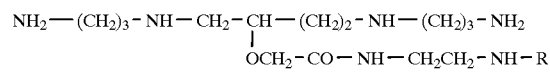

(16)

where R=-α-CO-aconityl-γ-COHNC—(OCH$_2$CH$_2$NHCO(CH$_2$)$_5$NH—R')$_3$ and R'=Pep24 (SEQ ID NO:54)-SS—CH$_2$CH$_2$CO—

Figure 25A:
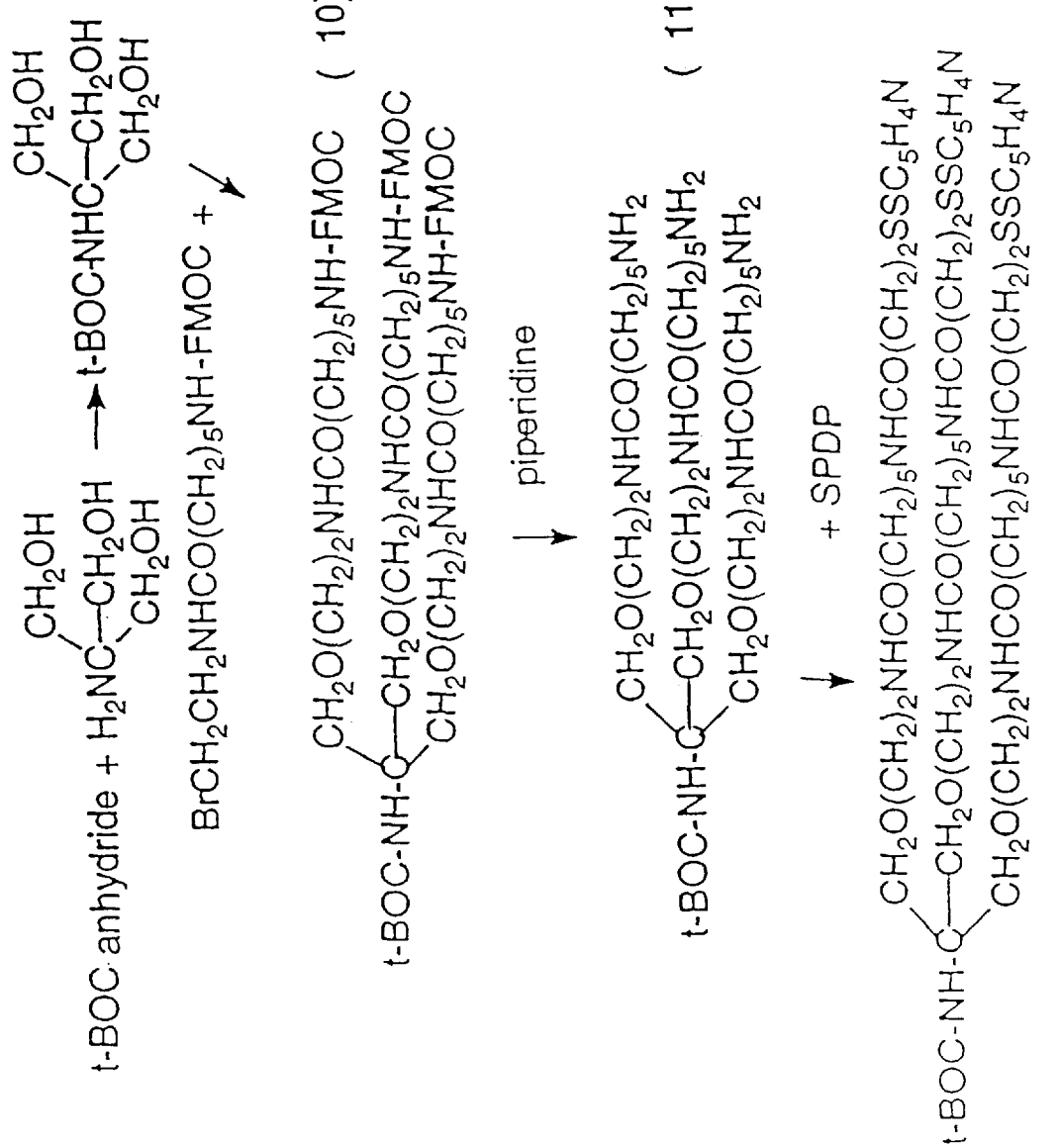
Figure 25B:
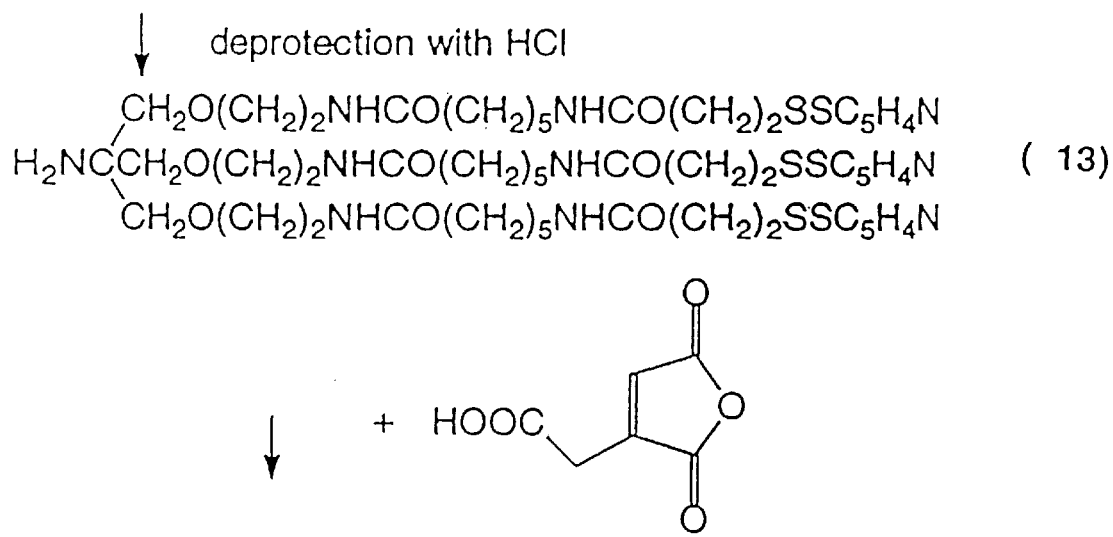
Figure 25C:
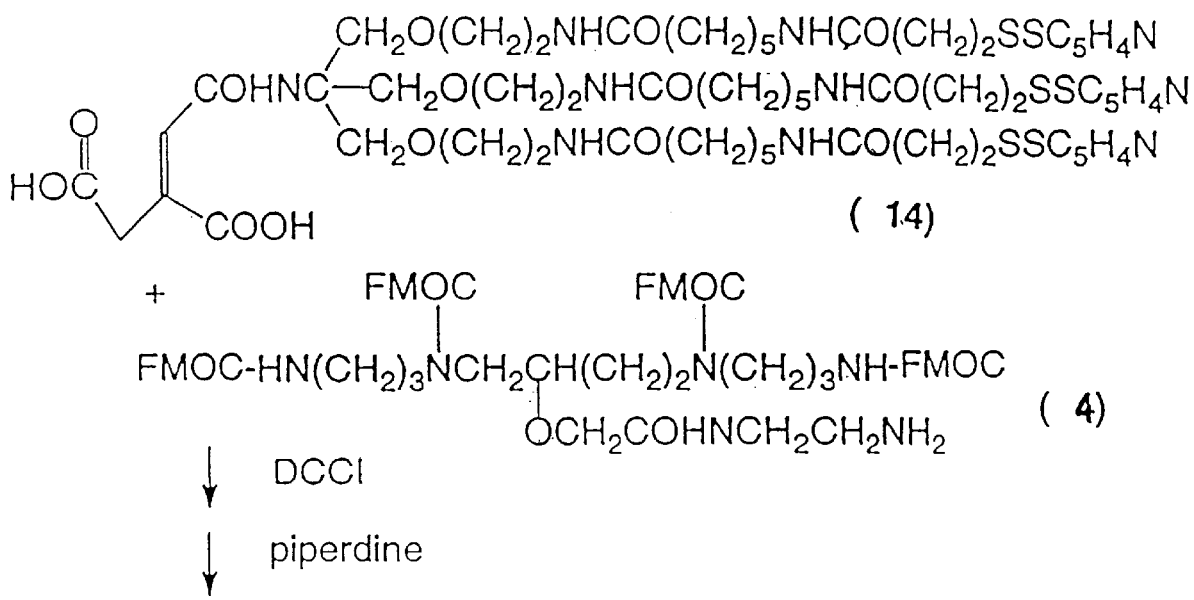

The Series II synthetic route (New compounds 10–16) is shown in FIG. 25. Detailed procedures are as follows.

Add 4 ml of dry benzene to 1 mmol K$_2$CO$_3$ and 2 mmol 18-crown-6 and stir for 20 min. Add 2 mmol N-t-BOC-tris-(hydroxymethyl)methane in 4 ml of dry benzene, followed by 20 mmol 1-bromo-2-(N-5-FMOC-aminohexanoyl)-aminoethane in 2 ml benzene. After 4 hr, add 25 ml of water and extract with 3 portions of 25 ml benzene. Remove the solvent in vacuo and dissolve the residue 10 in 10 ml 50% piperidine in DMF (v/v). After 6 hr, remove the solvents in vacuo, solubilize the residue in 20 ml ethyl acetate, wash with water until neutral and dry over molecular sieve before solid phase extraction and chromatography on octadecyl-silica, using a gradient of acetonitrile to 100%. Pool the appropriate fractions to obtain 11.

Combine 2 mmol of 11 in 20 ml acetonitrile with 7 mmol of succinimidyl 3(2-pyridyldithio)-propionate in ethanol. After 60 min, dilute with sufficient water to create a slight turbidity and apply to octadecyl-silica, again using a gradient of acetonitrile from 0 to 100%. Pool the appropriate fractions to obtain 12.

Dissolve 1 mmol of 12 in 20 ml 3N HCl at 4° and allow to stand for 60 min before the solution is taken to dryness in vacuo. The residue is resuspended in water and solubilized with the minimum amount of acetonitrile and chromatographed on octadecyl-silica, again using a gradient of acetonitrile from 0 to 100%. Pool the appropriate fractions to obtain 13.

Dissolve 1 mmol of 13 in 2 ml dry DMF, add 3 mmol cis-aconityl anhydride and stir under N$_2$ overnight at 4°. Remove the solvents in vacuo, solubilize the residue in 0.1 M NH$_4$OH, and apply to an anion exchange resin equilibrated in degassed 0.05 M NH$_4$CO$_3$ containing 20% acetonitrile and eluted with a gradient of 0 to 0.25 M acetonitrile in 0.1 M NH$_4$CO$_3$. The appropriate fractions are pooled and lyophilized to obtain the product 14.

Dissolve 1 mmol of 14 in 2 ml dry DMF, add 1.1 mmol N-hydroxysuccinimide and 1.1 mmol dicyclohexylcarbodiimide and continue stirring for another 6 hr at 4°. One mmol of 4 in 0.5 ml dry dimethylformamide, is added dropwise to the preceding reaction mixture and stirring continued for an additional 4 hr. Remove the solvent in vacuo and dissolve the residue in 10 ml 50% piperidine in DMF (v/v). Again remove the solvents in vacuo, solubilize the residue in 0.1 M NH$_4$OH, and apply to an anion exchange resin equilibrated in degassed 0.05 M NH$_4$CO$_3$ containing 20% acetonitrile and eluted with a gradient of 0 to 0.25 M acetonitrile in 0.1 M NH$_4$CO$_3$. The appropriate fractions are pooled and lyophilized to obtain the product 15.

To a stirred solution of 0.5 mmol of lytic peptide Pep24 (SEQ ID NO:54) in 5 ml PBS, pH 7.4, at 4°, add 0.1 mmol of 15 in PBS dropwise. After 18 hr. chromatograph over a molecular sieve to separate the product 16 from unreacted starting materials.

C3. Trimeric fusogenic peptide covalently linked to a polycation through an acid sensitive, reducible spacer.

(20)

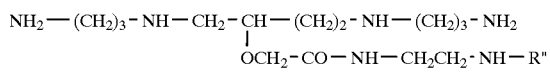

where R" =

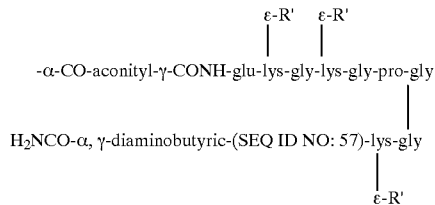

with the γ-carboxyl of glu$^1$ in amide linkage with the γ-amino of α,γ-diaminobutyric acid$^{10}$ and R'=Pep24-SS—CH$_2$CH$_2$CO— (SEQ ID NO:54).

Figure 26A:
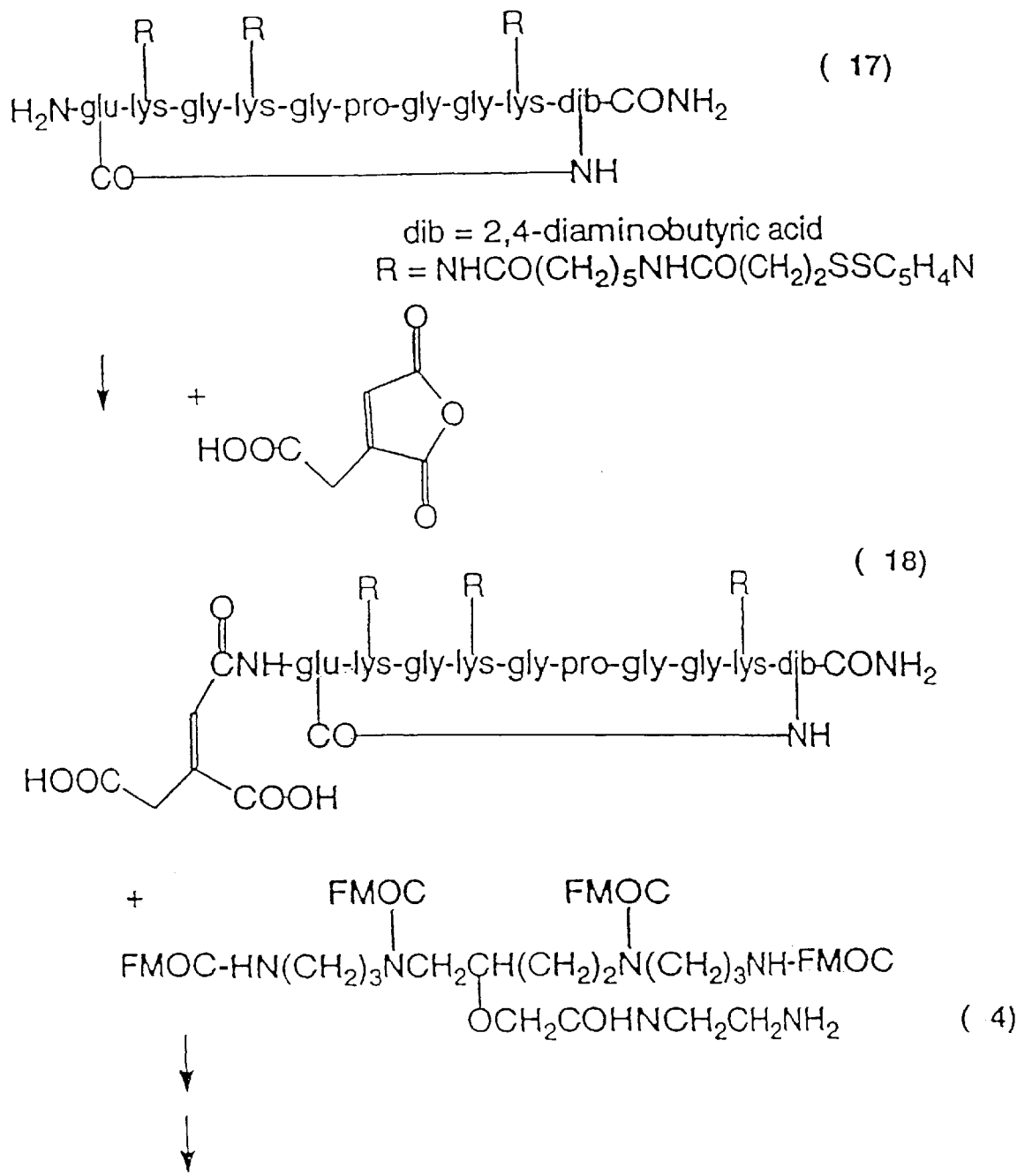
FIGS. 26A (SEQ ID NO:57) and 26B (SEQ ID NOS:57 and 59) is a schematic representation of the synthetic route for a trimeric fusogenic peptide.

The Series III synthetic route (New compounds 17–20) is shown in FIG. 26. Detailed experimental procedures are as follows.

Solid phase peptide synthesis with conventional reagents and procedures gives 17. It is obvious to one skilled in the art that homologs of 2,4-diaminobutyric acid, such as orinithine and lysine, could be substituted for this residue and that other amino acids, such as serine, alanine, and aspartic acid, could be substituted for gly.

Dissolve 1 mmol of 17 in 2 ml dry DMF, add 3 mmol cis-aconityl anhydride and stir under N$_2$ overnight at 4°. Remove the solvents in vacuo, solubilize the residue in 0.1 M NH$_4$OH, and apply to an anion exchange resin equilibrated in degassed 0.05 M NH$_4$CO$_3$ containing 20% acetonitrile and eluted with a gradient of 0 to 0.25 M acetonitrile in 0.1 M NH$_4$CO$_3$. The appropriate fractions are pooled and lyophilized to obtain the product 18.

Dissolve 1 mmol of 18 in 2 ml dry DMF, add 1.1 mmol N-hydroxysuccinimide and 1.1 mmol dicyclohexylcarbodiimide and continue stirring for another 6 hr at 4°. One mmol of 4 in 0.5 ml dry dimethylformamide, is added dropwise to the preceding reaction mixture and stirring continued for an additional 4 hr. Remove the solvent in vacuo and dissolve the residue in 10 ml 50% piperidine in DMF (v/v). Again remove the solvents in vacuo, solubilize the residue in 0.1 M NH$_4$OH, and apply to an anion exchange resin equilibrated in degassed 0.05 M NH$_4$CO$_3$ containing 20% acetonitrile and eluted with a gradient of 0 to 0.25 M acetonitrile in 0.1 M NH$_4$CO$_3$. The appropriate fractions are pooled and lyophilized to obtain the product 19.

To a stirred solution of 0.5 mmol of lytic peptide Pep24 (SEQ ID NO:54) in 5 ml PBS, pH 7.4, at 4°, add 0.1 mmol of 19 in PBS dropwise. After 18 hr, chromatograph over a molecular sieve to separate the product 20 from unreacted starting materials.

C4. Monomeric fusogenic peptide covalently linked to a polycation through an acid sensitive, reducible spacer.

(24)

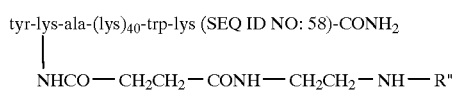

where R=Pep24 (SEQ ID NO:54)-SS—CH$_2$CH$_2$NH-α-CO-aconityl-γ-CO—

Figure 27:
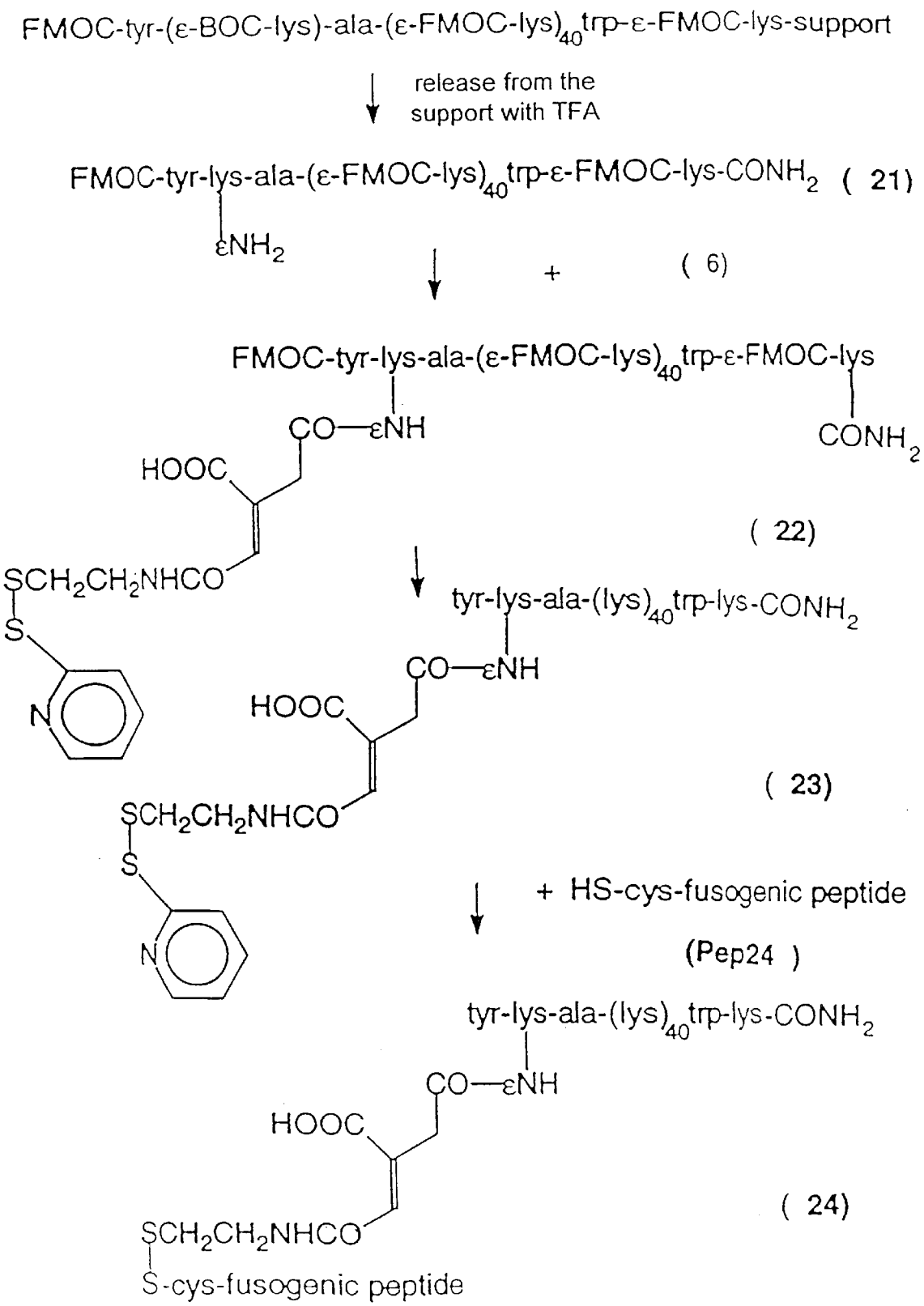
FIG. 27 is a schematic representation of a synthetic route for a monomeric fusogenic peptide.

The Series IV synthetic route (New compounds 21–24) is shown in FIG. 27. Detailed experimental procedures are as follows.

Solid phase peptide synthesis with conventional reagents and procedures gives 21. Dissolve 1 mmol of 21 in 2 ml dry DMF, add 3 ml of 6 and stir under N$_2$ overnight at 4°. Remove the solvents in vacuo, solubilize the residue in acetonitrile and apply to an anion exchange resin equilibrated in degassed 0.05 M NH$_4$CO$_3$ containing 20% acetonitrile and eluted with a gradient of 0 to 1.0 M acetonitrile in 0.1 M NH$_4$CO$_3$. The appropriate fractions are pooled and lyophilized to obtain the product 22.

Dissolve 1 mmol of 22 in 10 ml 50% piperidine in DMF (v/v). Remove the solvents in vacuo, solubilize the residue in 0.1 M NH$_4$OH, and apply to an anion exchange resin equilibrated in degassed 0.05 M NH$_4$CO$_3$ and elute with a gradient to 1 M NH$_4$CO$_3$. The appropriate fractions are pooled and lyophilized to obtain the product 23.

To a stirred solution of 0.5 mmol of lytic peptide Pep24 (SEQ ID NO:54) in 5 ml PBS, pH 7.4, at 4°, add 0.1 mmol of 23 in PBS dropwise. After 18 hrs, chromatograph over a molecular sizing column to separate the product 24 from unreacted starting materials.

C5. Trimeric fusogenic peptide covalently linked to a polycation through an acid sensitive, reducible spacer.

(27)

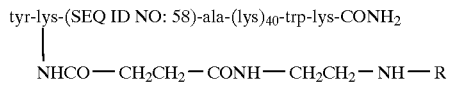

where R=-α-CO-aconityl-γ-COHNC—(OCH$_2$CH$_2$NHCO(CH$_2$)$_5$NH—R')$_3$ and R'=Pep24 (SEQ ID NO:54)-SS—CH$_2$CH$_2$CO—

Figure 28A:
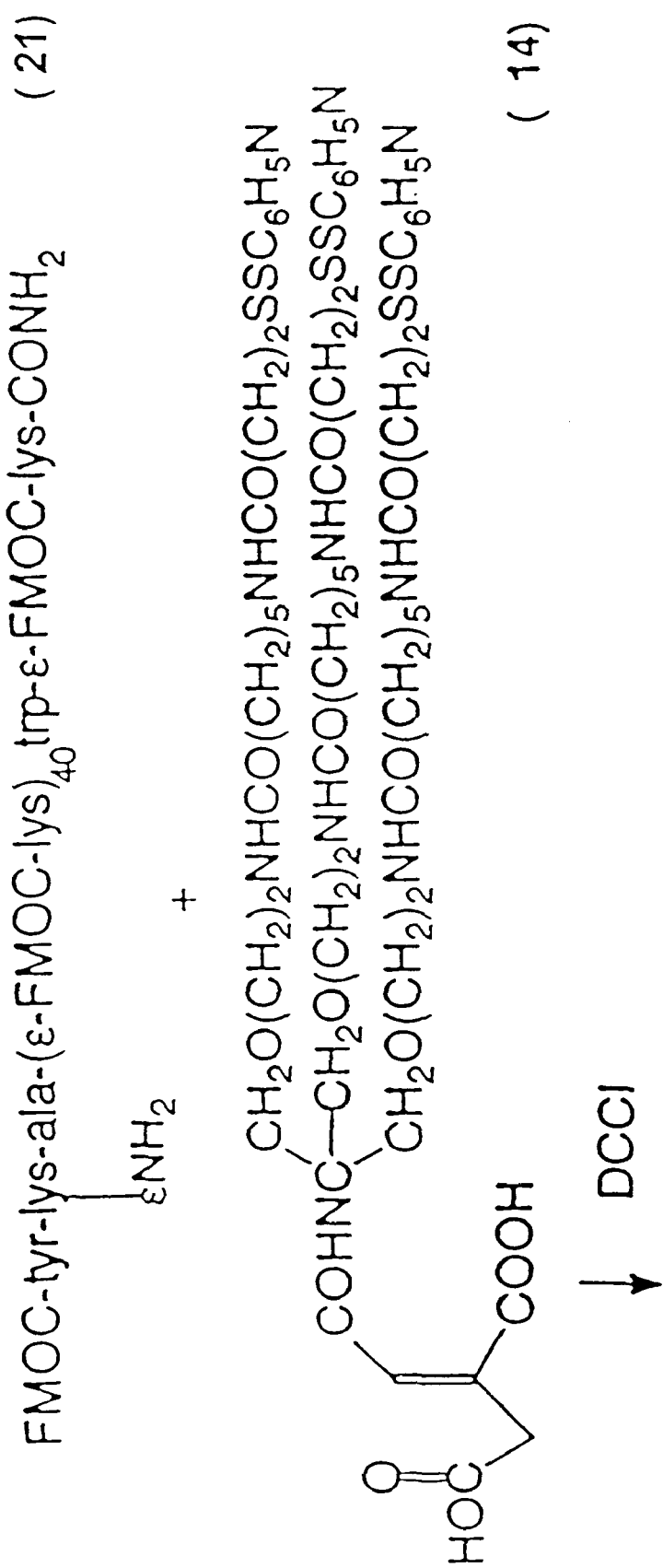
Figure 28C:
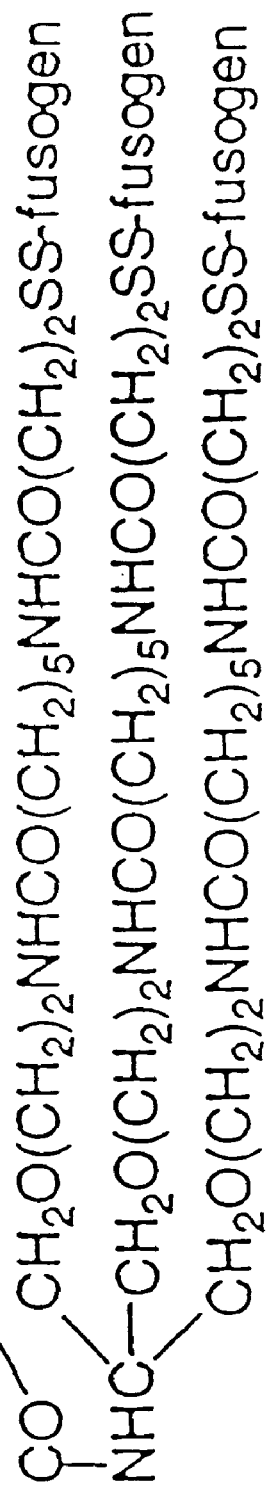

The Series V synthetic route (New compounds 25–27) is shown in FIG. 28. Detailed experimental procedures are as follows.

Dissolve 1 mmol of 14 in 2 ml dry DMF, add 1.1 mmol N-hydroxysuccinimide and 1.1 mmol dicyclohexylcarbodiimide and continue stirring for another 6 hr at 4°. One mmol of 21 in 0.5 ml dry dimethylformamide, is added dropwise to the preceding reaction mixture and stirring continued under N$_2$ overnight at 4°. Remove the solvents in vacuo, solubilize the residue in acetonitrile and apply to an anion exchange resin equilibrated in degassed 0.05 M NH$_4$CO$_3$ containing 20% acetonitrile and eluted with a gradient of 0 to 1.0 M acetonitrile in 0.1 M NH$_4$CO$_3$. The appropriate fractions are pooled and lyophilized to obtain the product 25.

Dissolve 1 mmol of 25 in 10 ml 50% piperidine in DMF (v/v). Remove the solvents in vacuo, solubilize the residue in 0.1 M NH$_4$OH, and apply to an anion exchange resin equilibrated in degassed 0.05 M NH$_4$CO$_3$ and elute with a gradient to 1 M NH$_4$CO$_3$. The appropriate fractions are pooled and lyophilized to obtain the product 26.

To a stirred solution of 0.5 mmol of lytic peptide Pep24 (SEQ ID NO:54) in 5 ml PBS, pH 7.4, at 4°, add 0.1 mmol of 23 in PBS dropwise. After 18 hr, chromatograph over a molecular sizing column to separate the product 27 from unreacted starting materials.

C6. Trimeric fusogenic peptide covalently linked to a polycation through an acid sensitive, reducible spacer.

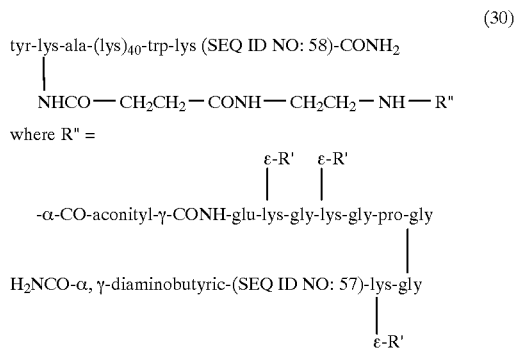

(30)

with the γ-carboxyl of glu¹ in amide linkage with the γ-amino of α,γ-diaminobutyric acid¹⁰ and R'=Pep24 (SEQ ID NO:54)-SS—CH₂CH₂CO—

Figure 29A:
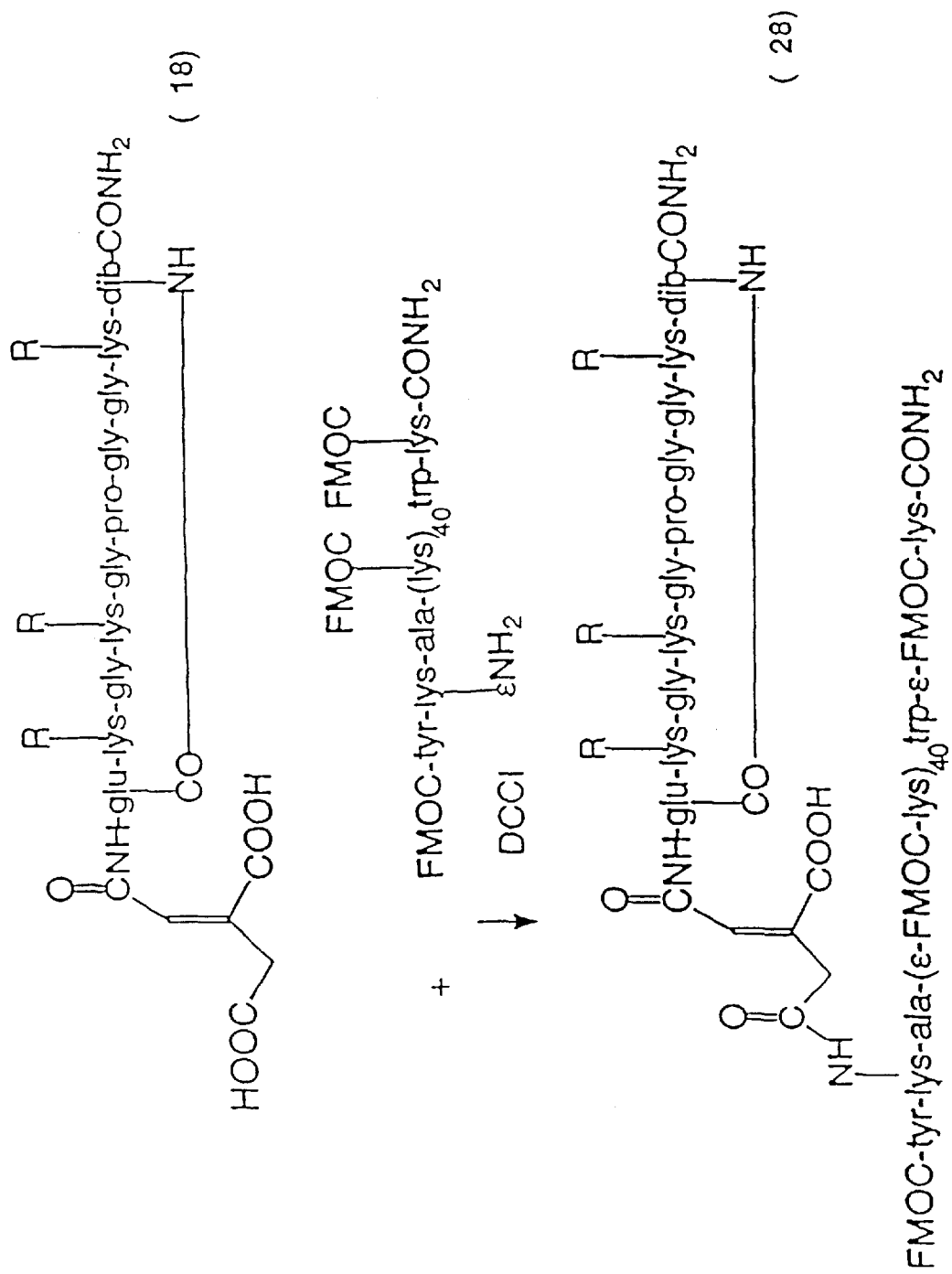
FIGS. 29A (SEQ ID NOS:57 and 58), 29B (SEQ ID NOS:54, 57 and 58), and 29C (SEQ ID NO:57 and 58) is a schematic representation of a synthetic route for a trimeric fusogenic peptide.
Figure 29B:
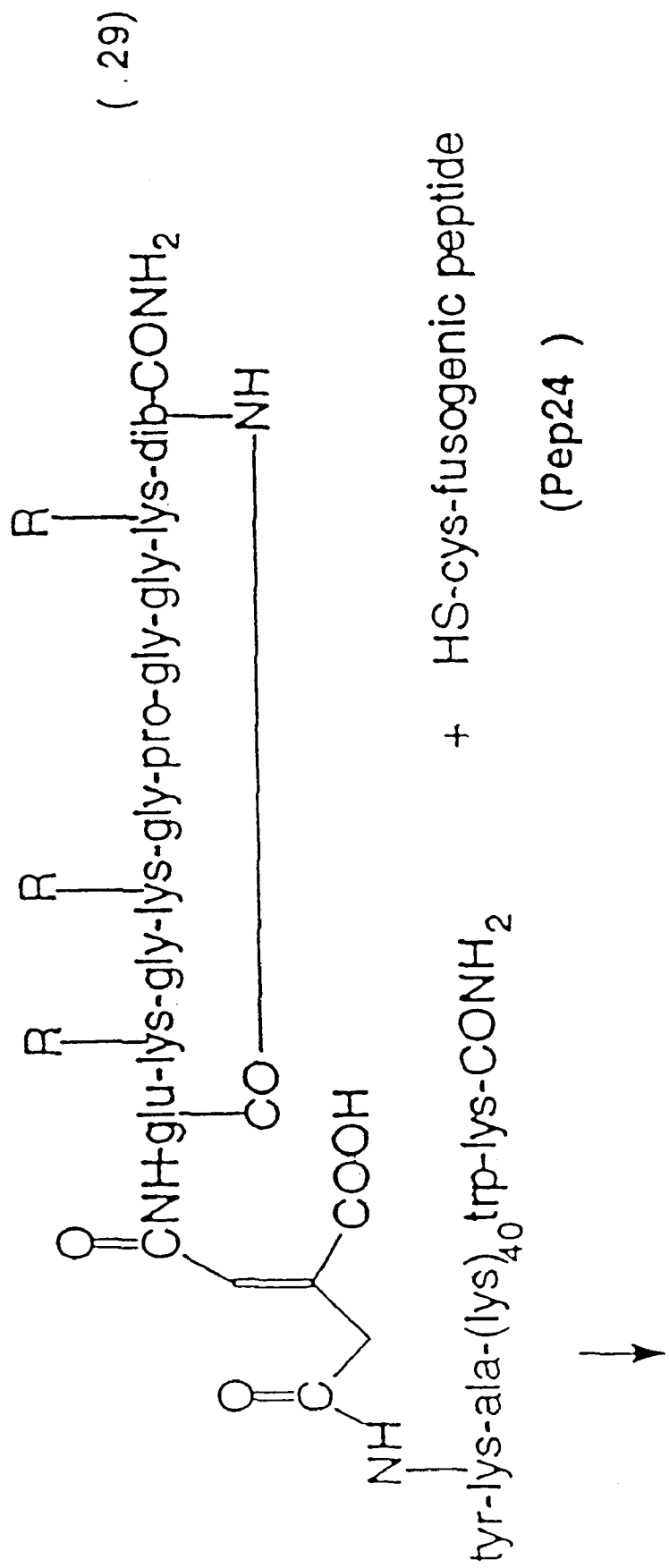
Figure 29C:
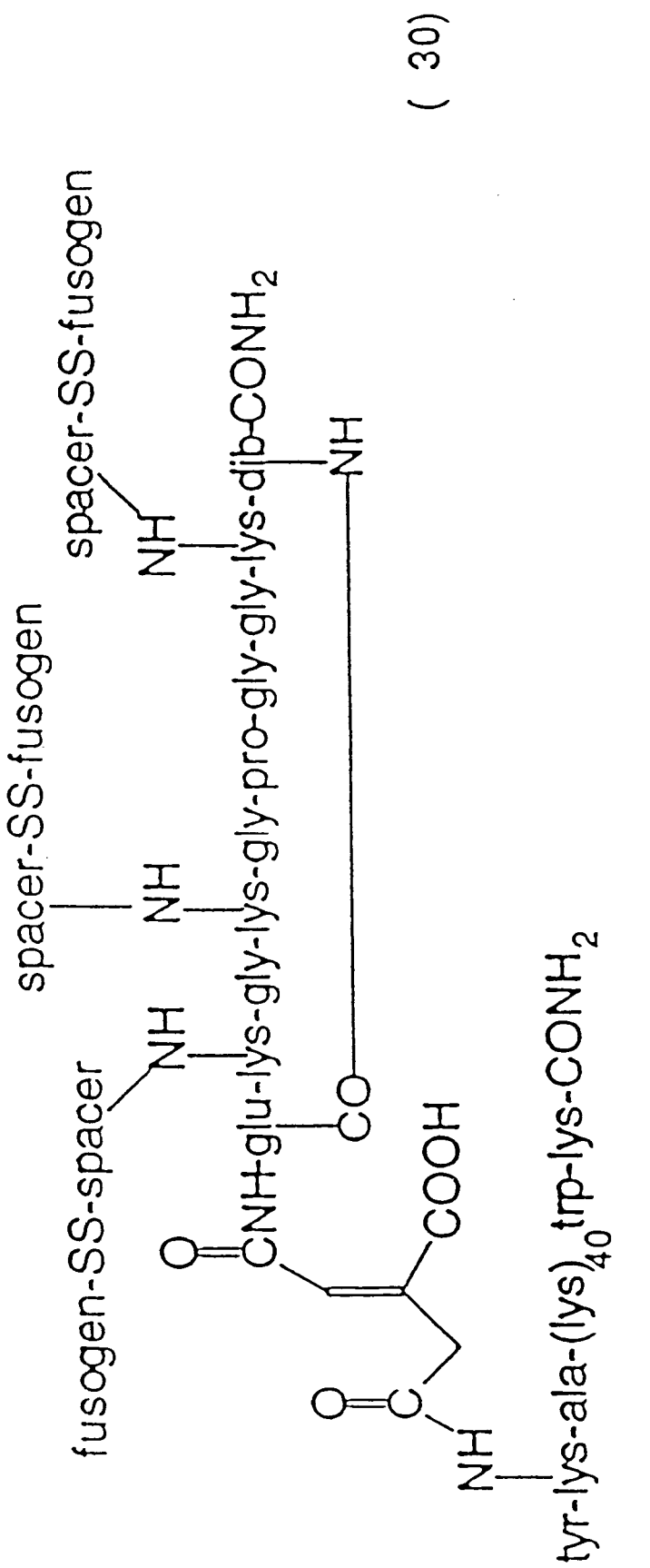

The Series VI synthetic route (New compounds 28–30)is shown in FIG. 29. Detailed experimental procedures are as follows.

Dissolve 1 mmol of 18 in 2 ml dry DMF, add 1.1 mmol N-hydroxysuccinimide and 1.1 mmol dicyclohexylcarbodiimide and continue stirring for another 6 hr at 4°. One mmol of 21 in 0.5 ml dry dimethylformamide, is added dropwise to the preceding reaction mixture and stirring continued under N₂ overnight at 4°. Remove the solvents in vacuo, solubilize the residue in acetonitrile and apply to an anion exchange resin equilibrated in degassed 0.05 M NH₄CO₃ containing 20% acetonitrile and eluted with a gradient of 0 to 1.0 M acetonitrile in 0.1 M NH₄CO₃. The appropriate fractions are pooled and lyophilized to obtain the product 28.

Dissolve 1 mmol of 28 in 10 ml 50% piperidine in DMF (v/v). Remove the solvents in vacuo, solubilize the residue in 0.1 M NH₄OH, and apply to an anion exchange resin equilibrated in degassed 0.05 M NH₄CO₃ and elute with a gradient to 1 M NH₄CO₃. The appropriate fractions are pooled and lyophilized to obtain the product 29.

To a stirred solution of 0.5 mmol of lytic peptide Pep24 (SEQ ID NO:54) in 5 ml PBS, pH 7.4, at 4°, add 0.1 mmol of 29 in PBS dropwise. After 18 hr, chromatograph over a molecular sizing column to separate the product 30 from unreacted starting materials.

D. Peptides such as Pep7 (SEQ ID NO:37) through Pep10 (SEQ ID NO:40) are nuclear localization sequences which are used to target the inserted nucleic acid to the nucleus. One skilled in the art recognizes that the peptides shown in FIG. 18 are only examples of this class of peptides and that there are a wide variety of other nuclear localization sequence peptides which can be used.

H₂N-Tyr-ε-N-lys-Pep11 (SEQ ID NO:61)—CONH, and γ-N-[N-2-methoxy-6-chloroacridinyl-HN-tyr-ε-N-lys-Pep11 (SEQ ID NO:61)-CO]-2-N-(2-methoxy-6-chloroacridinyl) diamino-butanoyl-CONH₂ were prepared by standard solid phase peptide synthesis. One skilled in the art recognizes that any amino acid polymer such as H₂N-(lys)$_n$ (SEQ ID NO:62)-COOH, H₂N-(arg-ala)$_n$ (SEQ ID NO:63)-COOH, histones and other DNA binding cationic polypeptides and proteins which form an α-helix, can be substituted for the lys-ala template. The —NH-(lys-ala)$_n$ (SEQ ID NO:64)-CO unit can be extended. The useful range is from 2 to greater than 100 depending on the sequence of the inserted DNA, the target, uptake and specificity. The sequence position of the ε-N-substituted-lys residue can be either amino-terminal or carboxyl-terminal. The substitution can be any amino reactive DNA binding dye as well as the acridine moiety. Examples of DNA binding dyes include thiaxanthenones, lucanthone, hycanthone, phenanthrenemethanol, metallointercalation reagents, tilorone, napthiophene, phenanthridiniums, dimidium, ethidium, propidium or quinacrine.

In further embodiments, the spacers can be attached to the α-amino group of the N-terminal amino acid, and/or the carboxyl group of the C-terminal amino acid, rather than the ε-amino group of lysine, to reduce immunological response to the ligand.

Figure 4:
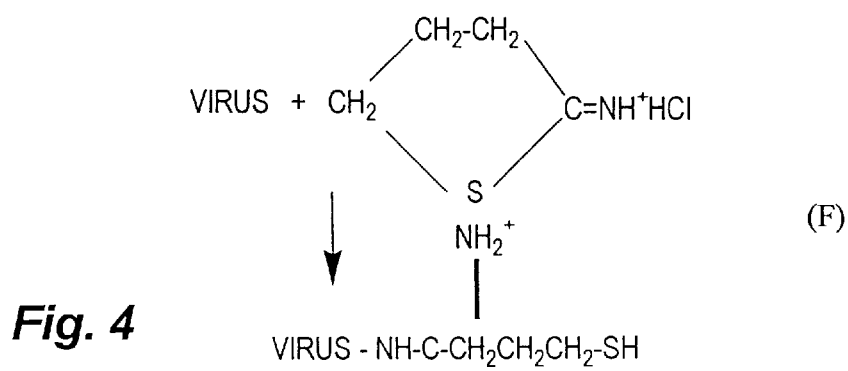
FIG. 4 shows a schematic synthesis of the virus ligand.

E. In addition to the above components, it has also been found that fusion competent virus can be used to target the inserted nucleic acid. FIG. 4 shows the schematic procedure for preparing a fusion competent virus for use in the present invention. A variety of fusion competent virus can be used. As an example, adenovirus can be prepared in two separate ways. To a stirred solution of 10 mg of fusion competent adenovirus in 5 ml PBS, pH 7.4, at 4°, add 0.3 ml of 20 mM succinimidyl 3(2-pyridyldithio)propionate in ethanol dropwise. After 60 min, dialyze against 3 changes of 0.5 L PBS, pH 7.4, at 4°, each for 2 hr. Alternatively, to a stirred solution of 10 mg of fusion competent adenovirus in 5 ml PBS, pH 7.4, at 4°, add 0.3 ml of 20 mM 2-iminothiolane HCl in ethanol dropwise. After 60 min, dialyze against 3 changes of 0.5 L PBS, pH 7.4, at 4°, each for 2 hr.

F. Recombinant Peptides 12 (SEQ ID NO:42), 13 (SEQ ID NO:43), and 16 (SEQ ID NO:46), 10 mg, prepared and purified by methods known in the art are dissolved in 10 ml 50 mM NH₄OH, pH 8.5. Aliquots are removed at 2 hr intervals to determine the extent of cyclization of N-terminal glutamine to pyroglutamate. When this reaction is complete, the solution is lypholyzed and then dissolved in 5 ml PBS, pH 7.4. Peptides 12 (SEQ ID NO:42), 13 (SEQ ID NO:43), 16 (SEQ ID NO:46), and 17 (SEQ ID NO:47) are further reacted with either succinimyl 3(2-pyridyldithio) propionate or 2-iminothiolane as described for adenovirus above.

G. Further, it has been found that either monoclonal or polyclonal IgG can be used to target the inserted nucleic acid. Generally, the IgG is cleaved with immobilized pepsin to yield (Fab__-S—)₂ which is selectively reduced to Fab__-SH. Specifically, this includes: adding dropwise 0.5 ml 0.1 mM dithiothreitol to a stirred 5 ml solution of 1 nmol IgG F(ab')₂ at 4°, which was prepared by standard methods with immobilized pepsin. After 60 min, dialyze against 3 changes of 0.5 L PBS, pH 7.4, at 4°, each for 2 hr.

H. Synthesis of component D. Standard continuous-flow solid phase synthetic methodologies are used to prepare H₂N-his-leu-arg-arg-leu-arg-arg-arg-leu-leu-arg-glu-ala-glu-glu-gly-CONH₂ (SEQ ID NO:18), which is released as a protected peptide, containing N$^{im}$-Fmoc-his, N⁹-4-methoxy-2,3,6-trimethylphenylsulfonyl-arg, and glu-γ-Fmoc ester. Coupling of this protected peptide using DCCI with the appropriate protected peptide on the solid support, gives

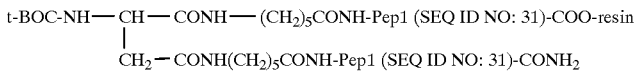

Deprotection of the asp-amino group, reaction with succinimidyl 3(2-pyridyldithio)propionate, deblocking and cleavage from the resin gives D.

I. Synthesis of the asialoglycoprotein receptor ligand, component E. Dissolve 1 mmol $N^\alpha$, $N^\beta$-bis{hexanamido [tris-(β-lactosylhydroxymethyl)methane]}aspartyl diamide, in 20 ml PBS, pH 7.4, and combine with 1 mmol succinimyl 3(2-pyridyldithio) propionate, in 2 ml phosphate-buffered saline, pH 7.4. Dilute the reaction mixture 20-fold with water, apply to a cation exchange column to separate the desired product from unreacted starting material and other products, using a linear gradient formed from equal volumes of water and 2.0 M HCl. The appropriate fractions are pooled and lyophilized to obtain the product E.

J. Preparation of Compound I. L-tyrosyl-L-aspartoyl-bis-{N-[6-[[6-O-phosphoryl-α-D-mannopyranosyl]oxy]hexyl]-L-alaninamide] is prepared as described in the art, except that N-t-BOC-L-tyrosine is used in lieu of N-acetyl-L-tyrosine.

Compound I is further reacted as described for compound E discussed above.

Synthesis of Tetracationic Nucleic Acid Binding Templates

Figure 5:
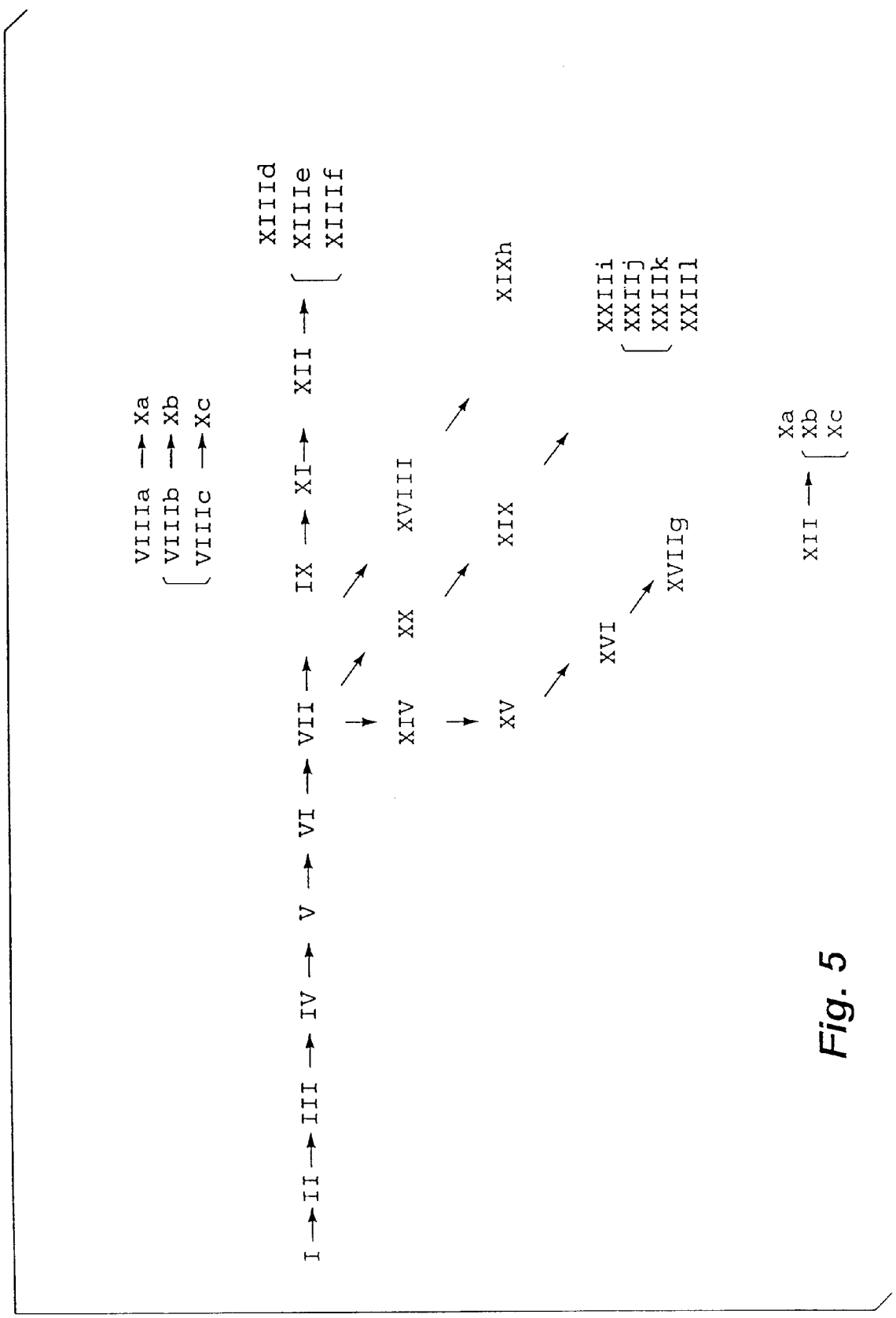

The overall schematic flow chart for the synthesis of these compounds is shown in FIG. 5. The chemical pathway of synthesis is shown below. The Roman numerals are used to identify the specific compounds.

Dissolve 2 mmol of free base 1,4-diaminobutan-2-ol (II) in 5 ml of ethanol, add 4.1 mmol of acrylonitrile and allow to stand overnight at room temperature. Cool in an ice bath and saturate the solution with anhydrous NH3 at 0°. Add about 5 ml of sponge nickel hydrogenation catalyst and shake under $H_2$ on a Paar low-pressure hydrogenator until the theoretical amount of $H_2$ is consumed. Remove the catalyst by filtration and wash the catalyst with ethanol. Combine filtrate and washings, then remove the ethanol in vacuo. Chromatograph on a cation exchange column to separate the desired products R, S and IV from unreacted starting material and other products, using a linear gradient formed from equal volumes of water and 2.0 M HCl. Resolve the enantiomers of IV on a chiral column such as (R)-N-3,5-dinitrobenzoylleucine-silica (Baker) by a gradient of 2-propanol, from 0 to 20% in hexane.

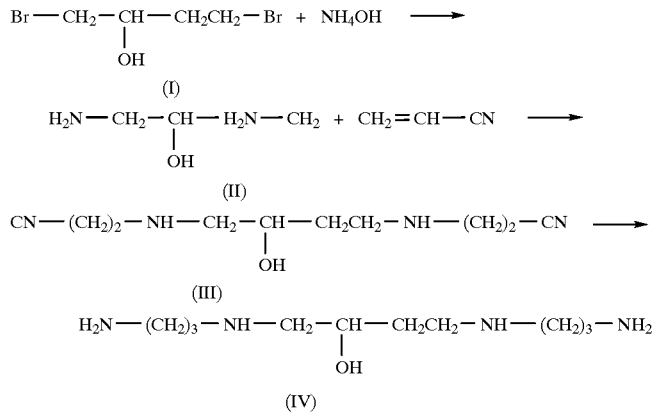

Next combine 2 mmol (S)-hydroxyspermine (IV), 8 mmol 4-pyrrolidinopyridine and 8.2 mmol benzyloxycarbonyl anhydride ($Z_2O$) in 40 ml anhydrous benzene and stir overnight at room temperature under $N_2$. Separate the desired product V by solid phase extraction on phenyl-silica and elution with a linear gradient of ethyl acetate from 0 to 50% in hexane. Pool the appropriate fractions and evaporate the solvent to obtain the product as an amorphous solid.

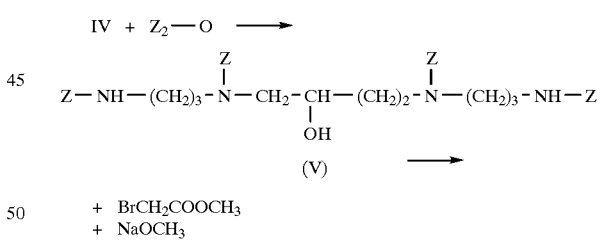

+ $BrCH_2COOCH_3$
+ $NaOCH_3$

Add 4 ml of dry benzene to 1 mmol $K_2CO_3$ and 2 mmol 18-crown-6 and stir for 20 min. Add 2 mmol V in 4 ml of dry benzene, followed by 2 mmol methyl bromoacetate in 2 ml benzene. After 4 hr, add 25 ml of water and extract with 3 portions of 25 ml benzene. Remove the solvent in vacuo and dissolve the residue IV in 10 ml ethanol containing 2 mmol potassium hydroxide. After overnight at room temperature, the solution is transferred to a separatory funnel, to which 2 mmol of HCl, 5 ml of water and 25 ml of benzene are added. After extraction with 3 additional portions of benzene, the combined organic phase is taken to dryness in vacuo, redissolved in a minimum volume of ethyl acetate, dried over 10% w/v anhydrous $Na_2SO_4$ overnight. The organic phase is decanted and diluted with a sufficient amount of petroleum ether to create slight turbidity and cooled at 4° to promote crystallization of VII (1,4,9,12-tetrabenzyloxycarbonyl-1,12-diamino-6-carboxymethoxy-4,9-diazadodecane).

odor of acetic acid is gone. Dissolve the solid in oxygen-free 0.1 M $NH_4OH$ and apply to an anion exchange resin equilibrated in degassed 0.1 M $NH_4CO_3$ containing 20%

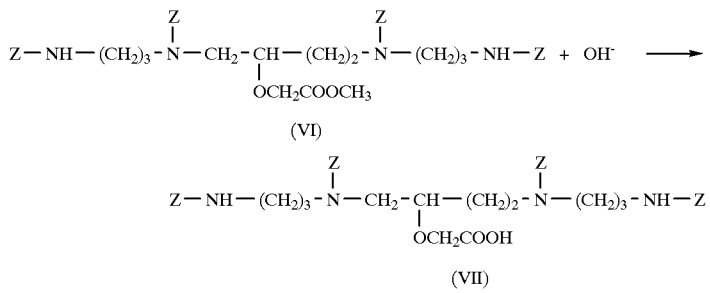

Dissolve 1 mmol of VII in 2 ml dry dimethylformamide, add 3.0 mmol 1-ethyl-3-[3-(dimethylamino)propyl)] carbodiimide, stir 2 hr, then add 1.1 mmol N-hydroxysuccinimide and stir for an additional 6 hr at room temperature. This solution is added dropwise to 1 mmol of A in 0.5 ml dry dimethylformamide. Stirring is continued in the dark under $N_2$ for an additional 4 hr. When the reaction is complete, as monitored by thin layer chromatography, 15 ml oxygen-free water is added to precipitate the product. The product is collected by centrifugation, washed and dissolved in oxygen-free 0.1 M $NH_4OH$. The solution is applied to an anion exchange resin equilibrated in degassed 0.1 M acetonitrile. The product Xa or Xb or Xc or XI is separated from unreacted starting materials by a gradient of 0 to 90% acetonitrile in 0.1 M $NH_4CO_3$. The appropriate fractions are pooled and lyophilized to obtain the product.

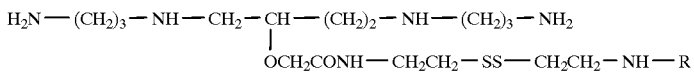

$NH_4CO_3$ containing 20% acetonitrile. The γ-isomer is separated from unreacted starting materials and the α-isomer by a gradient from 20% to 50% acetonitrile in 0.1 M $NH_4CO_3$. The appropriate fractions are pooled and lyophilized to obtain the product. Alternative compounds in this series, for example VIIIb and VIIIc, are made by substituting the appropriate starting material containing biotin, lipoic acid or other substituent.

Where R is A (Xa), B (Xb, G (Xc) or H (XI).

Dissolve 2 mmol XI purified by chromatography as was done for IV, in 10 ml oxygen-free 0.01 M $NH_4CO_3$ containing 2 mmol dithiothreitol and stir for 2 hr. Bring the solution to pH 5 with 1N HCl and apply the solution to a cation exchange resin equilibrated in degassed water. The

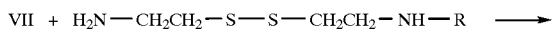

Where R is A, B, G, H, P, J, Pep$_{12}$
(SEQ ID NO: 32)-Pep$_{26}$ (SEQ ID NO: 36)

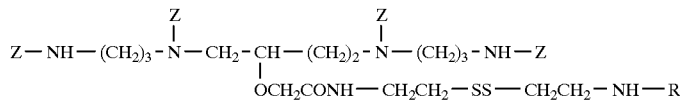

Where R is A (VIIIa), B (VIIIb), G (VIIIc) or H (IX).

Dissolve 1 mmol VIIIa or VIIIb or VIIIc or IX in 20 ml glacial acetic acid containing 30% HBr and stir overnight at room temperature in the dark under $N_2$. Add 30 ml diethyl ether to precipitate the product. Wash the product until the product XII is isolated by a gradient from 0.0005 M to 2.0 M HCl. The appropriate fractions are pooled and lyophilized to obtain the product. This is followed by reactions described above to yield XIIId, XIIIe and XIIIf.

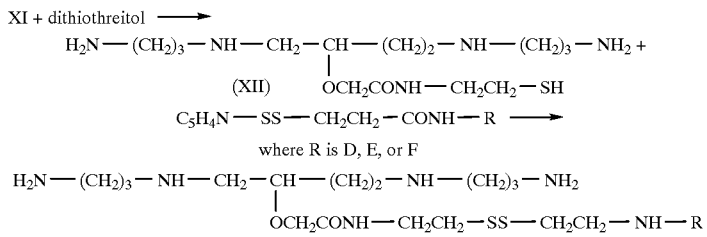

Where R is D (XIIId), E (XIIIe) or F (XIIIf).

Dissolve 1 mmol XII in 2 ml phosphate-buffered saline, pH 7.4, and combine with 1 mmol of further reacted A, B or G (as described above) in 2 ml phosphate-buffered saline, pH 7.4. Dilute the reaction mixture 20-fold with water, apply to an anion exchange resin equilibrated in degassed 0.1 M $NH_4CO_3$ containing 20% acetonitrile. The product XIa, XIb or XIc is separated from unreacted starting materials by chromatography in 0.1 M $NH_4CO_3$ containing 20% acetonitrile. The appropriate fractions are pooled and lyophilized to obtain the product.

in hexane. Pool the appropriate fractions and evaporate the solvent to obtain the product as an amorphous solid (XIV). Next combine 1 mmol XIV in dry 10 ml benzene with 1.1 mmol succinimidyl 3(2-pyridylthio)propionate, stir for 2 hr at room temperature, and then remove the solvent I in vacuo.

The resultant product is XV.

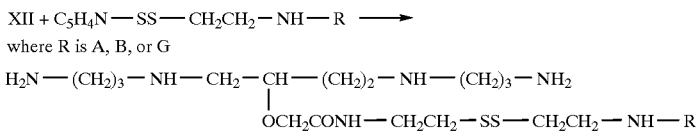

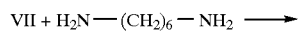

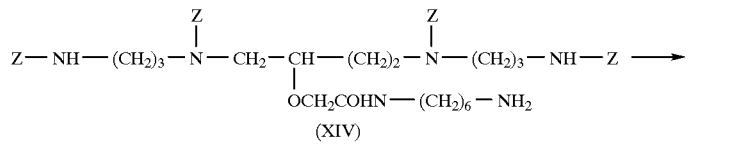

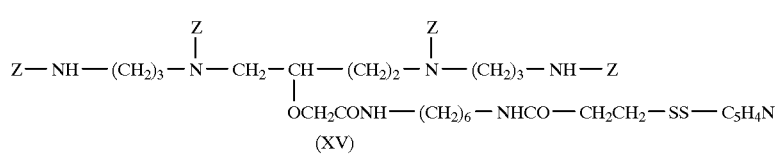

Where R is A (XIa), B (XIb) or G (XIc).

Dissolve 1 mmol of VII in 2 ml dry dimethylformamide, add 3 mmol 1-ethyl-3-[3-(dimethylamino)propyl) carbodiimide and stir 2 hr, then add 1.1 mmol N-hydroxysuccinimide and continue stirring for another 6 hr at room temperature. This solution is added dropwise to 5 mmol of 1,6-diaminohexane in 20 ml dry dimethylformamide, and stirring continued for an additional 24 hr. Remove the solvent in vacuo. Separate the desired product by solid phase extraction on phenyl-silica and elution with a linear gradient of ethyl acetate from 0 to 50%

Dissolve 1 mmol XV, in 20 ml glacial acetic acid containing 30% Hbr and stir overnight at room temperature in the dark under $N_2$. Add 30 ml diethyl ether to precipitate the product. Wash the product until the odor of acetic acid is gone. Dissolve the solid in oxygen-free 0.1 M $NH_4OH$. The solution is applied to an anion exchange resin equilibrated in degassed 0.1 M $NH_4CO_3$ containing 20% acetonitrile. The product is separated from unreacted starting materials by a gradient of 20 to 80% acetonitrile in 0.1 M $NH_4CO_3$. The appropriate fractions are pooled and lyophilized to obtain the product:

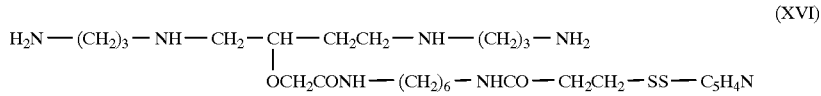

(XVI)

To a stirred solution of 10 mg of Fab__-SH in 5 ml PBS, pH 7.4, at 4°, add 0.3 ml of 10 mM XVI in ethanol dropwise. After 60 min. dialyze against 3 changes of 0.5 L PBS, pH 7.4, at 4°, each for 2 hrs.

elution with a linear gradient of ethyl acetate from 0 to 50% in hexane. Pool the appropriate fractions and evaporate the solvent to obtain the product XX as an amorphous solid.

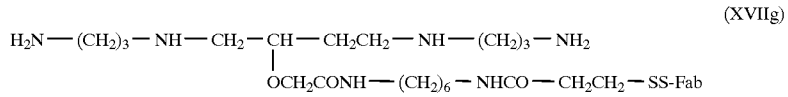

(XVIIg)

Combine 2 mmol IX, 2 mmol 4-pyrrolidinopyridine and 3 mmol succinic anhydride in 40 ml anhydrous benzene and stir overnight at room temperature under $N_2$. Separate the desired product by solid phase extraction on phenyl-silica and elution with a linear gradient of ethyl acetate to 50% in hexane. Pool the appropriate fractions and evaporate the solvent to obtain the product as an amorphous solid. This is followed with DCCI, in situ coupling with resin bound protected peptide, Pep2 (SEQ ID NO:32)-COOH, using standard solid phase synthetic techniques followed by deprotection and release from the resin to yield XIXh.

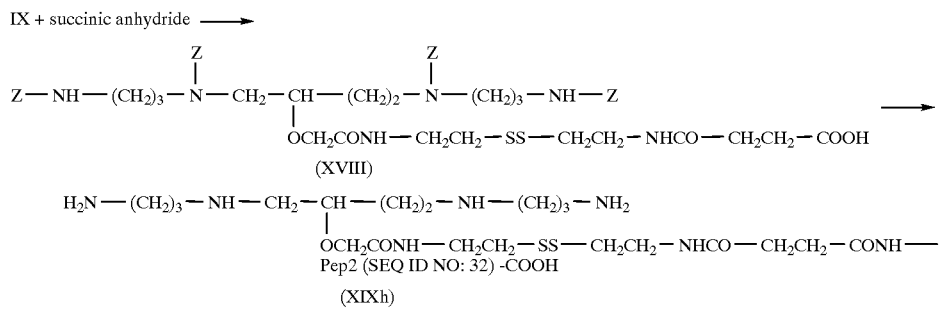

Dissolve 1 mmol of VII in 2 ml dry dimethylformamide, add 3.0 mmol 1-ethyl-3-[3-(dimethylamino)propyl) carbodiimide and stir 2 hr, then add 1.1 mmol

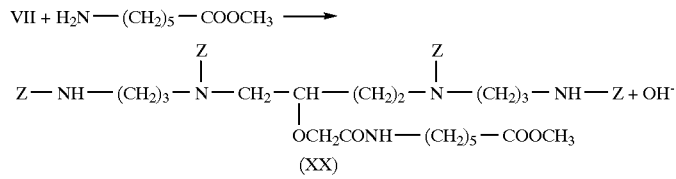

N-hydroxysuccinimide and continue stirring for another 6 hr at room temperature. This solution is added dropwise to 5 mmol of methyl 6-amonohexanoate in 20 ml dry dimethylformamide, and stirring continued for an additional 24 hr. Remove the solvent in vacuo. Separate the desired product by solid phase extraction on phenyl-silica and Dissolve 2 mmol XX in 10 ml ethanol containing 2 mmol potassium hydroxide. After overnight at room temperature, the solution is transferred to a separate funnel, to which 2 mmol of HCl, 5 ml of water and 25 ml of benzene is added. After extraction with 3 additional portions of benzene, the combined organic phase is taken to dryness in vacuo. Separate the desired product by solid phase extraction on phenyl-silica and elution with a linear gradient of ethyl acetate from 0 to 50% in hexane. Pool the appropriate fractions and evaporate the solvent to obtain the product XXI as an amorphous solid. Next, couple XXI to the amino terminal of the peptide on the support using standard solid phase peptide methods.

Where R is D (XXVId), E (XXVIe) or F (XXVIf).

After derivatization of the ε-N-succinyl-lys with $H_2N$—$CH_2CH_2$—S—S—$CH_2CH_2$—NH-t-BOC and deblocking, the ligand Pep2 (SEQ ID NO:32) is synthesized on the resin using standard solid phase techniques. Deblocking and cleavage from the resin yields XXVIIh.

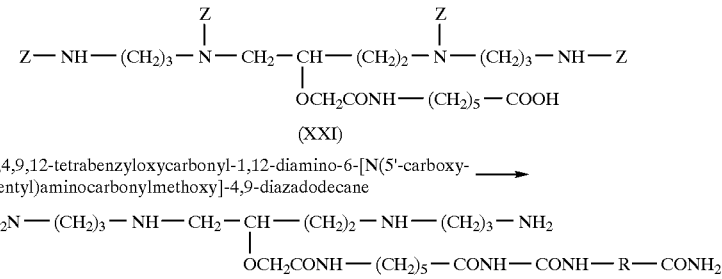

Where R is: Pep3 (SEQ ID NO:33) (XXIIi), Pep4 (SEQ ID NO:34) (XXIIj), Pep5 (SEQ ID NO:35) (XXIIk) or Pep6 (SEQ ID NO:36) (XXIII)

Further Tetracationic DNA Binding Templates

The overall schematic flow chart of the synthesis of these compounds is shown in FIG. 6. The chemical pathway of synthesis is shown below.

A. After derivatization of the ε-N-lys with succinic anhydride it is coupled to the ligands shown below:

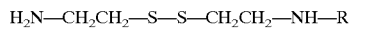

Where R is A, B, G or H.
Deprotection and release from the resin yields:

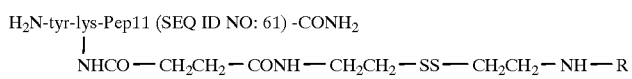

Where R is A (XXIIIa), B (XXIIIb), G (XXIIIc) or H (XXIV).

Following the procedures described for the synthesis of XII and XIII but substituting XXIV for XI yields XXV and XXVI.

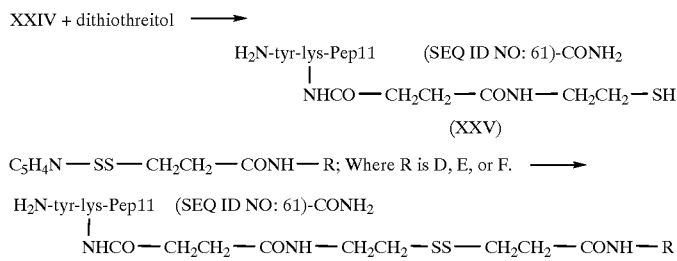

(XXVIIh)
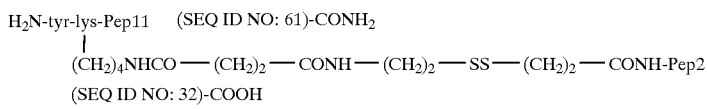

The resin bound lys-ε-NH—CO(CH$_2$)$_5$NH$_2$ intermediate was coupled with succinimidyl 3(2-pyridyldithio)propionate and then deprotected and cleaved to yield XXVIII.

(XXVIII)
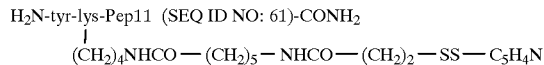

To a stirred solution of 10 mg of FAB__-SH in 5 ml PBS, pH 7.4, at 4°, add 0.3 ml of 10 mM XVI in PBS, pH 7.4, dropwise. After 60 min. dialyze against 3 changes of 0.5 L PBS, pH 7.4, at 4°, each for 2 hr.

(XXIXg)
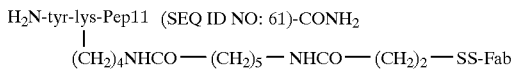

The nuclear localization sequence was added by standard solid phase synthetic methods to the lys-ε-NH—CO(CH$_2$)$_5$NH$_2$ intermediate of the resin bound protected peptide for carboxyl to amino orientation or to the N-succinyl derivative of ε-N-lys for amino to carboxyl orientation. Deprotection and release from the resin yields:

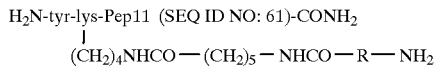

Where R is Pep7 (SEQ ID NO:37) (XXXi), Pep8 (SEQ ID NO:38) (XXXj), Pep9 (SEQ ID NO:39) (XXXk) or Pep10 (SEQ ID NO:40) (XXXl) or

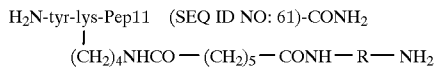

Where R is Pep3 (SEQ ID NO:33) (XXXIi), Pep4 (SEQ ID NO:34) (XXXIj), PepS (SEQ ID NO:35) (XXXIk) or Pep6 (SEQ ID NO:36) (XSSIl)

B. Parent compound, N-(ligand moiety)-HN-tyr-lys-lys-ala-lys-ala-lys-ala-lys-CONH$_2$ (SEQ ID NO:61) (SEQ ID NO:61), was prepared by standard solid phase peptide synthesis. An amino acid polymer, such as H$_2$N-(lys)n (SEQ ID NO:62)-COOH, H$_2$N-(arg-ala)$_n$ (SEQ ID NO:63)-COOH, histones, and other nucleic acid binding cationic polypeptides and proteins which form an α-helix, can be used for the lys-ala template. The —HN-(lys-ala)$_n$ (SEQ ID NO:64)-CO unit can be extended from 4 to more than 100. The sequence position of the residue bearing the spacer-ligand moiety can be either amino-terminal or carboxyl-terminal. In another embodiment, the ligand-spacer moiety is linked through a disulfide bond to cys as either the N-terminal or C-terminal residue.

The resin bound protected peptide containing a deblocked α-amino-tyr moiety is the synthetic intermediate for preparation of templates for reductive release of a plasma membrane receptor ligand. After derivatization of the α-amino-tyr with succinic anhydride, the following ligands are coupled to the resin bound protected peptide.

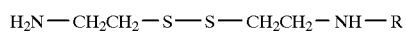

where

| | |
|---|---|
| R = γ-amide of the glutamyl moiety of folic acid | (A) |
| = biotin | (B) |
| = lipoic acid | (C) |
| = H | |

Deprotection and release from the resin gives:

tyr-lys-lys-ala-lys-ala-lys-ala-lys-CONH$_2$   (SEQ ID NO: 61)
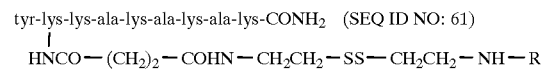

where

| | |
|---|---|
| R = γ-amide of the glutamyl moiety of folic acid | XXIIIa |
| = biotin | XXIIIb |
| = lipoic acid | XXIIIc |
| = H | |

Synthesis of Hexacationic DNA Binding Template

A schematic flow chart of the synthesis of these compounds is shown in FIG. 7. The chemical pathway of synthesis is shown below.

Dissolve 2 mmol of succinic monoamide in 2 ml dry DMF, add 4.0 mmol 1-ethyl-3-[3-(dimethylamino)propyl) carbodiimide and stir 2 hr. Then add 2.1 mmol N-hydroxysuccinimide and continue stirring for another 6 hr at room temperature. Combine this in dropwise fashion to 1 mmol (S)-hydroxyspermine (IV) in 2 ml dry DMF. After stirring overnight at room temperature, remove the solvent in vacuo, dissolve in water, and apply the solution to a cation exchange resin. The product is isolated by a gradient to 2.0 M HCl. The appropriate fractions are pooled and lyophilized to obtain XXXII.

Dissolve 2 mmol XXXII in 5 ml dry toluene and add 10 mmol sodium bis(2-methoxyethoxy)aluminum hydride in toluene in small aliquots over 30 min. After 2 hr, add 10 ml ethyl acetate, then remove the solvents in vacuo. Dissolve the solids in water, adjust the pH to 3 with HCl and apply to a cation exchange resin. The product is isolated by a gradient to 2.0 M HCl. The appropriate fractions are pooled and lyophilized to obtain the product.

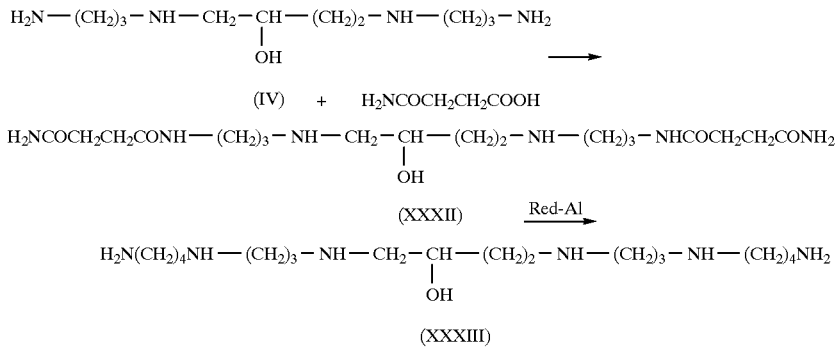

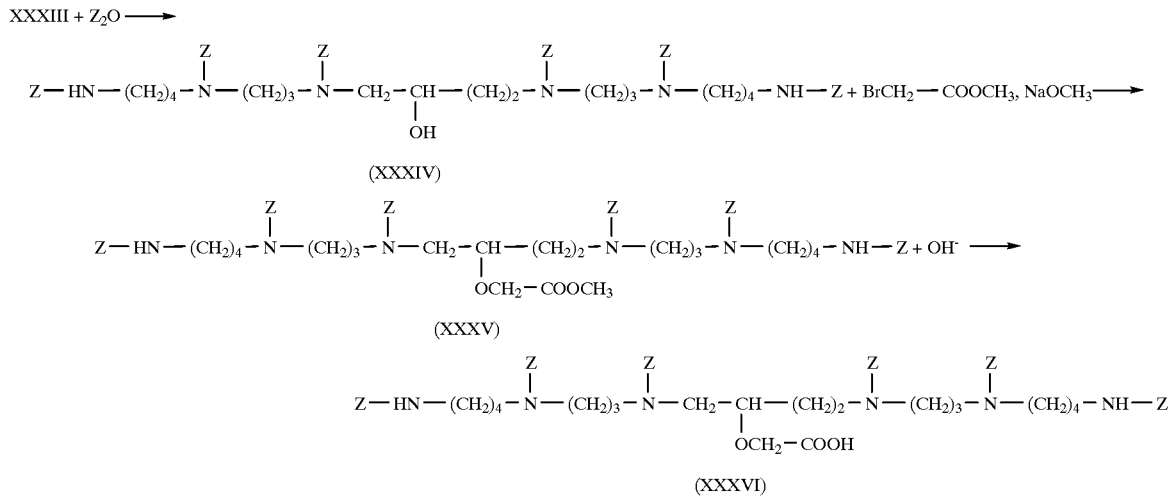

It is obvious to one skilled in the art that homologs with additional —$(CH_2)_4$—$NH_2$, or —$(CH_2)_3$—$NH_2$ units can be made by repeating the reactions using XXXIII in lieu of IV with $H_2NCOCH_2CH_2COOH$ or $CH_2$=CHCN.

In reactions similar to the above reaction where IV is converted to VII, XXXIII can be converted to XXVI.

1,5,9,14,18,22-hexabenzyloxycarbonyl-1,22-diamino-11-carboxymethyl-5,9,14,18-tetraazadocosane In reactions similar to the above reactions where VII is converted to the VII and XI series, XXXVI can be converted to the XXXVII and XXXIX series.

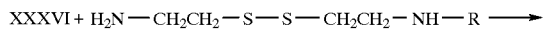

Where R is A, B, G or H.

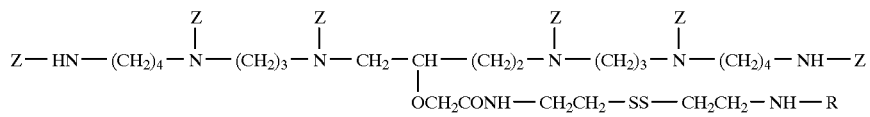

Where R is A (XXXVIIa), B (XXXVIIb), G (XXXVIIc) or H (XXXVIII).

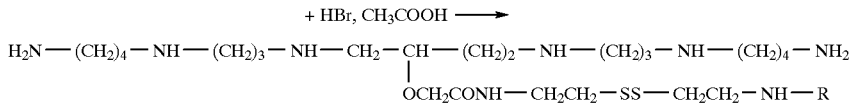

Where R is A (XXXIXa), B (XXXIXb), G (XXXIXc) or H (XL).

In reactions similar to the above for the conversion of XI to the XIII series XL is converted to the XLII series.

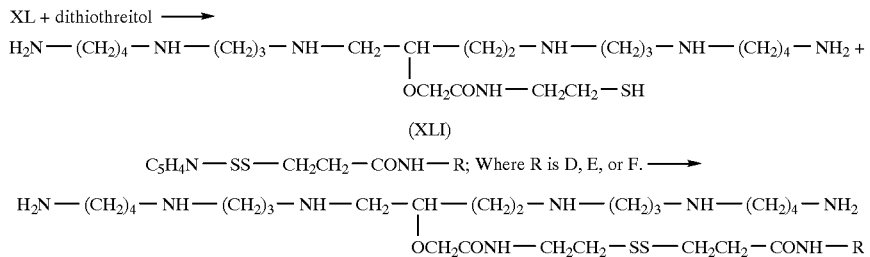

Where R is D (XLIId), E (XLIIe) or F (XLIIf)

In reactions similar to the above conversion of XII to the XI series, XLI is converted to the XXXIX series.

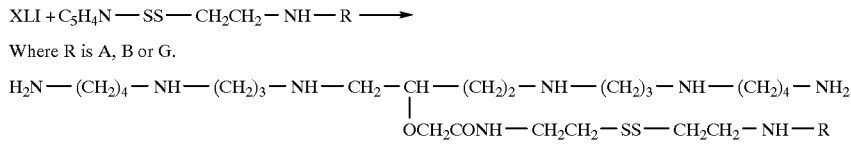

Where R is A (XXXIXa), B (XXXIXb) or G (XXXIXc).

In reactions similar to the above conversion of VII to XIV and XVIIg, XXXVI is converted to XLIV and XLVIg.

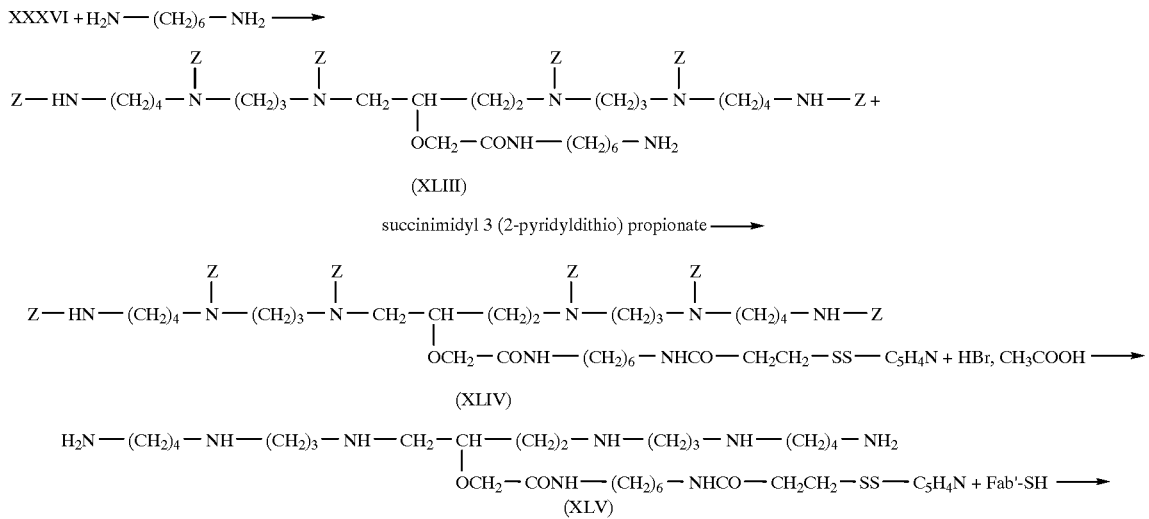

-continued

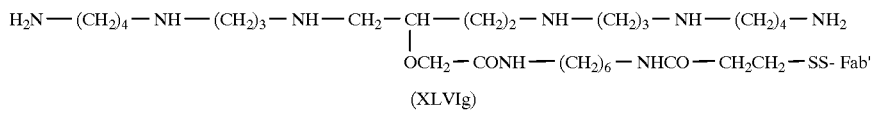

(XLVIg)

In reactions similar to the above conversion of IX to XIXh, XXXVIII is converted to XLVIIIh.

Combine 2 mmol III (resolved S enantiomer), 4 mmol 4-pyrrolidinopyridine and 4.1 mmol benzyloxycarbonyl XXXVIII + succinic anhydride ⟶

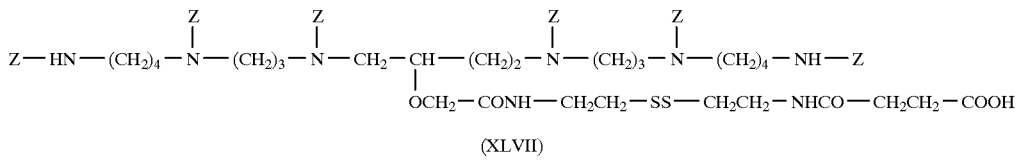

In reactions similar to the above conversion of VII to XXII series, XXXVI is converted to the LI series.

anhydride in 40 ml anhydrous benzene and stir overnight at room temperature under $N_2$. Separate the desired product by

XXXVI + $H_2N$—$(CH_2)_5$—$COOCH_3$ ⟶

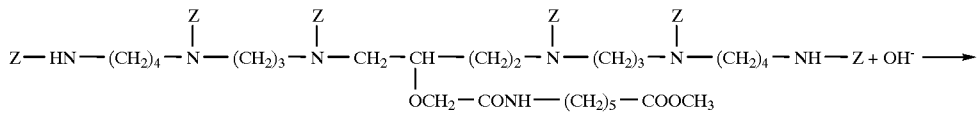

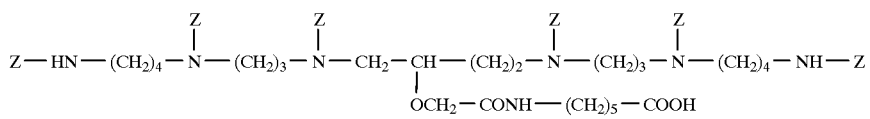

1,5,9,14,18,22-hexabenzyloxycarbonyl-1,22-diamino-11-[N(5'-carboxypentyl)carbonylmethyoxy-5,9,14,18-tetraazadocosane

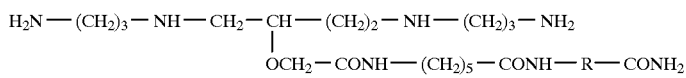

Where R is: Pep3 (SEQ ID NO:33) (LIi), Pep4 (SEQ ID NO:34) (LIj), Pep5 (SEQ ID NO:35) (LIk) or Pep6 (SEQ ID NO:36) (LIl)

Intercalating Hexacationic DNA Binding Templates

Figure 8:
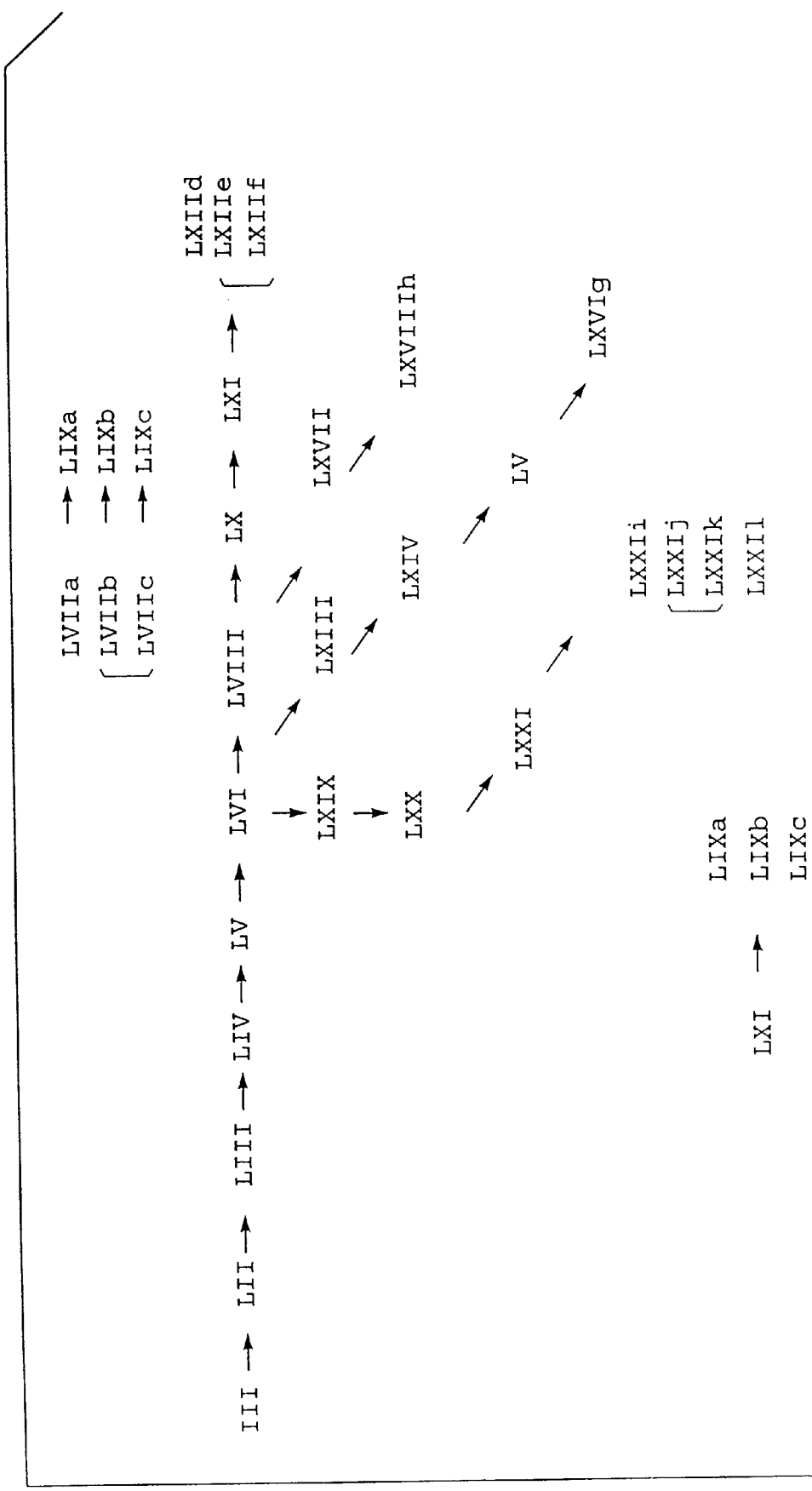

A schematic flow chart for the synthesis of these compounds is shown in FIG. 8. The chemical pathway of synthesis is shown below.

solid phase extraction on phenyl-silica and elution with a linear gradient of ethyl acetate to 50% in hexane. Pool the appropriate fractions and evaporate the solvent to obtain the product LII as an amorphous solid.

III (resolved S enantiomer) + t-BOC₂O ⟶

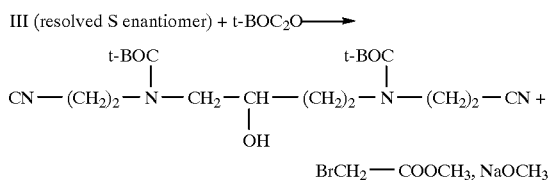

BrCH₂—COOCH₃, NaOCH₃

Add 4 ml of dry benzene to 1 mmol K₂CO₃ and 2 mmol 18-crown-6 and stir for 20 min. Add 2 mmol LIII in 4 ml of dry benzene, followed by 2 mmol methyl bromoacetate in 2 ml benzene. After 4 hr, add 25 ml of water and extract with 3 portions of 25 ml benzene. Remove the solvent in vacuo to obtain the product:

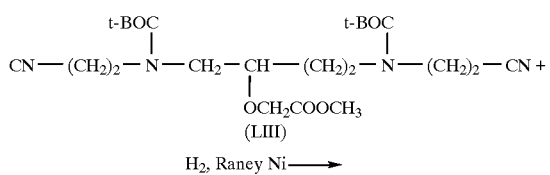

(LIII)

H₂, Raney Ni ⟶

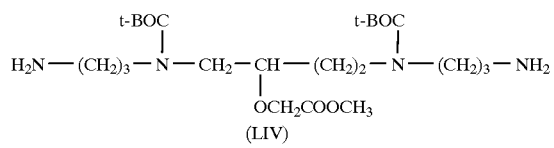

(LIV)

Dissolve 5 mmol LIV in 10 ml dry pyridine containing 0.1 mmol dimethylaminopyridine and 15 mmol triethylamine. Add dropwise 11 mmol 6,9-dichloro-2-methoxyacridine on any DNA binding dye that reacts specifically with amino group in 10 ml dry pyridine to the stirred solution. Stir for over 1 hr at room temperature. The solvents are removed in vacuo, and the mixture is redissolved in acetonitrile for solid phase extraction on phenyl-silica and elution with a linear gradient of acetonitrile to 50% in hexane. The appropriate fractions were pooled and the solvent evaporated to obtain the product as an amorphous solid.

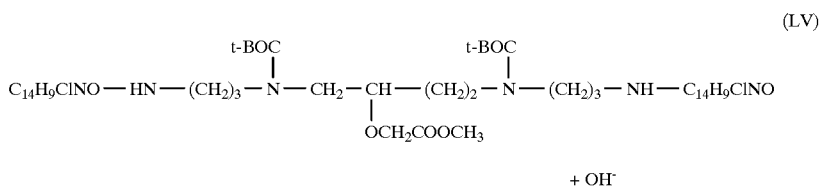

+ OH⁻

Dissolve 2 mmol LV in 10 ml ethanol containing 2 mmol potassium hydroxide. After overnight at room temperature, the solution is transferred to a separatory funnel, to which 2 mmol of HCl, 5 ml of water and 25 ml of benzene is added. After extraction with 3 additional portions of benzene, the combined organic phase is taken to dryness in vacuo. Dissolve in dry DMF for standard solid phase peptide synthesis.

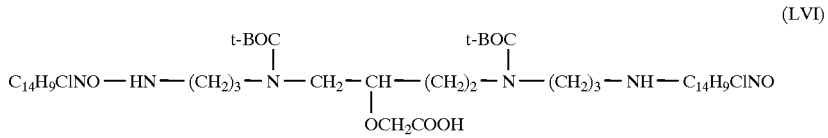

1,12-N,N'-di(2-methoxy-6-chloroacridinyl)amino-4,9-di-t-butyoxycarbonyl-6-carboxymethoxy-4,9-diaza-dodecane In reactions similar to the conversions in Example 2, the following products are obtained. One skilled in the art will recognize that the reaction conditions are similar, but that the starting material and end product will be different.

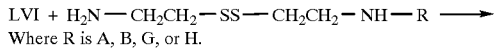

Where R is A, B, G, or H.

-continued
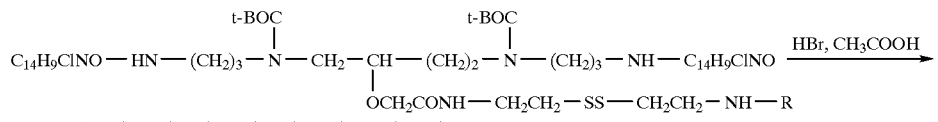
Where R is A (LVIIa), B (LVIIb), G (LVIIc) or H (LVIII).
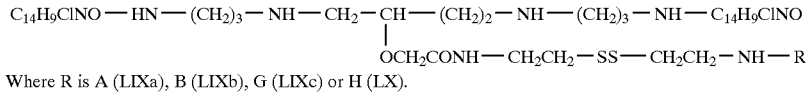
Where R is A (LIXa), B (LIXb), G (LIXc) or H (LX).
LX + dithiothreitol ⟶
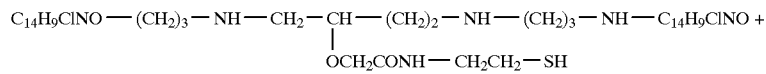
$C_5H_4N$—SS—$CH_2CH_2$—CONH—R; Where R is D, E or F. ⟶
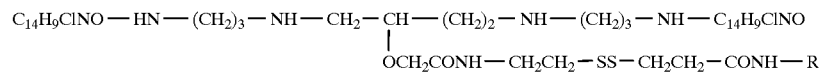
Where R is D (LXIId), E (LXIIe), or F (LXIIf).
LXI + $C_5H_4N$—SS—$CH_2CH_2$—NH—R; Where R is A, B, or G. ⟶
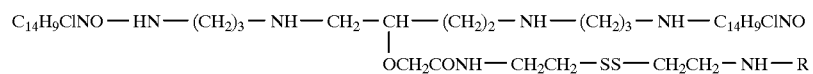
Where R is A (LIXa) B (LIXb) or G (LIXc).
LVI + $H_2N$—$(CH_2)_6$—$NH_2$ ⟶
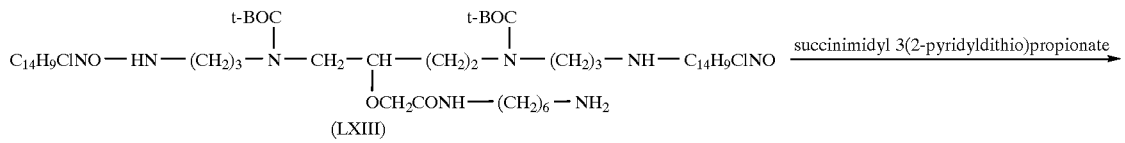
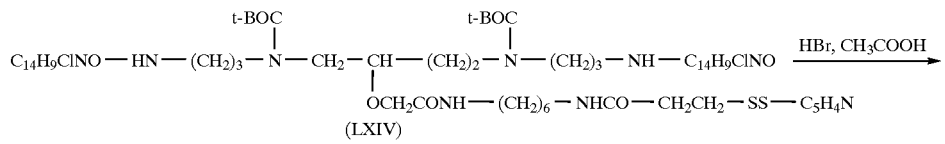
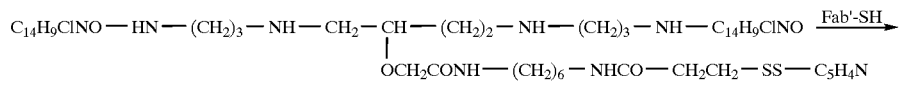
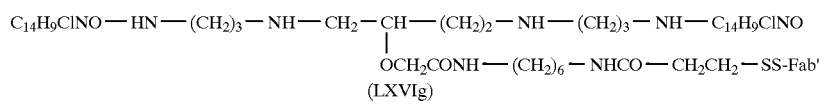
LVI + succinic anhydride ⟶
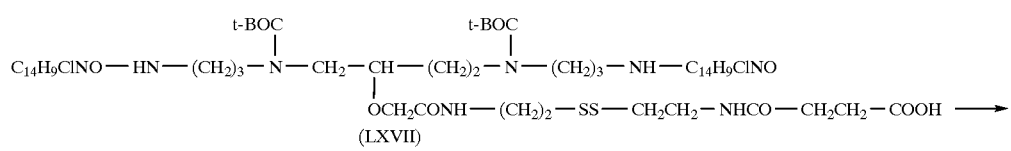
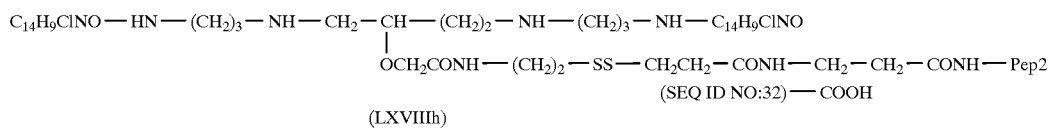
LVI + $H_2N$—$(CH_2)_5$—$COOCH_3$ ⟶
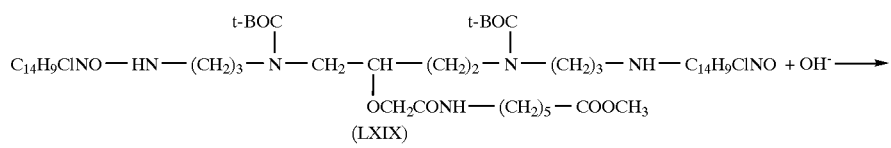

-continued

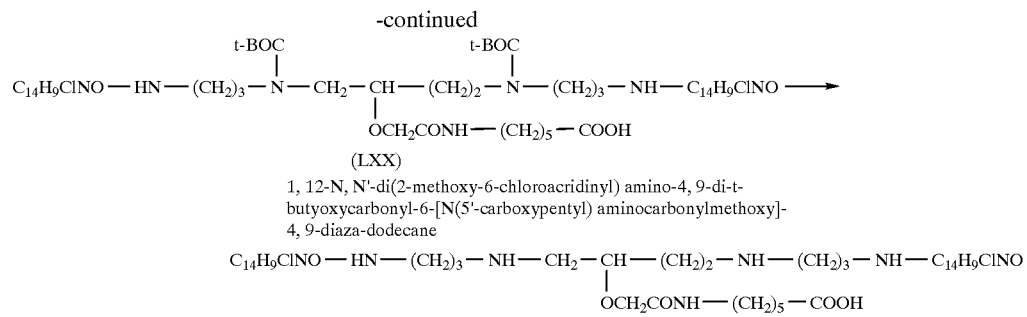

(LXX)

1, 12-N, N'-di(2-methoxy-6-chloroacridinyl) amino-4, 9-di-t-butyoxycarbonyl-6-[N(5'-carboxypentyl) aminocarbonylmethoxy]-4, 9-diaza-dodecane C$_{14}$H$_9$ClNO — HN — (CH$_2$)$_3$ — NH — CH$_2$ — CH — (CH$_2$)$_2$ — NH — (CH$_2$)$_3$ — NH — C$_{14}$H$_9$ClNO
$\quad\quad\quad\quad\quad\quad\quad\quad\quad\quad\quad\quad\quad\quad\quad\quad$|
$\quad\quad\quad\quad\quad\quad\quad\quad\quad\quad\quad\quad\quad\quad\quad$OCH$_2$CONH — (CH$_2$)$_5$ — COOH Where R is Pep3 (SEQ ID NO:33) (LXXIi), Pep4 (SEQ ID NO:34) (LXXIj), Pep5 (SEQ ID NO:35) (LXXIk) or Pep6 (SEQ ID NO:36) (LXXIl)

Further Intercalating Hexacationic DNA Binding Template

Figure 9:
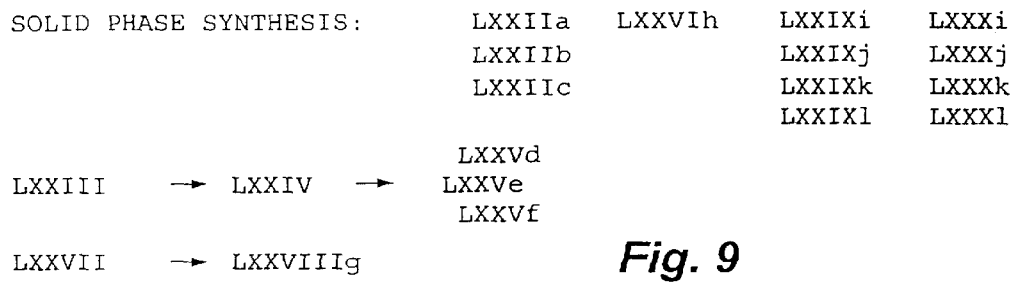

A schematic flow chart for the synthesis of these compounds is shown in FIG. 9. The chemical pathway of synthesis is shown below.

In reactions similar to the conversions disclosed above, the following products are obtained. One skilled in the art will recognize that the reaction conditions are similar, but that the starting material and end products will be different.

After derivatization of the ε-N-lys with succinic anhydride, the following ligands are coupled to the resin bound protected peptide.

H$_2$N—CH$_2$CH$_2$—S—S—CH$_2$CH$_2$—NH—R

Where R is A, B, G or H.

deprotection and release from the resin yields:

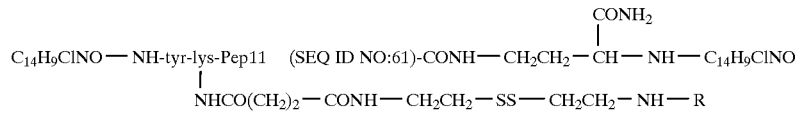

Where R is A (LXXIIa), B (LXXIIb), G (LXXIIc) or H (LXXIII).

LXXIII + dithiothreitol ⟶

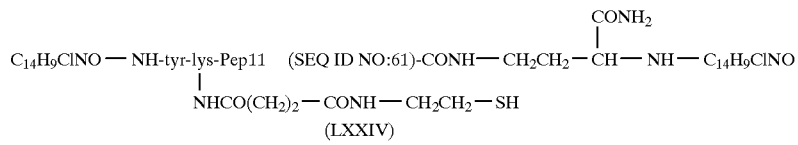

(LXXIV)

C$_5$H$_4$N — SS — CH$_2$CH$_2$ — CONH — R; Where R is D, E, or F. ⟶

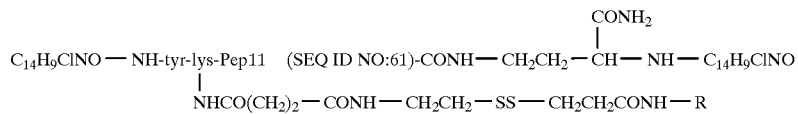

Where R is D (LXXVd), E (LXXVe) or F (LXXVf).

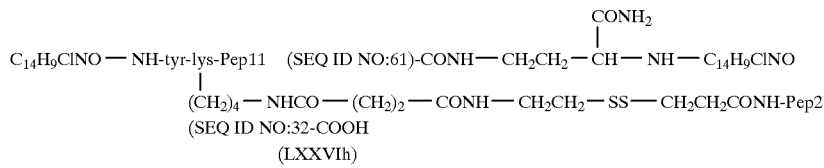

(LXXVIh)

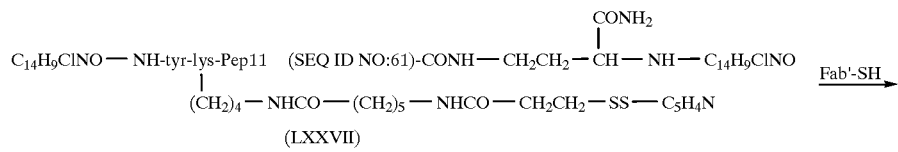

(LXXVII)

Fab'-SH ⟶

-continued

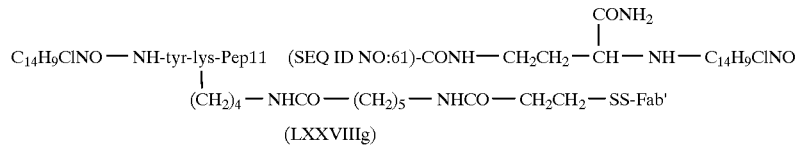

(LXXVIIIg)

The addition of the nuclear localization sequence yields:

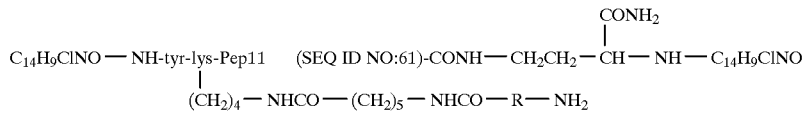

where R is Pep7 (SEQ ID NO:37) (LXXIXi), Pep8 (SEQ ID NO:38) (LXXIXj), Pep9 (SEQ ID NO:39), (LXXIXk) or Pep10 (SEQ ID NO:40) (LXXIXl).

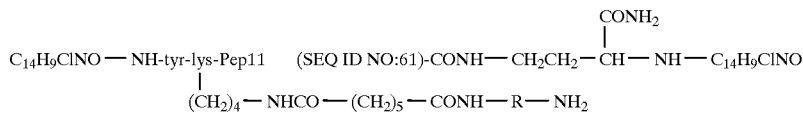

where R is Pep3 (SEQ ID NO:33) (LXXXi), Pep4 (SEQ ID NO:34) (LXXXj), Pep5 (SEQ ID NO:35) (LXXXk) or Pep6 (SEQ ID NO:36) (LXXXl).

Dimeric Octacationic DNA Binding Templates

Figure 10:
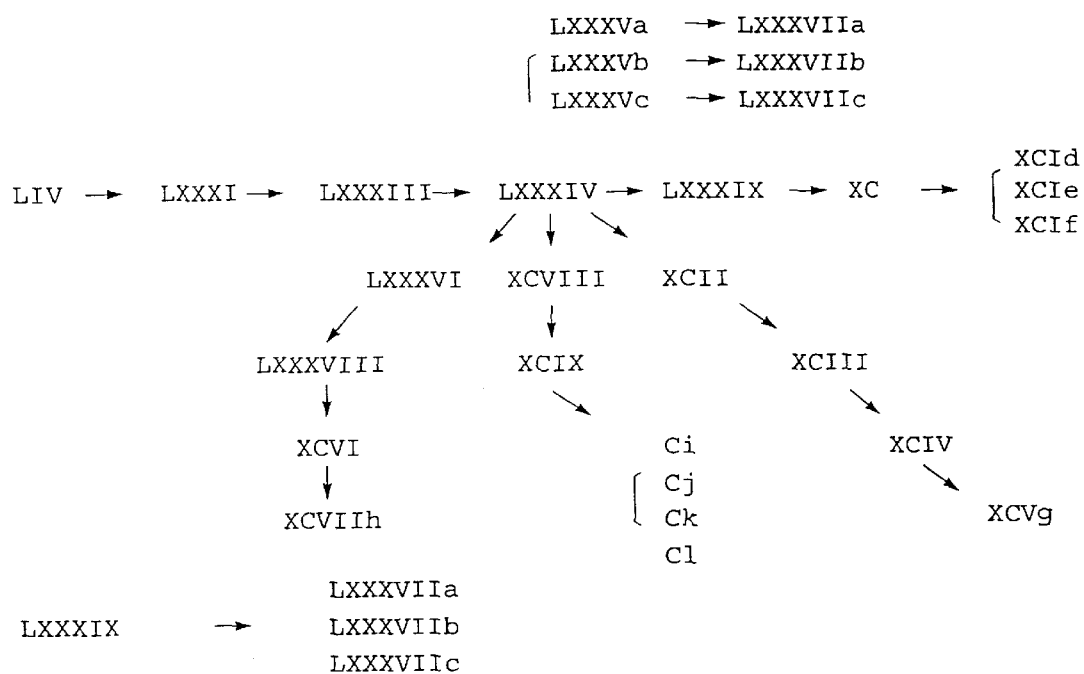

A schematic flow chart for the synthesis of these compounds is shown in FIG. 10. The chemical pathway of synthesis is shown below.

Combine 2 mmol LIV, 1 mmol 4-pyrrolidinopyridine and 1.0 mmol benzyloxycarbonyl anhydride in 40 ml anhydrous benzene and stir overnight at room temperature under $N_2$. Separate the product by solid phase extraction on phenyl-silica and elution with a linear gradient of ethyl acetate, 0 to 50% in hexane. Pool the appropriate fractions and evaporate the solvent to obtain the produce LXXXI as an amorphous solid.

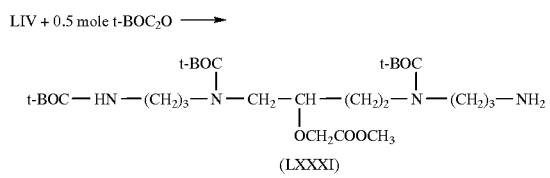

(LXXXI)

Combine 2 mmol LXXXI, 2 mmol 4-pyrrolidinopyridine and 3 mmol bis-(3-carboxyethyl)dithiol in 40 ml anhydrous benzene and stir overnight at room temperature under $N_2$. Separate the desired product by solid phase extraction on phenyl-silica and elution with a linear gradient of ethyl acetate to 50% in hexane. Pool the appropriate fractions and evaporate the solvent to obtain the product LXXXII as an amorphous solid.

(LXXXII)

t-BOC—HN—(CH$_2$)$_3$—N(t-BOC)—CH$_2$—CH(OCH$_2$COOCH$_3$)—(CH$_2$)$_2$—N(t-BOC)—(CH$_2$)$_3$—NHCO—CH$_2$CH$_2$—SS—CH$_2$CH$_2$—COOH

Dissolve 2 mmol LXXXII in 2 ml dry DMF, add 4.0 mmol 1-ethyl-3-[3-(dimethyl-amino)propyl)carbodiimide and stir 2 hr, then add 2.1 mmol N-hydroxysuccinimide and continue stirring for another 6 hr at room temperature, then combine with 2 mmol 3-[(3"-N-t-BOC-aminopropyl)-4'-N-t-BOC-aminobutyl]-N-t-BOC-aminopropylamine in 21 ml dry DMF. After stirring overnight at room temperature, remove the solvent in vacuo, separate the product by solid phase extraction on phenyl-silica and elution with a linear gradient of ethyl acetate, 0 to 50% in hexane. Pool the appropriate fractions and evaporate the solvent to obtain the product LXXXIII as an amorphous solid.

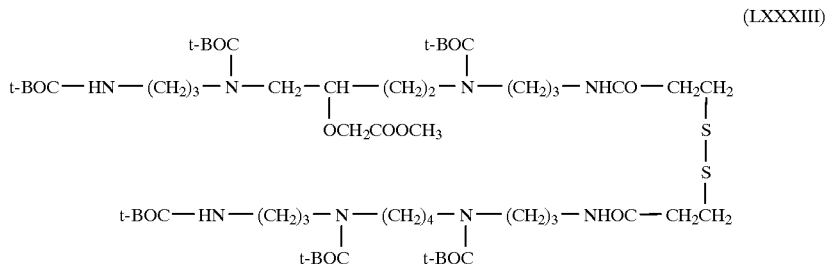

(LXXXIII)

Dissolve 2 mmol LXXXIII in 10 ml ethanol containing 2 mmol potassium hydroxide. After overnight at room temperature, the solution is transferred to a separatory funnel, to which 2 mmol of HCl, 5 ml of water and 25 ml of benzene is added. After extraction with 3 additional portions of benzene, the combined organic phase is taken to dryness in vacuo. Separate the desired product by solid phase extraction on phenyl-silica and elution with a linear gradient of ethyl acetate to 50% in hexane. Pool the appropriate fractions and evaporate the solvent to obtain the product LXXXIV as an amorphous solid.

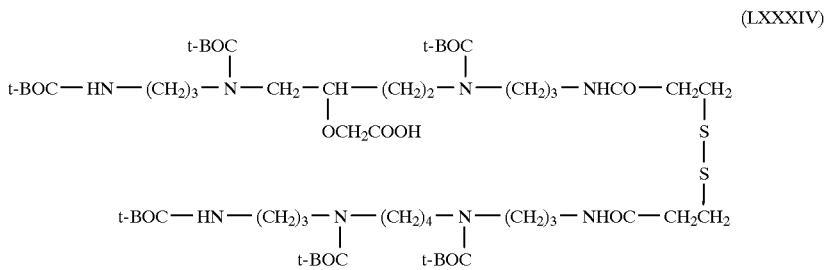

(LXXXIV)

Dissolve 1 mmol of LXXXIV in 2 ml dry dimethylformamide, add 3.0 mmol 1-ethyl-3-[3-(dimethylamino)propyl)carbodiimide and stir 2 hrs, then add

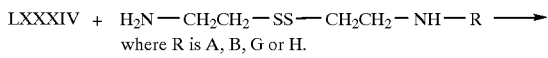

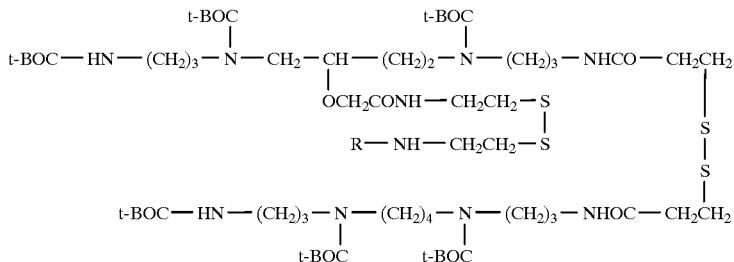

1.1 mmol n-hydroxysuccinimide and continue stirring for another 6 hrs at room temperature. This solution is added dropwise to 3 mmol of $H_2N$—$CH_2CH_2$—$NH$—R (where R=A, B, G or H) in 20 ml dry dimethylformamide, and stirring continued for an additional 24 hrs. Remove the solvent in vacuo. Separate the desired product by solid phase extraction on phenyl-silica and elution with a linear gradient of ethyl acetate from 0 to 50% in hexane. Pool the appropriate fractions and evaporate the solvent to obtain the product as an amorphous solid.

where R is A (LXXXVa), B (LXXXVb), G (LXXXVc) or H (LXXXVI).

Dissolve LXXXVa, 1 mmol, in 29 ml glacial acetic acid containing 30% HBr and stir overnight at room temperature in the dark under $N_2$. Add 30 ml diethyl ether to precipitate the product. Wash the product until the odor of acetic acid is gone. Dissolve the solid in oxygen-free 0.1 M $NH_4OH$. The solution is applied to an anion exchange resin equilibrated in degassed 0.1 M $NH_4CO_3$ containing 20% acetonitrile. The product is separated from unreacted starting materials by a gradient of 20 to 80% acetonitrile in 0.1 M $NH_4CO_3$. The appropriate fractions are pooled and lyophilized to obtain the product:

ture 20-fold with water, apply to an anion exchange resin equilibrated in degassed 0.1 M $NH_4CO_3$ containing 20% acetonitrile. The product XIa is separated from unreacted

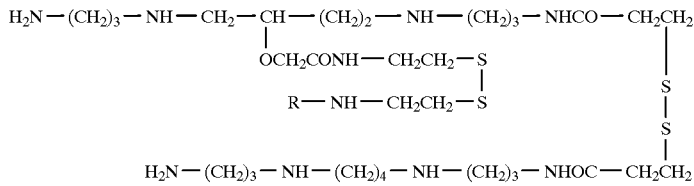

where R is A (LXXXVIIa) B (LXXXVIIb), G (LXXXVIIc) or H (LXXXVIII).

Use the same procedures as for LXXXVa–LXXXVc, except substitute S-t-BOC-mercaptoethylamine for $H_2N-CH_2CH_2-SS-CH_2CH_2-NH-R$. Then use the same procedures as for LXXXVIIa–LXXXVIIc.

starting materials by a gradient of 20 to 80% acetonitrile in 0.1 M $NH_4CO_3$. The appropriate actions are pooled by lyophilized to obtain the product.

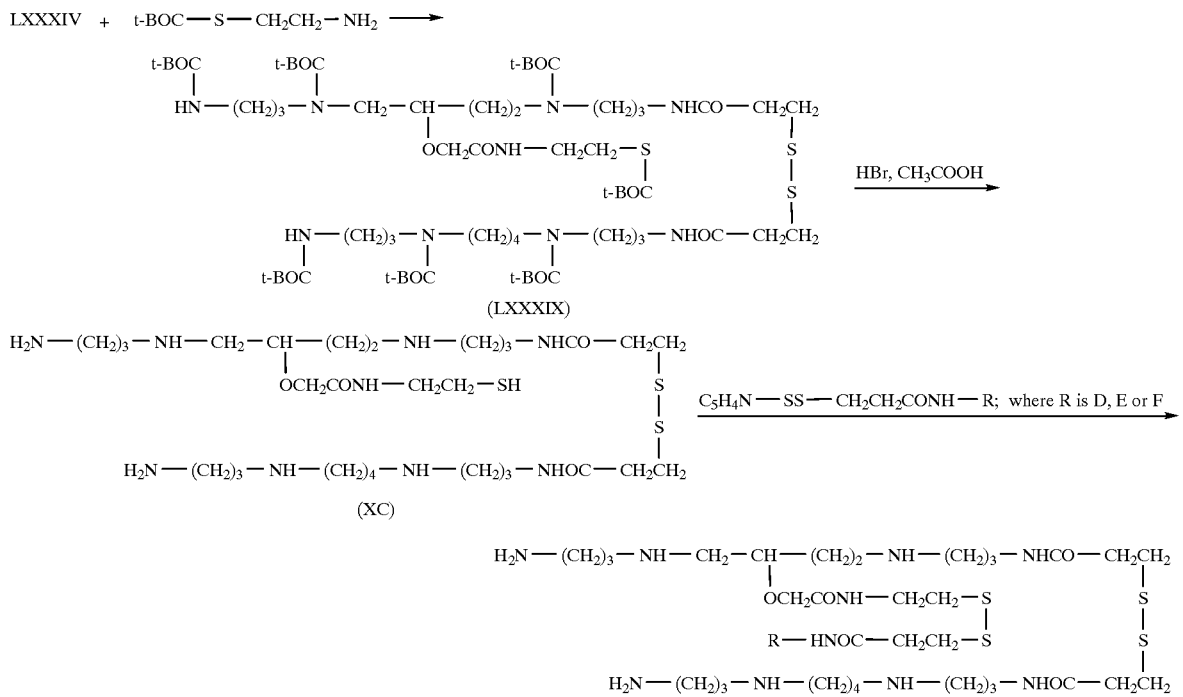

where R is D (XCId), E (XCIe) or F (XCIf)

Dissolve 1 mmol XC in 2 ml phosphate-buffered saline, pH 7.4, and combine with 1 mmol A', also dissolved in 2 ml phosphate-buffered saline, pH 7.4. Dilute the reaction mix

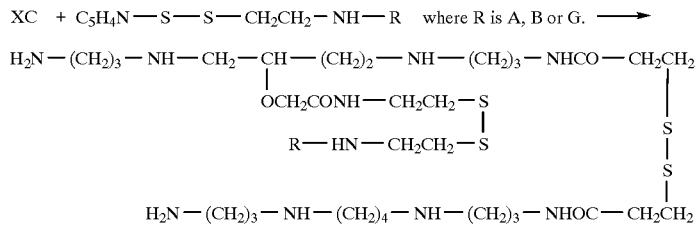

where R is A (LXXXVIIa), B (LXXXVIIb) or G (LXXXVIIc).

Dissolve 1 mmol of LXXXIV in 2 ml dry dimethylformamide, add 3.0 mmol 1-ethyl-3-[3-(diethylamino)propyl] carbodiimide and stir 2 hr, then add 1.1 mmol N-hydroxysuccinimide and continue stirring for another 6 hr at room temperature. This solution is added dropwise to 5 mmol of 1,6-diaminohexane in 20 ml dry diamethylformamide, and stirring continued for an additional 24 hours. Remove the solvent in vacuo. Separate the desired product by solid phase extraction on phenyl-silica and elution with a linear gradient of ethyl acetate from 0 to 50% in hexane. Pool the appropriate fractions and evaporate the solvent to obtain the product as an amorphous solid.

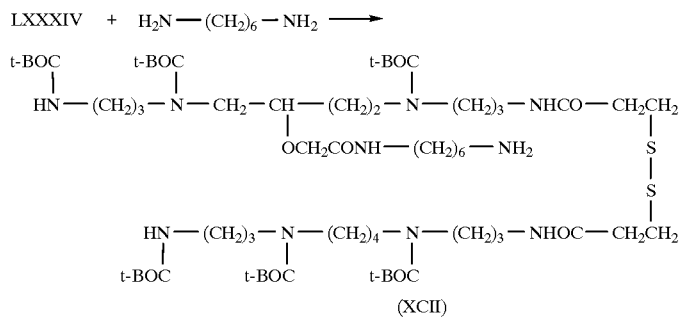

Combine 1 mmol XCII in dry 10 ml benzene with 1.1 mmol succinimidyl 3(2-pyridylthio) propionate, stir for 2 hr at room temperature, and then remove the solvent in vacuo.

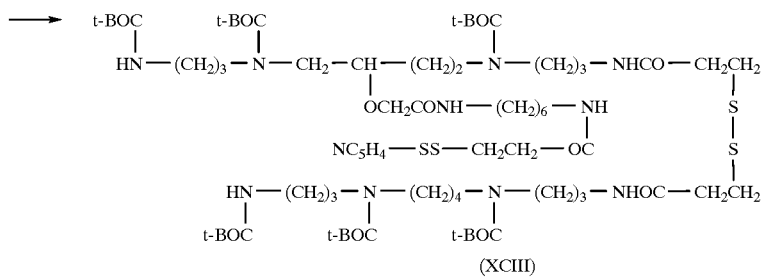

Dissolve XCIII, 1 mmol, in 20 ml glacial acetic acid containing 30% HBr and stir overnight at room temperature

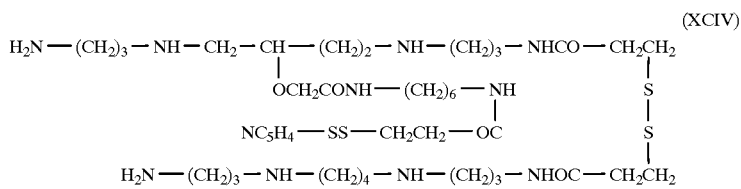

in the dark under $N_2$. Add 30 ml diethyl ether to precipitate the product. Wash the product until the odor of acetate acid is gone. Dissolve the solid in oxygen-free 0.1 M $NH_4CO_3$. The solution is applied to an anion exchange resin equilibrated in degassed 0.1 M $NH_4CO_3$ containing 20% acetonitrile. The product is separated from unreacted starting materials by a gradient of 20 to 80% acetonitrile in 0.1 M $NH_4CO_3$. The appropriate fractions are pooled and lyophilized to obtain the product.

To a stirred solution of 10 mg of Fab'-SH in 5 ml PBS, pH 7.4, at 4°, add 0.3 ml of 10 mM XCIV in PBS, pH 7.4, dropwise. After 60 min, dialyze against 3 changes of 0.5 L PBS, pH 7.4, at 4°, each for 2 hr.

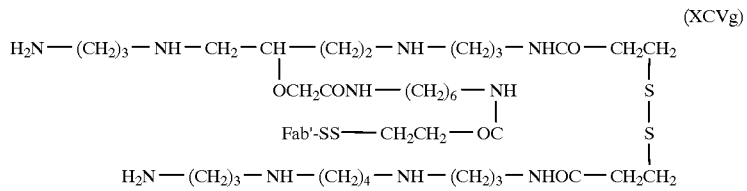
(XCVg)

Combine 2 mmol LXXXVI, 2 mmol 4-pyrrolidinopyridine and 3 mmol succinic anhydride in 40 ml anhydrous benzene and stir overnight at room temperature under $N_2$. Separate the desired product by solid phase extraction on phenyl-silica and elution with a linear gradient of ethyl acetate to 50% in hexane. Pool the appropriate fractions and evaporate the solvent to obtain the product XCVI as an amorphous solid.

continue stirring for another 6 hr at room temperature, then combine with 2 mmol methyl 6-aminohexanoate in 2 ml dry DMF. After stirring overnight at room temperature, remove the solvent in vacuo, separate the product by solid phase extraction on phenyl-silica and elution with a linear gradient of ethyl acetate, 0 to 50% in hexane. Pool the appropriate fractions and evaporate the solvent to obtain the product as an amorphous solid.

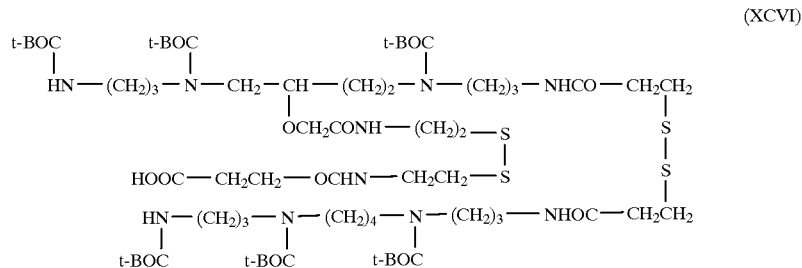
(XCVI)

Couple XCVI to the amino terminal of the peptide on the support using standard solid phase peptide methods, cleave from the resin and deprotect, and purify by ion exchange chromatography.

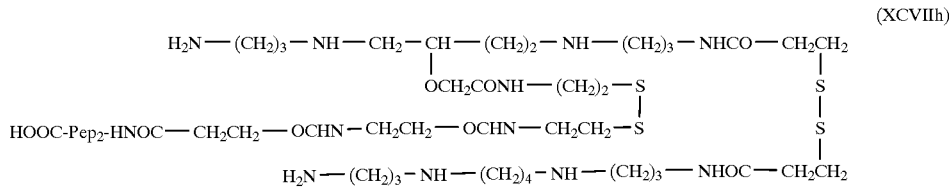
(XCVIIh)

Dissolve 2 mmol LXXXIV in 2 ml dry DMF, add 4.0 mmol 1-ethyl-3-[3-(dimethylamino)propyl)carbodiimide and stir 2 hr, then add 2.1 mmol N-hydroxysuccinimide and

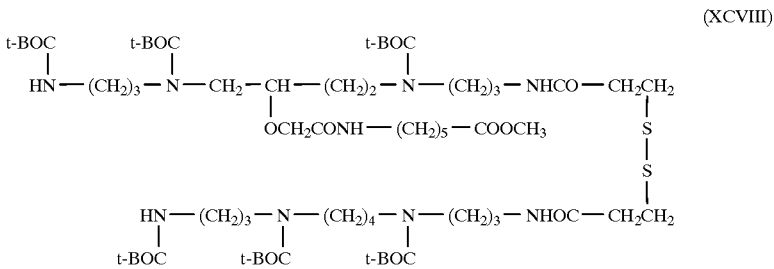
(XCVIII)

+ OH⁻

Dissolve 2 mmol XCVIII in 10 ml ethanol containing 2 mmol potassium hydroxide. After overnight at room temperature, the solution is transferred to a separatory funnel, to which 2 mmol of HCl, 5 ml of water and 25 ml of benzene is added. After extraction with 3 additional portions of benzene, the combined organic phase is taken to dryness in vacuo. Separate the desired product by solid phase extraction on phenyl-silica and elution with a linear gradient of ethyl acetate to 100% in hexane. Pool the appropriate fractions and evaporate the solvent to obtain the product as an amorphous solid.

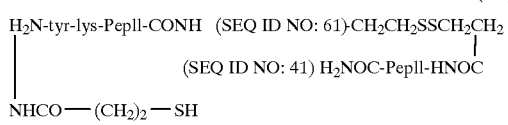

(CII)

To a stirred solution of 10 mg of D or E in 5 ml PBS, pH 7.4, at 4°, add 0.3 ml of 10 mM CII in PBS, pH 7.4, dropwise. After 60 min. dilute the reaction mixture 20-fold

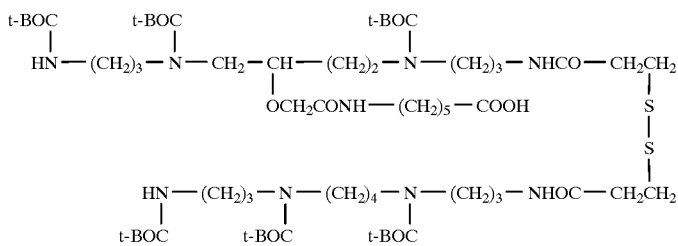

(XCVIX)

Couple XCIX to the amino terminal of the appropriate peptide on the support using standard solid phase peptide methods, cleave from the resin and deprotect, and purify by ion exchange chromatography.

with water, apply to a cation exchange column to separate the desired product from unreacted starting material and other products, using a linear gradient formed from equal volumes of water and 2.0 M HCl. The appropriate fractions are

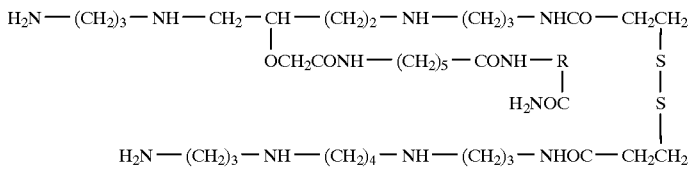

where R is Pep3 (SEQ ID NO:33) (XCXi), Pep4 (SEQ ID NO:34) (XCXj), Pep5 (SEQ ID NO:35) (XCXk) or Pep6 (SEQ ID NO:36) (XCXl).

Further Dimeric Octacationic DNA Binding Templates

Figure 11:
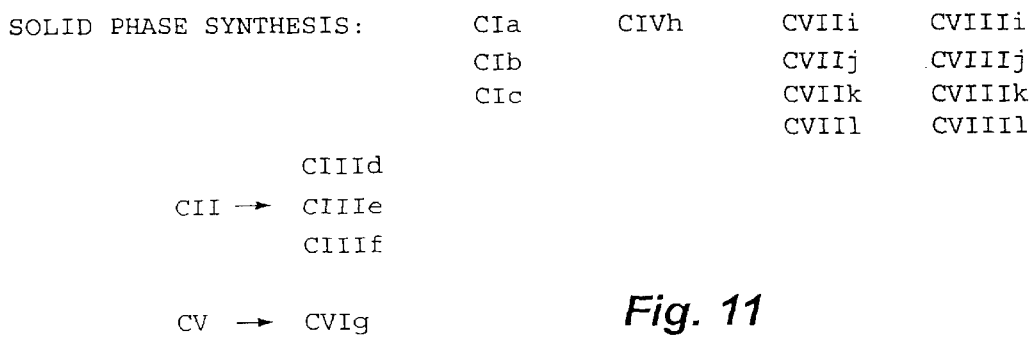

A schematic flow chart for the synthesis of these compounds is shown in FIG. 11 The chemical pathways of synthesis are shown below.

After derivatization of the ε-N-Lys or α-N-Tyr with succinic anhydride the following ligands are coupled to the resin bound protective peptide: H₂N—CH₂CH₂—S—S—CH₂CH₂—NH—R where R is A, B or G.

Deprotection and release from the resin yields:

pooled and lyophilized to obtain the product. Alternatively, to a stirred solution of 10 mg of F or F__ in 5 ml PBS, pH 7.4, at 4° add 0.3 ml of 10 mM CII in PBS, pH 7.4, dropwise. After 60 min, dialyze against 3 changes of 0.5 L PBS, pH 7.4, at 4°, each for 2 hr.

+ C₅H₄N—S—S—CH₂CH₂—CONH—R;

where R is D, E OR F. 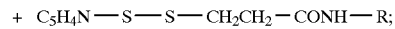

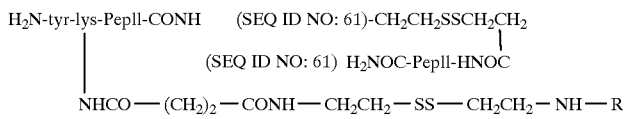

where R is A (CIa), B (CIb) or G (CIc).

After derivatization of the ε-N Lys with t-BOC-S-(CH₂)₂—COOH, deprotection and release from the support yields:

-continued

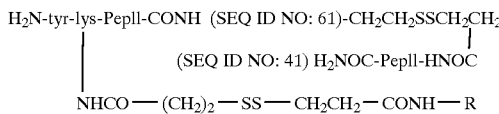

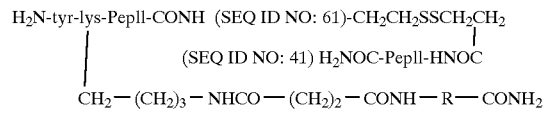

where R is D (CIIId), E (CIIIe) or F (CIIIf).

After derivatization of the ε-N-succinyl-lys with H$_2$N—CH$_2$—CH$_2$—S—S—CH$_2$CH$_2$—NH-t-BOC and deblocking, the ligand Pep2 is synthesized on the resin using standard solid phase technique. Deblocking and cleavage from the resin yields:

where R is Pep3 (SEQ ID NO:33) (CVIIIi), Pep4 (SEQ ID NO:34) (CVIIIj), Pep5 (SEQ ID NO:35) (CVIIIk) or Pep6 (SEQ ID NO:36) (CVIIIl).

(CIVh)

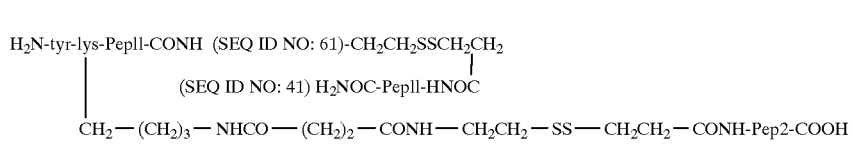

The resin bound Lys-εNH—CO(CH$_2$)$_5$ NH2 intermediate is coupled with succinimidyl 3(2-pyridyldithio) propionate and then deprotected and cleaved to yield:

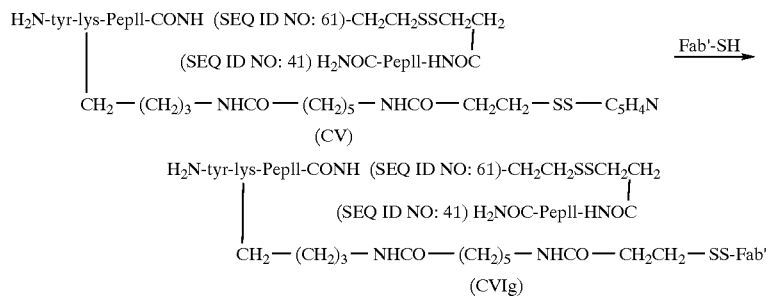

The addition of the nuclear localization sequence yields:

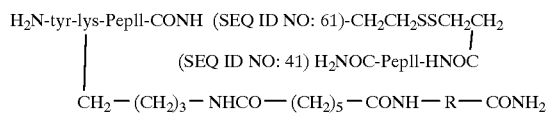

where R is Pep7 (SEQ ID NO:37) (CVIIi), Pep8 (SEQ ID NO:38) (CVIIj), Pep9 (SEQ ID NO:39) (CVIIk) or Pep10 (SEQ ID NO:40) (CVIIl).

Octacationic DNA Binding Templates with Dual Ligands

With at least 8 DNA binding templates and at least 12 receptor ligands, there are many possible combinations which can be used. Representative examples include polyamine templates with either a cleavable or non-cleavable spacer joining the templates and oligopeptide templates with either a cleavable or non-cleavable spacer joining the template.

A schematic flow chart for the synthesis of these compounds is shown in FIG. 12. The chemical pathway of synthesis is shown below for polyamine templates:

Final coupling are the same for each peptide as described for the A, A__, B, B__, G, G__ ligands. Reaction conditions for D, E, F and the Fab__ are comparable.

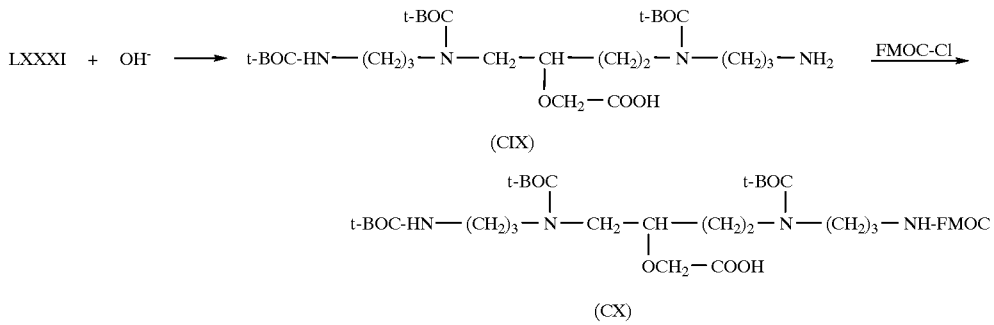

In reactions similar to those in Example 7 the following products are found. One skilled in the art will recognize that the starting material and resulting products are different but the reaction is the same.

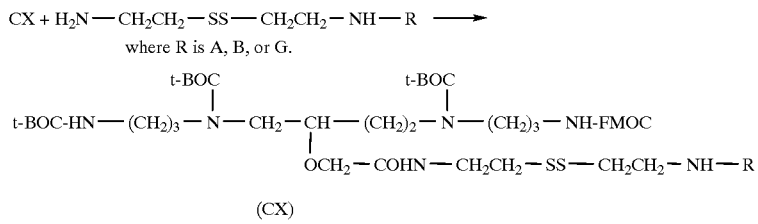

where R is A (CXIa), B (CXIb) or G (CXIc).

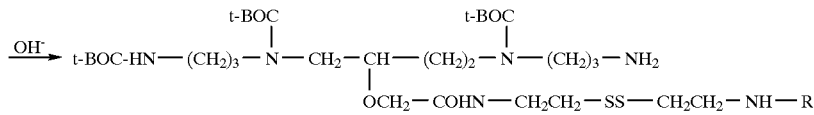

where R is A (CXIIa), B (CXIIb) or G (CXIIc).

Dissolve 2 mmol CX in 2 ml dry DMF, add 4.0 mmol 1-ethyl-3-[3 (dimethylamino)propyl] carbondiimide and stir 2 hr, then add 2.1 mmol N-hydroxysuccinimide and continue stirring for another 6 hr at room temperature, then combine with 2 mmol S(2-aminoethyl) S__ (2-pyridyl)-dithiol in 2 ml dry DMF. After stirring overnight at room temperature, remove the solvent in vacuo, separate the product by solid phase extraction on phenyl-silica and elution with a linear gradient of ethyl acetate, 0 to 50% in hexane. Pool the appropriate fractions and evaporate the solvent to obtain the product as an amorphous solid.

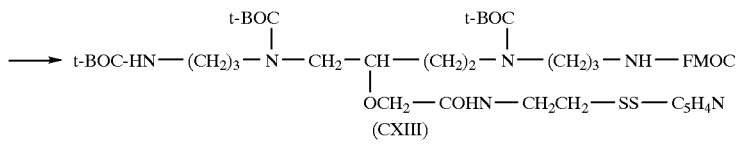

Dissolve 2 mmol CVIII in 10 ml ethanol containing 20 mmol piperidine. After overnight at room temperature, the solution is transferred to a separatory funnel, to which 50 mmol of HCl, 5 ml of water and 25 ml of benzene is added. After extraction with 3 additional portions of benzene, the combined organic phase is taken to dryness in vacuo. Separate the desired product by solid phase extraction on phenyl-silica and elution with a linear gradient of ethyl acetate to 100% in hexane. Pool the appropriate fractions and evaporate the solvent to obtain the product as an amorphous solid.

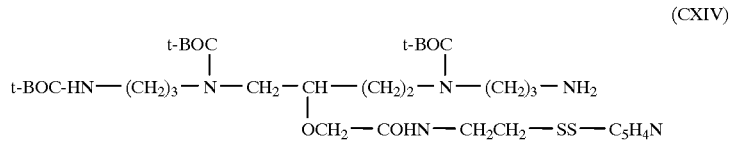

Using the same procedures for CXIII, except substituting S-t-BOC-mercaptoethylamine for H₂N—CH₂CH₂—SS—C₅H₄N.

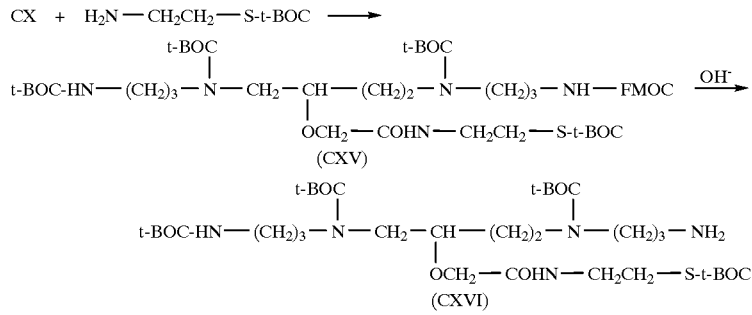

The nuclear localization sequences are added. Standard continuous-flow solid phase synthetic methodologies are used to couple the commercially available 5-(N-t-BOC) aminohexanoic acid to the protected peptide on the solid support and the subsequent reaction to give CXVIIa–c, CXVIII and CXIX, as the final products after deprotection and release from the support and chromatographic isolation.

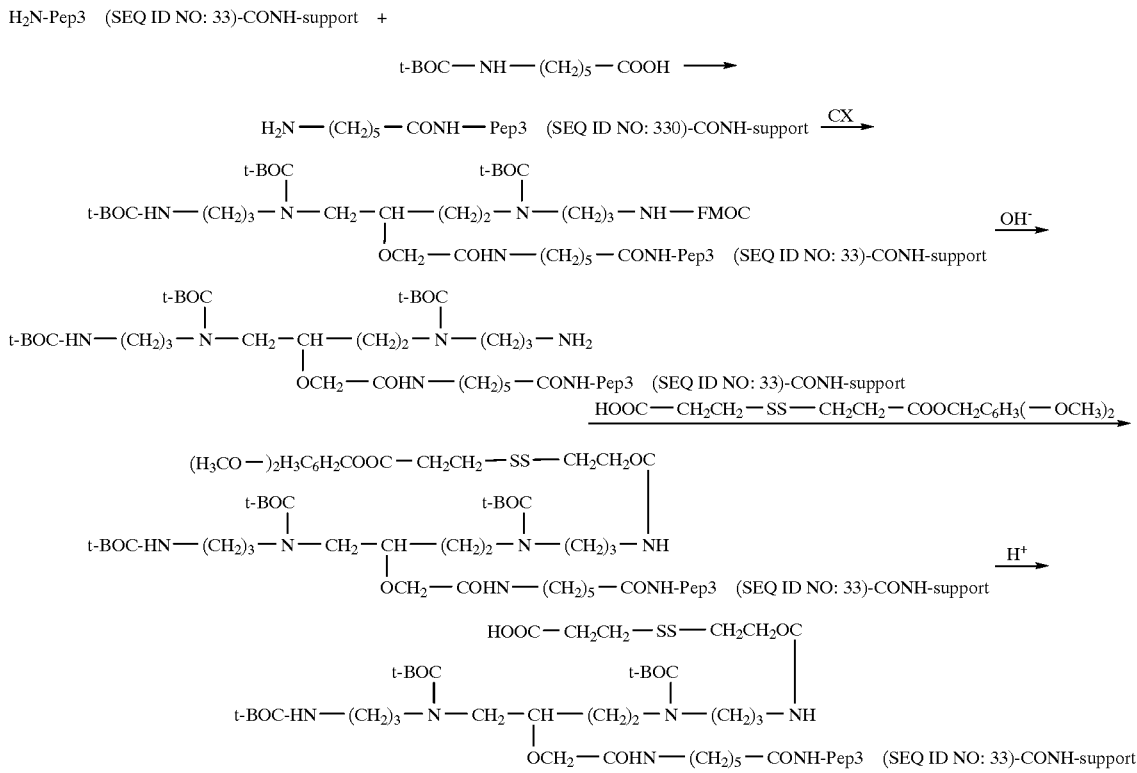

-continued

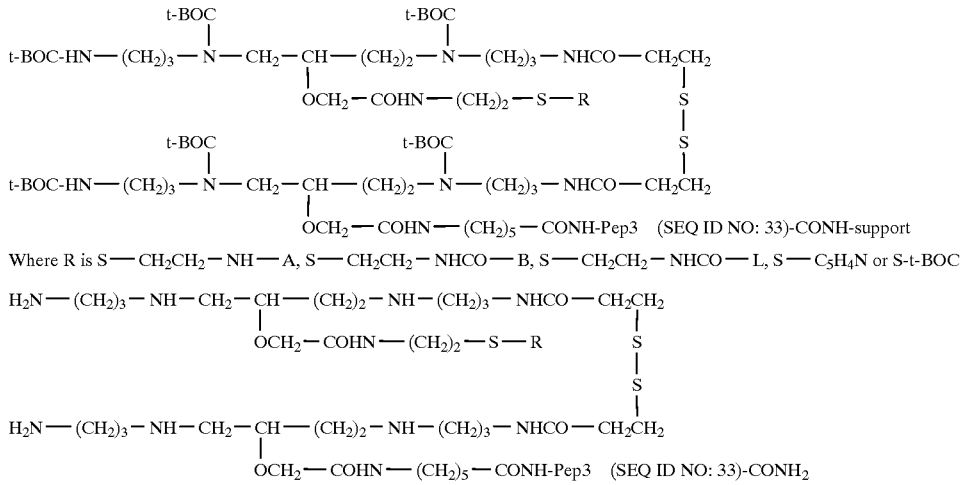

Where R is S—CH$_2$CH$_2$—NH—A, S—CH$_2$CH$_2$—NHCO—B, S—CH$_2$CH$_2$—NHCO—L, S—C$_5$H$_4$N or S-t-BOC Where R is S—CH$_2$CH$_2$—NH—A (CXVIIa), S—CH$_2$CH$_2$—NHCO—B (CXVIIb), S—CH$_2$CH$_2$—NHCO—G (CXVIIc), S—C$_5$H$_4$N (CXVIII) or SH (CXIX).

To a stirred solution of 10 mg of Fab__—SH in 5 ml PBS, pH 7.4, at 4°, add 0.3 ml of 10 CXVIII in PBS, pH 7.4, dropwise. After 60 min, dialyze against 3 changes of 0.5 L PBS pH 7.4, at 4°, each for 2 hr. Alternatively to a stirred solution of HS—CH$_2$CH$_2$—CONH-Pep2 (SEQ ID NO: 32)—COOH, prepared by standard solid phase peptide methodology, 10 mg in 5 ml PBS, pH 7.4, at 4°, add 0.3 ml of 10 mM CXVIII in PBS, pH 7.4, dropwise. After 60 min, Substitution of succinic anhydride for HOOC—CH$_2$CH$_2$—S—S—CH$_2$CH$_2$—COOH$_2$—C$_6$H$_3$(—OCH$_3$)$_2$ at the fourth stage of synthesis gives a noncleavable intermediate which is further modified according to the reaction sequences for CXVIIa, CXVIIb, CXXg, CXXh. CXXId, CXXIe and CXXIf to give the following products for gene delivery.

Standard continuous-flow solid phase synthetic methodologies are used to couple succinic anhydride to the protected peptide on the solid support and the subsequent reaction to give CXXIIa–c, and CXXVh, as the final prod-

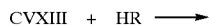
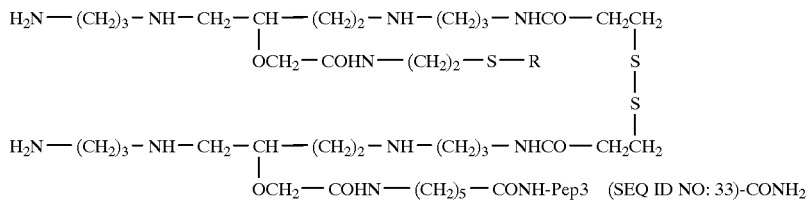

Where R is S-Fab' (CXXg) or S—CH$_2$CH$_2$—CONH-Pep2 (SEQ ID NO: 32)—COOH (CXXh).

Using similar reaction conditions as for preparing CIIId–f ucts after deprotection and release from the support and chromatographic isolation. The intermediates corresponding to CXVIII and CXIX, are deprotected, released from the

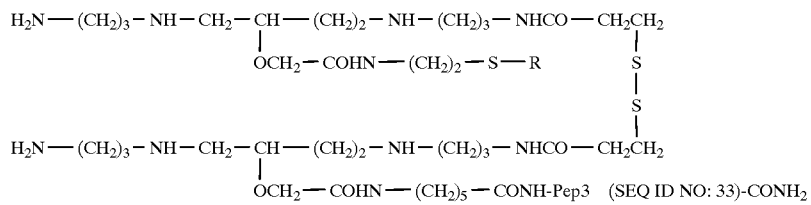

where R is D (CXXId), E (CXXIe) or F (CXXIf).

support, chromatographically purified, and reacted with the appropriate intermediates to give CXXVg, CXXVId–f, as described for the CXX and CXXI series.

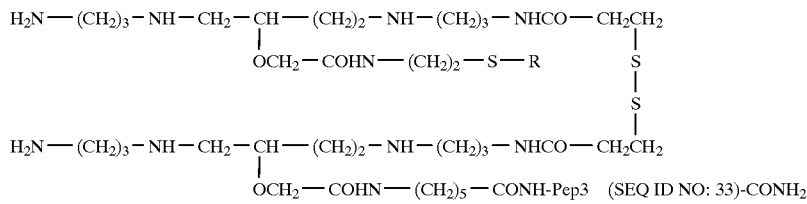

where R is S—CH$_2$CH$_2$—NH—A (CXXIIa), S—CH$_2$CH$_2$—NHCO—B (CXXIIb), S—CH$_2$CH$_2$—NHCO-G (CXXIIc), S-Fab' (CXXVg), S—CH$_2$CH$_2$—CONH-Pep1 (SEQ ID NO: 31)—CONH2 (CXXVh), S—CH$_2$CH$_2$CO-D (CXXVId), S—CH$_2$CH$_2$—CO-E (CXXVIe) or S—CH$_2$CH$_2$—CONH-F (CXXVIf)

Further Octacationic DNA Binding Templates with Dual Ligands

A schematic flow chart for the synthesis of these compounds is shown in FIG. 13. The chemical pathway of synthesis is shown below.

Final coupling are the same for each peptide as described for the A, A', B, B', G, G' ligands. Reaction conditions for D, E, F and the Fab' are comparable.

For oligopeptide template

After derivatization of the ε-N-lys with succinic anhydride the ligands (X) are coupled to the resin bound protective peptide.

X where X is H$_2$N—CH$_2$CH$_2$—S—S—C$_5$H$_4$N, H$_2$N—CH$_2$CH$_2$—S-t-BOC or H$_2$N—CH$_2$CH$_2$—S—S—CH$_2$CH$_2$—NH—R and where R is A, B or G.

Although not necessary, it is sometimes desirable to derivatize the amino-terminal tyr with a 2-methoxy-6-chloracridinyl moiety. If not, then deprotection and release from the resin yields:

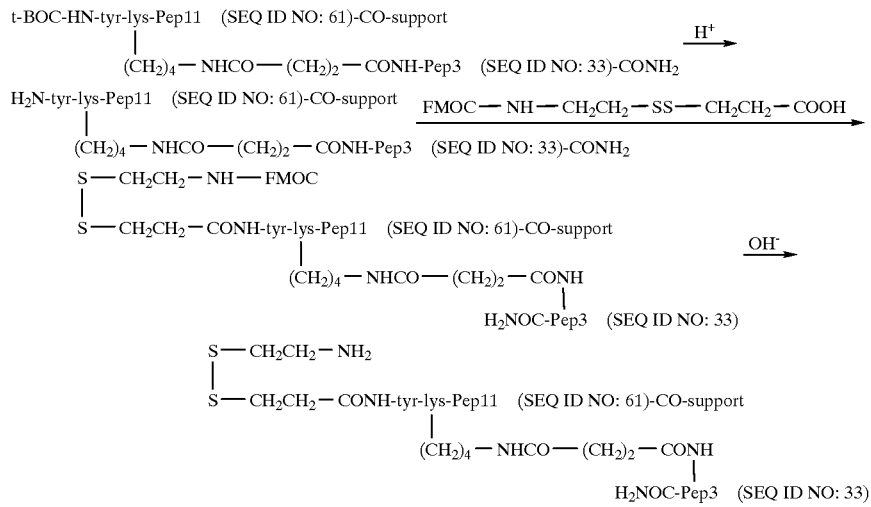

Further extension of template yields:

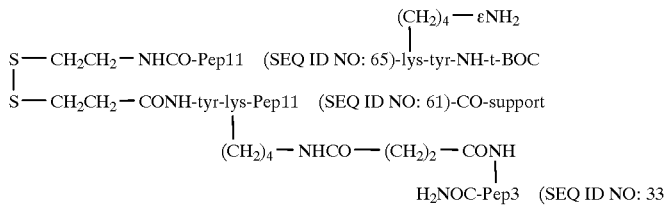

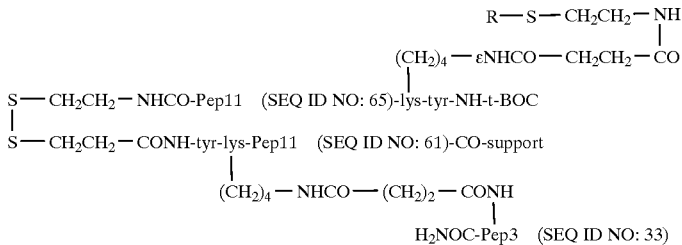

Where R is S—CH$_2$CH$_2$—NHCO-A (CXXVIIa), S—CH$_2$CH$_2$—NHCO-B (CXXVIIb), S—CH$_2$CH$_2$—NHCO-G (CXXVIIc), S—C$_5$H$_4$N (CXXIX) or SH (CXXX).

intermediate, which is further modified according to the reaction sequence for the CXXVII series, CXXXg, CXXXIIIh and the CXXXI series to give the following products for gene delivery.

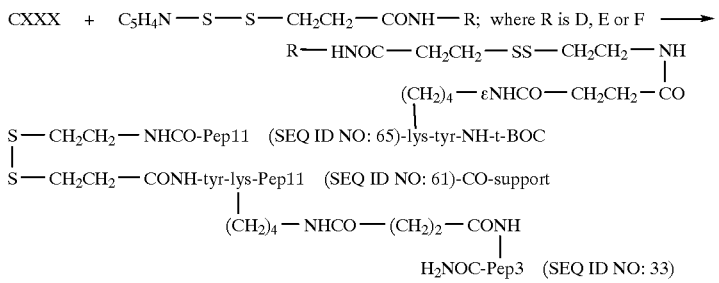

Where R is D (CXXXId), E (CXXXIe) or F (CXXXIf)

After derivatization of the ε-N-succinyl-lys with H$_2$N—CH$_2$CH$_2$—S—S—CH$_2$CH$_2$—NH-t-BOC and deblocking the ligand Pep3 (SEQ ID NO: 33) is synthesized on the resin using standard solid phase techniques. Deblocking and cleavage from the resin yields:

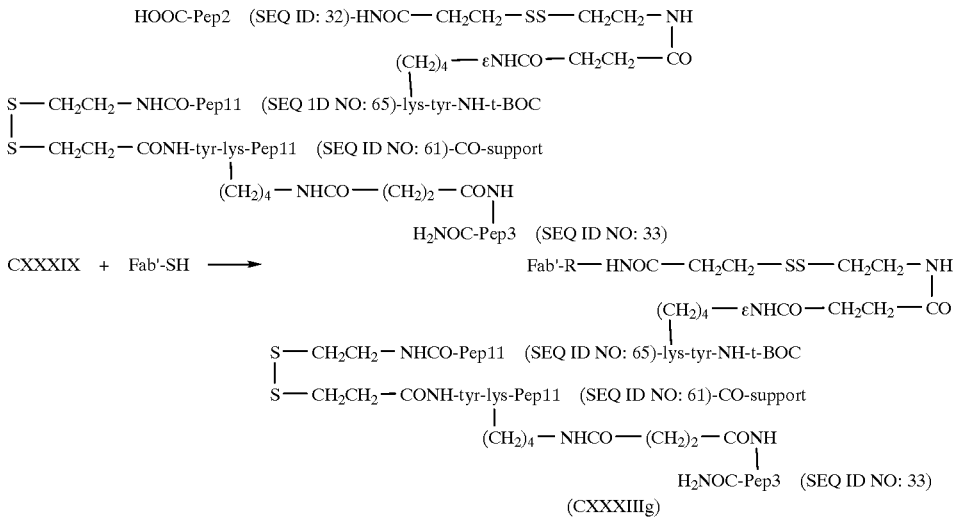

Substitution of t-BOC—NH—(CH$_2$)$_5$—COOH for FMOC—NH—CH$_2$CH$_2$—S—S—CH$_2$—CH$_2$—COOH at the second stage of synthesis gives a noncleavable

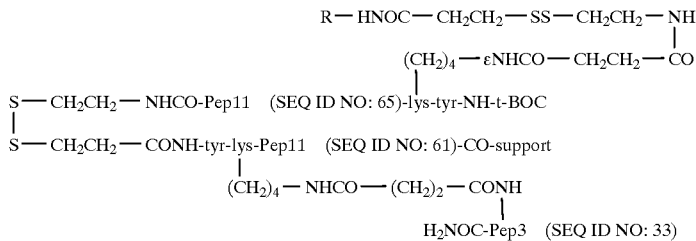

where R is S—CH$_2$CH$_2$—NH-A (CXXXIVa), S—CH$_2$CH$_2$—NHCO-B (CXXXIVb), S—CH$_2$CH$_2$—NHCO-L (CXXXIVC), S-Fab' (CXXXIXg), S—CH$_2$CH$_2$—CONH-Pep1 (SEQ ID NO: 31)—CONH$_2$ (CXXXVIIIh), S—CH$_2$CH$_2$—CO-D (CXXXVIId), S—CH$_2$CH$_2$—CO-E (CXXXVIIe), S—CH$_2$CH$_2$—CONH-F (CXXXVIIIf).

Oligonucleotides Containing Receptor Ligands

FIG. 14 show a double stranded DNA vector with a single stranded DNA attached to a ligand containing both a plasma membrane and nuclear membrane receptors. Two different functions can be shown for this single stranded pyrimidine deoxyoligonucleotide modified at the 3_ and 5_ terminal nucleotides with a space molecule derivatized with a ligand for either a plasma membrane receptor or nuclear membrane receptor and/or a nucleotide containing a modified base conjugated with a ligand for either a plasma membrane receptor or a nuclear membrane receptor.

The first function is to target double stranded vectors to specific cells and then to the nucleus of the targeted cell for expression of the vector and/or integration of the vector sequences into the host genome. One to ten copies of the double stranded target sequences either individually or clustered will be inserted in non-coding regions of the vector.

The second function is to deliver therapeutic single stranded DNA for treatment of cancer, infectious disease and cardiovascular disease. Targeting the single stranded DNA to specific cells and then to the nucleus of the targeted cell will form a triplex structure that prevents transcription of the specified genes.

Figure 15A:
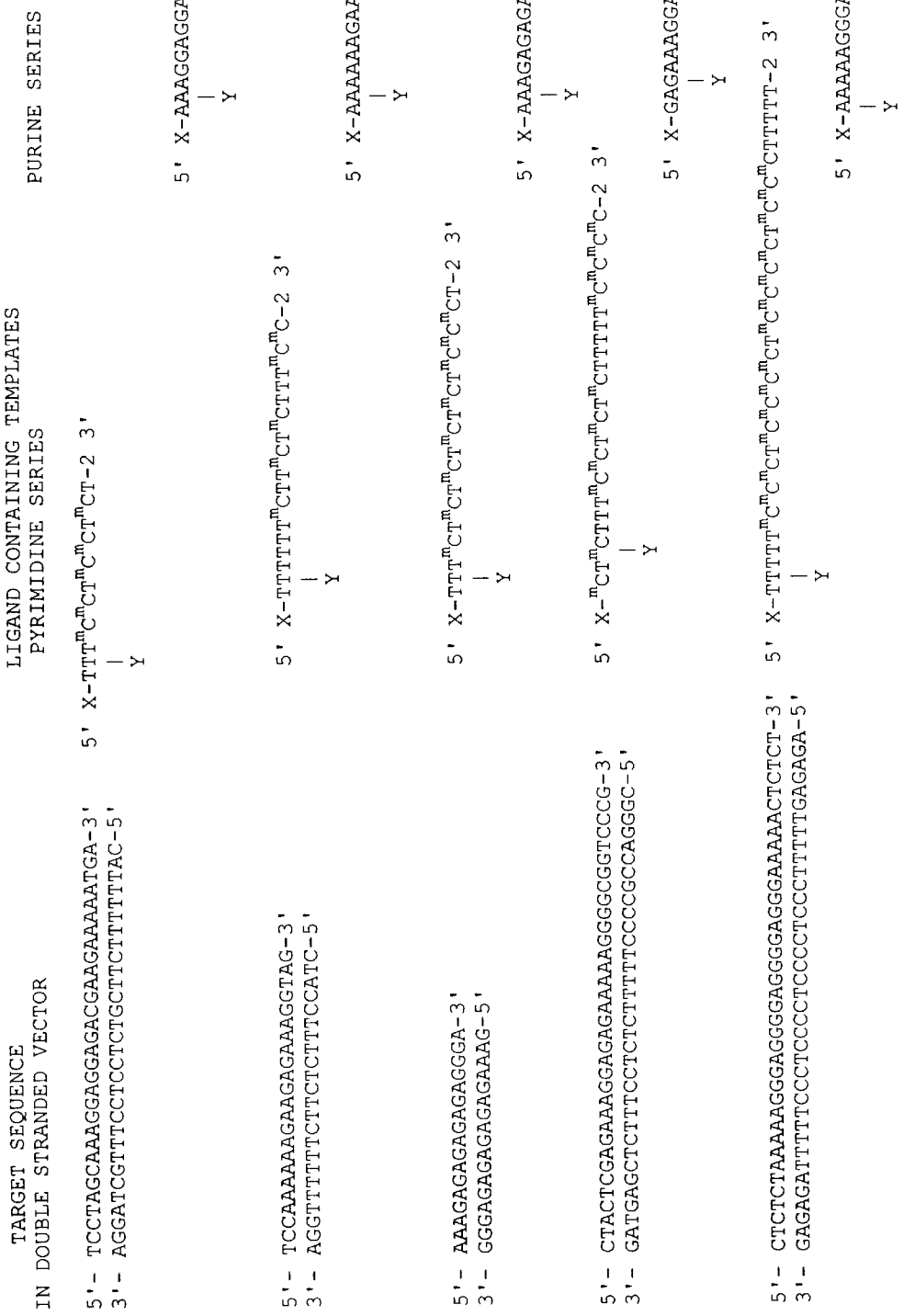
FIG. 15A is a schematic representation of using a ligand to target to a triplex forming oligonucleotide to a duplex nucleic acid (Double stranded DNA sequences (1.) represent Seq. ID Nos. 1, 4, 7, and 10 respectively top to bottom of page; single stranded nucleic acid sequences (middle) represent Seq. ID Nos. 2, 5, 8, 11, and 14 respectively top to bottom of page; single stranded nucleic acid sequences (right) represent Seq. ID Nos. 3, 6, 7 or 9, 12, and 15 respectively top to bottom of page).

In FIG. 15A is shown single stranded DNA as a DNA-binding template containing a single receptor ligand. Cm is the 5-methyl cytosine derivative.

Figure 15B:
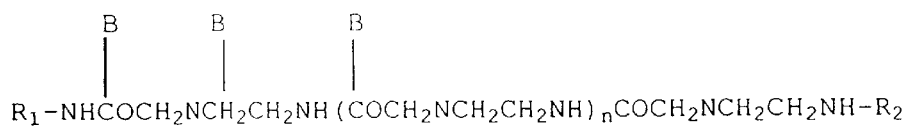
FIG. 15B depicts a specific ligand for targeting muscle.

In FIG. 15B is shown single stranded DNA-binding template in which N-(2-ethylamino)glycine replaces the deoxyribose-phosphate backbone of the nucleic acid polymer.

Figure 15C:
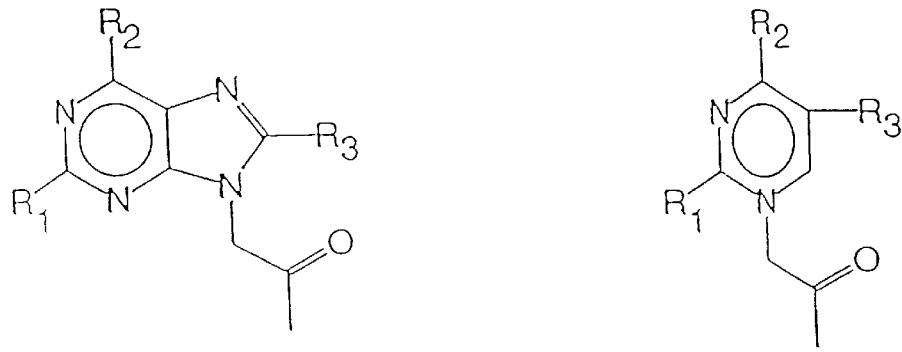
FIG. 15C shows analogs useful in the compound of 15A.

Derivatives and analogs of FIG. 15 are shown in FIGS. 15C.

Figure 15D:
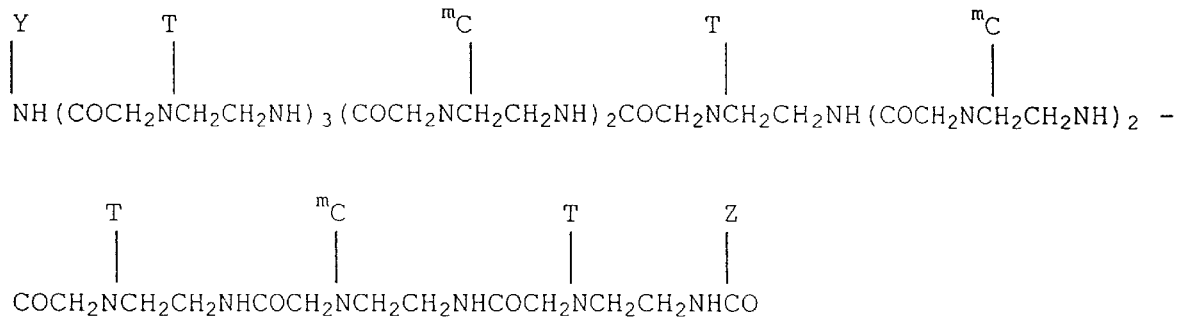
FIG. 15D depicts an analog of 15A.

In FIG. 15D is an example of a ligand containing template in the pyrimidine series. With at least 18 binding templates and at least 12 receptor ligands there are many possible combinations for use. It is obvious to one skilled in the art that two different DNA binding templates could be linked 5_(3_) to 3_(5_) with a dithio bridge so that the single stranded DNA bearing the plasma membrane ligand would disassociate from the double stranded DNA vector. The oligonucleotides are made by conventional solid phase synthesis. The 5_ and 3_ nucleotides contained in an amino group in lieu of the 5_ and 3_ hydroxyl moieties, respectively, of the terminal nucleotides. The nucleotide T-Y is 5-(N-[N-{N-ligand-5-aminohexanoyl}-4-aminobutanoyl]-3-aminoallyl]-2_-deoxyuridine moiety.

The nucleotide A-Y is 8-[N-[N-ligand-5-aminohexanoyl]-8-aminohexylamino]-2_-deoxyadenosine moiety.

Figure 16:
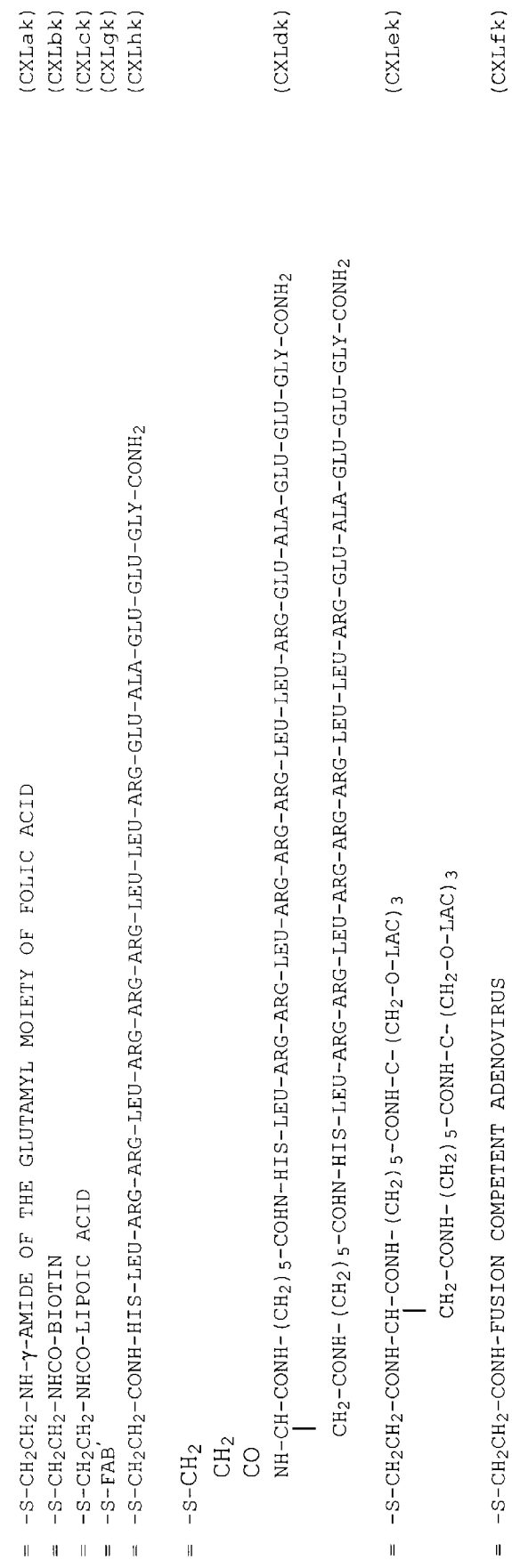
FIG. 16 shows a specific targeting of a ligand for the SV40 sequences (single stranded nucleic acid sequence (top of page.) represents Seq. ID No.16; ten peptide sequence (middle of page) represents Seq. ID No.17; sixteen peptide sequence (bottom of page) represents Seq. ID No.18).
Figure 19:
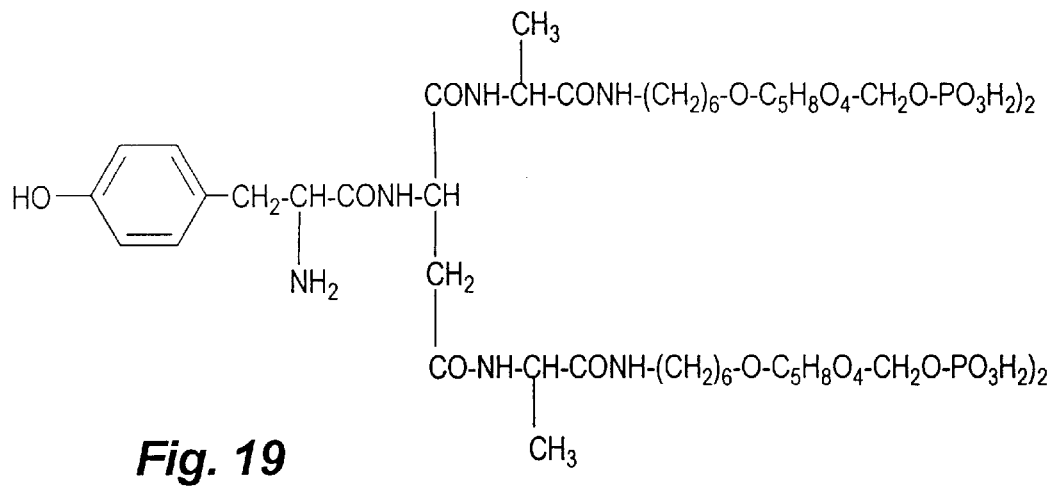
FIG. 19 shows the schematic synthesis of receptor ligands.
Figure 21:
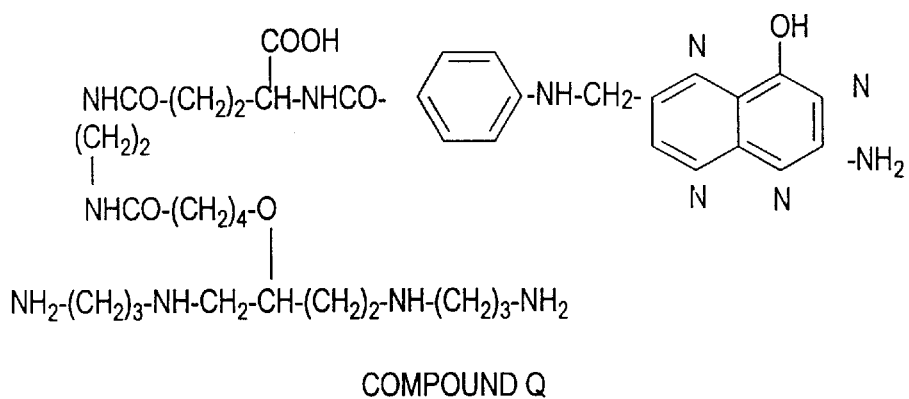
FIG. 21 shows the folyl-spermine derivative.
Figure 22:
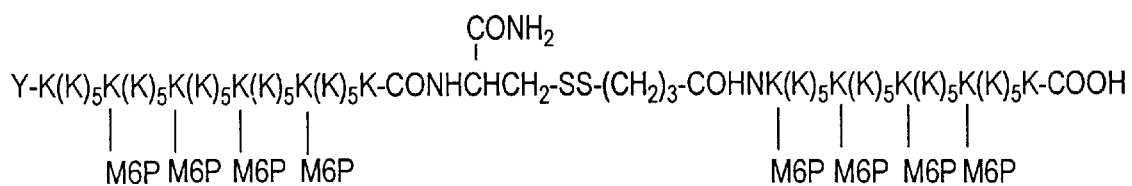
FIG. 22 shows a specific ligand for targeting muscle.

The ligand for SV-40 sequences is shown in FIG. 16. Therapeutic single stranded DNA for the treatment of cancer, infectious disease and cardiovascular disease can be delivered to specific cells and then to the nucleus of the targeted cell where it forms triplex structures that prevent transcription of the specified genes. An initial template will contain two different single stranded DNA templates linked 5_(3_) to 3_(5_) with a dithio bridge, so that as a result of reduction in the cytoplasm, both the single stranded DNA and the plasma membrane ligand will disassociate from the double stranded DNA vectors as separate molecules. The spacer for the plasma membrane ligand also contains a dithio moiety so that the cellular targeting ligand will be released when the complex is present in the cytoplasm. The oligonucleotides are made by conventional solid phase synthesis. The 5_ and 3_ nucleotides contain an amino group in lieu of the 5_ and 3_ hydroxyl moiety, respectively, of the terminal nucleotides. FIG. 17 shows an example of this for the C-myc promoter.

In FIG. 17, the deoxyoligonucleotide strands are synthesized on an automated DNA synthesizer using a solid-phase cyanoethylphosphoramidate method. Commercially available reagents are used to provide a 3' terminal thiol which is reacted further with reacted A after deblocking and release of the oligonucleotide from the support. Dissolve 2 mmol of the protected peptide N-succinyl-Pep5 (SEQ ID NO: 35)—CONH$_2$ released from the peptide support in 2 ml dry DMF, and add 4.0 mmol 1-ethyl-3-[3-(dimethylamino)propyl) carbodiimide.

Stir for 2 hr, then add 2.1 mmol N-hydroxysuccinimide. Stir for another 6 hr at room temperature, then couple with the deprotected side chain amino group of 5-(N-[N-{N-ligand-5-aminohexanoyl}-4-aminobutanoyl]-3-aminoallyl)-2'-deoxyuridine moiety on the solid support. The nucleotide is terminated with the commercially available Uni-Link AminoModifier. The terminal Fmoc amino protecting group is removed and reacted with 6,9-dichloro-2-methoxyacridine before the substituted oligonucleotide is cleaved from the support.

Adenovirus Production

Adenovirus (d1312) was grown in 293 cells and purified by double banding on CsCl gradients and then dialyzed against 2× filtered HEPES Buffered Saline (HBS; 150 mM NaCl, 20 mM HEPES, pH 7.3). The concentration of the virus was determined by U.V. spectrophotometric analysis and either stored in 10% glycerol at −20° C. or further modified for DNA complex formation. Adenovirus was thawed and the appropriate amount added directly to hepatocytes for analysis.

Hepatocyte Isolation and Culture

Mouse hepatocytes isolation and culture was by ollagenase perfusion technique. Briefly, themice are nesthetized, the abdomens opened and a cannula is rapiidly inserted into the portal vein for infusion of Earle's balanced salt solution (w/o Mg, w/o Ca) supplemented with 0.5 mM EGTA and 10 mM HEPES pH 7.4. After 5 min, the liver is perfused for 10 to 12 min with regular Earle's balanced salt solution containing 10 mM HEPES pH 7.4, 0.3 mg/ml collagenase, and 0.04 mg/ml soybean trypsin inhibitor. Next, the liver is transferred and dispersed with forceps into a petri-dish containing regular incubation media. The suspension is then filtered through two layers of nylon mesh and the cells are separated from debris by centirfuging and resuspending them 3 times with media. The desired number of hepatocytes are then plated in a Primaria dish (e.g., $3 \times 10^5$ cells/well of a 6 well plate) in regular incubation media.

Cell Lines and Hepatocyte Isolation

The rat embryo fibroblast 208F cell lines were grown in High glucose DMEM containing 10% heat inactivated hyclone, 1 mM glutamine, 100 μl/ml streptomycin and 100 units/ml penicillin. Mouse hepatocytes were isolated by the collagenase perfusion method and then cultured by methods known in the art. The cultured hepatocytes and liver tissue were tested with X-gal histochemical staining.

Preparation of ASOR and Uptake Studies in Primary Hepatocytes

Orosomucoid was desialylated with neuraminidase to form asialoorosomucoid (ASOR). Residual sialic acid was determined to be less than 5% by the thiobutyric acid assay. The labeling of ASOR was performed by using $^3$H-borohydride. Hepatocyte isolation from 10–12 week old C57-B6 mice and 10–12 week old PAH deficient mice was done by collagenase perfusion. The hepatocytes were plated at a density of $3 \times 10^5$/well in 6 well Primaria plates and grown in 2 ml of Low Glucose complete media (Low Glucose DMEM, 10% fetal calf serum, 10mM HEPES, 0.5% MEM amino acids, 2 mM glutamine, 100 units/ml penicillin, and 100 pg/ml streptomycin). All uptake studies in hepatocytes were done 2–4 hours after the hepatocytes were plated out, allowing the hepatocytes to attach to the plate. The uptake studies of $^3$H-ASOR were performed by incubating the protein with the hepatocytes for the specified period of time after which, the media containing the protein was removed, the cells were washed with PBS (Phosphate Buffered Saline, minus $Ca^{2+}$ and minus $Mg^+$), 1 ml of trypsin added to each well and the cells incubated for 10 minutes at room temperature. The trypsinized cells were removed from the plate and pelleted after which the pellet was washed with PBS minus and then the cells were lysed with 0.5 NaOH. Internalized tritium counts were determined from the cell lysates by scintillation counting.

Preparation of ASOR/Poly-L-Lysine/DNA Complexes

Poly-L-lysine (PLL) MW. 20,500, was coupled to ASOR in a 1 to 2.0 ratio by using 1-ethyl-3-(3-dimethylamniopropyl) carbodiimide (EDC) at pH 7.3. The reaction was incubated for 24 hours at room temperature after which it was concentrated and resuspended in 2M Guanidine-HCl, 50 mM HEPES, pH 7.3, and fractionated by gel filtration on a Superose 6 column with a Fast Protein Liquid Chromatography system (FPLC). Once the conjugate was made and purified, fractions from the FPLC were analyzed on an SDS-PAGE gel to determine those fractions that contained modified ASOR (ASOR/PLL conjugate) only. These fractions were then pooled and dialyzed against 150 mM NaCl, 20 mM HEPES, pH 7.3. prior to complex formation. The DNA plasmid CMV/B-gal containing the *E. coli* β-galactosidase gene under the control of the CMV enhancer and promoter and the DNA plasmid CMV/hPAH containing the human phenylalanine hydroxylase cDNA under the control of the CMV enhancer and promoter were used as reporter genes. All plasmids were isolated and purified by double CsCl banding. Conjugate/DNA complexes were prepared by diluting the conjugate in 150 μl of HES (150 mM NaCl per 20 mM HEPES, pH 7.3) and diluting 6 μl of DNA, in 350 μl of HBS. The diluted DNA was added directly to the diluted conjugate while mixing. The reaction was allowed to incubate at room temperature for 30 minutes before analysis. Immediately following the incubation, all complexes were analyzed on 0.8% agarose gels and electro-phoresed in TBE, or added directly to hepatocytes for uptake analysis.

Analysis of Complex Uptake and Expression in Primary Hepatocytes

Before adding the complex to the hepatocytes, the complete media was removed and replaced with 1 ml of Low Glucose DMEM containing, 5 mM $Ca^{2+}$ and 2% fetal calf serum. Three micrograms of DNA in complex form was then added to the hepatocytes, followed by the immediate addition of the appropriate amount of adenovirus stock. After a 2 hour incubation at 37° C., 1.5 ml of complete media was added to the hepatocytes and the incubation continued for 24 hours at 37° C. The analysis of β-galactosidase (β-gal) activity was done by staining the cells, using X-gal as a substrate. To quantify the actual amount of β-galactosidase produced, ONPG was used as a substrate with aliquots of cell extracts. Phenylalanine hydroxylase activity in cells extracts was measured as the percent conversion of phenylalanine to tyrosine from cell extracts. Protein concentration in cell extracts was determined by the BCA Micro-Protein assay.

Receptor-Mediated Uptake of ASOR in Primary Hepatocytes

The target tissue for this DNA delivery system is the liver, with the specific delivery directed to hepatocytes. A hepatocyte has approximately 500,000 ASOR receptors, compared to HepG2 cells which contain approximately half the number of ASOR receptors. To determine if the desialylated orosomucoid could be internalized by primary hepatocytes in a receptor-mediated process, a dose-response curve was performed by incubating increasing amounts of $^3$H-ASOR with $3 \times 10^5$ hepatocytes. After a 2 hour incubation, the cells were isolated and the internalized $^3$H counts were measured. The dose response curve shows that maximal uptake of $^3$H-ASOR is 6.5 ng of ASOR/$3 \times 10^5$ hepatocytes, which is equivalent to $3.2 \times 10^5$ molecules/cell. The dose response curve is similar for HepG2 cells, but because of the lower number of ASOR receptors, the maximal ASOR uptake is $1.5 \times 10^5$ molecules/cell. No uptake of ASOR occurs in NIH3T3 cells as this cell line contains no ASOR receptors.

To determine the kinetics of ASOR uptake in cultured hepatocytes, a time course analysis was performed. Tritium labeled ASOR (2 μg) was incubated with $3 \times 10^5$ hepatocytes and time points were taken at 0, 30, 50, 90, 120, and 240 minutes after addition of the $^3$H-ASOR to the hepatocytes. The time course analysis shows that the internalized amount of $^3$H-ASOR increases linearly with time for up to 1 hour and reaches saturation level at 2 hours from the initial incubation with the $^3$H-ASOR. When the same analysis is done with HepG2 cells, the internalized amount of $^3$H-ASOR increases at lower levels and does not reach saturation as seen in primary hepatocytes.

DNA Delivery to Hepatocytes By Receptor-Mediated Endocytosis

The ASOR was conjugated to poly-L-lysine with the water soluble carbodiimide EDC and after purification, increasing concentrations of the conjugate were incubated with DNA. The extent of ASOR/PLL/DNA complex formation was determined by agarose gel electrophoresis. Based on charge neutralization, as seen by the reduction of electrophoretic mobility of the DNA, interaction between the ASOR/PLL conjugate and DNA started at a molar ratio of 10 to 1. The DNA is completely retarded at molar ratios of 100 to 1 and greater. To assess if the complexes formed were capable of being internalized and also allowed expression of the DNA, the complexes were incubated with primary hepatocytes for 24 hours, after which time, the hepatocytes were analyzed for β-galactosidase activity. The results of X-gal staining showed few or no blue hepatocytes.

To increase the efficiency of DNA delivery and expression in the cells, the replication defective adenovirus d1312 was incorporated into the analysis. The complex was incubated with $3 \times 10^5$ hepatocytes and with increasing adenoviral titer ranging from zero to $3 \times 10^{10}$ viral particles. The results of the analysis show that the adenovirus alone or the complex alone do not produce any blue staining cells, but hepatocytes can be quantitatively stained when $3 \times 10^9$ adenoviral particles are used. When the hepatocytes are incubated with both the complex and increasing titers of adenovirus, there is a correlative increase in the number of blue cells after X-gal staining. To determine quantitatively the amount of β-galactosidase being produced, ONPG analysis was done on cellular extracts from the hepatocytes that had been incubated with complex only, adenovirus only, or with the complex and increasing titers of adenovirus. The analysis shows that 0.006 units per mg of protein of β-galactosidase activity occurs when the complex alone is used and this activity increases to 6.4 units per mg of protein when $3 \times 10^9$ adenoviral particles are also included. This represents a 1000-fold increase in activity.

To determine if this delivery was specifically through the ASOR receptor, hepatocytes were incubated with the ASOR/DNA complex and $3 \times 10^9$ adenoviral particles in the presence of increasing concentrations of free ASOR. The analysis shows that the delivery of the DNA by the complex in the presence of adenovirus is competable by excess ASOR, verifying that the majority of DNA uptake occurs specifically through the ASOR receptor.

Expression of Human Phenylalanine Hydroxylase After Receptor-Mediated Gene Delivery to Deficient Hepatocytes To determine if the system could be used to reconstitute enzymatic activities in PKU, a plasmid containing the human phenylalanine hydroxylase (PAH) cDNA under the control of the CMV enhancer/promoter was used for complex formation. A PAH-deficient mouse strain has been developed and the hepatic enzyme level is only 3% of normal. Hepatocytes isolated from PAH deficient mice were incubated with complex made with a ratio of ASOR to DNA of 250 to 1. This complex shows maximal hPAH expression over a 24 hour period in hepatocyte extracts that have been incubated with 3 μg of DNA in complex form and $3 \times 10^9$ adenoviral particles. After 24 hours, analysis of the extract from these hepatocytes resulted in the conversion of 2.2% of the phenylalanine substrate to tyrosine, as compared to 0.3% conversion with extracts from the untreated PAH-deficient mouse hepatocytes. When the deficient hepatocytes are incubated with 15 μg and 30 μg of DNA in complex form, the amount of phenylalanine conversion increases to 20% and 26% respectively, which is comparable to the activity that occurs in extracts from normal mouse hepatocytes.

To show that the presence of hPAH activity was due to the DNA/Protein complex and not due to non-specific uptake of the increased level of DNA, the hepatocytes were incubated with $3 \times 10^9$ adenoviral particles along with 30 μg of free CMV/hPAH DNA. The results of the analysis showed that no increase in activity occurs over the activity in the PAH deficient hepatocytes with only a 0.3% conversion of phenylalanine to tyrosine, confirming that the uptake occurs specifically through the presence of the DNA/Protein complex.

Receptor-Mediated Uptake of ASOR/Spermine/ DNA Complexes in Primary Hepatocytes ASOR and spermine complexes were coupled as described above using 1-ethyl-3-(3-dimethylaminopropyl) carbodiimide (EDC). The conjugate is purified and fractions from the FPLC analyzed on SDS-PAGE gel for fractions containing modified ASOR (ASOR/spermine). Fractions are then pooled and dialyzed prior to complex formation. The DNA plasmid CMV/B-gal containing the *E. coli* β-galactosidase gene under the control of the CMV enhancer and promoter and the DNA plasmid CMV/hPAH containing the human phenylalanine hydroxylase cDNA under the control of the CMV enhancer and promoter were used as reporter genes. All plasmids were isolated and purified by double CsCl banding. Conjugate/DNA complexes were prepared by diluting both the conjugate and DNA in HBS (150 mM NaCl per 20 mM HEPES, pH 7.3). The diluted DNA was added directly to the diluted conjugate while mixing. The reaction was allowed to incubate at room temperature for 30 minutes before analysis. Immediately following the incubation, all complexes were analyzed on agarose gels and electrophoresed in TBE, or added directly to hepatocytes for uptake analysis.

Before adding the complex to the hepatocytes, the complete media was removed from the cells and replaced with 1 ml of Low Glucose DMEM containing, 5 mM $Ca^{2+}$ and 2% fetal calf serum. DNA in complex form was then added to the hepatocytes, followed by the immediate addition of the appropriate amount of adenovirus stock. After a 2 hour incubation at 37° C., 1.5 ml of complete media was added to the hepatocytes and the incubation continued for 24 hours at 37° C. The analysis of β-galactosidase (β-gal) activity was done by staining the cells, using X-gal as a substrate. To quantify the actual amount of β-galactosidase produced, ONPG was used as a substrate with aliquots of cell extracts. Phenylalanine hydroxylase activity in cells extracts was measured as the percent conversion of phenylalanine to tyrosine from cell extracts. Protein concentration in cell extracts was determined by the BCA Micro-Protein assay.

As noted above, the complexes were incubated with primary hepatocytes for 24 hours, after which time, the hepatocytes were analyzed for β-galactosidase activity. The results of X-gal staining showed few or no blue hepatocytes. The replication defective adenovirus d1312 was incorporated into the analysis to increase the efficiency of DNA delivery and expression in the cells. The complex was incubated with hepatocytes and with increasing adenoviral titer.

When the hepatocytes are incubated with both the complex and increasing titers of adenovirus, there is a correlative increase in the number of blue cells after X-gal staining. To determine quantitatively the amount of β-galactosidase being produced, ONPG analysis was done on cellular extracts from the hepatocytes that had been incubated with complex only, adenovirus only, or with the complex and increasing titers of adenovirus. In addition, expression of hPAH after receptor-mediated gene delivery to deficient hepatocytes was determined as discussed above.

Preparation and Cellular Uptake of ASOR/Nuclear Ligand/DNA Complexes

The nuclear ligand peptide GYGPPKKKRKVEAPYKA(K)$_{40}$WK (SEQ ID NO: 60) was coupled to PLL to form the nuclear binding molecule by the same procedures as described above. This peptide contains a tyrosine for incorporation or $^{125}$I to quantify binding parameters and to determine stiochiometry of the DNA complex. Binding of the peptide to DNA quenches tryptophan fluourescence and allows the kinetics and thermodynamics of complex formation to be determined. The function of the EAP sequence is to extend the nuclear localization sequence at right angles to the PLL backbone. The peptide is homogeneous by reversed phase HPLC and has the expected molecular weight, determined by fast atom bombardment mass spectroscopy.

ASOR-PLL complexes were prepared as described above. The DNA plasmid CMV/B-gal containing the *E. coli* β-galactosidase gene under the control of the CMV enhancer and promoter and the DNA plasmid CMV/hPAH containing the human phenylalanine hydroxylase cDNA under the control of the CMV enhancer and promoter were used as reporter genes. All plasmids were isolated and purified by double CsCl banding. ASOR/nuclear ligand/DNA complexes were prepared by diluting the ASOR-PLL and nuclear ligand-PLL conjugates in HBS (150 mM NaCl per 20 mM HEPES, pH 7.3) and diluting the DNA in HBS. The diluted DNA was added directly to the diluted conjugate while mixing. The reaction was allowed to incubate at room temperature for 30 minutes before analysis. Immediately following the incubation, all complexes were analyzed on agarose gels and electrophoresed in TBE, or added directly to hepatocytes for uptake analysis.

Before adding the complex to the hepatocytes, the complete media was removed and replaced with 1 ml of Low Glucose DMEM containing, 5 mM $Ca^{2+}$ and 2% fetal calf serum. DNA in complex form was then added to the hepatocytes, followed by the immediate addition of the appropriate amount of adenovirus stock. After a 2 hour incubation at 37° C., 1.5 ml of complete media was added to the hepatocytes and the incubation continued for 24 hours at 37° C. The analysis of β-galactosidase (β-gal) activity was done by staining the cells, using X-gal as a substrate. To quantify the actual amount of β-galactosidase produced, ONPG was used as a substrate with aliquots of cell extracts. Phenylalanine hydroxylase activity in cells extracts was measured as the percent conversion of phenylalanine to tyrosine from cell extracts. Protein concentration in cell extracts was determined by the BCA Micro-Protein assay.

As noted above, to assess if the complexes formed were capable of being internalized and also allowed expression of the DNA, the complexes were incubated with primary hepatocytes for 24 hours, after which time, the hepatocytes were analyzed for β-galactosidase activity. The results of X-gal staining showed few or no blue hepatocytes.

To increase the efficiency of DNA delivery and expression in the cells, the replication defective adenovirus dl312 was incorporated into the analysis. The complex was incubated with hepatocytes and with increasing adenoviral titers. The results of the analysis show that the adenovirus alone or the complex alone do not produce any blue staining cells, but hepatocytes can be quantitatively stained when adenoviral particles are used. When the hepatocytes are incubated with both the complex and increasing titers of adenovirus, there is a correlative increase in the number of blue cells after X-gal staining. To determine quantitatively the amount of β-galactosidase being produced, ONPG analysis was done on cellular extracts from the hepatocytes that had been incubated with complex only, adenovirus only, or with the complex and increasing titers of adenovirus.

Delivery of DNA into the nucleus is determined by using radiolabeled amino acids. The nuclear ligand is labeled with C14 by procedures well known in the art. The nuclear fraction is then isolated by separation techniques known in the art. Radioactivity levels are measured to determine delivery of DNA to the nucleus.

Potocytosis Mediated DNA Delivery

The ability of DNA/folate/adenovirus complexes were analyzed for delivery of DNA directly into the cytosol of cells. Folate was activated with 1-ethyl-3-(3-dimethylamino-propyl)carbodiimide (EDC) in dimethylsulfoxide and was then coupled under hydrous conditions to poly-L-lysine (PLL) under procedures as described above. Adenovirus was attached to PLL with the help of EDC under conditions which inactivates the adenovirus binding domain for its receptor, but leaves the endosomal lysis domain intact. The DNA/folate/adenovirus complexes were used to deliver the *E. coli* β-galactosidase gene into human epidermoid carcinoma cell line (KB). Twenty-four hours after addition of the complex to the cells, histological staining showed that 20–30% of the cells could be positively stained with X-GAL.

In addition to DNA, other macromolecules including RNA, proteins, lipids and carbohydrates can also be delivered into the cytosol using this delivery system. Folate can also be exchanged by other ligands that are taken up into the cells by caveolae. Other water soluble molecules are taken up into cells via this mechanism as well. The adenovirus can also be replaced by other endosomal or potosomal lysis agents, including but not limited to, viruses, bacteria, proteins, peptides and lipids.

Efficient Non-Viral DNA Delivery with the Endosomal Lysis Agent Listeriolysin

A nucleic acid transporter was formed using the above-described methods. Listeriolysin are only a part of the toxin, harboring the active site, was coupled to PLL. In addition, asialoglycoprotein was coupled to PLL as described above. The DNA/ASOR/LIS complexes were then tested in mammalian cells in vitro and in vivo. DNA was delivered directly into the cells through receptor-mediated endocytosis and was capable of escaping the endosome due to the listeriolysin. Gene expression was elevated in the cytoplasm and the nucleus as compared to use of a DNA/ASOR complex without the use of listeriolysin. As discussed above, the hepatocytes express specifically the asialoglycoprotein receptor which recognizes the asialooromucoid protein used in the DNA complex described herein. The asialooromucoid protein is delivered to the cell interior via receptor-mediated endocytosis.

The listeriolysin toxin forms pores in the endosomal membrane. The diameter of the pores are between 50–100 nanometers (nm), which is large enough for macromolecules to pass through. The pH optimum for listeriolysin is between pH 5.5–7.0. The listeriolysin is membranolytic active between these pHs. The harboring active site which can be used with the above-described procedure, is located in the C-terminal region of listeriolysin. Although the above efficiency of DNA delivery is tested in hepatocytes, listeriolysin can be coupled with other ligands to form nucleic acid complexes and used for nucleic acid delivery to other cell types, depending only upon the ligand being used. Furthermore, all similar microbial toxins and their active subfragments can be incorporated into the nucleic acid complexes for endosomal escape.

Preparation of Folate Labeled Conjugates and DNA/Folate Complexes

Folic acid was dissolved in dimethyl sulfoxide and incubated with an 10 fold excess of 1-ethyl-3-(3-dimethylaminopropyl)carbodiimide (EDC) for 30 min at room temperature. A 30-fold excess of the activated vitamin was added to $^{125}$I-bovine serum albumin (BSA) (89 kBq/μg;NEN) in phosphate buffer and incubated for 4 hours at room temperature. The reaction was quenched with a 50-fold excess of ethanolamine and free folate was separated from the $^{125}$I-BSA-folate conjugate by passing the reaction mixture over a Sephadex G-25 column equilibrated with phosphate buffered saline, pH 7.4. To estimate the number of folate molecules coupled to BSA under these conditions the same protocol was used with the exception that $^{3}$H-folic acid (2.01 Gbq/mmol;NEN) was used with unlabeled BSA. A similar protocol was used to couple folate to poly-L-lysine ($M_r$-20,500) with a molar ratio of activated vitamin to poly-L-lysine of 2 to 1. After purification the folate/poly-L-lysine conjugate was dialyzed against 150 mM NaCl, 20 mM Hepes, pH 7.3 (HBS).

The DNA plasmid CMV/β-gal containing the *E. coli* β-galactosidase gene under the control of the early CMV enhancer and promoter was used as a reporter gene. DNA/folate complexes were prepared by diluting the folate/PLL conjugate in 150 μl HBS to which 6 μg DNA (in 350 μl HBS) was added. After 30 minutes of incubation at room temperature the complexes were analyzed on 0.8% agarose gels or added directly to cells for further analysis.

Uptake of $^{3}$H-Folate and Folate Conjugated $^{125}$I-BSA Into Cells

KB, Hela, Caco-2, SW620 and SKOV-3 cells were purchased from the American Type Tissue Collection (ATCC) and maintained in Dulbecco's modified Eagle's medium (DMEM) supplemented with 10% fetal calf serum, penicillin (100 units/ml) streptomycin (100 μg/ml), and 2 mM L-glutamine. For the culture of Caco-2 cells nonessential amino acids were added. The cells were grown for two passages in folate deficient DMEM containing the above-mentioned supplements 8 to 10 days before each experiment. Normal DMEM has a folate concentration 1000 fold above in vivo levels. The supplemented folate deficient DMEM has sufficient folate to sustain cell growth.

Cells were incubated for up to 2 hours with 25 nM $^{3}$H-folic acid. At the indicated time points the cells were washed once with ice cold PBS, followed by a 30 sec wash with ice cold acid saline (0.15 M NaCl, adjusted to pH 3.0 with glacial acetic acid) to remove surface bound folate and then harvested by scraping in ice cold PBS. The cells were pelleted, washed with PBS, and then dissolved in 0.1 M NaOH. One-half was used for protein determination (BCA-Protein assay) and the other half was counted in a scintillation counter. For $^{125}$I-BSA-folate uptake the KB cells were incubated with 1–10 μg $^{125}$-BSA-folate/ml for 2 hours. Cells were harvested to determine internalized radioactivity using the protocol described for folic acid. For competition a 100 fold molar excess of folate was added prior to incubation with the DNA complexes.

Analysis of DNA Complex Uptake in KB, Hela, Caco-2, SW620, and SKOV-3 cells

The cells were harvested 24 hours prior to each experiment and 2×10$^5$ cells per well were plated in a 6 well plate, to give about 3–4×10$^5$ cells per well on the day of the experiment. Before adding the complexes to the cells the media was replaced by 1 ml of folate deficient DMEM without supplements. 3 μg of DNA in the form of DNA/folate complexes were incubated with the cells for 2 hours and after addition of 2 ml of regular folate deficient media the incubation was continued for 24 hours. For experiments using adenovirus, 3–4×10$^8$ viral particles were added immediately after the addition of the DNA/folate complexes to the media. The analysis of β-galactosidase activity was done by using X-gal as a substrate for staining and for quantification of the β-galactosidase activity o-nitrophenylgalactose (ONPG) was used. For competition experiments, a 100 fold molar excess of folate was added prior to incubation with the complexes.

Uptake of Folate and Folate Conjugated BSA in KB Cells

Figure 30:
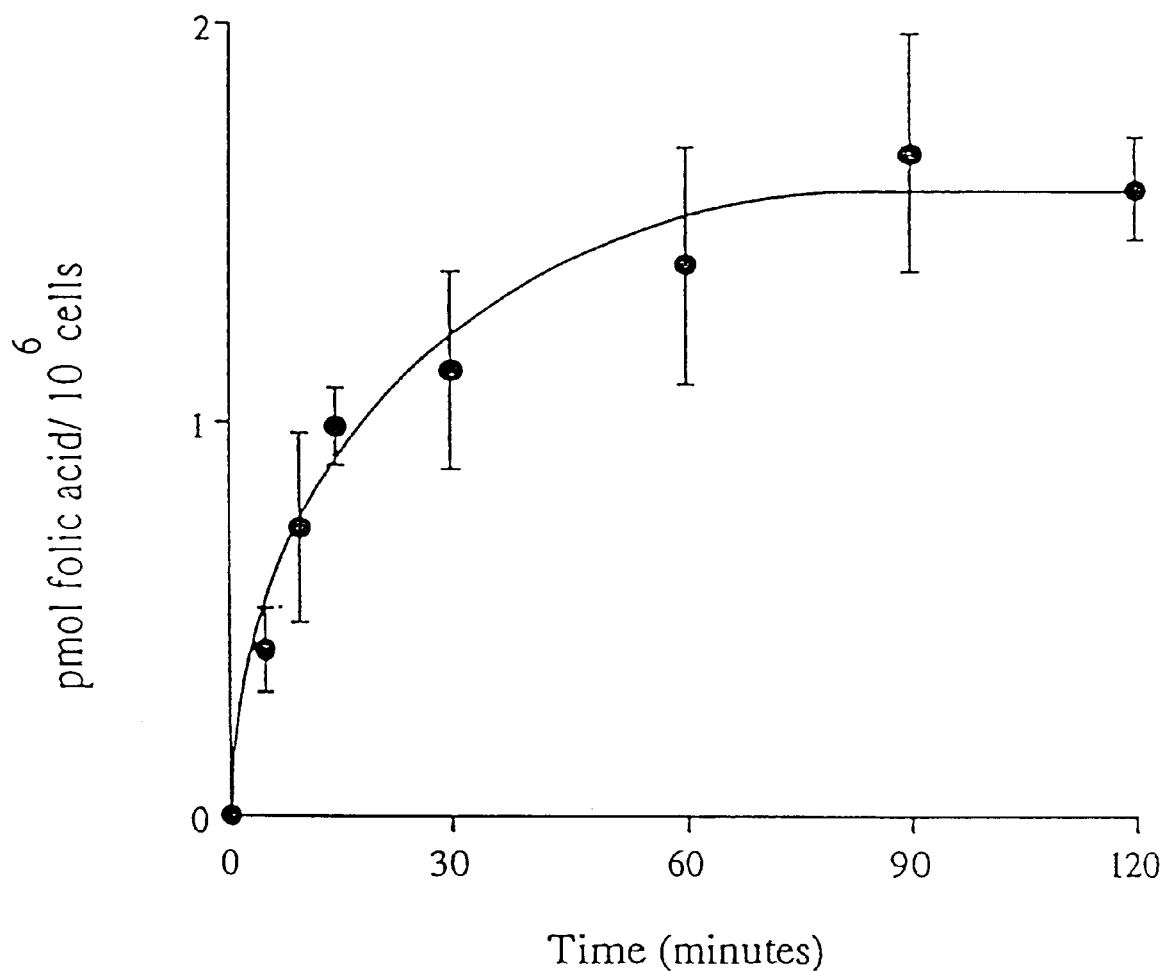
FIG. 30 is a time course analysis of $^3$H-folic acid uptake in KB cells.

Folate uptake studies were conducted with a physiological concentration of extracellular folate, ranging between 5 to 50 nM. To show that KB cells internalize folic acid, cells were incubated with 25 nM $^{3}$H-folic acid, with samples taken at 0, 15, 30, 60, 90, and 120 minutes. The cells were isolated to measure the internalized $^{3}$H-radioactivity. Within 120 minutes of incubation the uptake of $^{3}$H-folic acid reached saturation and a maximum of 1.5 pmol folic acid/ 10$^6$ cells became internalized (FIG. 30).

Figure 31:
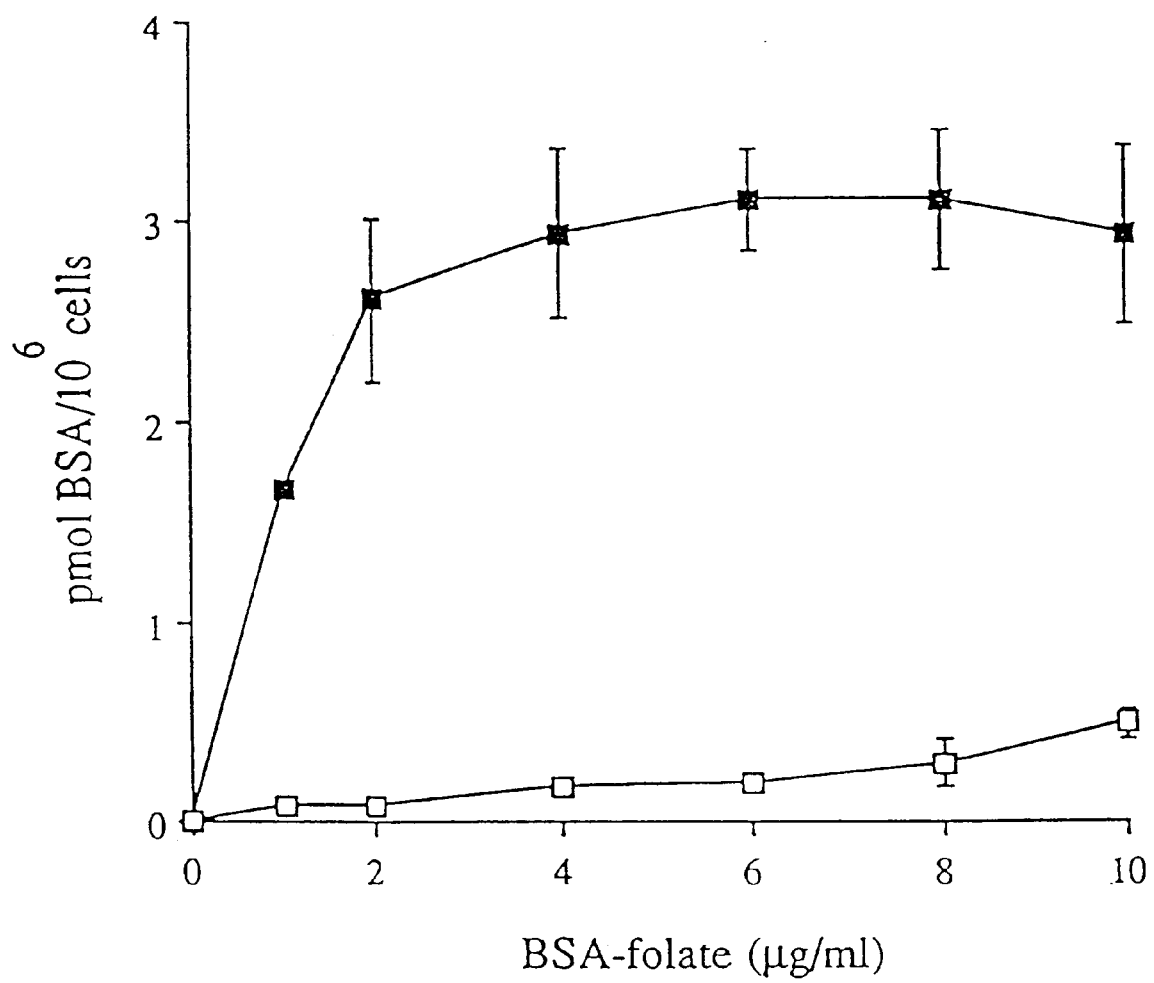
FIG. 31 is a time course analysis of $^{125}$I-BSA folate uptake in KB cells.

To confirm that conjugation of folic acid to a macromolecule does not impair recognition of folate by its receptor, folic acid was covalently coupled to $^{125}$I-BSA with the water soluble carbodiimide EDC. Under these coupling conditions an average of 3 folate molecules were conjugated to BSA as based on $^{3}$H-folate content. KB cells were incubated for 120 minutes with increasing concentrations of $^{125}$I-BSA-folate and after cell isolation internalized $^{125}$I-radioactivity was measured (FIG. 31). The uptake of $^{125}$I-BSA-folate was saturable at a BSA concentration between 2 and 4 μg/ml (FIG. 31; closed squares). To show that the BSA uptake is specific for folic acid, the experiment was repeated in the presence of a 100 fold molar excess of folate. Under these conditions more than 90% of the cellular uptake of $^{125}$I-BSA-folate was inhibited (FIG. 31; open squares).

Delivery of DNA/Folate Complexes in KB Cells

Figure 32:
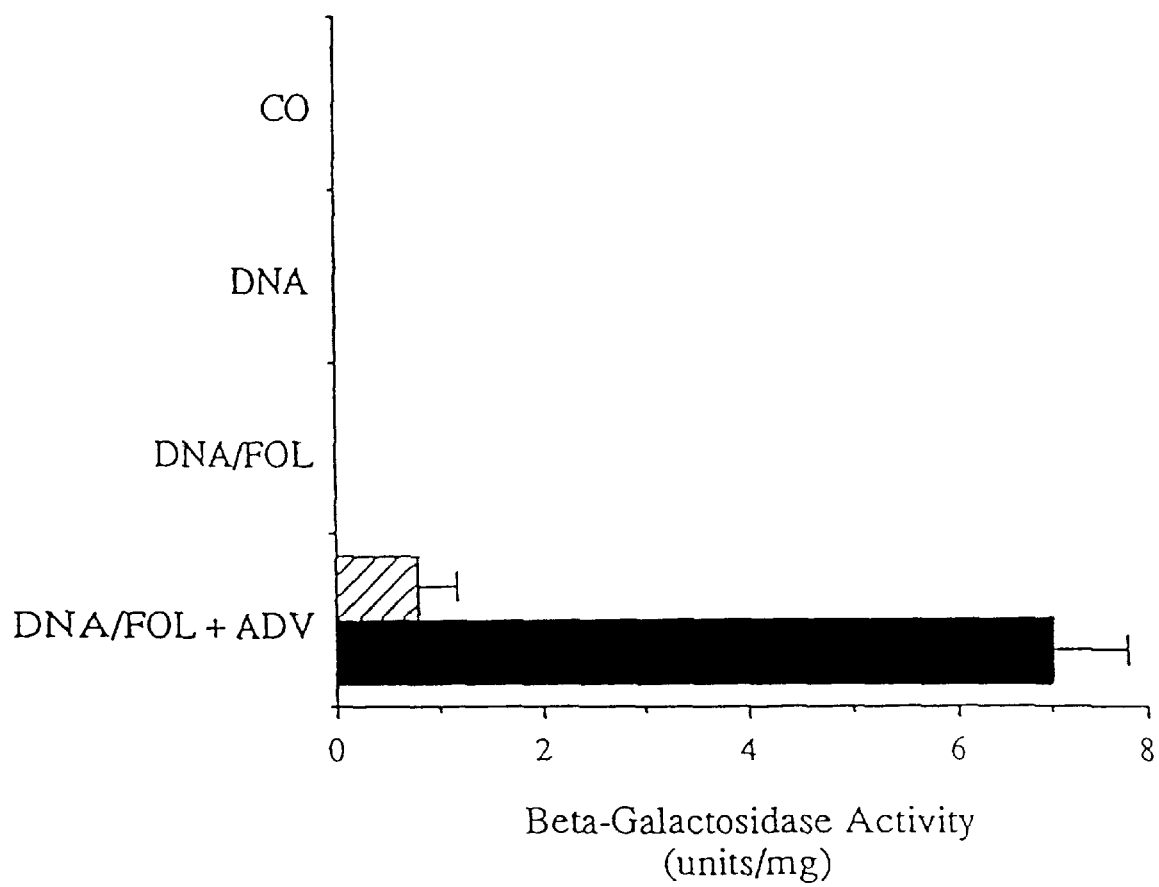
FIG. 32 is a quantitation of β-galactosidase expression in KB after gene delivery.

Folic acid was conjugated to poly-L-lysine as described for BSA to give folate/poly-L-lysine conjugates containing 1–2 folates per poly-L-lysine (PLL) molecule. Increasing concentrations of the folate/PLL conjugate were incubated with DNA and the extent of DNA/folate/PLL complex formation was determined by agarose gel electrophoresis. Based on charge neutralization, as shown by reduction of the electrophoretic mobility of the DNA, the interaction between folate/PLL conjugate and DNA could be detected at a molar ratio of 10 to 1. The movement of the DNA was completely retarded at a molar PLL/DNA ratio of greater 100 to 1. To assess if these complexes could be internalized to allow DNA expression in KB cells, the *E. coli* β-galactosidase gene was used as a reporter gene. Twenty-four hours after addition of the complex to the cells histological staining showed that less than 0.1 of the cells were positively stained with X-gal. To determine quantitatively the β-galactosidase gene expression ONPG analysis was done on cellular extracts, showing less than 0.005 units β-galactosidase activity per mg protein (FIG. 32).

To determine if adenovirus enhanced gene delivery via the folate receptor internalized through caveolae, replication-defective adenovirus dl312 was incorporated in the protocol. KB cells ($4\times10^5$) were incubated with DNA/folate complexes in the presence of $4\times10^8$ viral particles and twenty-four hours later the cells were analyzed for β-galactosidase expression. With X-gal staining approximately 20 to 30% of the cells were positively stained blue, a dramatic increase in comparison to DNA/folate complexes alone. Quantitative ONPG-analysis on cellular extracts showed 7.0 units of β-galactosidase activity per mg protein, corresponding to an at least 1000 fold increase of activity. The majority of DNA uptake occurred specifically through the folate receptor, since it was competable by a 100 fold excess of free folate (FIG. 32).

Delivery of DNA/Folate Complexes into Tumor Cells Overexpressing the Folate Receptor To show that folate mediated gene delivery is not restricted to KB cells, other tumor cell lines were selected (Hela, Caco-2, SW 620, and SKOV3 cells), which all overexpress the folate receptor. To determine if the cell lines could take up folic acid, cells were incubated with 25 nM $^3$H-folic acid for two hours, after which internalized $^3$H-radioactivity was determined. Internalization of folic acid by Hela cells was similar to that of KB cells. By contrast the amount of folic acid internalization in Caco-2, SW620, and SKOV-3 cells was ten to twenty fold lower. This difference in uptake corresponds very well to the differences in mRNA levels of the folate receptor, which have been determined for Hela, Caco-2, and SKOV-3 cells.

Figure 33:
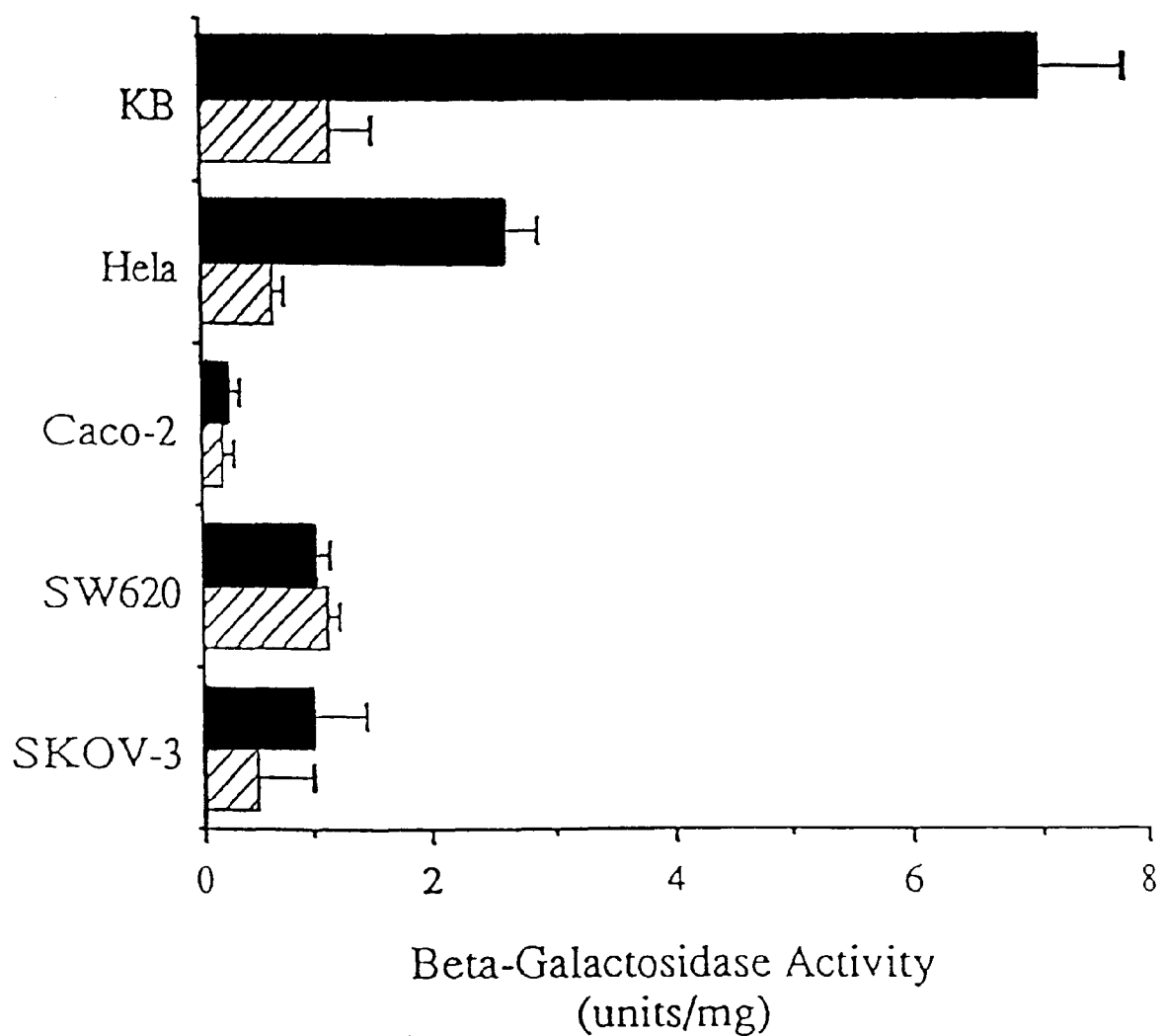
FIG. 33 is a quantitation of folate mediated gene delivery in tumor cells.

Hela, Caco-2, SW620, and SKOV-3 cells were incubated with DNA/folate complexes in the presence or absence of replication-defective adenovirus as described for KB cells. After 24 hours incubation the β-galactosidase activity was determined on cellular extracts by using ONPG analysis. Without replication-defective adenovirus less than 0.005 units β-galactosidase activity per mg protein was detected in all four cell lines. Coincubation with replication-defective adenovirus caused an at least 500 fold increase of β-galactosidase activity only in Hela cells, which was specific for folate, since it was competable by a 100 fold excess of free folate (FIG. 33). By contrast, replication-defective adenovirus did not cause a folate specific enhancement of β-galactosidase activity in Caco-2, SW620, and SKOV-3 cells (FIG. 33).

To exclude the possibility that this result is due to differences in the susceptibility of the cell lines to adeno-viral infection, the efficiency of viral infection was determined with the help of a recombinant adenovirus expressing the *E. coli* β-galactosidase gene. The recombinant adenoviral vector Ad.RSVBgal containing β-galactosidase under the transcriptional control of the RSV-LTR promoter is a replication-deficient human adenovirus. Adenovirus was prepared as described in the art. Briefly, this involved growing 293 cells in 150 mm petri-dishes in Dulbecco's Modified Eagle's Medium with high Glucose (HGDMEN) supplemented with penicillin/streptomycin, glutamine and 10% fetal calf serum. At a confluency of 90%, the media is removed and replication-defective adenovirus at a PFU of 10 per cell is added in 5 ml of media onto the cells. Next, the cells are incubated at 37° C. and every 15 min the plates are gently rocked to redistribute the media over the entire plate. After 1 hour of incubation 15 ml of media is added to each plate and the plates are incubated for 36–48 hr. The cells are harvested and the virus is then purified by two rounds of cesium chloride ultracentrifugation. The purified virus was dialysed in 10 mM Tris HCl (pH 7.4), 1 mM $MgCl_2$ and stored at 4° C. in CsCl for immediate use. Viral titers were determined by O.D. (particles per ml) and by plaque assay. In most experiments the plaque titer was within one log of the O.D. titer.

$4\times10^5$ KB, Hela, Caco-2, SW 620, and SKOV-3 cells were incubated with $4\times10^8$ viral particles and after 24 h the cells were stained with X-gal. For all five cell lines greater than 95% of the cells stained blue, indicating an equal susceptibility towards adenovirus infection. Therefore, folate mediated DNA delivery does not only require a membrane disruption agent, but is also dependent on high levels of expression of the folate receptor.

Adenovirus Modification and DNA Complex Formation

Freshly isolated adenovirus, as described above, ($1.4\times10^{11}$ particles) was combined with Poly-1-Lysine (PLL) M.W.-20,500, at a concentration of 16 μM, along with 1-ethyl-3-(3-dimethylaminopropyl)carbodiimide (EDC) at a final concentration of either 130 μM (low EDC) or 2600 μM (high EDC) in a final volume of 4 milliliters. After incubation on ice for four hours after which time, the unreacted components were removed by ultra-centrifugation (150,000 ×g) for 18 hours on a CsCl gradient at a CsCl concentration of 1.35 g/ml. The adenovirus was then either dialyzed against 2M NaCl and then stored at −20° C. in 10% glycerol or stored in 10% glycerol.

The DNA used in complex formation was either the plasmid pCMV/βGal, which contains the beta-galactosidase gene under the control of the CMV enhancer and promoter or the plasmid pCMV/cFIX. This plasmid was constructed as follows. The canine factor IX (cFIX) cDNA (kozak translation sequence constructed as known in the art) was cloned into the Xho I/Cla I sites of the spCMV plasmid. The Xho I/Sal I fragment containing the CMV promoter-enhancer and factor IX cDNA was then cloned into the Xho I site of the N2 retroviral vector in the forward orientation. All plasmid DNA was purified by banding twice in CsCl gradients.

The modified ADV-PLL/DNA complexes were made in a two step procedure. The first step involved the addition of 10 μg of DNA, in 250 μl of HBS, to the ASOR/PLL conjugate in 250 μl, with continuous mixing, followed by incubation at room temperature for 30 minutes. The ASOR/PLL conjugate was synthesized and purified as before. Sufficient ASOR/PLL conjugate to neutralize 75% of the charge on the DNA molecule was used. The second step involved the addition of the modified adenovirus, in 330 μl of HBS, to the DNA/ASOR/PLL mixture, with continuous mixing, followed by incubation for an additional 30 minutes at room temperature. After complex formation, the complexes were either analyzed by electron microscopy or added to the hepatocytes for analysis.

Analysis of Complex Uptake and Expression in Primary Hepatocytes

Hepatocyte isolation from 10–12 week old C57-B6 mice was done by collagenase perfusion. The hepatocytes were plated at a density of 3×10⁵/well in 6 well Primaria plates and grown in 2 ml of Low Glucose complete media (Low Glucose DMEM, 10% fetal calf serum, 10 mM HEPES, 0.5% MEM amino acids, 2 mM glutamine, 100 units/ml penicillin, and 100 μg/ml streptomycin). All uptake studies in hepatocytes were done within 2–4 hours after the hepatocytes were plated, allowing for the hepatocytes to attach to the surface. Before adding the DNA complexes to the hepatocytes, the complete media was removed and replaced with 1 ml of Low Glucose incomplete media (Low Glucose DMEM containing, 5 mM $Ca^{+2}$ and 2% fetal calf serum). The modified adenovirus/DNA complexes were incubated with cells in incomplete media for 2 hours at 37° C. in a $CO_2$ incubator, after which the media was removed and replaced with 1 ml of media and the incubation was allowed to continue at 37° C. in a $CO_2$ incubator.

The analysis of β-galactosidase (β-gal) activity was done by staining the cells, using X-gal as a substrate. The measurement of factor IX levels were analyzed from the supernatants of cultured hepatocytes that were incubated in media for various times. The levels of cFIX in the samples were determined according to a protocol known in the art, utilizing an ELISA based assay. Protein concentration in cell extracts was determined by the BCA Micro-Protein assay.

Receptor Mediated Endocytosis and Adenoviral Mediated Endosomal Release of DNA The ASOR in the ASOR-PLL/DNA complex functions as a receptor ligand to target the DNA to hepatocytes, while the PLL functions to attach DNA to ASOR through ionic interactions. To achieve efficient cellular delivery of DNA without subsequent lysosomal degradation, the complex can be co-incubated with a replication defective adenovirus. A fraction of the DNA toroids and the adenovirus are internalized in the same endosome, leading to the release of the DNA from the endosome, escaping lysosomal degradation. To reduce the viral titers while enhancing the efficiency of DNA delivery, the adenovirus can be coupled directly to the DNA complex. As a result, the ASOR-PLL/DNA/PLL-ADV complex is co-internalized, either through the adenovirus receptor or the ASOR receptor. After co-internalization, the adenovirus causes endosomal lysis and results in the release of the ASOR/PLL/DNA complex into the cytoplasm.

Ultra-Structure of ADV-PLL/DNA Complexes

The ultra-structure of the ADV-PLL/DNA complexes was determined by electron microscopy. When the ASOR-PLL conjugate is combined with DNA in the proper ratio to achieve charge neutralization on the DNA molecule, a DNA toroid results. After conjugation with PLL, the adenoviral particle retains its natural structure. When the PLL conjugated ADV is incubated with DNA toroids, complexes between DNA toroids and adenoviral particles are formed. When PLL is conjugated to the adenoviral particle at low concentrations of EDC and used in DNA complex formation, the viral particles are linked to DNA toroids in limited numbers. The coupling of a DNA toroid with 1–3 adenovirus particles, usually occurs in the coupling procedure and gives a complex that is less than 200 nm in size. When PLL is conjugated to adenovirus under high EDC concentrations and then used for complex formation, however, multiple viral particles bound to the DNA toroids are frequently observed. These complexes are greater than 200–300 nm in diameter.

Dose Response of Adenovirus/DNA Complexes on Primary Hepatocytes

To analyze the ability of the ADV-PLL/DNA complexes to deliver DNA, primary mouse hepatocytes were used as recipient cells to measure gene expression. Primary hepatocytes (3×10⁵) were incubated with increasing titers of adenovirus, ranging from 0 to 10³ particles in free and conjugated forms. When the cells were incubated with ASOR-PLL/DNA complexes along with free adenovirus, the percentage of cells that express β-gal was 9% when 10³ particles/cell was used. The amount of free virus that is needed to transduce 100% of cells is 10⁴ particles/cell. In contrast, when adenovirus conjugated with PLL at low EDC concentrations was used at 10³ adenoviral particles/cell, the percentage of cells staining positive for beta-gal reached 100%. When adenovirus conjugated with PLL at high EDC concentrations was used, 80% of cells stained blue at 10³ particles/cell.

To determine the percentage of cells that internalized DNA specifically through the ASOR receptor, the same dose response analysis was done as before, but in the presence of a 1000-fold excess of free ASOR. The cells incubated with ASOR-PLL/DNA complexes and free adenovirus showed a decrease in the percentage of cells expressing β-gal to less than 2%, when 10³ particles/cell was used, demonstrating that most of the DNA uptake specifically occurred through the ASOR receptor. Competition of the complex containing adenovirus conjugated with PLL at low EDC concentrations showed a minimal decrease in the percentage of cells staining positive for beta-gal from 100% to about 80% at 10³ adenovirus particles/cell. This result shows that the majority of the DNA uptake of this complex into recipient cells was through the adenovirus receptor. When the adenovirus conjugated with PLL at high EDC concentrations was used however, the percentage of cells staining blue decreases from 80% to less than 30%, when 10³ particles/cell are used, indicating that the majority of the DNA delivered by this complex occurs through the ASOR receptor.

To further determine the basis for uptake by these complexes, the ADV-PLL/DNA complex was made with PLL instead of the ASOR-PLL conjugate and then incubated with cells. This complex, when used to deliver DNA in the presence of free adenovirus resulted in less than 2% of the cells staining positive for Beta-gal. When the low EDC modified adenovirus was used the percentage of blue cells was 80% at 10³ particles/cell. When this was done with the high EDC modified adenovirus, the percentage of blue cells was 37% at 10³ particles/cell. The results were in complete agreement with the competition experiment, suggesting that the residual uptake is due to other interactions between the adenovirus and the cells. Analysis of the cytopathic effect of the complexes on the cells after a 96-hour incubation showed no toxic effects when either the low or high EDC modified ADV-PLL/DNA complexes were used at 10³ particles/cell.

In studies with adenovirus coupled to PLL and included in a DNA/ASOR-PLL complex, the controls confirmed endocytosis by the asialoglycoprotein receptor and not the adenovirus receptor. Uptake of the DNA/ASOR-PLL/adenovirus-PLL complex by hepatocytes gave results identical to those observed with ten-fold higher free virus. With adenovirus/PLL in the DNA complex, little if any cytopathic effect was found after prolonged incubations. SDS gel analysis showed extensive cross-linking of viral proteins by the carbodiimide, therefore, the role of adenovirus is limited to endosome lysis.

Expression of Canine Factor IX in the Primary Mouse Hepatocytes

Figure 34:
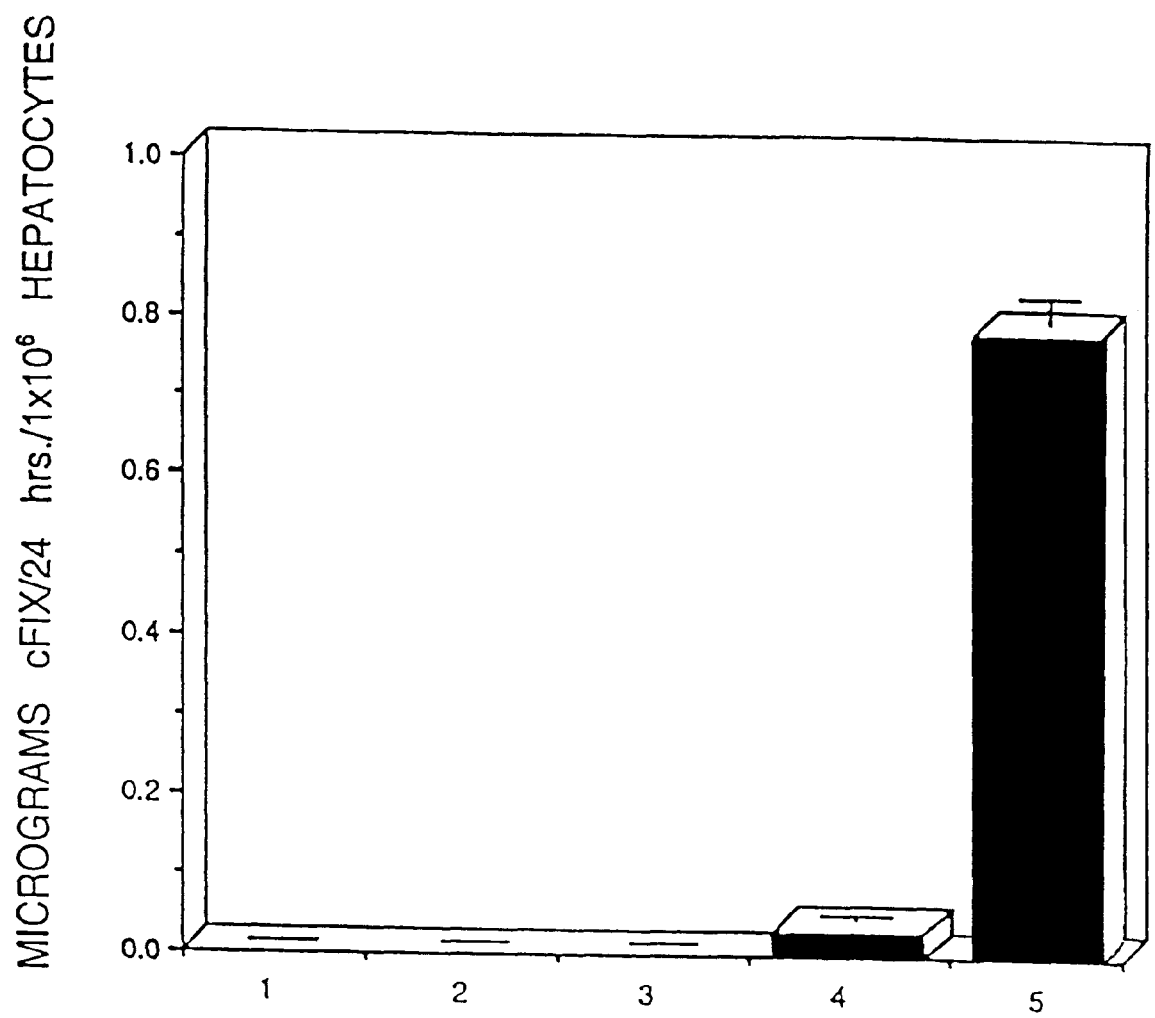
FIG. 34 is a representation of Factor IX expression after nucleic acid delivery to primary hepatocytes by ADV-PLL/DNA complexes.

To quantitatively compare the levels of gene expression achieved with the ADV-PLL/DNA complexes with those achieved with the free adenovirus, the complexes were used to deliver a canine factor IX (cFIX) cDNA into primary mouse hepatocytes (FIG. 34). Adenovirus modified with high EDC concentrations was used to deliver the DNA, since the complexes made with this conjugated adenovirus deliver the DNA primarily through the ASOR receptor. No cFIX activity was observed when the adenovirus alone was used (FIG. 34, Lane 2). When DNA in toroid form was used along with free adenovirus at a titer of $10^3$ particles/cell, the level of cFIX increased to 0.032 μg/$10^6$ cells/24 hours (FIG. 34, lane 4). In contrast, when the conjugated adenovirus was used to deliver DNA at $10^3$ particles/cell, the levels of cFIX increase to 0.79 μg/$10^6$ cells/24 hours (FIG. 34, lane 5). This represents a 25-fold enhancement of cFIX expression over that achieved with the complex and free adenovirus at the same titer.

The above nucleic acid transporter system can be used to deliver cFIX gene to Hemophilia B dogs. Administration of the appropriate concentration of the transporter to obtain a final concentration of 2–5 ng/ml of cFIX in the plasma of treated dogs will result in partial phenotypic correction of hemophilia B. The same can be utilized with the Factor IX gene for hemophiliacs. Likewise, the above transporter system can be used for treating other metabolic disorders such as phenylketonuria and familial hypercholesterolemia.

Use of Perfringolysin O ("PFO") as a Lysis Agent
Dose Response of PFO

Figure 35:
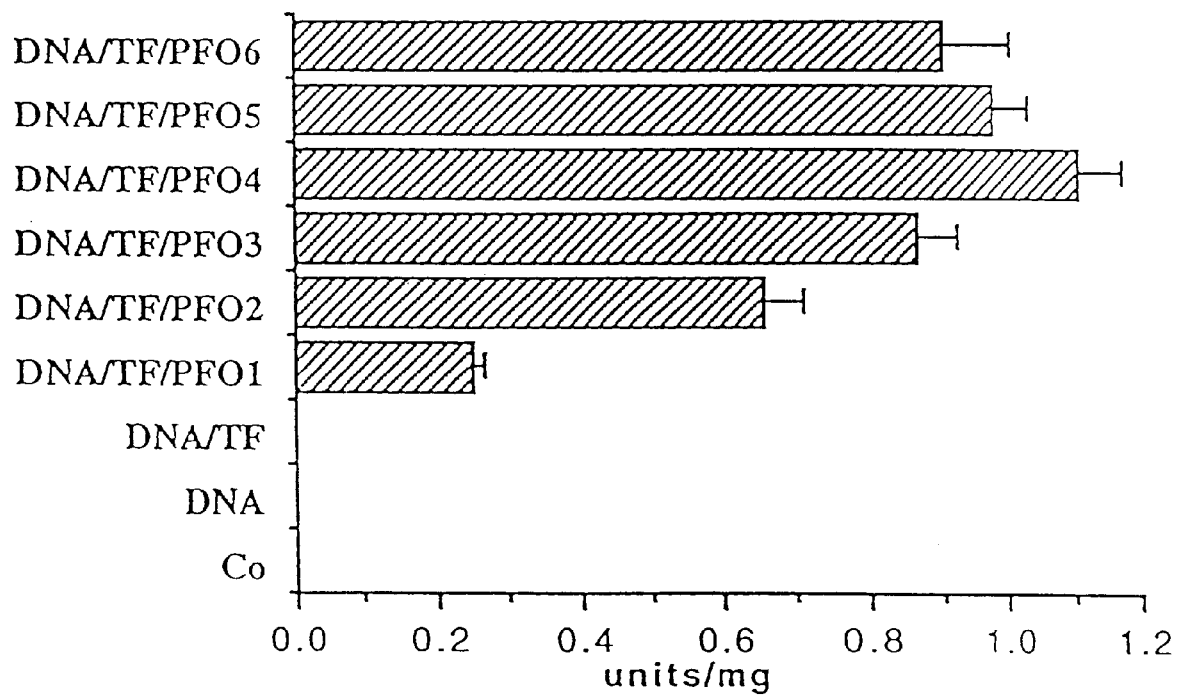
FIG. 35 is a representation of β-galactosidase expression after nucleic acid delivery by Transferrin/DNA/PFO complexes.

Sol 8 (muscle cell line) cells were incubated with DNA/Transferrin Perfringolysin O (DNA/TF/PFO) complexes. The DNA plasmid CMV/β-Gal, which contains the *E. coli* β-galactosidase gene, as described above, was used. The DNA/TF/PFO complex was prepared as described above. TF and PFO were conjugated with PLL using the techniques discussed above. 3 μg DNA/TF/PFO complex was added to 5×$10^5$ cells and after 24 hours the cells ONPG-Analysis was done (FIG. 35). PFO1 to PFO6 represent increasing amounts of PFO in the complexes. β-gal activity increased from PFO1 to PFO4. Above PFO4 the specific β-gal activity goes down due to toxic effects of PFO. Toxicity can be avoided by using Listeriolysin O. Comparison of DNA/TF/PFO to DNA/PFO complexes shows that approximately 50% of the β-gal activity is independent of transferrin.

Dose Response of DNA/TF/PFO Complexes

Using the complexes above, 3, 4.5 or 6 μg of the DNA/TF/PFO was added to 5×$10^5$ cells and β-gal activity was assayed 24 hours later. An increase of β-gal activity is seen for both complexes. Quantitative analysis of β-gal expression using DNA/TF/PFO4 provided over 25% of the cells to exhibit β-gal activity. DNA/TF/PFO3 exhibited over 20% β-gal activity.

Comparison of PFO and Adenovirus as an Endosomal Lysis Agent

The DNA/TF/PFO complex (PFO4) was compared with adenovirus as to the effect on β-gal expression. The adenovirus is separate from the DNA/TF/PFO complexes. The amount of adenovirus was chosen in such a way that 100% of the cells are blue on X-gal stain. Expression using the adenovirus was greater than tenfold over the use of PFO as a lysis agent.

Liposome Leakage Assay

Liposome membrane activity was measured by testing liposomal leakage. Briefly, a fluorescent dye (calcein) is encapsulated into liposomes at a concentration where the fluorescence of the dye is greatly reduced (self-quenching). When the liposomes are destroyed by the lysis agent, the fluorescent dye leaks out of the liposomes and is diluted in the incubation buffer. This causes a great increase of fluorescence (dequenching) which can be followed in a fluorescence spectrotrophotometer.

Figure 36:
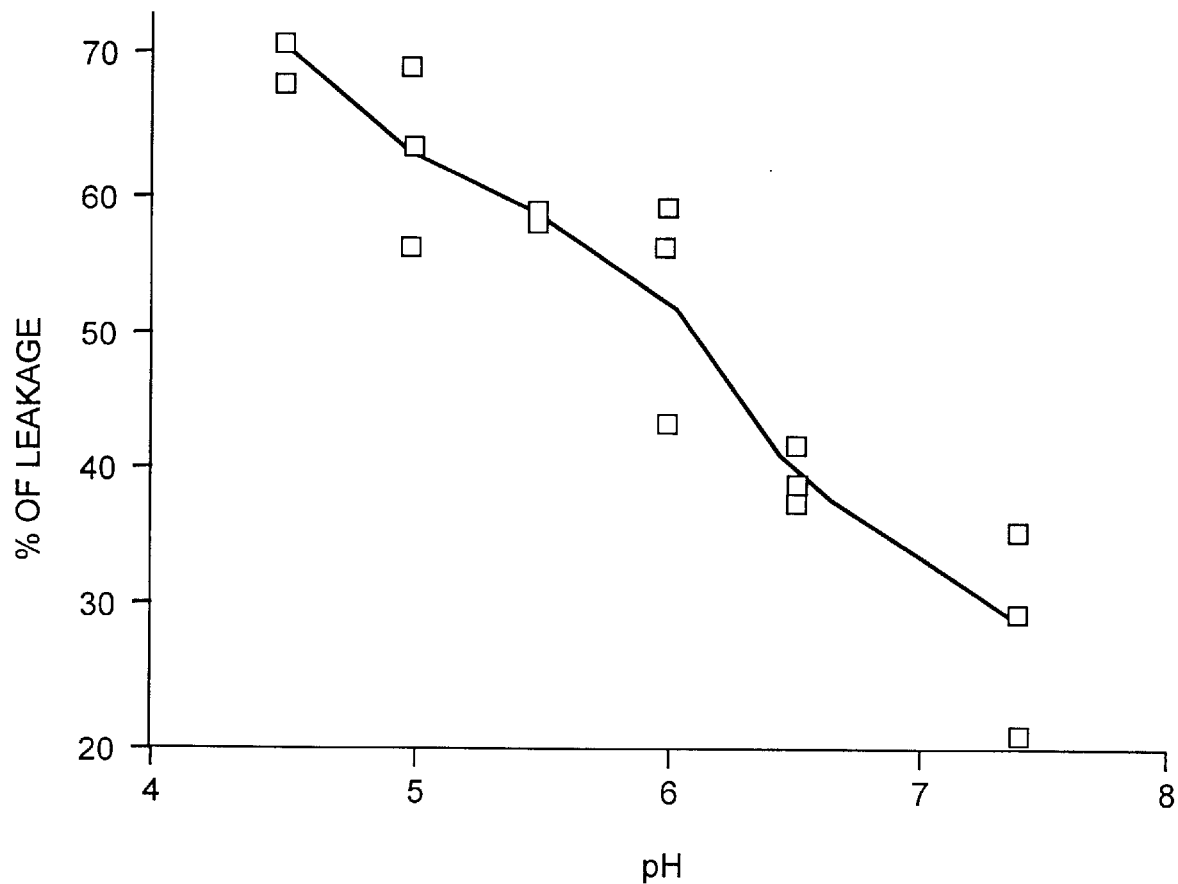
FIG. 36 is a representation of liposome leakage using a monomeric form of the HA$_2$-fusiogenic peptide.
Figure 37:
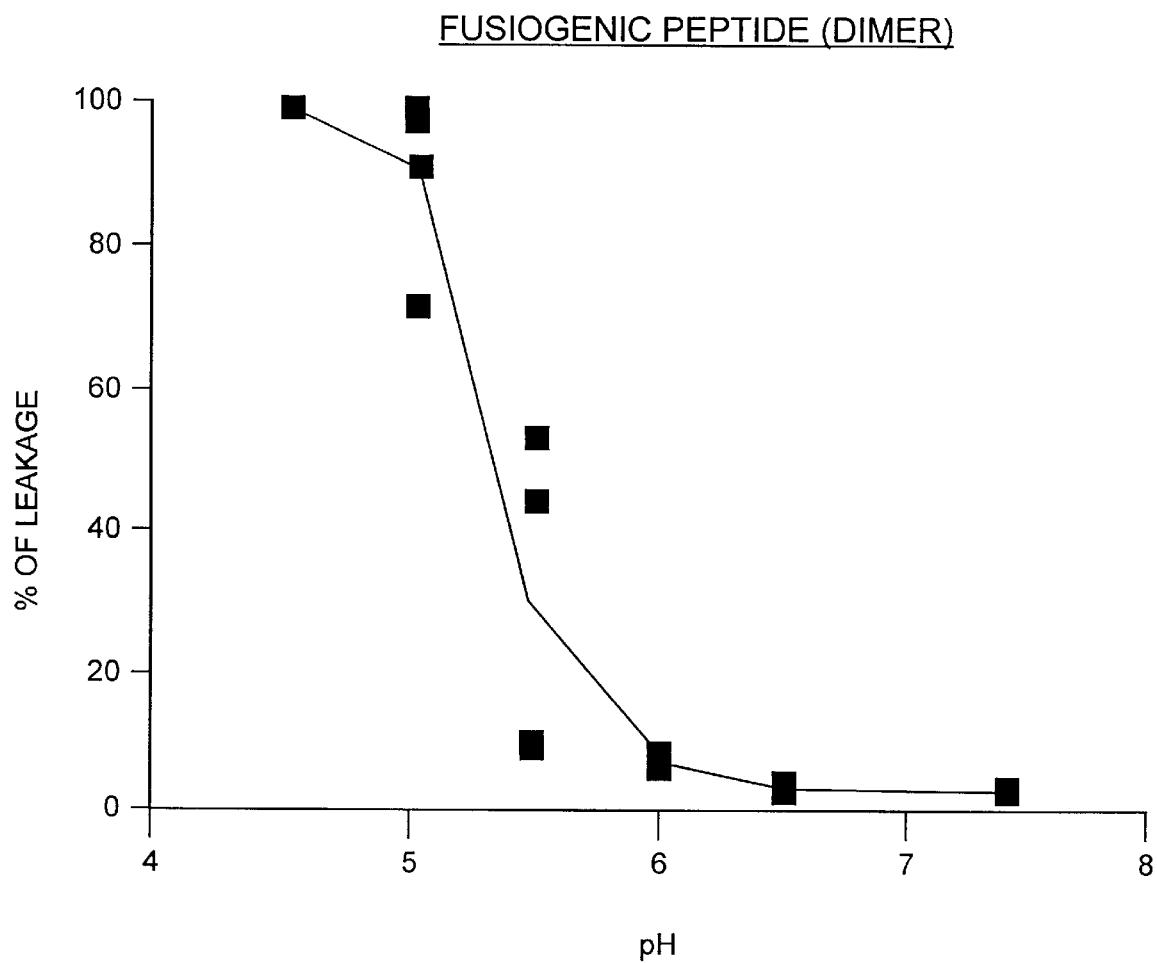
FIG. 37 is a representation of liposome leakage using a dimeric form of the HA$_2$-fusiogenic peptide.

Liposomes were incubated with monomeric or dimeric forms of the $HA_2$-fusiogenic peptide at a concentration of 0.5 μg/ml in a sodium-citrate buffer with a pH ranging from 4.5 to 7.4. Before and 5 min after the addition of the lysis agent peptides, the fluorescence was determined. The fluorescence corresponding to 100% leakage was determined by complete lysis of the liposomes with a detergent (Triton X-100; final concentration 0.5%) and the values obtained for the monomeric and dimeric form were plotted as percentage leakage (FIGS. 36 and 37). As seen in FIGS. 36 and 37, the dimeric form of the $HA_2$-fusiogenic peptide is more potent and its activity is far better controlled by the pH than the activity of the monomeric form.

Treatment of Cardiovascular Disease

In order to treat cardiovascular diseases, it is best to achieve high serum concentrations of High Density Lipoproteins (HDL) and low levels of Low Density Lipoproteins (LDL). This can be accomplished by over expressing a combination of seven proteins in the liver. The proteins are cholesterol-7α-hydroxylase, truncated apolipoprotein B, lipoprotein lipase, apolipoprotein E, apolipoprotein A1, LDL receptor, scavenger receptor, molecular variants of each, and combinations thereof.

Nucleic acid transporters containing DNA coding for human cholesterol-7α-hydroxylase, truncated apolipoprotein B, lipoprotein lipase, apolipoprotein E, apolipoprotein A1, LDL receptor, scavenger receptor, molecular variants of each, or combinations thereof can be constructed. A full-length cDNA clone of human cholesterol-7α-hydroxylase containing all of the coding sequences is used. The same strategy is used to incorporate truncated apolipoprotein B, lipoprotein lipase, apolipoprotein E, apolipoprotein A1, LDL receptor, scavenger receptor, molecular variants of each, and combinations thereof. In some cases, more than one gene, a molecular variant of the given gene, and possibly all seven genes or their molecular variants can be used with the nucleic acid transporters. One example is cholesterol-7α-hydroxylase and apolipoprotein B truncated.

Because of its ease in producing hypercholesterolemia by cholesterol feeding, the heterozygote Watanabe hereditary hyperlipidemic rabbit is a good example for showing the effect of these vectors. The efficacy of this therapeutic approach is monitored by a simple observation of serum cholesterol and triglyceride levels, lipoprotein profiles and apoprotein levels. After intravenous injection of the nucleic acid transporter in experimental animals, (1) the tissue localization of the DNA, (2) the tissue specificity for gene expression, (3) how long the new gene can be expressed and (4) function is determined.

Cell Transformation

One embodiment of the present invention includes cells transformed with nucleic acid associated with the nucleic acid transporter systems described above. Once the cells are transformed, the cells will express the protein, polypeptide or RNA encoded for by the nucleic acid. Cells included but are not limited to liver, muscle and skin. This is not intended to be limiting in any manner.

The nucleic acid which contains the genetic material of interest is positionally and sequentially oriented within the host or vectors such that the nucleic acid can be transcribed into RNA and, when necessary, be translated into proteins or polypeptides in the transformed cells. A variety of proteins and polypeptides can be expressed by the sequence in the nucleic acid cassette in the transformed cells. These proteins or polypeptides which can be expressed include hormones, growth factors, enzymes, clotting factors, apolipoproteins, receptors, drugs, tumor antigens, viral antigens, parasitic antigens and bacterial antigens.

Transformation can be done either by in vivo or ex vivo techniques. One skilled in the art will be familiar with such techniques for transformation. Transformation by ex vivo techniques includes co-transfecting the cells with DNA containing a selectable marker. This selectable marker is used to select those cells which have become transformed. Selectable markers are well known to those who are skilled in the art.

For example, one approach to gene therapy for hepatic diseases is to remove hepatocytes from an affected individual, genetically alter them in vitro, and reimplant them into a receptive locus. The ex vivo approach includes the steps of harvesting hepatocytes, cultivating the hepatocytes, transducing or transfecting the hepatocytes, and introducing the transfected hepatocytes into the affected individual.

The hepatocytes may be obtained in a variety of ways. They may be taken from the individual who is to be later injected with the hepatocytes that have been transformed or they can be collected from other sources, transformed and then injected into the individual of interest.

Once the ex vivo hepatocyte is collected, it may be transformed by contacting the hepatocytes with media containing the nucleic acid transporter and maintaining the cultured hepatocytes in the media for sufficient time and under conditions appropriate for uptake and transformation of the hepatocytes. The hepatocytes may then be introduced into an orthotopic location (the body of the liver or the portal vasculature) or heterotopic locations by injection of cell suspensions into tissues. One skilled in the art will recognize that the cell suspension may contain: salts, buffers or nutrients to maintain viability of the cells; proteins to ensure cell stability; and factors to promote angiogenesis and growth of the implanted cells.

In an alternative method, harvested hepatocytes may be grown ex vivo on a matrix consisting of plastics, fibers or gelatinous materials which may be surgically implanted in an orthotopic or heterotopic location after transduction. This matrix may be impregnated with factors to promote angiogenesis and growth of the implanted cells. Cells can then be reimplanted.

Administration

Administration as used herein refers to the route of introduction of the nucleic acid transporters into the body. Administration includes intravenous, intramuscular, topical, or oral methods of delivery. Administration can be directly to a target tissue or through systemic delivery.

In particular, the present invention can be used for administering nucleic acid for expression of specific nucleic acid sequence in cells. Routes of administration include intramuscular, aerosol, oral, topical, systemic, ocular, intraperitoneal and/or intrathecal. A preferred method of administering nucleic acid transporters is by intraveneous delivery. Another preferred method of administration is by direct injection into the cells.

The special delivery route of any selected vector construct will depend on the particular use for the nucleic acid associated with the nucleic acid transporter. In general, a specific delivery program for each nucleic acid transporter used will focus on uptake with regard to the particular targeted tissue, followed by demonstration of efficacy. Uptake studies will include uptake assays to evaluate cellular uptake of the nucleic acid and expression of the specific nucleic acid of choice. Such assays will also determine the localization of the target nucleic acid after uptake, and establishing the requirements for maintenance of steady-state concentrations of expressed protein. Efficacy and cytotoxicity is then tested. Toxicity will not only include cell viability but also cell function.

Incorporated DNA into transporters, as described herein, which undergo endocytosis increases the range of cell types that will take up foreign genes form the extracellular space.

The chosen method of delivery should result in cytoplasmic accumulation and optimal dosing. The dosage will depend upon the disease and the rough of administration but should be between 1–1000 mg/kg of body weight/day. This level is readily determinable by standard methods. It could be more or less depending on the optimal dosing. The duration of treatment will extend through the course of the disease symptoms, possibly continuously. The number of doses will depend upon disease delivery vehicle and efficacy data from clinical trials.

Establishment of therapeutic levels of DNA within the cell is dependent upon the rate of uptake and degradation. Decreasing the degree of degradation will prolong the intracellular half-life of the DNA.

Direct DNA Delivery to Muscle

The muscular dystrophies are a group of diseases that result in abnormal muscle development, due to many different reasons. These diseases can be treated by using the direct delivery of genes with the nucleic acid transporters of the present invention resulting in the production of normal gene product. Delivery to the muscle using the present invention is done to present genes that produce various antigens for vaccines against a multitude of infections of both viral and parasitic origin. The detrimental effects caused by aging can also be treated using the nucleic acid delivery system described herein. Since the injection of the growth hormone protein promotes growth and proliferation of muscle tissue, the growth hormone gene can be delivered to muscle, resulting in both muscle growth and development, which is decreased during the later portions of the aging process. Genes expressing other growth related factors can be delivered, such as Insulin Like Growth Factor-1 (IGF-1). Furthermore, any number of different genes may be delivered by this method to the muscle tissue.

IGF-1 can be used to deliver DNA to muscle, since it undergoes uptake into cells by receptor-mediated endocytosis. This polypeptide is 70 amino acids in length and is a member of the growth promoting polypeptides structurally related to insulin. It is involved in the regulation of tissue growth and cellular differentiation affecting the proliferation and metabolic activities of a wide variety of cell types, since the polypeptide has receptors on many types of tissue. As a result, the nucleic acid transporter delivery system of the present invention utilizes IGF-1 as a ligand for tissue-specific nucleic acid delivery to muscle. The advantage of the IGF-1/nucleic acid delivery system is that the specificity and the efficiency of the delivery is greatly increased due to a great number of cells coming into contact with the ligand/ nucleic acid complex with uptake through receptor-mediated endocytosis. Using the nucleic acid described above in the delivery systems of the present invention with the use of specific ligands for the delivery of nucleic acid to muscle cells provides treatment of diseases and abnormalities that affect muscle tissues.

Direct DNA Delivery to Osteogenic Cells

There are many other problems that occur during the aging process, but one major problem is osteoporosis, which is the decrease in overall bone mass and strength. The direct nucleic acid delivery system of the present invention can be used to deliver genes to cells that promote bone growth. The osteoblasts are the main bone forming cell in the body, but there are other cells that are capable of aiding in bone formation. The stromal cells of the bone marrow are the source of stem cells for osteoblasts. The stromal cells differentiate into a population of cells known as Inducible Osteoprogenitor Cells (IOPC), which then under induction of growth factors, differentiate into Determined Osteoprogenitor Cells (DOPC). It is this population of cells that mature directly into bone producing cells. The IOPCs are also found in muscle and soft connective tissues. Another cell involved in the bone formation process is the cartilage-producing cell known as the chondrocyte.

The factor that has been identified to be involved in stimulating the IOPCs to differentiate is known as Bone Morphogenetic Protein (BMP). This 19,000 MW protein was first identified from demineralized bone. Another factor similar to BMP is Cartilage Induction Factor (CIF), which functions to stimulate IOPCs to differentiate also, starting the pathway of cartilage formation, cartilage calcification, vascular invasion, resorption of calcified cartilage, and finally induction of new bone formation. Cartilage Induction Factor has been identified as being homologous to Transforming Growth Factor β.

Since osteoblasts are involved in bone production, genes that enhance osteoblast activity can be delivered directly to these cells. Genes can also be delivered to the IOPCs and the chondrocytes, which can differentiate into osteoblasts, leading to bone formation. BMP and CIF are the ligands that can be used to deliver genes to these cells. Genes delivered to these cells promote bone formation or the proliferation of osteoblasts. The polypeptide, IGF-1 stimulates growth in hypophysectomized rats which could be due to specific uptake of the polypeptide by osteoblasts or by the interaction of the polypeptide with chondrocytes, which result in the formation of osteoblasts. Other specific bone cell and growth factors can be used through the interaction with various cells involved in bone formation to promote osteogenesis.

Non-limiting examples of genes expressing the following growth factors which can be delivered to these cell types are Insulin, Insulin-Like Growth Factor-1, Insulin-Like Growth Factor-2, Epidermal Growth Factor, Transforming Growth Factor α, Transforming Growth Factor β, Platelet Derived Growth Factor, Acidic Fibroblast Growth Factor, Basic Fibroblast Growth Factor, Bone Derived Growth Factors, Bone Morphogenetic Protein, Cartilage Induction Factor, Estradiol, and Growth Hormone. All of these factors have a positive effect on the proliferation of osteoblasts, the related stem cells, and chondrocytes. As a result, BMP or CIF can be used as conjugates to deliver genes that express these growth factors to the target cells by the intravenous injection of the nucleic acid/Protein complexes of the present invention. Using the nucleic acid described above in the delivery systems of the present invention with the use of specific ligands for the delivery of nucleic acid to bone cells provides treatment of diseases and abnormalities that affect bone tissues.

One skilled in the art would readily appreciate that the present invention is well adapted to carry out the objects and obtain the ends and advantages mentioned as well as those inherent therein. The nucleic acid transporter systems along with the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed here in without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

We claim:

1. A method for transformation of a cell comprising the step of contacting said cell with a nucleic acid transporter system for delivering nucleic acid into a cell for a sufficient time to transform said cell, said nucleic acid transporter system comprising a nucleic acid binding complex comprising (i) a first binding molecule noncovalently bound to said nucleic acid and covalently linked to; (ii) a cell-surface ligand, (iii) a nuclear ligand; and (iv) a lysis agent.

2. The method of claim 1, wherein said nucleic acid transporter system further comprises a plurality of nucleic acid binding complexes, wherein each said nucleic acid binding complex comprises a binding molecule noncovalently bound to said nucleic acid.

3. The method of claim 2, wherein each said nucleic acid binding complex is bound to said nucleic acid simultaneously.

4. The method of claim 1, wherein said transformation of said cell is in vitro.

5. The method of claim 1, wherein said cell is a hepatocyte.

6. The method of claim 1, wherein said cell is a muscle cell.

7. The method of claim 1, wherein said cell is a bone forming cell.

8. The method of claim 1, wherein said surface ligand is specific to said cell to be transformed.

9. The method of claim 1, wherein said first binding molecule is selected from the group consisting of spermine, spermine derivative, spermidine, polylysine, histones, and cationic peptides.

10. The method of claim 9 wherein said first binding molecule is a spermine derivative.

11. The method of claim 1, wherein said surface ligand is an asialoorosomucoid protein.

12. The method of claim 11, wherein the ratio of said asialoorosomucoid protein to said nucleic acid is between 10:1 and 1,000:1.

13. The method of claim 12, wherein the ratio of said asialoorosomucoid protein to said nucleic acid is 250:1.

14. The method of claim 1, wherein said surface ligand is insulin-like growth factor I.

15. The method of claim 1, wherein said surface ligand is bone morphogenetic or cartilage induction factor.

16. The method of claims 1, wherein said surface ligand is folate.

17. The method of claim 1, wherein said lysis agent is a replication-defective adenovirus.

18. The method of claim 17, wherein the amount of said adenovirus delivered to said cell is between $10^3$ and $10^5$ particles of virus.

19. The method of claim 1 wherein said first binding molecule is attached to said cell surface ligand by a spacer.

20. The method of claim 1 wherein said first binding molecule is attached to said lysis agent by a spacer.

21. The method of claim 1 wherein said first binding molecule is attached to said nuclear ligand by a spacer.

22. The method of any one of claims 19–21, wherein said spacer is hydrophilic and has from 6–30 carbons.

23. The method of any one of claims 19–21, wherein said spacer has from 6–16 carbons.

24. The method of any one of claims 19–21, wherein said spacer is a disulfide having the structure of

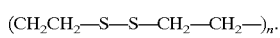

25. The method of any one of claims 19–21, wherein said spacer comprises a hydrophilic polymer of $[(gly)_I(ser)_j]_k$ wherein I ranges from 1–6, j ranges from 1–6, and k ranges from 3–20.

* * * * *

SEQUENCE LISTING (1) GENERAL INFORMATION:

(iii) NUMBER OF SEQUENCES:65

(2) INFORMATION FOR SEQ ID NO:1:

(i) SEQUENCE CHARACTERISTICS:
      (A) LENGTH:          31 base pairs
      (B) TYPE:            nucleic acid
      (C) STRANDEDNESS:    double
      (D) TOPOLOGY:        linear (ii) MOLECULE TYPE:cDNA (xi) SEQUENCE DESCRIPTION: SEQ ID NO: 1:

```
TCCTAGCAAA GGAGGAGACG AAGAAAAATG A                           31
```

(2) INFORMATION FOR SEQ ID NO: 2:

(i) SEQUENCE CHARACTERISTICS:
        (A) LENGTH:           11 base pairs
        (B) TYPE:             nucleic acid
        (C) STRANDEDNESS:     single
        (D) TOPOLOGY:         linear (ii) MOLECULE TYPE:       Other nucleic acid (ix) FEATURE:
        (D) OTHER INFORMATION:   "C" stands for 5-methylcytosine (xi) SEQUENCE DESCRIPTION: SEQ ID NO: 2:

```
TTTCCTCCTC T                                                 11
```

(2) INFORMATION FOR SEQ ID NO: 3:

(i) SEQUENCE CHARACTERISTICS:
        (A) LENGTH:           11 base pairs
        (B) TYPE:             nucleic acid
        (C) STRANDEDNESS:     single
        (D) TOPOLOGY:         linear (ii) MOLECULE TYPE:       cDNA (xi) SEQUENCE DESCRIPTION: SEQ ID NO: 3:

```
AAAGGAGGAG A                                                 11
```

(2) INFORMATION FOR SEQ ID NO: 4:

(i) SEQUENCE CHARACTERISTICS:
        (A) LENGTH:           23 bases
        (B) TYPE:             nucleic acid
        (C) STRANDEDNESS:     double
        (D) TOPOLOGY:         linear (ii) MOLECULE TYPE:       Genomic cDNA (xi) SEQUENCE DESCRIPTION: SEQ ID NO: 4:

```
TCCAAAAAAG AAGAGAAAGG TAG                                    23
```

(2) INFORMATION FOR SEQ ID NO: 5:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (ii) MOLECULE TYPE:       Other nucleic acid (ix) FEATURE:
        (D) OTHER INFORMATION:   "C" stands for 5-methylcytosine (xi) SEQUENCE DESCRIPTION: SEQ ID NO: 5:

```
TTTTTTCTTC TCTTTCC                                           17
```

(2) INFORMATION FOR SEQ ID NO: 6:

(i) SEQUENCE CHARACTERISTICS:
        (A) LENGTH:           17 base pairs
        (B) TYPE:             nucleic acid
        (C) STRANDEDNESS:     single
        (D) TOPOLOGY:         linear (ii) MOLECULE TYPE:       cDNA (xi) SEQUENCE DESCRIPTION: SEQ ID NO: 6:

```
      AAAAAAGAAG AGAAAGG                                                    17

(2) INFORMATION FOR SEQ ID NO: 7:

(i) SEQUENCE CHARACTERISTICS:
        (A) LENGTH:             17 base pairs
        (B) TYPE:               nucleic acid
        (C) STRANDEDNESS:       double
        (D) TOPOLOGY:           linear (ii) MOLECULE TYPE:         cDNA (xi) SEQUENCE DESCRIPTION: SEQ ID NO: 7:

AAAGAGAGAG AGAGGGA                                                    17

(2) INFORMATION FOR SEQ ID NO: 8:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (ii) MOLECULE TYPE:         Other nucleic acid (ix) FEATURE:
        (D) OTHER INFORMATION:  "C" stands for 5-methylcytosine (xi) SEQUENCE DESCRIPTION: SEQ ID NO: 8:

TTTCTCTCTC TCTCCCT                                                    17

(2) INFORMATION FOR SEQ ID NO: 9:

(i) SEQUENCE CHARACTERISTICS:
        (A) LENGTH:             17 base pairs
        (B) TYPE:               nucleic acid
        (C) STRANDEDNESS:       single
        (D) TOPOLOGY:           linear (ii) MOLECULE TYPE:         cDNA (xi) SEQUENCE DESCRIPTION: SEQ ID NO: 9:

AAAGAGAGAG AGAGGGA                                                    17

(2) INFORMATION FOR SEQ ID NO: 10:

(i) SEQUENCE CHARACTERISTICS:
        (A) LENGTH:             35 base pairs
        (B) TYPE:               nucleic acid
        (C) STRANDEDNESS:       double
        (D) TOPOLOGY:           linear (ii) MOLECULE TYPE:         cDNA (xi) SEQUENCE DESCRIPTION: SEQ ID NO: 10:

CTACTCGAGA AAGGAGAGAA AAAGGGGCGG TCCCG                                35

(2) INFORMATION FOR SEQ ID NO: 11:

(i) SEQUENCE CHARACTERISTICS:
        (A) LENGTH:             21 base pairs
        (B) TYPE:               nucleic acid
        (C) STRANDEDNESS:       single
        (D) TOPOLOGY:           linear (ii) MOLECULE TYPE:         Other nucleic acid (ix) FEATURE:
        (D) OTHER INFORMATION:  "C" stands for 5-methylcytosine
```

```
        (xi) SEQUENCE DESCRIPTION: SEQ ID NO: 11:

CTCTTTCCTC TCTTTTTCCC C                                              21

(2) INFORMATION FOR SEQ ID NO: 12:

(i) SEQUENCE CHARACTERISTICS:
          (A) LENGTH:          21 base pairs
          (B) TYPE:            nucleic acid
          (C) STRANDEDNESS:    single
          (D) TOPOLOGY:        linear (ii) MOLECULE TYPE:        cDNA (xi) SEQUENCE DESCRIPTION: SEQ ID NO: 12:

GAGAAAGGAG AGAAAAAGGG G                                              21

(2) INFORMATION FOR SEQ ID NO: 13:

(i) SEQUENCE CHARACTERISTICS:
          (A) LENGTH:          39 base pairs
          (B) TYPE:            nucleic acid
          (C) STRANDEDNESS:    double
          (D) TOPOLOGY:        linear (ii) MOLECULE TYPE:        cDNA (xi) SEQUENCE DESCRIPTION: SEQ ID NO: 13:

CTCTCTAAAA AGGGAGGGGA GGGGAGGGAA AAACTCTCT                            39

(2) INFORMATION FOR SEQ ID NO: 14:

(i) SEQUENCE CHARACTERISTICS:
          (A) LENGTH:          27 base pairs
          (B) TYPE:            nucleic acid
          (C) STRANDEDNESS:    single
          (D) TOPOLOGY:        linear (ii) MOLECULE TYPE:        Other nucleic acid (ix) FEATURE:
          (D) OTHER INFORMATION: "C" stands for 5-methylcytosine (xi) SEQUENCE DESCRIPTION: SEQ ID NO: 14:

TTTTTCCCTC CCCTCCCCTC CCTTTTT                                        27

(2) INFORMATION FOR SEQ ID NO: 15:

(i) SEQUENCE CHARACTERISTICS:
          (A) LENGTH:          27 base pairs
          (B) TYPE:            nucleic acid
          (C) STRANDEDNESS:    single
          (D) TOPOLOGY:        linear (ii) MOLECULE TYPE:        cDNA (xi) SEQUENCE DESCRIPTION: SEQ ID NO: 15:

AAAAAGGGAG GGGAGGGGAG GGAAAAA                                        27

(2) INFORMATION FOR SEQ ID NO: 16:

(i) SEQUENCE CHARACTERISTICS:
          (A) LENGTH:          11 base pairs
          (B) TYPE:            nucleic acid
          (C) STRANDEDNESS:    single
          (D) TOPOLOGY:        linear (ii) MOLECULE TYPE:        Other nucleic acid (ix) FEATURE:
          (D) OTHER INFORMATION: "C" stands for 5-methylcytosine
```

(xi) SEQUENCE DESCRIPTION: SEQ ID NO: 16:

TTTCCTCCTC T                                                                                        11

(2) INFORMATION FOR SEQ ID NO: 17:

(i) SEQUENCE CHARACTERISTICS:
        (A) LENGTH:             10 amino acids
        (B) TYPE:               amino acid
        (C) STRANDEDNESS:       single
        (D) TOPOLOGY:           linear (ii) MOLECULE TYPE:         peptide (xi) SEQUENCE DESCRIPTION: SEQ ID NO: 17:

Gly Tyr Ser Thr Pro Gly Arg Lys Lys Arg
1               5                   10

(2) INFORMATION FOR SEQ ID NO: 18:

(i) SEQUENCE CHARACTERISTICS:
        (A) LENGTH:             16 amino acids
        (B) TYPE:               amino acid
        (C) STRANDEDNESS:       single
        (D) TOPOLOGY:           linear (ii) MOLECULE TYPE:         peptide (xi) SEQUENCE DESCRIPTION: SEQ ID NO: 18:

His Leu Arg Arg Leu Arg Arg Leu Leu Arg Glu Ala Glu Glu Gly
1               5                   10                  15

(2) INFORMATION FOR SEQ ID NO: 19:

(i) SEQUENCE CHARACTERISTICS:
        (A) LENGTH:             27 base pairs
        (B) TYPE:               nucleic acid
        (C) STRANDEDNESS:       single
        (D) TOPOLOGY:           linear (ii) MOLECULE TYPE:         cDNA (xi) SEQUENCE DESCRIPTION: SEQ ID NO: 19:

TGGGGAGGGA GGGGAGGGAG GGGAAGG                                                                       27

(2) INFORMATION FOR SEQ ID NO: 20:

(i) SEQUENCE CHARACTERISTICS:
        (A) LENGTH:             39 base pairs
        (B) TYPE:               nucleic acid
        (C) STRANDEDNESS:       single
        (D) TOPOLOGY:           linear (ii) MOLECULE TYPE:         cDNA (xi) SEQUENCE DESCRIPTION: SEQ ID NO: 20:

TAGAGGAGGC CGCAGGGGCT GGGCAGGAAG GAGGTGAAT                                                           39

(2) INFORMATION FOR SEQ ID NO: 21:

(i) SEQUENCE CHARACTERISTICS:
        (A) LENGTH:             21 base pairs
        (B) TYPE:               nucleic acid
        (C) STRANDEDNESS:       single
        (D) TOPOLOGY:           linear (ii) MOLECULE TYPE:         cDNA (ix) FEATURE:
        (D) OTHER INFORMATION:      "C" stands for 5-methylcytosine (xi) SEQUENCE DESCRIPTION: SEQ ID NO: 21:

CTCTTTCCTC TCTTTTTCCC C                        21

(2) INFORMATION FOR SEQ ID NO: 22:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (ii) MOLECULE TYPE:     cDNA (xi) SEQUENCE DESCRIPTION: SEQ ID NO: 22:

TGGGGAGGGA GGGGAGGGAG GGGAAGG                  27

(2) INFORMATION FOR SEQ ID NO: 23:

(i) SEQUENCE CHARACTERISTICS:
        (A) LENGTH:         15 amino acids
        (B) TYPE:           amino acid
        (C) STRANDEDNESS:   single
        (D) TOPOLOGY:       linear (ii) MOLECULE TYPE:     peptide (xi) SEQUENCE DESCRIPTION: SEQ ID NO: 23:

Pro Asp Glu Val Lys Arg Lys Lys Lys Pro Thr Ser Tyr Gly
1               5                   10                  15

(2) INFORMATION FOR SEQ ID NO: 24:

(i) SEQUENCE CHARACTERISTICS:
        (A) LENGTH:         12 amino acids
        (B) TYPE:           amino acid
        (C) STRANDEDNESS:   single
        (D) TOPOLOGY:       linear (ii) MOLECULE TYPE:     peptide (xi) SEQUENCE DESCRIPTION: SEQ ID NO: 24:

Pro Arg Arg Arg Thr Lys Pro Pro Thr Ser Tyr Gly
1               5                   10

(2) INFORMATION FOR SEQ ID NO: 25:

(i) SEQUENCE CHARACTERISTICS:
        (A) LENGTH:         10 amino acids
        (B) TYPE:           amino acid
        (C) STRANDEDNESS:   single
        (D) TOPOLOGY:       linear (ii) MOLECULE TYPE:     peptide (xi) SEQUENCE DESCRIPTION: SEQ ID NO: 25:

Arg Lys Lys Arg Gly Pro Thr Ser Tyr Gly
1               5                   10

(2) INFORMATION FOR SEQ ID NO: 26:

(i) SEQUENCE CHARACTERISTICS:
        (A) LENGTH:         13 amino acids
        (B) TYPE:           amino acid
        (C) STRANDEDNESS:   single
        (D) TOPOLOGY:       linear (ii) MOLECULE TYPE:     peptide (xi) SEQUENCE DESCRIPTION: SEQ ID NO: 26:

Trp Arg Arg Arg Arg Asn Arg Arg Pro Thr Ser Tyr Gly

```
              1               5                   10
```

(2) INFORMATION FOR SEQ ID NO: 27:

(i) SEQUENCE CHARACTERISTICS:
        (A) LENGTH:          15 amino acids
        (B) TYPE:            amino acid
        (C) STRANDEDNESS:    single
        (D) TOPOLOGY:        linear (ii) MOLECULE TYPE:      peptide (xi) SEQUENCE DESCRIPTION: SEQ ID NO: 27:

```
Gly Tyr Ser Thr Pro Pro Lys Lys Arg Lys Val Glu Asp Pro
1               5                   10                  15
```

(2) INFORMATION FOR SEQ ID NO: 28:

(i) SEQUENCE CHARACTERISTICS:
        (A) LENGTH:          12 amino acids
        (B) TYPE:            amino acid
        (C) STRANDEDNESS:    single
        (D) TOPOLOGY:        linear (ii) MOLECULE TYPE:      peptide (xi) SEQUENCE DESCRIPTION: SEQ ID NO: 28:

```
Gly Tyr Ser Thr Pro Pro Lys Thr Arg Arg Arg Pro
1               5                   10
```

(2) INFORMATION FOR SEQ ID NO: 29:

(i) SEQUENCE CHARACTERISTICS:
        (A) LENGTH:          10 amino acids
        (B) TYPE:            amino acid
        (C) STRANDEDNESS:    single
        (D) TOPOLOGY:        linear (ii) MOLECULE TYPE:      peptide (xi) SEQUENCE DESCRIPTION: SEQ ID NO: 29:

```
Gly Tyr Ser Thr Pro Gly Arg Lys Lys Arg
1               5                   10
```

(2) INFORMATION FOR SEQ ID NO: 30:

(i) SEQUENCE CHARACTERISTICS:
        (A) LENGTH:          13 amino acids
        (B) TYPE:            amino acid
        (C) STRANDEDNESS:    single
        (D) TOPOLOGY:        linear (ii) MOLECULE TYPE:      peptide (xi) SEQUENCE DESCRIPTION: SEQ ID NO: 30:

```
Gly Tyr Ser Thr Pro Arg Arg Asn Arg Arg Arg Arg Trp
1               5                   10
```

(2) INFORMATION FOR SEQ ID NO: 31:

(i) SEQUENCE CHARACTERISTICS:
        (A) LENGTH:          16 amino acids
        (B) TYPE:            amino acid
        (C) STRANDEDNESS:    single
        (D) TOPOLOGY:        linear (ii) MOLECULE TYPE:      peptide (xi) SEQUENCE DESCRIPTION: SEQ ID NO: 31:

His Leu Arg Arg Leu Arg Arg Arg Leu Leu Arg Glu Ala Glu Glu Gly (2) INFORMATION FOR SEQ ID NO: 32:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

His Leu Arg Arg Leu Arg Arg Arg Leu Leu Arg Glu Ala Glu Glu
1             5                   10              15

(2) INFORMATION FOR SEQ ID NO: 33:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Gly Tyr Ser Thr Pro Pro Lys Lys Lys Arg Lys Val Glu Asp Pro
1             5                   10              15

(2) INFORMATION FOR SEQ ID NO: 34:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

Gly Tyr Ser Thr Pro Pro Lys Thr Arg Arg Arg Pro
1             5                   10

(2) INFORMATION FOR SEQ ID NO: 35:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

Gly Tyr Ser Thr Pro Gly Arg Lys Lys Arg
1             5                   10

(2) INFORMATION FOR SEQ ID NO: 36:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

Gly Tyr Ser Thr Pro Arg Arg Asn Arg Arg Arg Arg Trp (2) INFORMATION FOR SEQ ID NO: 37:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

Pro Asp Glu Val Lys Arg Lys Lys Pro Thr Ser Tyr Gly
1          5                10             15

(2) INFORMATION FOR SEQ ID NO: 38:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

Pro Arg Arg Arg Thr Lys Pro Thr Ser Tyr Gly
1          5                10

(2) INFORMATION FOR SEQ ID NO: 39:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

Arg Lys Lys Arg Gly Pro Thr Ser Tyr Gly
1          5                10

(2) INFORMATION FOR SEQ ID NO: 40:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

Trp Arg Arg Arg Arg Asn Arg Arg Pro Thr Ser Tyr Gly
1          5                10

(2) INFORMATION FOR SEQ ID NO: 41:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

Lys Ala Lys Ala Lys Ala Lys (2) INFORMATION FOR SEQ ID NO: 42:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: "Lys" in position 66 has an n-X substitution.

(xi) SEQUENCE DESCRIPTION: SEQ ID NO: 42:

```
Gln Ala Tyr Arg Pro Ser Glu Thr Leu Cys Gly Gly Glu Leu Val Asp
 1               5                  10                  15

Thr Leu Gln Phe Val Cys Gly Asp Arg Gly Phe Leu Phe Ser Arg Pro
            20                  25                  30

Ala Ser Arg Val Ser Arg Arg Ser Arg Gly Ile Val Glu Glu Cys Cys
        35                  40                  45

Phe Arg Ser Cys Asp Leu Ala Leu Leu Glu Thr Tyr Cys Ala Thr Pro
    50                  55                  60

Ala Lys Ser Glu
65
```

(2) INFORMATION FOR SEQ ID NO: 43:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: "Lys" in position 4 has an n-X substitution.

(xi) SEQUENCE DESCRIPTION: SEQ ID NO: 43:

```
Gln Ala Tyr Lys Pro Ser Glu Thr Leu Cys Gly Gly Glu Leu Val Asp
 1               5                  10                  15

Thr Leu Gln Phe Val Cys Gly Asp Arg Gly Phe Leu Phe Ser Arg Pro
            20                  25                  30

Ala Ser Arg Val Ser Arg Arg Ser Arg Gly Ile Val Glu Glu Cys Cys
        35                  40                  45

Phe Arg Ser Cys Asp Leu Ala Leu Leu Glu Thr Tyr Cys Ala Thr Pro
    50                  55                  60

Ala Arg Ser Glu
65
```

(2) INFORMATION FOR SEQ ID NO: 44:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: "Lys" in position 25 has an n-X substitution.

(xi) SEQUENCE DESCRIPTION: SEQ ID NO: 44:

Tyr Ala Cys Asp Thr Ala Thr Cys Val Thr His Arg Leu Ala Gly Leu
1               5                   10                  15

Leu Ser Arg Ser Gly Gly Val Val Lys Asn Asn Phe Val Pro Thr Asn
            20                  25                  30

Val Gly Ser Lys Ala Phe
            35

(2) INFOR FOR SEQ ID NO: 45:

(i) SEQUENCE CHARACTERISTICS:
      (A) LENGTH:         35 amino acids
      (B) TYPE:           amino acid
      (C) STRANDEDNESS:   single
      (D) TOPOLOGY:      linear (ii) MOLECULE TYPE:     peptide (ix) FEATURE:
      (D) OTHER INFORMATION:   "Xaa" stands for an unnatural amino
          acid with R group forming a ring
          attached to "Asp" in position 1.
          "Lys" in position 22 has an
          n-X substitution.

(xi) SEQUENCE DESCRIPTION: SEQ ID NO: 45:

Asp Thr Ala Thr Xaa Tyr Thr His Arg Leu Ala Gly Leu Leu Ser Arg
1               5                   10                  15

Ser Gly Gly Val Val Lys Asn Asn Phe Val Pro Thr Asn Val Gly Ser
            20                  25                  30

Lys Ala Phe
            35

(2) INFOR FOR SEQ ID NO: 46:

(i) SEQUENCE CHARACTERISTICS:
      (A) LENGTH:         68 amino acids
      (B) TYPE:           amino acid
      (C) STRANDEDNESS:   single
      (D) TOPOLOGY:      linear (ii) MOLECULE TYPE:     peptide (ix) FEATURE:
      (D) OTHER INFORMATION:   "Lys" in position 55 has an
          n-X substitution.

(xi) SEQUENCE DESCRIPTION: SEQ ID NO: 46:

Gln Ala Tyr Arg Pro Ser Glu Thr Leu Cys Gly Gly Glu Leu Val Asp
1               5                   10                  15

Thr Leu Gln Phe Val Cys Gly Asp Arg Gly Phe Leu Phe Ser Arg Pro
            20                  25                  30

Ala Ser Arg Val Ser Arg Arg Ser Arg Gly Ile Val Glu Glu Cys Cys
            35                  40                  45

Phe Arg Ser Cys Asp Leu Lys Arg Leu Glu Thr Tyr Cys Ala Thr Pro
            50                  55                  60

Ala Arg Ser Glu
65

(2) INFORMATION FOR SEQ ID NO: 47:

(i) SEQUENCE CHARACTERISTICS:
      (A) LENGTH:         78 amino acids
      (B) TYPE:           amino acid
      (C) STRANDEDNESS:   single

```
           (D) TOPOLOGY:            linear (ii) MOLECULE TYPE:           peptide (xi) SEQUENCE DESCRIPTION: SEQ ID NO: 47:

Asn Thr Leu Cys Gly Ala Glu Leu Val Asp Ala Leu Gln Phe Val Cys
      1               5                   10                  15

Gly Asp Arg Gly Phe Tyr Phe Asn Lys Pro Thr Gly Tyr Gly Ser Ser
                      20                  25                  30

Ser Arg Arg Ala Pro Gln Thr Gly Ile Val Asp Glu Cys Cys Phe Arg
                  35                  40                  45

Ser Cys Asp Leu Arg Arg Leu Glu Met Tyr Cys Ala Pro Leu Arg Pro
                  50                  55                  60

Ala Arg Ser Ala Arg Ser Val Arg Ala Gln Arg His Thr Asp
      65                  70                  75

(2) INFORMATION FOR SEQ ID NO: 48:

(i) SEQUENCE CHARACTERISTICS:
           (A) LENGTH:              49 amino acids
           (B) TYPE:                amino acid
           (C) STRANDEDNESS:        single
           (D) TOPOLOGY:            linear (ii) MOLECULE TYPE:           peptide (ix) FEATURE:
           (D) OTHER INFORMATION:   "Lys" in position 1 has an
               n-X substitution.

(xi) SEQUENCE DESCRIPTION: SEQ ID NO: 48:

Lys Gly Leu Pro Lys Glu Val Pro Ala Val Leu Thr Lys Gln Lys Leu
      1               5                   10                  15

Lys Ser Glu Leu Val Ala Asn Gly Val Thr Leu Pro Ala Gly Glu Met
                      20                  25                  30

Arg Lys Asp Val Tyr Val Glu Leu Tyr Leu Gln His Leu Thr Ala Leu
                  35                  40                  45

(2) INFORMATION FOR SEQ ID NO: 49:

(i) SEQUENCE CHARACTERISTICS:
           (A) LENGTH:              48 amino acids
           (B) TYPE:                amino acid
           (C) STRANDEDNESS:        single
           (D) TOPOLOGY:            linear (ii) MOLECULE TYPE:           peptide (ix) FEATURE:
           (D) OTHER INFORMATION:   "Lys" in position 4 has an
               n-X substitution.

(xi) SEQUENCE DESCRIPTION: SEQ ID NO: 49:

Gly Leu Pro Lys Glu Val Pro Ala Val Leu Thr Lys Gln Lys Leu Lys
      1               5                   10                  15

Ser Glu Leu Val Ala Asn Gly Val Thr Leu Pro Ala Gly Glu Met Arg
                      20                  25                  30

Lys Asp Val Tyr Val Glu Leu Tyr Leu Gln His Leu Thr Ala Leu His
                  35                  40                  45

(2) INFOR FOR SEQ ID NO: 50:

(i) SEQUENCE CHARACTERISTICS:
           (A) LENGTH:              697 amino acids
           (B) TYPE:                amino acid
           (C) STRANDEDNESS:        single
```

```
          (D) TOPOLOGY:              linear (ii) MOLECULE TYPE:              peptide (xi) SEQUENCE DESCRIPTION: SEQ ID NO: 50:

Gln Arg Lys Arg Arg Asn Thr Ile His Glu Phe Lys Lys Ser Ala Lys
  1               5                  10                  15

Thr Thr Leu Ile Lys Ile Asp Pro Ala Leu Lys Ile Lys Thr Lys Lys
             20                  25                  30

Val Asn Thr Ala Asp Gln Cys Ala Asn Arg Cys Thr Arg Asn Lys Gly
         35                  40                  45

Leu Pro Phe Thr Cys Lys Ala Phe Val Phe Asp Lys Ala Arg Lys Gln
     50                  55                  60

Cys Leu Trp Phe Pro Phe Asn Ser Met Ser Ser Gly Val Lys Lys Glu
 65                  70                  75                  80

Phe Gly His Glu Phe Asp Leu Tyr Glu Asn Lys Asp Tyr Ile Arg Asn
                 85                  90                  95

Cys Ile Ile Gly Lys Gly Arg Ser Tyr Lys Gly Thr Val Ser Ile Thr
                100                 105                 110

Lys Ser Gly Ile Lys Cys Gln Pro Trp Ser Ser Met Ile Pro His Glu
            115                 120                 125

His Ser Phe Leu Pro Ser Ser Tyr Arg Gly Lys Asp Leu Gln Glu Asn
        130                 135                 140

Tyr Cys Arg Asn Pro Arg Gly Glu Glu Gly Gly Pro Trp Cys Phe Thr
145                 150                 155                 160

Ser Asn Pro Glu Val Arg Tyr Glu Val Cys Asp Ile Pro Gln Cys Ser
                165                 170                 175

Glu Val Glu Cys Met Thr Cys Asn Gly Glu Ser Tyr Arg Gly Leu Met
            180                 185                 190

Asp His Thr Glu Ser Gly Lys Ile Cys Gln Arg Trp Asp His Gln Thr
        195                 200                 205

Pro His Arg His Lys Phe Leu Pro Glu Arg Tyr Pro Asp Lys Gly Phe
    210                 215                 220

Asp Asp Asn Tyr Cys Arg Asn Pro Asp Gly Gln Pro Arg Pro Trp Cys
225                 230                 235                 240

Tyr Thr Leu Asp Pro His Thr Arg Trp Glu Tyr Cys Ala Ile Lys Thr
                245                 250                 255

Cys Ala Asp Asn Thr Met Asn Asp Thr Asp Val Pro Leu Glu Thr Thr
            260                 265                 270

Glu Cys Ile Gln Gly Gln Gly Glu Gly Tyr Arg Gly Thr Val Asn Thr
        275                 280                 285

Ile Trp Asn Gly Ile Pro Cys Gln Arg Trp Asp Ser Gln Tyr Pro His
    290                 295                 300

Glu His Asp Met Thr Pro Glu Asn Phe Lys Cys Lys Asp Leu Arg Glu
305                 310                 315                 320

Asn Tyr Cys Arg Asn Pro Asp Gly Ser Glu Ser Pro Trp Cys Phe Thr
                325                 330                 335

Thr Asp Pro Asn Ile Arg Val Gly Tyr Cys Ser Gln Ile Pro Asn Cys
            340                 345                 350

Asp Met Ser His Gly Gln Asp Cys Tyr Arg Gly Asn Gly Lys Asn Tyr
        355                 360                 365

Met Gly Asn Leu Ser Gln Thr Arg Ser Gly Leu Thr Cys Ser Met Trp
    370                 375                 380

Asp Lys Asn Met Glu Asp Leu His Arg His Ile Phe Trp Glu Pro Asp
385                 390                 395                 400
```

```
    Ala Ser Lys Leu Asn Glu Asn Tyr Cys Arg Asn Pro Asp Asp Asp Ala
                405                 410                 415
    His Gly Pro Trp Cys Tyr Thr Gly Asn Pro Leu Ile Pro Trp Asp Tyr
                420                 425                 430
    Cys Pro Ile Ser Arg Cys Glu Gly Asp Thr Thr Pro Thr Ile Val Asn
                435                 440                 445
    Leu Asp His Pro Val Ile Ser Cys Ala Lys Thr Lys Gln Leu Arg Val
                450                 455                 460
    Val Asn Gly Ile Pro Thr Arg Thr Asn Ile Gly Trp Met Val Ser Leu
    465                 470                 475                 480
    Arg Tyr Arg Asn Lys His Ile Cys Gly Gly Ser Leu Ile Lys Glu Ser
                485                 490                 495
    Trp Val Leu Thr Ala Arg Gln Cys Phe Pro Ser Arg Asp Leu Lys Asp
                500                 505                 510
    Tyr Glu Ala Trp Leu Gly Ile His Asp Val His Gly Arg Gly Asp Glu
                515                 520                 525
    Lys Cys Lys Gln Val Leu Asn Val Ser Gln Leu Val Tyr Gly Pro Glu
                530                 535                 540
    Gly Ser Asp Leu Val Leu Met Lys Leu Ala Arg Pro Ala Val Leu Asp
    545                 550                 555                 560
    Asp Phe Val Ser Thr Ile Asp Leu Pro Asn Tyr Gly Cys Thr Ile Pro
                565                 570                 575
    Glu Lys Thr Ser Cys Ser Val Tyr Gly Trp Gly Tyr Thr Gly Leu Ile
                580                 585                 590
    Asn Tyr Asp Gly Leu Leu Arg Val Ala His Leu Tyr Ile Met Gly Asn
                595                 600                 605
    Glu Lys Cys Ser Gln His His Arg Gly Lys Val Thr Leu Asn Glu Ser
                610                 615                 620
    Glu Ile Cys Ala Gly Ala Glu Lys Ile Gly Ser Gly Pro Cys Glu Gly
    625                 630                 635                 640
    Asp Tyr Gly Gly Pro Leu Val Cys Glu Gln His Lys Met Arg Met Val
                645                 650                 655
    Leu Gly Val Ile Val Pro Gly Arg Gly Cys Ala Ile Pro Asn Arg Pro
                660                 665                 670
    Gly Ile Phe Val Arg Val Ala Tyr Tyr Ala Lys Trp Ile His Lys Ile
                675                 680                 685
    Ile Leu Thr Tyr Lys Val Pro Gln Ser
                690                 695

(2) INFORMATION FOR SEQ ID NO: 51:

(i) SEQUENCE CHARACTERISTICS:
        (A) LENGTH:          21 amino acids
        (B) TYPE:            amino acid
        (C) STRANDEDNESS:    single
        (D) TOPOLOGY:        linear (ii) MOLECULE TYPE:      peptide (xi) SEQUENCE DESCRIPTION: SEQ ID NO: 51:

Cys Ser Cys Ser Ser Leu Met Asp Lys Glu Cys Val Tyr Phe Cys His
    1               5                   10                  15

Leu Asp Ile Ile Trp
                20

(2) INFORMATION FOR SEQ ID NO: 52:
```

```
        (i) SEQUENCE CHARACTERISTICS:
            (A) LENGTH:          14 amino acids
            (B) TYPE:            amino acid
            (C) STRANDEDNESS:    single
            (D) TOPOLOGY:        linear (ii) MOLECULE TYPE:       peptide (xi) SEQUENCE DESCRIPTION: SEQ ID NO: 52:

Asp Glu Glu Ala Val Tyr Phe Ala His Leu Asp Ile Ile Trp
 1               5                  10

(2) INFORMATION FOR SEQ ID NO: 53:

(i) SEQUENCE CHARACTERISTICS:
            (A) LENGTH:          28 amino acids
            (B) TYPE:            amino acid
            (C) STRANDEDNESS:    single
            (D) TOPOLOGY:        linear (ii) MOLECULE TYPE:       peptide (xi) SEQUENCE DESCRIPTION: SEQ ID NO: 53:

Ser Leu Arg Arg Ser Ser Cys Phe Gly Gly Arg Met Asp Arg Ile Gly
 1               5                  10                  15

Ala Gln Ser Gly Leu Gly Cys Asn Ser Phe Arg Tyr
            20                  25

(2) INFORMATION FOR SEQ ID NO: 54:

(i) SEQUENCE CHARACTERISTICS:
            (A) LENGTH:          23 amino acids
            (B) TYPE:            amino acid
            (C) STRANDEDNESS:    single
            (D) TOPOLOGY:        linear (ii) MOLECULE TYPE:       peptide (xi) SEQUENCE DESCRIPTION: SEQ ID NO: 54:

Gly Leu Phe Glu Ala Ile Ala Asp Phe Ile Glu Asn Gly Trp Glu Gly
 1               5                  10                  15

Met Ile Asp Gly Gly Gly Cys
            20

(2) INFORMATION FOR SEQ ID NO: 55:

(i) SEQUENCE CHARACTERISTICS:
            (A) LENGTH:          19 amino acids
            (B) TYPE:            amino acid
            (C) STRANDEDNESS:    single
            (D) TOPOLOGY:        linear (ii) MOLECULE TYPE:       peptide (xi) SEQUENCE DESCRIPTION: SEQ ID NO: 55:

Lys Val Tyr Thr Gly Val Tyr Pro Phe Met Trp Gly Gly Ala Tyr Cys
 1               5                  10                  15

Phe Cys Asp (2) INFORMATION FOR SEQ ID NO: 56:

(i) SEQUENCE CHARACTERISTICS:
            (A) LENGTH:          23 amino acids
            (B) TYPE:            amino acid
            (C) STRANDEDNESS:    single
            (D) TOPOLOGY:        linear (ii) MOLECULE TYPE:       peptide
```

(xi) SEQUENCE DESCRIPTION: SEQ ID NO: 56:

```
Gly Gly Tyr Cys Leu Thr Arg Trp Met Leu Ile Glu Ala Glu Leu Lys
1               5                   10                  15
Cys Phe Gly Asn Thr Ala Val
                20
```

(2) INFORMATION FOR SEQ ID NO: 57:

(i) SEQUENCE CHARACTERISTICS:
        (A) LENGTH:         9 amino acids
        (B) TYPE:           amino acid
        (C) STRANDEDNESS:   single
        (D) TOPOLOGY:       linear (ii) MOLECULE TYPE:      peptide (xi) SEQUENCE DESCRIPTION: SEQ ID NO: 57:

```
Glu Lys Gly Lys Gly Pro Gly Gly Lys
1               5
```

(2) INFORMATION FOR SEQ ID NO: 58:

(i) SEQUENCE CHARACTERISTICS:
        (A) LENGTH:         45 amino acids
        (B) TYPE:           amino acid
        (C) STRANDEDNESS:   single
        (D) TOPOLOGY:       linear (ii) MOLECULE TYPE:      peptide (xi) SEQUENCE DESCRIPTION: SEQ ID NO: 58:

```
Tyr Lys Ala Lys Lys Lys Lys Lys Lys Lys Lys Lys Lys Lys Lys Lys
1               5                   10                  15
Lys Lys Lys Lys Lys Lys Lys Lys Lys Lys Lys Lys Lys Lys Lys Lys
                20                  25                  30
Lys Lys Lys Lys Lys Lys Lys Lys Lys Lys Lys Trp Lys
        35                  40                  45
```

(2) INFORMATION FOR SEQ ID NO: 59:

(i) SEQUENCE CHARACTERISTICS:
        (A) LENGTH:         24 amino acids
        (B) TYPE:           amino acid
        (C) STRANDEDNESS:   single
        (D) TOPOLOGY:       linear (ii) MOLECULE TYPE:      peptide (xi) SEQUENCE DESCRIPTION: SEQ ID NO: 59:

```
Cys Gly Leu Phe Glu Ala Ile Ala Asp Phe Ile Glu Asn Gly Trp Glu
1               5                   10                  15
Gly Met Ile Asp Gly Gly Gly Cys
                20
```

(2) INFORMATION FOR SEQ ID NO: 60:

(i) SEQUENCE CHARACTERISTICS:
        (A) LENGTH:         59 amino acids
        (B) TYPE:           amino acid
        (C) STRANDEDNESS:   single
        (D) TOPOLOGY:       linear (ii) MOLECULE TYPE:      peptide (xi) SEQUENCE DESCRIPTION: SEQ ID NO: 60:

```
Gly Tyr Gly Pro Pro Lys Lys Lys Arg Lys Val Glu Ala Pro Tyr Lys
1               5                   10                  15
```

Ala Lys Lys Lys Lys Lys Lys Lys Lys Lys Lys Lys Lys Lys
      20                   25                 30

Lys Lys Lys Lys Lys Lys Lys Lys Lys Lys Lys Ly
    35                40               45

Lys Lys Lys Lys Lys Lys Lys Lys Trp Lys
    50                55

(2) INFORMATION FOR SEQ ID NO: 61:

(i) SEQUENCE CHARACTERISTICS:
        (A) LENGTH:         9 amino acids
        (B) TYPE:           amino acid
        (C) STRANDEDNESS:   single
        (D) TOPOLOGY:       linear (ii) MOLECULE TYPE:      peptide (xi) SEQUENCE DESCRIPTION: SEQ ID NO: 61:

Tyr Lys Lys Ala Lys Ala Lys Ala Lys
1             5

(2) INFORMATION FOR SEQ ID NO: 62:

(i) SEQUENCE CHARACTERISTICS:
        (A) LENGTH:         100 amino acids
        (B) TYPE:           amino acid
        (C) STRANDEDNESS:   single
        (D) TOPOLOGY:       linear (ii) MOLECULE TYPE:      peptide (ix) FEATURE:
        (D) OTHER INFORMATION:   "Lys" in positions 3 to 100 may be
            present or absent.

(xi) SEQUENCE DESCRIPTION: SEQ ID NO: 62:

Lys Lys Lys Lys Lys Lys Lys Lys Lys Lys Lys Lys Lys Lys Lys
1            5               10              15

Lys Lys Lys Lys Lys Lys Lys Lys Lys Lys Lys Lys Lys Lys Lys
    20                25               30

Lys Lys Lys Lys Lys Lys Lys Lys Lys Lys Lys Lys Lys Lys Lys
    35                40               45

Lys Lys Lys Lys Lys Lys Lys Lys Lys Lys Lys Lys Lys Lys Lys
    50                55               60

Lys Lys Lys Lys Lys Lys Lys Lys Lys Lys Lys Lys Lys Lys Lys
    65                70               75              80

Lys Lys Lys Lys Lys Lys Lys Lys Lys Lys Lys Lys Lys Lys Lys
          85               90              95

Lys Lys Lys Lys
          100

(2) INFORMATION FOR SEQ ID NO: 63:

(i) SEQUENCE CHARACTERISTICS:
        (A) LENGTH:         100 amino acids
        (B) TYPE:           amino acid
        (C) STRANDEDNESS:   single
        (D) TOPOLOGY:       linear (ii) MOLECULE TYPE:      peptide (ix) FEATURE:
        (D) OTHER INFORMATION:   "Arg Ala" in positions 3 to 100 may
            be present or absent.

(xi) SEQUENCE DESCRIPTION: SEQ ID NO: 63:

-continued

```
Arg Ala Arg Ala Arg Ala Arg Ala Arg Ala Arg Ala Arg Ala Arg Ala
 1               5                  10                  15

Arg Ala Arg Ala Arg Ala Arg Ala Arg Ala Arg Ala Arg Ala Arg Ala
            20                  25                  30

Arg Ala Arg Ala Arg Ala Arg Ala Arg Ala Arg Ala Arg Ala Arg Ala
        35                  40                  45

Arg Ala Arg Ala Arg Ala Arg Ala Arg Ala Arg Ala Arg Ala Arg Ala
    50                  55                  60

Arg Ala Arg Ala Arg Ala Arg Ala Arg Ala Arg Ala Arg Ala Arg Ala
65                  70                  75                  80

Arg Ala Arg Ala Arg Ala Arg Ala Arg Ala Arg Ala Arg Ala Arg Ala
                85                  90                  95

Arg Ala Arg Ala
            100
```

(2) INFORMATION FOR SEQ ID NO: 64:

(i) SEQUENCE CHARACTERISTICS:
        (A) LENGTH:        100 amino acids
        (B) TYPE:          amino acid
        (C) STRANDEDNESS:   single
        (D) TOPOLOGY:      linear (ii) MOLECULE TYPE:     peptide (ix) FEATURE:
        (D) OTHER INFORMATION:  "Lys Ala" in positions 3 to 100 may
            be present or absent.

(xi) SEQUENCE DESCRIPTION: SEQ ID NO: 64:

```
Lys Ala Lys Ala Lys Ala Lys Ala Lys Ala Lys Ala Lys Ala Lys Ala
 1               5                  10                  15

Lys Ala Lys Ala Lys Ala Lys Ala Lys Ala Lys Ala Lys Ala Lys Ala
            20                  25                  30

Lys Ala Lys Ala Lys Ala Lys Ala Lys Ala Lys Ala Lys Ala Lys Ala
        35                  40                  45

Lys Ala Lys Ala Lys Ala Lys Ala Lys Ala Lys Ala Lys Ala Lys Ala
    50                  55                  60

Lys Ala Lys Ala Lys Ala Lys Ala Lys Ala Lys Ala Lys Ala Lys Ala
65                  70                  75                  80

Lys Ala Lys Ala Lys Ala Lys Ala Lys Ala Lys Ala Lys Ala Lys Ala
                85                  90                  95

Lys Ala Lys Ala
            100
```

(2) INFORMATION FOR SEQ ID NO: 65:

(i) SEQUENCE CHARACTERISTICS:
        (A) LENGTH:        9 amino acids
        (B) TYPE:          amino acid
        (C) STRANDEDNESS:   single
        (D) TOPOLOGY:      linear (ii) MOLECULE TYPE:     peptide (xi) SEQUENCE DESCRIPTION: SEQ ID NO: 65:

```
Lys Ala Lys Ala Lys Ala Lys Lys Tyr
 1               5
```